United States Patent
Atkins et al.

(10) Patent No.: US 10,865,001 B2
(45) Date of Patent: Dec. 15, 2020

(54) FILLABLE VAPORIZER CARTRIDGE AND METHOD OF FILLING

(71) Applicant: JUUL Labs, Inc., San Francisco, CA (US)

(72) Inventors: Ariel Atkins, San Francisco, CA (US); Steven Christensen, San Mateo, CA (US); Aaron Keller, Santa Rosa, CA (US); James Monsees, San Francisco, CA (US)

(73) Assignee: JUUL Labs, Inc., San Francisco, CA (US)

( * ) Notice: Subject to any disclaimer, the term of this patent is extended or adjusted under 35 U.S.C. 154(b) by 0 days.

(21) Appl. No.: 16/404,693

(22) Filed: May 6, 2019

(65) Prior Publication Data
US 2019/0256231 A1  Aug. 22, 2019

Related U.S. Application Data

(63) Continuation of application No. 15/430,284, filed on Feb. 10, 2017, now Pat. No. 10,279,934.
(Continued)

(51) Int. Cl.
*B65B 3/00* (2006.01)
*A24F 47/00* (2020.01)
(Continued)

(52) U.S. Cl.
CPC ............ *B65B 3/003* (2013.01); *A24F 47/008* (2013.01); *A61M 15/06* (2013.01); *B65B 3/14* (2013.01);
(Continued)

(58) Field of Classification Search
CPC ......... A24F 47/008; B65B 3/003; B65B 3/14; B65B 3/18
See application file for complete search history.

(56) References Cited

U.S. PATENT DOCUMENTS 374,584 A ‡ 12/1887 Name Not Available ................... E05F 1/1066
16/72
576,653 A ‡ 2/1897 Name Not Available ................... A24F 15/18
206/92

(Continued)

FOREIGN PATENT DOCUMENTS

AT          507187 A4       3/2010
AU       2014206215 A1 ‡   8/2014
(Continued)

OTHER PUBLICATIONS

"Commission Regulation (EC) no. 1275/2008," Official Journal of the European Union, Dec. 17, 2008.‡
(Continued)

*Primary Examiner* — Timothy P. Kelly
(74) *Attorney, Agent, or Firm* — Mintz Levin Cohn Ferris Glovsky and Popeo, P.C.

(57) ABSTRACT

Vaporizer device cartridges are provided. In some implementations, a cartridge comprises a storage compartment having first and second opposing ends, a sealing material sealing the second end, and a wick positioned proximate to the first end. The storage compartment is configured to hold a liquid vaporizable material. The sealing material is configured for insertion of a needle through the sealing material for dispensing the liquid vaporizable material into the storage compartment. The wick comprises opposing ends in communication with the storage compartment and is configured to allow a volume of air to exit the storage compartment through the wick when the storage compartment is being filled with the liquid vaporizable material.

28 Claims, 9 Drawing Sheets

Related U.S. Application Data

(60) Provisional application No. 62/294,285, filed on Feb. 11, 2016.

(51) Int. Cl.
  *B65B 3/14* (2006.01)
  *B65B 3/18* (2006.01)
  *A61M 15/06* (2006.01)
  *B65B 25/04* (2006.01)
  *A61M 11/04* (2006.01)

(52) U.S. Cl.
  CPC .............. *B65B 3/18* (2013.01); *B65B 25/041* (2013.01); *A61M 11/042* (2014.02); *A61M 2209/045* (2013.01)

(56) References Cited

U.S. PATENT DOCUMENTS

| | | | | |
|---|---|---|---|---|
| 595,070 A ‡ | 12/1897 | Name Not Available | ................... | B65D 43/168 220/82 |
| 720,007 A ‡ | 2/1903 | Name Not Available | ................... | A24D 1/14 131/34 |
| 799,844 A ‡ | 9/1905 | Name Not Available | ................... | A24F 27/10 206/13 |
| 968,160 A ‡ | 8/1910 | Name Not Available | ................... | A24F 1/22 131/19 |
| 969,076 A ‡ | 8/1910 | Name Not Available | ................... | A24F 27/00 206/12 |
| 1,067,531 A ‡ | 7/1913 | Name Not Available | ................... | B42F 17/00 40/339 |
| 1,163,183 A ‡ | 12/1915 | Name Not Available | ................... | B65D 85/1009 206/25 |
| 1,299,162 A ‡ | 4/1919 | Name Not Available | ................... | B65D 85/1009 206/25 |
| 1,505,748 A ‡ | 8/1924 | Tamis | ..................... | A24F 15/12 206/25 |
| 1,552,877 A ‡ | 9/1925 | Phillipps | ................. | A24F 25/02 239/53 |
| 1,632,335 A ‡ | 6/1927 | Hiering | ................... | A24F 15/00 131/23 |
| 1,706,244 A ‡ | 3/1929 | Meyerson | ............... | A24F 15/18 131/24 |
| 1,845,340 A ‡ | 2/1932 | Woller | .................... | A24F 15/18 131/18 |
| 1,972,118 A ‡ | 9/1934 | McDill | .................. | A24F 25/00 131/32 |
| 1,998,683 A ‡ | 4/1935 | Montgomery | ....... | A24B 15/282 206/20 |
| 2,031,363 A ‡ | 2/1936 | Erikson | ................. | A45C 15/00 206/23 |
| 2,039,559 A ‡ | 5/1936 | Segal | ..................... | A24F 15/18 206/23 |
| 2,104,266 A ‡ | 1/1938 | McCormick | .......... | A24F 47/008 131/17 |
| 2,159,698 A ‡ | 5/1939 | Harris | ..................... | A24F 1/00 131/19 |
| 2,177,636 A ‡ | 10/1939 | Coffelt | ................... | A24F 13/14 131/17 |
| 2,195,260 A ‡ | 3/1940 | Rasener | ................... | A24F 5/06 131/19 |
| 2,231,909 A ‡ | 2/1941 | Hempel | ............... | A45C 13/005 |
| 2,327,120 A ‡ | 8/1943 | McCoon | ................ | A24F 15/14 206/25 |
| D142,178 S ‡ | 8/1945 | Name Not Available | ..... | D27/18 |
| 2,460,427 A ‡ | 2/1949 | Musselman | ............... | F23Q 2/06 206/89 |
| 2,483,304 A ‡ | 9/1949 | Vogel | ..................... | A24F 15/12 16/226 |
| 2,502,561 A ‡ | 4/1950 | Ebert | ..................... | B65D 5/524 206/75 |
| 2,765,949 A ‡ | 10/1956 | Hillman | ................... | E05D 1/06 16/257 |
| 2,830,597 A ‡ | 4/1958 | Kummli | ................. | A24F 47/002 131/21 |
| 2,860,638 A ‡ | 11/1958 | Bartolomeo | .......... | A24F 47/002 128/20 |
| 2,897,958 A ‡ | 8/1959 | Tarleton | .................. | A24F 15/12 206/25 |
| 2,935,987 A ‡ | 5/1960 | Ackerbauer | ............. | A24D 1/14 131/34 |
| 3,085,145 A | 4/1963 | Wray | | |
| 3,146,937 A ‡ | 9/1964 | Vesak | ............... | B65D 5/46032 229/11 |
| 3,258,015 A ‡ | 6/1966 | Drummond | ........... | A24F 47/004 |
| 3,271,719 A ‡ | 9/1966 | Ovshinsky | ............. | H01C 11/00 327/51 |
| 3,292,634 A ‡ | 12/1966 | Beucler | .................... | A24D 1/14 131/18 |
| D207,887 S ‡ | 6/1967 | Name Not Available | ..... | D9/439 |
| 3,373,915 A ‡ | 3/1968 | Anderson | ............... | A24F 23/02 206/24 |
| 3,420,360 A ‡ | 1/1969 | Young | ...................... | B65D 5/72 206/25 |
| 3,443,827 A ‡ | 5/1969 | Boezi | .................... | E21B 17/046 24/303 |
| 3,456,645 A ‡ | 7/1969 | Brock | ............... | A61M 15/0091 128/20 |
| 3,479,561 A ‡ | 11/1969 | Janning | ................... | F21S 6/001 200/81 |
| 3,567,014 A ‡ | 3/1971 | Feigelman | ........... | B65D 5/5246 206/76 |
| 3,675,661 A ‡ | 7/1972 | Weaver | ..................... | A24F 1/08 131/21 |
| 3,707,017 A ‡ | 12/1972 | Paquette | ................... | E05D 1/00 16/385 |
| 3,723,048 A ‡ | 3/1973 | Russell | ..................... | F23Q 2/06 431/15 |
| 3,792,704 A ‡ | 2/1974 | Parker | ..................... | A24D 1/14 131/34 |
| 3,815,597 A ‡ | 6/1974 | Goettelman | .......... | A61M 15/06 131/19 |
| 3,861,523 A ‡ | 1/1975 | Fountain | .................. | A24F 15/12 206/23 |
| 3,918,451 A | 11/1975 | Steil | | |
| 3,934,117 A | 1/1976 | Schladitz | | |
| 3,941,300 A ‡ | 3/1976 | Troth | ...................... | B65D 5/12 229/5 |
| 4,020,853 A ‡ | 5/1977 | Nuttall | ..................... | A24F 1/22 131/19 |
| 4,049,005 A ‡ | 9/1977 | Hernandez | ............. | A24F 13/04 131/18 |
| 4,066,088 A ‡ | 1/1978 | Ensor | ..................... | A24F 13/00 131/18 |
| D250,485 S ‡ | 12/1978 | Cuthbertson | .................. | D27/16 |
| 4,171,000 A | 10/1979 | Uhle | | |
| D255,548 S ‡ | 6/1980 | Grodin | .......................... | D9/439 |
| 4,207,976 A ‡ | 6/1980 | Herman | ............... | B65D 85/109 206/24 |
| 4,215,708 A ‡ | 8/1980 | Bron | ..................... | A24F 13/04 131/33 |
| 4,219,032 A ‡ | 8/1980 | Tabatznik | .................. | A24F 1/00 131/17 |
| D260,690 S ‡ | 9/1981 | Stutzer | .......................... | D27/15 |
| 4,303,083 A ‡ | 12/1981 | Burruss, Jr. | ........... | A61M 15/06 131/19 |
| D271,255 S ‡ | 11/1983 | Rousseau | ..................... | D3/207 |
| 4,492,480 A | 1/1985 | Wadso et al. | | |
| 4,506,683 A ‡ | 3/1985 | Cantrell | ................ | A24D 3/043 131/33 |

(56) References Cited

U.S. PATENT DOCUMENTS

| | | | |
|---|---|---|---|
| 4,519,319 A ‡ | 5/1985 | Howlett | A47F 5/116 108/18 |
| 4,520,938 A ‡ | 6/1985 | Finke | B65D 50/041 215/22 |
| D280,494 S ‡ | 9/1985 | Abel | D10/10 |
| 4,548,454 A | 10/1985 | Zeller et al. | |
| 4,595,024 A ‡ | 6/1986 | Greene | A24D 1/00 131/36 |
| 4,625,737 A ‡ | 12/1986 | Keritsis | A24B 15/14 131/35 |
| 4,648,393 A ‡ | 3/1987 | Landis | A61M 15/0091 128/20 |
| 4,708,151 A ‡ | 11/1987 | Shelar | A24D 1/14 131/35 |
| 4,735,217 A ‡ | 4/1988 | Gerth | A24F 47/008 128/20 |
| 4,745,705 A | 5/1988 | Yamamoto et al. | |
| 4,771,796 A ‡ | 9/1988 | Myer | A24F 47/002 131/27 |
| 4,793,365 A ‡ | 12/1988 | Sensabaugh, Jr. | A24B 15/165 131/19 |
| 4,794,323 A ‡ | 12/1988 | Zhou | G01K 7/223 324/71 |
| 4,798,310 A ‡ | 1/1989 | Kasai | B43K 23/001 206/22 |
| 4,811,731 A | 3/1989 | Newell et al. | |
| 4,813,536 A ‡ | 3/1989 | Willis | B65D 5/5206 206/45 |
| 4,819,665 A ‡ | 4/1989 | Roberts | A24F 47/004 131/19 |
| 4,830,028 A ‡ | 5/1989 | Lawson | A24B 15/30 131/31 |
| D301,837 S ‡ | 6/1989 | Peterson | D9/529 |
| 4,836,224 A ‡ | 6/1989 | Lawson | A24B 15/30 131/33 |
| 4,846,199 A ‡ | 7/1989 | Rose | A24B 15/165 131/32 |
| 4,848,374 A ‡ | 7/1989 | Chard | A24F 47/004 131/33 |
| 4,848,563 A ‡ | 7/1989 | Robbins | B65D 5/4802 206/31 |
| D302,659 S ‡ | 8/1989 | Peterson | D9/529 |
| D303,722 S ‡ | 9/1989 | Marlow | D27/18 |
| 4,870,748 A ‡ | 10/1989 | Hensgen | A24F 47/004 131/80 |
| D304,771 S ‡ | 11/1989 | Katayama | D27/16 |
| 4,893,639 A ‡ | 1/1990 | White | A24B 15/14 131/35 |
| 4,896,683 A ‡ | 1/1990 | Cohen | A24D 3/16 131/33 |
| 4,907,606 A ‡ | 3/1990 | Lilja | A24B 15/18 131/27 |
| 4,924,883 A ‡ | 5/1990 | Perfetti | A24F 47/004 131/33 |
| 4,938,236 A ‡ | 7/1990 | Banerjee | A24B 15/165 131/19 |
| 4,941,483 A ‡ | 7/1990 | Ridings | F24V 30/00 131/19 |
| 4,944,317 A ‡ | 7/1990 | Thal | A24D 1/14 131/34 |
| D310,171 S ‡ | 8/1990 | Cusenza | D9/529 |
| 4,945,929 A ‡ | 8/1990 | Egilmex | A24F 47/002 128/20 |
| 4,947,874 A ‡ | 8/1990 | Brooks | A24F 47/008 128/20 |
| 4,947,875 A ‡ | 8/1990 | Brooks | A24F 47/006 128/20 |
| D310,349 S ‡ | 9/1990 | Rowen | D13/16 |
| 4,955,397 A ‡ | 9/1990 | Johnson | A24B 15/165 131/19 |
| 4,984,588 A ‡ | 1/1991 | Stewart, Jr. | A24D 1/00 131/33 |
| D315,032 S ‡ | 2/1991 | Hayes | D27/16 |
| 4,993,436 A | 2/1991 | Bloom, Jr. | |
| 5,005,759 A ‡ | 4/1991 | Bouche | B65D 15/22 206/44 |
| 5,019,122 A ‡ | 5/1991 | Clearman | A24F 47/004 131/19 |
| 5,020,548 A ‡ | 6/1991 | Farrier | A24B 15/165 131/19 |
| 5,027,836 A ‡ | 7/1991 | Shannon | A24F 47/004 131/19 |
| 5,031,646 A ‡ | 7/1991 | Lippiello | A24B 15/30 131/27 |
| 5,040,551 A ‡ | 8/1991 | Schlatter | A24B 15/165 131/33 |
| 5,050,621 A ‡ | 9/1991 | Creighton | A24B 15/165 131/19 |
| 5,060,671 A ‡ | 10/1991 | Counts | A24F 47/008 131/32 |
| 5,065,776 A ‡ | 11/1991 | Lawson | A24B 15/165 131/36 |
| 5,076,297 A ‡ | 12/1991 | Farrier | A24B 15/165 131/35 |
| 5,101,838 A ‡ | 4/1992 | Schwartz | A24F 47/002 131/27 |
| 5,105,831 A ‡ | 4/1992 | Banerjee | A24F 47/004 131/19 |
| 5,105,836 A ‡ | 4/1992 | Gentry | A24B 15/14 131/35 |
| 5,105,838 A ‡ | 4/1992 | White | A24D 1/00 131/19 |
| 5,117,482 A | 5/1992 | Hauber | |
| 5,123,530 A ‡ | 6/1992 | Lee | A24F 15/14 206/24 |
| 5,133,368 A ‡ | 7/1992 | Neumann | A24F 47/004 131/33 |
| 5,141,004 A ‡ | 8/1992 | Porenski | A24B 15/16 131/19 |
| 5,144,962 A ‡ | 9/1992 | Counts | A24F 47/008 131/19 |
| 5,148,817 A ‡ | 9/1992 | Houminer | C07D 213/16 131/27 |
| 5,152,456 A ‡ | 10/1992 | Ross | A61M 15/0085 128/20 |
| 5,183,062 A ‡ | 2/1993 | Clearman | A24F 47/004 131/19 |
| D336,346 S ‡ | 6/1993 | Miller | D25/12 |
| 5,224,498 A ‡ | 7/1993 | Deevi | A24F 47/008 128/20 |
| 5,228,460 A ‡ | 7/1993 | Sprinkel | H05B 3/10 128/20 |
| 5,240,012 A ‡ | 8/1993 | Ehrman | A24F 47/004 131/18 |
| 5,249,586 A ‡ | 10/1993 | Morgan | A24F 47/008 128/20 |
| 5,259,786 A | 11/1993 | Huang | |
| 5,261,424 A ‡ | 11/1993 | Sprinkel, Jr. | A24F 47/008 128/20 |
| 5,269,237 A ‡ | 12/1993 | Baker | A01C 5/064 111/12 |
| 5,269,327 A ‡ | 12/1993 | Counts | A24F 47/008 128/20 |
| H001271 H | 1/1994 | Shouse | |
| 5,296,685 A ‡ | 3/1994 | Burstein | H05B 3/44 219/53 |
| 5,303,720 A ‡ | 4/1994 | Banerjee | A24F 47/004 |
| 5,322,075 A ‡ | 6/1994 | Deevi | H05B 3/44 131/19 |
| 5,324,498 A ‡ | 6/1994 | Streusand | C01G 41/04 423/48 |
| 5,345,951 A ‡ | 9/1994 | Serrano | A24B 15/165 131/19 |
| 5,369,723 A ‡ | 11/1994 | Counts | H05B 3/145 392/38 |
| 5,372,148 A ‡ | 12/1994 | McCafferty | A24F 47/008 131/19 |

(56) References Cited

U.S. PATENT DOCUMENTS

| | | | | |
|---|---|---|---|---|
| 5,388,574 A ‡ | 2/1995 | Ingebrethsen | A61M 15/0085 | |
| | | | 128/20 | |
| 5,449,078 A ‡ | 9/1995 | Akers | B65D 41/06 | |
| | | | 215/22 | |
| 5,456,269 A ‡ | 10/1995 | Kollasch | A24F 1/00 | |
| | | | 131/19 | |
| 5,472,001 A ‡ | 12/1995 | Nicholson | A24F 13/00 | |
| | | | 131/18 | |
| 5,479,948 A | 1/1996 | Counts et al. | | |
| D367,605 S ‡ | 3/1996 | Moore | D9/529 | |
| 5,497,791 A ‡ | 3/1996 | Bowen | A24F 13/00 | |
| | | | 131/17 | |
| D368,552 S ‡ | 4/1996 | Adams | D27/19 | |
| 5,529,078 A ‡ | 6/1996 | Rehder | A24F 13/00 | |
| | | | 131/17 | |
| D371,633 S ‡ | 7/1996 | Chenard | D27/16 | |
| 5,545,904 A ‡ | 8/1996 | Orbach | H01L 23/5256 | |
| | | | 257/20 | |
| 5,564,442 A ‡ | 10/1996 | MacDonald | A24F 13/00 | |
| | | | 131/19 | |
| 5,579,934 A ‡ | 12/1996 | Buono | B65D 50/041 | |
| | | | 215/21 | |
| 5,591,368 A ‡ | 1/1997 | Fleischhauer | A24F 47/008 | |
| | | | 131/19 | |
| 5,605,226 A ‡ | 2/1997 | Hernlein | A24F 15/18 | |
| | | | 206/49 | |
| D379,810 S ‡ | 6/1997 | Giordano, Jr. | D14/13 | |
| 5,641,064 A ‡ | 6/1997 | Goserud | B65D 39/16 | |
| | | | 206/31 | |
| D380,293 S ‡ | 7/1997 | Cudmore | D3/208 | |
| 5,649,552 A ‡ | 7/1997 | Cho | A24B 3/182 | |
| | | | 131/29 | |
| D382,146 S ‡ | 8/1997 | Sandy | D25/12 | |
| 5,661,329 A | 8/1997 | Hiramoto et al. | | |
| 5,666,977 A ‡ | 9/1997 | Higgins | A24F 47/008 | |
| | | | 128/20 | |
| 5,666,978 A ‡ | 9/1997 | Counts | A24F 47/008 | |
| | | | 131/19 | |
| 5,682,050 A | 10/1997 | Williams | | |
| 5,708,258 A ‡ | 1/1998 | Counts | A24F 47/008 | |
| | | | 131/19 | |
| 5,730,118 A ‡ | 3/1998 | Hermanson | A45F 5/00 | |
| | | | 128/2 | |
| 5,730,158 A ‡ | 3/1998 | Collins | A24F 47/008 | |
| | | | 131/19 | |
| 5,746,587 A ‡ | 5/1998 | Racine | A24F 15/18 | |
| | | | 206/85 | |
| D397,504 S ‡ | 8/1998 | Zelenik | D27/18 | |
| D398,150 S ‡ | 9/1998 | Vonarburg | D28/85 | |
| 5,810,164 A ‡ | 9/1998 | Rennecamp | B65D 85/1081 | |
| | | | 131/26 | |
| 5,819,756 A ‡ | 10/1998 | Mielordt | A24F 47/008 | |
| | | | 131/33 | |
| 5,845,649 A ‡ | 12/1998 | Saito | A24B 15/165 | |
| | | | 131/35 | |
| D405,007 S ‡ | 2/1999 | Naas, Sr. | D27/18 | |
| 5,865,185 A ‡ | 2/1999 | Collins | A24F 47/008 | |
| | | | 131/19 | |
| 5,865,186 A ‡ | 2/1999 | Volsey, II | A24F 47/006 | |
| | | | 131/19 | |
| 5,881,884 A ‡ | 3/1999 | Podosek | B65D 5/5445 | |
| | | | 206/73 | |
| 5,894,841 A ‡ | 4/1999 | Voges | A24F 47/008 | |
| | | | 128/20 | |
| D411,332 S ‡ | 6/1999 | Zelenik | D27/18 | |
| D412,279 S ‡ | 7/1999 | Brice | D7/629 | |
| 5,931,828 A ‡ | 8/1999 | Durkee | B65D 51/002 | |
| | | | 215/24 | |
| 5,934,289 A ‡ | 8/1999 | Watkins | A24F 47/008 | |
| | | | 128/20 | |
| 5,938,018 A ‡ | 8/1999 | Keaveney | A24F 15/18 | |
| | | | 206/26 | |
| 5,944,025 A ‡ | 8/1999 | Cook | A24F 47/006 | |
| | | | 131/33 | |
| 5,954,979 A ‡ | 9/1999 | Counts | A24F 47/008 | |
| | | | 131/19 | |
| D414,893 S ‡ | 10/1999 | Moore | D27/19 | |
| 5,967,310 A ‡ | 10/1999 | Hill | A24F 23/04 | |
| | | | 131/32 | |
| 5,975,415 A ‡ | 11/1999 | Zehnal | B65D 5/541 | |
| | | | 206/80 | |
| 5,979,460 A ‡ | 11/1999 | Matsumura | A24D 3/10 | |
| | | | 131/33 | |
| 5,994,025 A ‡ | 11/1999 | Iwasa | G03F 7/0045 | |
| | | | 430/27 | |
| 5,996,589 A ‡ | 12/1999 | St Charles | A24F 47/002 | |
| | | | 131/27 | |
| 6,024,097 A ‡ | 2/2000 | Von Wielligh | A24F 47/002 | |
| | | | 131/27 | |
| 6,026,820 A ‡ | 2/2000 | Baggett, Jr. | A24F 47/008 | |
| | | | 131/37 | |
| 6,040,560 A ‡ | 3/2000 | Fleischhauer | A24F 47/008 | |
| | | | 128/20 | |
| D422,884 S ‡ | 4/2000 | Lafond | D8/354 | |
| 6,053,176 A ‡ | 4/2000 | Adams | A24F 47/008 | |
| | | | 128/20 | |
| D424,236 S ‡ | 5/2000 | Reed | D27/16 | |
| 6,089,857 A ‡ | 7/2000 | Matsuura | A61M 15/06 | |
| | | | 431/14 | |
| 6,090,082 A | 7/2000 | King et al. | | |
| 6,095,153 A ‡ | 8/2000 | Kessler | A24F 47/008 | |
| | | | 131/19 | |
| 6,102,036 A ‡ | 8/2000 | Slutsky | A61M 15/0045 | |
| | | | 128/20 | |
| 6,119,684 A ‡ | 9/2000 | Nohl | A61M 15/009 | |
| | | | 128/20 | |
| 6,125,853 A ‡ | 10/2000 | Susa | A24F 47/008 | |
| | | | 131/27 | |
| D433,532 S ‡ | 11/2000 | Higgins | D27/18 | |
| 6,155,268 A ‡ | 12/2000 | Takeuchi | A24F 47/008 | |
| | | | 131/27 | |
| 6,164,287 A ‡ | 12/2000 | White | A24F 47/008 | |
| | | | 131/19 | |
| D436,686 S ‡ | 1/2001 | Fujisawa | D27/16 | |
| 6,196,218 B1 | 3/2001 | Voges | | |
| 6,196,232 B1 ‡ | 3/2001 | Chkadua | A24F 1/00 | |
| | | | 131/17 | |
| 6,203,339 B1 | 3/2001 | Nieminen | | |
| 6,216,705 B1 ‡ | 4/2001 | Ossepian | A24F 47/002 | |
| | | | 128/20 | |
| D442,328 S ‡ | 5/2001 | Barmes | D27/16 | |
| 6,234,169 B1 ‡ | 5/2001 | Bulbrook | A61M 15/06 | |
| | | | 128/20 | |
| 6,265,789 B1 ‡ | 7/2001 | Honda | H01F 38/14 | |
| | | | 307/33 | |
| D447,276 S ‡ | 8/2001 | Gustafson | D27/16 | |
| 6,269,966 B1 ‡ | 8/2001 | Pallo | A45C 5/02 | |
| | | | 220/4 | |
| 6,283,610 B1 | 9/2001 | Alajajian | | |
| D450,313 S ‡ | 11/2001 | Koinuma | D14/21 | |
| D450,662 S ‡ | 11/2001 | Kwok | D13/16 | |
| 6,324,261 B1 ‡ | 11/2001 | Merte | H04M 1/0291 | |
| | | | 379/10 | |
| 6,349,728 B1 ‡ | 2/2002 | Pham | A24F 13/00 | |
| | | | 131/17 | |
| D454,079 S ‡ | 3/2002 | Fong | D10/40 | |
| 6,381,739 B1 ‡ | 4/2002 | Breternitz, Jr. | G06F 8/443 | |
| | | | 714/37 | |
| 6,386,371 B1 ‡ | 5/2002 | Parsons | B65D 5/504 | |
| | | | 206/48 | |
| 6,407,371 B1 ‡ | 6/2002 | Toya | H05B 3/0047 | |
| | | | 118/72 | |
| 6,418,938 B1 ‡ | 7/2002 | Fleischhauer | A24F 9/04 | |
| | | | 131/24 | |
| 6,431,363 B1 ‡ | 8/2002 | Hacker | B65D 5/5038 | |
| | | | 206/48 | |
| 6,443,146 B1 ‡ | 9/2002 | Voges | A24F 47/002 | |
| | | | 128/20 | |

(56) References Cited

U.S. PATENT DOCUMENTS

| | | | |
|---|---|---|---|
| 6,446,793 B1 ‡ | 9/2002 | Layshock | A24F 15/18 |
| | | | 206/85 |
| D465,660 S ‡ | 11/2002 | Doeing | D19/90 |
| 6,510,982 B2 ‡ | 1/2003 | White | A47F 5/112 |
| | | | 206/73 |
| 6,516,796 B1 | 2/2003 | Cox et al. | |
| D471,104 S ‡ | 3/2003 | Hunt | D9/435 |
| 6,532,965 B1 ‡ | 3/2003 | Abhulimen | A24F 47/004 |
| | | | 131/17 |
| 6,536,442 B2 ‡ | 3/2003 | St. Charles | A24F 47/004 |
| | | | 131/18 |
| 6,557,708 B2 ‡ | 5/2003 | Polacco | B65D 77/042 |
| | | | 206/59 |
| 6,598,607 B2 ‡ | 7/2003 | Adiga | A24F 47/004 |
| | | | 131/19 |
| D477,920 S ‡ | 8/2003 | McCarty | D6/310 |
| D478,569 S ‡ | 8/2003 | Hussaini | D14/21 |
| D478,897 S ‡ | 8/2003 | Tsuge | D14/21 |
| 6,603,924 B2 ‡ | 8/2003 | Brown | A01M 1/2077 |
| | | | 219/54 |
| 6,606,998 B1 ‡ | 8/2003 | Gold | A24F 47/002 |
| | | | 128/20 |
| 6,612,404 B2 ‡ | 9/2003 | Sweet | H03K 17/97 |
| | | | 187/39 |
| 6,615,840 B1 ‡ | 9/2003 | Fournier | A24D 1/02 |
| | | | 131/19 |
| 6,622,867 B2 ‡ | 9/2003 | Menceles | B65D 11/02 |
| | | | 206/46 |
| 6,637,430 B1 ‡ | 10/2003 | Voges | A61M 15/0065 |
| | | | 128/20 |
| 6,655,379 B2 ‡ | 12/2003 | Clark | A61K 9/0073 |
| | | | 128/20 |
| D485,639 S ‡ | 1/2004 | Stronski | D27/17 |
| 6,672,762 B1 ‡ | 1/2004 | Faircloth | B65D 5/029 |
| | | | 206/27 |
| 6,688,313 B2 ‡ | 2/2004 | Wrenn | A24C 5/478 |
| | | | 131/19 |
| 6,707,274 B1 ‡ | 3/2004 | Karr | H01M 10/46 |
| | | | 320/10 |
| 6,708,846 B1 ‡ | 3/2004 | Fuchs | A61M 15/0028 |
| | | | 222/82 |
| 6,726,006 B1 ‡ | 4/2004 | Funderburk | B65B 19/20 |
| | | | 206/25 |
| 6,743,030 B2 ‡ | 6/2004 | Lin | H01R 31/065 |
| | | | 439/13 |
| 6,752,649 B2 ‡ | 6/2004 | Arkin | H01R 31/065 |
| | | | 439/49 |
| D494,315 S ‡ | 8/2004 | Cartier | D27/19 |
| 6,769,436 B2 ‡ | 8/2004 | Horian | A61M 15/06 |
| | | | 128/20 |
| 6,772,756 B2 ‡ | 8/2004 | Shayan | A61M 15/00 |
| | | | 128/20 |
| D495,599 S ‡ | 9/2004 | Biesecker | D7/391 |
| 6,799,576 B2 ‡ | 10/2004 | Farr | A24F 47/002 |
| | | | 128/20 |
| 6,803,545 B2 ‡ | 10/2004 | Blake | H05B 3/58 |
| | | | 131/19 |
| 6,803,744 B1 ‡ | 10/2004 | Sabo | H02J 50/90 |
| | | | 320/10 |
| 6,805,545 B2 ‡ | 10/2004 | Slaboden | B65B 1/24 |
| | | | 425/35 |
| 6,810,883 B2 ‡ | 11/2004 | Felter | A24F 47/008 |
| | | | 131/19 |
| D500,301 S ‡ | 12/2004 | Deguchi | D14/48 |
| D500,302 S ‡ | 12/2004 | Deguchi | D14/48 |
| 6,827,573 B2 ‡ | 12/2004 | St. Charles | F23D 14/105 |
| | | | 431/32 |
| 6,854,470 B1 ‡ | 2/2005 | Pu | A61M 15/06 |
| | | | 128/20 |
| 6,874,507 B2 ‡ | 4/2005 | Farr | A24F 47/002 |
| | | | 128/20 |
| D505,922 S ‡ | 6/2005 | Mayo | D13/16 |
| D506,447 S ‡ | 6/2005 | Mayo | D13/16 |
| D506,731 S ‡ | 6/2005 | Mayo | D13/16 |
| 6,909,840 B2 ‡ | 6/2005 | Harwig | A01M 1/2077 |
| | | | 392/39 |
| D507,244 S ‡ | 7/2005 | Mayo | D13/16 |
| 6,923,890 B2 ‡ | 8/2005 | Ricatto | B01J 19/088 |
| | | | 204/16 |
| 6,954,979 B2 ‡ | 10/2005 | Logan | A47G 1/105 |
| | | | 227/11 |
| 6,994,096 B2 ‡ | 2/2006 | Rostami | A24F 47/008 |
| | | | 131/19 |
| 7,000,775 B2 ‡ | 2/2006 | Gelardi | B65D 15/08 |
| | | | 206/48 |
| 7,015,796 B2 ‡ | 3/2006 | Snyder | A24F 47/00 |
| | | | 131/27 |
| 7,025,066 B2 ‡ | 4/2006 | Lawson | A24B 15/18 |
| | | | 131/29 |
| D523,171 S ‡ | 6/2006 | Mitten | D27/18 |
| D525,948 S ‡ | 8/2006 | Blair | D13/16 |
| 7,082,825 B2 ‡ | 8/2006 | Aoshima | G01F 1/6842 |
| | | | 73/204 |
| D528,992 S ‡ | 9/2006 | Hobart | D13/16 |
| D529,044 S ‡ | 9/2006 | Andre | D14/20 |
| 7,109,876 B2 ‡ | 9/2006 | Smith | G06F 1/28 |
| | | | 340/5 |
| D530,340 S ‡ | 10/2006 | Andre | D14/20 |
| D531,190 S ‡ | 10/2006 | Lee | D14/20 |
| 7,117,707 B2 ‡ | 10/2006 | Adams | B21J 1/06 |
| | | | 72/342 |
| D534,921 S ‡ | 1/2007 | Andre | D14/20 |
| D535,261 S ‡ | 1/2007 | Daniels | D13/16 |
| D535,308 S ‡ | 1/2007 | Andre | D14/20 |
| 7,185,659 B2 ‡ | 3/2007 | Sharpe | A24F 47/008 |
| | | | 131/19 |
| D539,813 S ‡ | 4/2007 | Chen | D14/20 |
| D540,687 S ‡ | 4/2007 | Egawa | D9/529 |
| D540,749 S ‡ | 4/2007 | Kaule | D13/16 |
| 7,214,075 B2 ‡ | 5/2007 | He | H01R 13/5213 |
| | | | 439/13 |
| D544,643 S ‡ | 6/2007 | Lin | D27/19 |
| D545,303 S ‡ | 6/2007 | Chang | D14/21 |
| D545,490 S | 6/2007 | Tai | |
| 7,234,593 B2 ‡ | 6/2007 | Fath | B65D 5/422 |
| | | | 206/23 |
| D545,904 S ‡ | 7/2007 | Chen | D19/66 |
| D546,782 S ‡ | 7/2007 | Poulet | D13/16 |
| D547,002 S ‡ | 7/2007 | Lin | D27/19 |
| D551,548 S ‡ | 9/2007 | Didier | D9/439 |
| D551,970 S ‡ | 10/2007 | Didier | D9/439 |
| 7,275,941 B1 ‡ | 10/2007 | Bushby | H01R 13/6397 |
| | | | 439/13 |
| D556,154 S ‡ | 11/2007 | Poulet | D13/16 |
| 7,290,549 B2 ‡ | 11/2007 | Banerjee | A24B 15/16 |
| | | | 131/19 |
| D557,209 S ‡ | 12/2007 | Ahlgren | D13/10 |
| D558,060 S ‡ | 12/2007 | Sír | D9/687 |
| 7,318,435 B2 | 1/2008 | Pentafragas | |
| D562,151 S ‡ | 2/2008 | Larocca | D9/529 |
| D565,496 S ‡ | 4/2008 | Disla | D12/30 |
| D566,709 S | 4/2008 | Kim et al. | |
| D568,298 S ‡ | 5/2008 | Lundgren | D14/21 |
| D569,727 S ‡ | 5/2008 | Moretti | D9/454 |
| 7,374,048 B2 ‡ | 5/2008 | Mazurek | B65D 15/08 |
| | | | 206/48 |
| D571,202 S ‡ | 6/2008 | Vogt | D9/439 |
| D571,556 S ‡ | 6/2008 | Raile | D3/265 |
| D573,474 S ‡ | 7/2008 | Beam | D9/423 |
| 7,415,982 B1 ‡ | 8/2008 | Sheridan | A24F 1/28 |
| | | | 131/19 |
| D576,619 S ‡ | 9/2008 | Udagawa | D14/43 |
| D577,019 S ‡ | 9/2008 | Udagawa | D14/43 |
| D577,150 S ‡ | 9/2008 | Bryman | D27/16 |
| D577,591 S ‡ | 9/2008 | Bouroullec | D9/529 |
| 7,428,905 B2 ‡ | 9/2008 | Mua | A24B 3/14 |
| | | | 131/36 |
| 7,434,584 B2 ‡ | 10/2008 | Steinberg | A24F 1/00 |
| | | | 131/19 |

(56) References Cited

U.S. PATENT DOCUMENTS

| | | | | |
|---|---|---|---|---|
| D580,756 S ‡ | 11/2008 | Seebold | ............................ | D9/439 |
| D585,077 S ‡ | 1/2009 | Sheba | ............................ | D14/43 |
| 7,488,171 B2 ‡ | 2/2009 | St. Charles | ............ | F23D 14/105 |
| | | | | 431/32 |
| D589,941 S ‡ | 4/2009 | Maier | ............................ | D14/21 |
| D590,988 S ‡ | 4/2009 | Hon | ............................ | D27/10 |
| D590,989 S ‡ | 4/2009 | Hon | ............................ | D27/10 |
| D590,990 S ‡ | 4/2009 | Hon | ............................ | D27/10 |
| D590,991 S ‡ | 4/2009 | Hon | ............................ | D27/10 |
| D591,758 S ‡ | 5/2009 | Lee | ............................ | D14/43 |
| 7,530,352 B2 ‡ | 5/2009 | Childers | ............ | A61M 15/0003 |
| | | | | 128/20 |
| 7,546,703 B2 ‡ | 6/2009 | Johnske | ............ | G09F 7/00 |
| | | | | 206/73 |
| D599,670 S ‡ | 9/2009 | Qin | ............................ | D9/529 |
| 7,581,540 B2 ‡ | 9/2009 | Hale | ............................ | A24F 47/006 |
| | | | | 128/20 |
| 7,621,403 B2 ‡ | 11/2009 | Althoff | ............ | A45D 40/24 |
| | | | | 206/44 |
| D605,509 S ‡ | 12/2009 | Leonardis | ............ | D9/435 |
| D606,505 S ‡ | 12/2009 | Seflic | ............................ | D14/13 |
| 7,633,270 B2 ‡ | 12/2009 | Wong | ............ | H02J 7/0052 |
| | | | | 320/10 |
| 7,644,823 B2 ‡ | 1/2010 | Gelardi | ............ | B65D 15/08 |
| | | | | 206/48 |
| 7,646,613 B2 | 1/2010 | Ligtenberg et al. | | |
| D610,588 S ‡ | 2/2010 | Chen | ............................ | D14/48 |
| D611,409 S ‡ | 3/2010 | Green | ............................ | D13/11 |
| D616,753 S ‡ | 6/2010 | Beam | ............................ | D9/420 |
| 7,726,320 B2 ‡ | 6/2010 | Robinson | ............ | A24F 47/008 |
| | | | | 131/20 |
| 7,753,055 B2 ‡ | 7/2010 | Bryman | ............ | A23F 3/00 |
| | | | | 131/18 |
| D621,357 S ‡ | 8/2010 | Dong | ............................ | D13/13 |
| 7,767,698 B2 ‡ | 8/2010 | Warchol | ............ | A61K 9/0078 |
| | | | | 514/34 |
| D624,238 S ‡ | 9/2010 | Turner | ............................ | D24/13 |
| 7,793,860 B2 ‡ | 9/2010 | Bankers | ............ | A01M 1/2044 |
| | | | | 206/22 |
| 7,793,861 B2 ‡ | 9/2010 | Bankers | ............ | A01M 1/2044 |
| | | | | 206/22 |
| 7,801,573 B2 ‡ | 9/2010 | Yazdi | ............ | H02J 7/0042 |
| | | | | 455/57 |
| 7,802,569 B2 | 9/2010 | Yeates et al. | | |
| D624,880 S ‡ | 10/2010 | Felegy, Jr. | ............ | D13/16 |
| 7,813,832 B2 ‡ | 10/2010 | Sundar | ............ | H01L 21/68707 |
| | | | | 414/22 |
| 7,815,332 B1 ‡ | 10/2010 | Smith | ............ | F21S 8/04 |
| | | | | 362/13 |
| D627,962 S ‡ | 11/2010 | Mudrick | ............ | D3/208 |
| 7,832,397 B2 ‡ | 11/2010 | Lipowicz | ............ | A61M 15/06 |
| | | | | 128/20 |
| 7,832,410 B2 ‡ | 11/2010 | Hon | ............ | A24F 47/008 |
| | | | | 131/27 |
| 7,845,359 B2 ‡ | 12/2010 | Montaser | ............ | A61M 15/0085 |
| | | | | 128/20 |
| D631,055 S ‡ | 1/2011 | Gilbert | ............ | D14/24 |
| D631,458 S ‡ | 1/2011 | Liao | ............ | D14/13 |
| 7,886,507 B2 ‡ | 2/2011 | McGuinness, Jr. | ...... | B65B 67/08 |
| | | | | 493/32 |
| D634,735 S ‡ | 3/2011 | Maier | ............ | D14/21 |
| 7,905,236 B2 ‡ | 3/2011 | Bryman | ............ | A24F 47/004 |
| | | | | 131/18 |
| 7,913,686 B2 ‡ | 3/2011 | Hughes | ............ | A61M 15/009 |
| | | | | 128/20 |
| 7,913,688 B2 | 3/2011 | Cross et al. | | |
| D639,303 S ‡ | 6/2011 | Ni | ............ | D14/48 |
| D639,782 S ‡ | 6/2011 | Kim | ............ | D14/21 |
| D641,718 S ‡ | 7/2011 | Sakai | ............ | D13/16 |
| D642,330 S ‡ | 7/2011 | Turner | ............ | D24/13 |
| D644,375 S ‡ | 8/2011 | Zhou | ............ | D27/10 |
| 7,987,846 B2 ‡ | 8/2011 | Hale | ............ | A24F 47/006 |
| | | | | 128/20 |
| 7,988,034 B2 ‡ | 8/2011 | Pezzoli | ............ | B65D 5/541 |
| | | | | 229/12 |
| 8,003,080 B2 ‡ | 8/2011 | Rabinowitz | ............ | A61K 9/007 |
| | | | | 128/20 |
| D645,817 S ‡ | 9/2011 | Sasada | ............ | D13/10 |
| D647,247 S ‡ | 10/2011 | Jones | ............ | D27/16 |
| 8,042,550 B2 ‡ | 10/2011 | Urtsev | ............ | A24F 47/008 |
| | | | | 131/19 |
| D649,708 S ‡ | 11/2011 | Oneil | ............ | D27/16 |
| D649,932 S ‡ | 12/2011 | Symons | ............ | D13/10 |
| 8,079,371 B2 ‡ | 12/2011 | Robinson | ............ | A24F 47/008 |
| | | | | 131/20 |
| 8,080,975 B2 ‡ | 12/2011 | Bessa | ............ | H02J 7/0044 |
| | | | | 320/10 |
| 8,091,558 B2 ‡ | 1/2012 | Martzel | ............ | A24F 47/008 |
| | | | | 131/27 |
| D653,803 S ‡ | 2/2012 | Timmermans | ............ | D27/16 |
| D656,496 S ‡ | 3/2012 | Andre | ............ | D14/34 |
| 8,141,701 B2 ‡ | 3/2012 | Hodges | ............ | A24C 5/608 |
| | | | | 206/26 |
| 8,156,944 B2 ‡ | 4/2012 | Han | ............ | A24F 47/008 |
| 8,157,918 B2 ‡ | 4/2012 | Becker | ............ | A24B 15/282 |
| | | | | 131/19 |
| D661,889 S ‡ | 6/2012 | Wu | ............ | D3/207 |
| D661,991 S ‡ | 6/2012 | Brummelhuis | ............ | D9/449 |
| 8,205,622 B2 ‡ | 6/2012 | Pan | ............ | A24F 47/008 |
| | | | | 131/27 |
| D664,146 S ‡ | 7/2012 | Hoehn | ............ | D14/43 |
| D664,636 S ‡ | 7/2012 | Robinson | ............ | D23/36 |
| 8,251,060 B2 ‡ | 8/2012 | White | ............ | A61M 11/041 |
| | | | | 128/20 |
| 8,282,995 B2 ‡ | 10/2012 | Calzia | ............ | C09D 11/037 |
| | | | | 427/38 |
| D670,272 S ‡ | 11/2012 | Suzuki | ............ | D14/21 |
| D670,659 S ‡ | 11/2012 | Ishikawa | ............ | D13/16 |
| 8,308,624 B2 ‡ | 11/2012 | Travers | ............ | A24D 3/0212 |
| | | | | 131/28 |
| 8,314,235 B2 ‡ | 11/2012 | Dixit | ............ | C07D 471/08 |
| | | | | 544/34 |
| D672,715 S ‡ | 12/2012 | Brunner | ............ | D13/11 |
| 8,322,350 B2 ‡ | 12/2012 | Lipowicz | ............ | A24F 47/002 |
| | | | | 131/27 |
| D674,182 S ‡ | 1/2013 | Copeland | ............ | D3/208 |
| D674,748 S ‡ | 1/2013 | Ferber | ............ | D13/10 |
| 8,344,693 B2 ‡ | 1/2013 | Budziszek | ............ | H02J 7/32 |
| | | | | 290/1 A |
| D676,741 S ‡ | 2/2013 | van Landsveld | ............ | D9/423 |
| 8,371,310 B2 ‡ | 2/2013 | Brenneise | ............ | A24F 47/008 |
| | | | | 131/19 |
| 8,375,957 B2 ‡ | 2/2013 | Hon | ............ | A24F 47/008 |
| | | | | 131/19 |
| 8,381,739 B2 ‡ | 2/2013 | Gonda | ............ | A24F 47/002 |
| | | | | 131/27 |
| 8,387,612 B2 ‡ | 3/2013 | Damani | ............ | A61M 11/041 |
| | | | | 126/26 |
| 8,393,331 B2 ‡ | 3/2013 | Hon | ............ | A24F 47/008 |
| | | | | 131/19 |
| 8,402,978 B2 ‡ | 3/2013 | Karles | ............ | A24B 15/283 |
| | | | | 131/27 |
| 8,424,539 B2 ‡ | 4/2013 | Braunshteyn | ........ | A24D 3/0283 |
| | | | | 131/33 |
| D681,445 S ‡ | 5/2013 | van Landsveld | ............ | D9/423 |
| D682,090 S ‡ | 5/2013 | Scatterday | ............ | D9/430 |
| D682,698 S ‡ | 5/2013 | Young | ............ | D9/529 |
| D682,841 S ‡ | 5/2013 | Suetake | ............ | D14/48 |
| 8,443,534 B2 ‡ | 5/2013 | Goodfellow | ............ | B65D 27/00 |
| | | | | 116/32 |
| D684,683 S ‡ | 6/2013 | Curti | ............ | D24/11 |
| 8,464,867 B2 ‡ | 6/2013 | Holloway | ............ | B65D 85/1054 |
| | | | | 206/25 |
| D686,336 S ‡ | 7/2013 | Horian | ............ | D24/22 |
| D686,987 S ‡ | 7/2013 | Vanstone | ............ | D13/10 |
| D687,042 S ‡ | 7/2013 | Yoneta | ............ | D14/48 |
| 8,479,747 B2 ‡ | 7/2013 | O'Connell | ............ | A24B 15/24 |
| | | | | 131/30 |
| 8,485,099 B2 | 7/2013 | Skidmore et al. | | |
| 8,485,180 B2 | 7/2013 | Smutney et al. | | |

(56) References Cited

U.S. PATENT DOCUMENTS

| | | | | |
|---|---|---|---|---|
| 8,490,629 B1 ‡ | 7/2013 | Shenassa | A24F 1/28 131/19 |
| 8,495,998 B2 ‡ | 7/2013 | Schennum | A24F 47/002 128/20 |
| 8,499,766 B1 ‡ | 8/2013 | Newton | A24F 47/002 131/27 |
| 8,511,318 B2 ‡ | 8/2013 | Hon | A24F 47/002 131/27 |
| D690,461 S ‡ | 9/2013 | Chen | D27/18 |
| 8,522,776 B2 | 9/2013 | Wright et al. | |
| 8,539,959 B1 ‡ | 9/2013 | Scatterday | A61M 15/06 131/19 |
| 8,541,401 B2 ‡ | 9/2013 | Mishra | A24B 15/30 514/18 |
| D691,324 S ‡ | 10/2013 | Saliman | D27/10 |
| D692,615 S ‡ | 10/2013 | Verleur | D27/18 |
| 8,550,069 B2 ‡ | 10/2013 | Alelov | A61M 11/005 128/20 |
| 8,552,691 B2 ‡ | 10/2013 | Wu | H02J 7/045 320/13 |
| D693,054 S ‡ | 11/2013 | Verleur | D27/18 |
| 8,578,942 B2 ‡ | 11/2013 | Schennum | A24F 47/002 131/27 |
| 8,578,943 B2 ‡ | 11/2013 | Luan | A24B 15/246 131/33 |
| D695,450 S ‡ | 12/2013 | Benassayag | D24/11 |
| D696,051 S ‡ | 12/2013 | Scatterday | D6/680 |
| 8,596,460 B2 ‡ | 12/2013 | Scatterday | B65D 5/54 206/73 |
| 8,646,462 B2 ‡ | 2/2014 | Yamada | A24F 47/002 128/20 |
| D700,572 S ‡ | 3/2014 | Esses | D13/10 |
| 8,671,952 B2 ‡ | 3/2014 | Winterson | A24B 13/00 131/35 |
| 8,678,012 B2 ‡ | 3/2014 | Li | A24F 47/008 128/20 |
| 8,689,789 B2 ‡ | 4/2014 | Andrus | A61M 15/0088 128/20 |
| 8,689,805 B2 ‡ | 4/2014 | Hon | A24F 47/008 131/27 |
| 8,695,794 B2 ‡ | 4/2014 | Scatterday | A24F 15/00 206/24 |
| 8,707,965 B2 ‡ | 4/2014 | Newton | A61M 15/06 128/20 |
| D704,629 S ‡ | 5/2014 | Liu | D13/10 |
| D704,634 S ‡ | 5/2014 | Eidelman | D13/10 |
| D705,918 S ‡ | 5/2014 | Robinson | D23/36 |
| 8,714,150 B2 ‡ | 5/2014 | Alelov | A61M 11/005 128/20 |
| 8,714,161 B2 ‡ | 5/2014 | Liu | A24F 47/008 128/20 |
| 8,733,345 B2 ‡ | 5/2014 | Siller | A24F 47/006 128/20 |
| 8,733,346 B2 ‡ | 5/2014 | Rinker | A24F 47/006 128/20 |
| D707,389 S ‡ | 6/2014 | Liu | D27/19 |
| D707,627 S ‡ | 6/2014 | Brunner | D13/11 |
| 8,739,788 B2 ‡ | 6/2014 | Yomtov | A61M 11/041 128/20 |
| 8,741,348 B2 ‡ | 6/2014 | Hansson | A61K 9/0058 424/48 |
| 8,752,545 B2 ‡ | 6/2014 | Buchberger | A24F 47/008 128/20 |
| 8,752,557 B2 ‡ | 6/2014 | Lipowicz | A24F 47/002 131/27 |
| 8,757,169 B2 ‡ | 6/2014 | Gysland | A24F 47/008 131/27 |
| D708,727 S ‡ | 7/2014 | Postma | D23/36 |
| 8,770,187 B2 ‡ | 7/2014 | Murphy | A24F 47/002 128/20 |
| 8,781,307 B2 ‡ | 7/2014 | Buzzetti | A61M 11/042 392/39 |
| 8,790,556 B2 ‡ | 7/2014 | Bundren | B29C 48/30 264/10 |
| 8,794,231 B2 ‡ | 8/2014 | Thorens | A24F 47/008 128/20 |
| 8,794,244 B2 ‡ | 8/2014 | Hammel | A24F 1/28 131/19 |
| 8,794,245 B1 ‡ | 8/2014 | Scatterday | A45C 13/005 131/27 |
| 8,807,140 B1 ‡ | 8/2014 | Scatterday | A24F 47/002 131/27 |
| 8,809,261 B2 ‡ | 8/2014 | Elsohly | C07D 311/80 |
| 8,813,747 B2 ‡ | 8/2014 | Gibson | A61M 11/041 128/20 |
| 8,813,759 B1 ‡ | 8/2014 | Horian | A61M 15/06 131/27 |
| 8,820,330 B2 ‡ | 9/2014 | Bellinger | A61M 11/041 131/27 |
| 8,829,395 B2 ‡ | 9/2014 | Bao | A61M 11/042 219/20 |
| 8,833,364 B2 | 9/2014 | Buchberger | |
| 8,851,068 B2 ‡ | 10/2014 | Cohen | A61M 11/042 128/20 |
| 8,851,081 B2 ‡ | 10/2014 | Fernando | A24F 47/008 131/19 |
| 8,851,083 B2 ‡ | 10/2014 | Oglesby | A61M 11/047 131/27 |
| 8,857,446 B2 ‡ | 10/2014 | Wu | A24F 47/008 128/20 |
| 8,863,752 B2 ‡ | 10/2014 | Hon | A24F 47/008 131/19 |
| 8,869,792 B1 ‡ | 10/2014 | Lee | A61M 15/06 128/20 |
| 8,881,737 B2 ‡ | 11/2014 | Collett | H05B 3/265 131/27 |
| 8,881,738 B2 ‡ | 11/2014 | Bryman | A24F 3/00 131/18 |
| 8,893,726 B2 ‡ | 11/2014 | Hon | A24F 47/008 |
| 8,897,628 B2 ‡ | 11/2014 | Conley | A24F 47/008 392/38 |
| D718,621 S ‡ | 12/2014 | Mitchell | D9/435 |
| D718,723 S ‡ | 12/2014 | Clymer | D13/16 |
| D718,933 S ‡ | 12/2014 | Brown, Jr. | D3/255 |
| D719,701 S ‡ | 12/2014 | Scatterday | D27/18 |
| D720,095 S ‡ | 12/2014 | Alima | D27/10 |
| D720,496 S ‡ | 12/2014 | Alima | D27/10 |
| D720,497 S ‡ | 12/2014 | Alima | D27/10 |
| 8,899,238 B2 ‡ | 12/2014 | Robinson | A24F 47/008 131/20 |
| 8,899,240 B2 ‡ | 12/2014 | Mass | A61M 15/06 131/19 |
| 8,905,040 B2 ‡ | 12/2014 | Scatterday | A61M 15/06 128/20 |
| 8,910,630 B2 ‡ | 12/2014 | Todd | A61M 11/042 128/20 |
| 8,910,639 B2 ‡ | 12/2014 | Chang | A24F 47/008 131/27 |
| 8,910,640 B2 ‡ | 12/2014 | Sears | F22B 1/28 131/27 |
| 8,910,641 B2 ‡ | 12/2014 | Hon | A24F 47/002 131/27 |
| 8,910,783 B2 ‡ | 12/2014 | Liu | A24F 15/12 206/26 |
| 8,915,254 B2 ‡ | 12/2014 | Monsees | A24F 47/006 131/27 |
| 8,919,561 B2 ‡ | 12/2014 | Boisseau | A61J 7/0069 206/23 |
| D721,202 S ‡ | 1/2015 | Liu | D27/10 |
| D721,577 S ‡ | 1/2015 | Scatterday | D9/432 |
| 8,925,555 B2 ‡ | 1/2015 | Monsees | A24F 47/006 131/27 |
| 8,928,277 B2 ‡ | 1/2015 | Xiang | A24F 47/08 320/10 |
| 8,931,492 B2 ‡ | 1/2015 | Scatterday | A61M 15/06 131/27 |
| D721,972 S ‡ | 2/2015 | Brewer | D9/529 |
| D722,023 S ‡ | 2/2015 | Brunner | D13/11 |

(56) References Cited

U.S. PATENT DOCUMENTS

| | | | |
|---|---|---|---|
| 8,948,578 B2 ‡ | 2/2015 | Buchberger | A61M 11/041 392/39 |
| 8,950,395 B2 ‡ | 2/2015 | Schennum | A61M 15/06 128/20 |
| 8,955,522 B1 ‡ | 2/2015 | Bowen | A24F 47/008 128/20 |
| 8,960,199 B2 ‡ | 2/2015 | Zhuang | A24B 15/14 131/19 |
| 8,963,725 B2 ‡ | 2/2015 | Xiang | G08B 17/10 340/62 |
| D723,735 S ‡ | 3/2015 | Liu | D27/18 |
| D723,736 S ‡ | 3/2015 | Liu | D27/18 |
| D724,037 S ‡ | 3/2015 | Yoshioka | D13/16 |
| D725,310 S ‡ | 3/2015 | Eksouzian | D27/10 |
| D725,821 S | 3/2015 | Levin et al. | |
| D725,823 S ‡ | 3/2015 | Scatterday | A24F 15/12 D27/18 |
| 8,967,382 B2 ‡ | 3/2015 | Liu | A24F 15/18 206/23 |
| 8,973,587 B2 ‡ | 3/2015 | Liu | A24F 47/008 131/27 |
| 8,975,764 B1 ‡ | 3/2015 | Abehasera | F03G 7/08 128/20 |
| 8,978,663 B2 ‡ | 3/2015 | Newton | A24F 47/008 131/34 |
| 8,991,402 B2 ‡ | 3/2015 | Bowen | A61M 11/041 131/19 |
| D726,727 S ‡ | 4/2015 | Holz | D14/40 |
| 9,010,335 B1 ‡ | 4/2015 | Scatterday | A24F 47/008 128/20 |
| 9,016,274 B1 ‡ | 4/2015 | White | A61M 15/00 128/20 |
| 9,018,899 B2 ‡ | 4/2015 | Xiang | A24F 47/00 320/10 |
| D728,855 S ‡ | 5/2015 | Liu | D27/16 |
| D729,030 S ‡ | 5/2015 | Novick | D8/98 |
| D729,277 S ‡ | 5/2015 | Uchida | D14/43 |
| D729,366 S ‡ | 5/2015 | Kauss | D23/36 |
| D729,439 S ‡ | 5/2015 | Scatterday | D27/10 |
| D729,444 S ‡ | 5/2015 | Leidel | D27/16 |
| D729,445 S ‡ | 5/2015 | Leidel | D27/16 |
| D730,571 S ‡ | 5/2015 | Chen | D27/10 |
| D730,572 S ‡ | 5/2015 | Leidel | D27/16 |
| 9,022,026 B2 ‡ | 5/2015 | Fang | A24F 47/008 128/20 |
| 9,022,039 B2 ‡ | 5/2015 | Hearn | A24F 47/002 131/27 |
| 9,025,291 B2 ‡ | 5/2015 | Xiang | G06F 1/26 361/93 |
| 9,028,808 B2 ‡ | 5/2015 | Huland | A61K 9/007 424/85 |
| 9,032,968 B2 ‡ | 5/2015 | Glasberg | A24F 47/008 131/27 |
| 9,038,626 B2 ‡ | 5/2015 | Yamada | A61M 11/041 128/20 |
| 9,038,642 B2 ‡ | 5/2015 | Liu | A24F 47/008 131/22 |
| D731,114 S ‡ | 6/2015 | Leidel | D27/16 |
| D732,733 S | 6/2015 | Spagnolo et al. | |
| D733,142 S ‡ | 6/2015 | Solomon | D14/43 |
| D733,356 S ‡ | 6/2015 | Leidel | D27/16 |
| 9,046,278 B2 ‡ | 6/2015 | Koller | A24F 47/006 |
| 9,050,431 B2 ‡ | 6/2015 | Turner | A61M 15/009 |
| 9,055,617 B2 ‡ | 6/2015 | Thorens | H05B 3/58 |
| 9,055,770 B2 ‡ | 6/2015 | Liu | A61M 15/06 |
| 9,060,388 B2 ‡ | 6/2015 | Liu | H05B 1/0244 |
| 9,060,548 B2 ‡ | 6/2015 | Zheng | H01R 13/66 |
| 9,066,543 B2 ‡ | 6/2015 | Cameron | A24F 15/18 |
| 9,072,321 B2 ‡ | 7/2015 | Liu | A24F 47/008 |
| 9,072,322 B2 ‡ | 7/2015 | Liu | A24F 47/008 |
| 9,078,472 B2 ‡ | 7/2015 | Liu | A24F 15/18 |
| 9,078,474 B2 ‡ | 7/2015 | Thompson | A24F 47/008 |
| 9,078,475 B2 ‡ | 7/2015 | Li | A24F 47/008 |
| 9,089,166 B1 ‡ | 7/2015 | Scatterday | A24F 15/12 |
| 9,089,168 B2 ‡ | 7/2015 | Liu | A61M 11/042 |
| 9,090,173 B2 ‡ | 7/2015 | Oishi | B60L 11/182 |
| D736,706 S ‡ | 8/2015 | Huang | D13/10 |
| D736,995 S ‡ | 8/2015 | Recio | D27/14 |
| D737,508 S ‡ | 8/2015 | Liu | D27/18 |
| 9,095,174 B2 ‡ | 8/2015 | Capuano | A24F 47/008 |
| 9,095,175 B2 ‡ | 8/2015 | Terry | A24F 47/008 |
| 9,099,873 B2 ‡ | 8/2015 | Xiang | H02J 7/0029 |
| 9,101,729 B2 ‡ | 8/2015 | Liu | A61M 15/06 |
| 9,113,659 B2 ‡ | 8/2015 | Liu | A24F 47/002 |
| D737,566 S ‡ | 9/2015 | Gaddis | D3/208 |
| D738,038 S ‡ | 9/2015 | Smith | D27/17 |
| D739,973 S ‡ | 9/2015 | Chao | D13/10 |
| 9,131,733 B2 ‡ | 9/2015 | Liu | A24F 47/008 |
| 9,132,248 B2 | 9/2015 | Qiu | |
| D741,001 S ‡ | 10/2015 | Alarcon | D27/16 |
| D741,002 S ‡ | 10/2015 | Liu | D27/18 |
| D741,541 S ‡ | 10/2015 | Liu | D27/18 |
| D742,063 S ‡ | 10/2015 | Recio | D27/14 |
| D742,064 S ‡ | 10/2015 | Leidel | D27/16 |
| 9,155,336 B2 ‡ | 10/2015 | Liu | A24F 47/008 |
| 9,166,424 B2 ‡ | 10/2015 | Oakley, Jr. | H01M 10/465 |
| 9,167,849 B2 ‡ | 10/2015 | Adamic | A24F 1/00 |
| 9,167,850 B2 ‡ | 10/2015 | Liu | A24F 15/12 |
| 9,167,852 B2 ‡ | 10/2015 | Xiu | A24F 47/008 |
| 9,167,853 B2 ‡ | 10/2015 | Xiang | H02J 7/045 |
| D742,492 S ‡ | 11/2015 | Robinson | D23/36 |
| D742,624 S ‡ | 11/2015 | Meyers | D2/857 |
| D743,099 S ‡ | 11/2015 | Oglesby | D27/10 |
| D744,159 S ‡ | 11/2015 | Lukas | D27/17 |
| 9,185,937 B2 ‡ | 11/2015 | Liu | A24F 47/008 |
| 9,197,726 B2 ‡ | 11/2015 | Stanimirovic | H04M 1/215 |
| D744,342 S ‡ | 12/2015 | Blasko | D9/516 |
| D744,419 S ‡ | 12/2015 | Bowen | D13/10 |
| D744,696 S ‡ | 12/2015 | Malhi | D27/16 |
| D745,004 S ‡ | 12/2015 | Kim | H04M 1/0268 D14/34 |
| D745,388 S ‡ | 12/2015 | Taylor | D9/418 |
| D746,291 S ‡ | 12/2015 | Solomon | D14/43 |
| 9,198,463 B2 ‡ | 12/2015 | Liu | A24F 15/12 |
| 9,198,464 B2 ‡ | 12/2015 | Liu | A24F 15/12 |
| 9,198,466 B2 ‡ | 12/2015 | Liu | A24F 47/008 |
| 9,204,670 B2 ‡ | 12/2015 | Liu | A24F 47/008 |
| 9,215,895 B2 ‡ | 12/2015 | Bowen | A24B 15/16 |
| 9,220,302 B2 ‡ | 12/2015 | Depiano | A24F 47/008 |
| 9,220,303 B2 ‡ | 12/2015 | Li | A24F 47/008 |
| D747,035 S ‡ | 1/2016 | Moradian | D27/10 |
| D747,265 S ‡ | 1/2016 | Marini | D13/10 |
| D747,546 S ‡ | 1/2016 | Liu | D27/10 |
| D747,603 S ‡ | 1/2016 | Gaddis | D3/208 |
| D747,722 S ‡ | 1/2016 | Webb | D14/43 |
| D747,852 S ‡ | 1/2016 | Meyers | D2/857 |
| D748,329 S ‡ | 1/2016 | Bagai | D27/18 |
| 9,226,525 B2 ‡ | 1/2016 | Liu | A24F 47/008 |
| 9,226,526 B2 ‡ | 1/2016 | Liu | A24F 47/008 |
| 9,233,217 B2 ‡ | 1/2016 | Jones | A61M 15/06 |
| 9,240,695 B2 ‡ | 1/2016 | Xiang | H02J 7/0047 |
| 9,240,697 B2 ‡ | 1/2016 | Xiang | H02J 7/0052 |
| D748,852 S ‡ | 2/2016 | Wu | D27/10 |
| D748,853 S ‡ | 2/2016 | Seibel | D27/10 |
| D749,260 S ‡ | 2/2016 | Wu | D27/10 |
| D749,261 S ‡ | 2/2016 | Chen | D27/16 |
| D749,505 S ‡ | 2/2016 | Verleur | D13/10 |
| D749,510 S ‡ | 2/2016 | Liu | D13/10 |
| D749,781 S ‡ | 2/2016 | Lane | D27/18 |
| D750,320 S ‡ | 2/2016 | Verleur | A24F 47/008 D27/10 |
| D750,321 S ‡ | 2/2016 | Chen | D27/19 |
| 9,247,773 B2 ‡ | 2/2016 | Memari | A24F 15/12 |
| 9,254,002 B2 ‡ | 2/2016 | Chong | A24B 15/30 |
| 9,254,005 B2 ‡ | 2/2016 | Liu | A24F 15/20 |
| 9,255,277 B2 ‡ | 2/2016 | Bakker | C12N 9/1051 |
| D750,835 S ‡ | 3/2016 | Wei | D27/10 |
| D751,250 S ‡ | 3/2016 | Vuong | D27/18 |
| D751,527 S ‡ | 3/2016 | Hinokio | D14/20 |
| D751,755 S ‡ | 3/2016 | Van Riper | D12/22 |
| D751,757 S ‡ | 3/2016 | Stern | D27/18 |
| D752,277 S ‡ | 3/2016 | Liu | D27/10 |

(56) References Cited

U.S. PATENT DOCUMENTS

| | | | |
|---|---|---|---|
| D752,278 S ‡ | 3/2016 | Verleur | D13/10 |
| D752,279 S ‡ | 3/2016 | Liu | D27/10 |
| D752,280 S ‡ | 3/2016 | Verleur | D27/16 |
| D752,282 S ‡ | 3/2016 | Doster | D27/18 |
| D752,283 S ‡ | 3/2016 | Doster | D27/18 |
| D752,284 S ‡ | 3/2016 | Doster | D27/18 |
| D752,285 S ‡ | 3/2016 | Doster | D27/18 |
| D752,286 S ‡ | 3/2016 | Doster | D27/18 |
| D752,808 S ‡ | 3/2016 | Hearn | D27/18 |
| 9,271,525 B2 ‡ | 3/2016 | Liu | A24F 15/18 |
| 9,271,526 B2 ‡ | 3/2016 | Liu | A24F 15/12 |
| 9,271,529 B2 ‡ | 3/2016 | Alima | A24F 47/008 |
| 9,272,103 B2 ‡ | 3/2016 | Storz | A61M 15/009 |
| 9,277,768 B2 ‡ | 3/2016 | Xiu | A24F 47/008 |
| 9,277,769 B2 ‡ | 3/2016 | Liu | A24F 47/008 |
| 9,281,705 B2 ‡ | 3/2016 | Xiang | H02J 7/045 |
| 9,282,772 B2 ‡ | 3/2016 | Tucker | H01C 17/00 |
| 9,282,773 B2 ‡ | 3/2016 | Greim | A24F 47/008 |
| 9,289,014 B2 ‡ | 3/2016 | Tucker | A24F 47/008 |
| 9,295,286 B2 ‡ | 3/2016 | Shin | A24F 47/008 |
| D753,090 S ‡ | 4/2016 | Langhammer | D14/20 |
| D753,338 S ‡ | 4/2016 | Chen | D27/16 |
| D753,873 S ‡ | 4/2016 | Schuessler | D27/10 |
| D753,874 S ‡ | 4/2016 | Moreno Medina | D27/10 |
| D754,919 S ‡ | 4/2016 | Alarcon | D27/10 |
| 9,301,545 B2 ‡ | 4/2016 | Li | A24F 15/18 |
| 9,301,549 B2 ‡ | 4/2016 | Liu | A24F 47/008 |
| 9,302,800 B2 ‡ | 4/2016 | Holmes | A24F 47/008 |
| 9,302,825 B2 ‡ | 4/2016 | Liu | B65D 43/163 |
| 9,308,336 B2 ‡ | 4/2016 | Newton | A61M 15/06 |
| 9,312,687 B2 ‡ | 4/2016 | Xiang | H02H 7/20 |
| 9,315,890 B1 ‡ | 4/2016 | Frick | F21V 33/0004 |
| 9,320,300 B2 ‡ | 4/2016 | Hon | A24F 47/008 |
| D755,057 S ‡ | 5/2016 | Mutter | D9/529 |
| D755,506 S ‡ | 5/2016 | Neely, III | D3/208 |
| D755,733 S ‡ | 5/2016 | Ikegaya | D13/16 |
| D755,735 S ‡ | 5/2016 | Kashimoto | D13/16 |
| D756,030 S ‡ | 5/2016 | Chen | D27/10 |
| D756,031 S ‡ | 5/2016 | Wu | D27/10 |
| D756,559 S ‡ | 5/2016 | Li | D13/14 |
| D757,352 S ‡ | 5/2016 | Bagai | D27/10 |
| D757,353 S ‡ | 5/2016 | Nunnelly | D27/10 |
| D757,690 S ‡ | 5/2016 | Lee | D13/16 |
| D757,994 S ‡ | 5/2016 | Moradian | D27/10 |
| D757,995 S ‡ | 5/2016 | Liu | D27/10 |
| 9,326,547 B2 ‡ | 5/2016 | Tucker | H01C 17/00 |
| 9,326,549 B2 ‡ | 5/2016 | Hon | A24F 47/008 |
| 9,332,787 B2 ‡ | 5/2016 | Liu | A24F 47/008 |
| 9,345,269 B2 ‡ | 5/2016 | Liu | A24F 47/008 |
| 9,345,541 B2 | 5/2016 | Greeley et al. | |
| 9,350,102 B2 ‡ | 5/2016 | Wu | H01R 13/111 |
| 9,350,178 B2 ‡ | 5/2016 | Xiang | H02J 7/0029 |
| 9,350,181 B2 ‡ | 5/2016 | Xiang | H02J 7/0042 |
| 9,351,522 B2 ‡ | 5/2016 | Safari | A24F 47/008 |
| D758,647 S ‡ | 6/2016 | Liu | D27/10 |
| D758,649 S ‡ | 6/2016 | Liu | D27/10 |
| D758,650 S ‡ | 6/2016 | Wu | D27/10 |
| D759,031 S ‡ | 6/2016 | Ozolins | D14/48 |
| D759,297 S ‡ | 6/2016 | Liu | D27/10 |
| D759,303 S ‡ | 6/2016 | Afridi | D27/10 |
| D760,431 S ‡ | 6/2016 | Liu | D27/18 |
| 9,357,802 B2 ‡ | 6/2016 | Liu | A24F 15/18 |
| 9,360,379 B2 ‡ | 6/2016 | Liu | G01K 13/002 |
| 9,364,025 B2 ‡ | 6/2016 | Liu | A24F 47/008 |
| 9,364,026 B2 ‡ | 6/2016 | Liu | A24F 47/008 |
| 9,364,027 B2 ‡ | 6/2016 | Hon | A24F 47/002 |
| 9,364,800 B2 ‡ | 6/2016 | Dubief | A24F 47/008 |
| 9,379,364 B2 ‡ | 6/2016 | Alima | H01M 10/48 |
| D760,952 S ‡ | 7/2016 | Mayor | D27/16 |
| D761,488 S ‡ | 7/2016 | Alarcon | D27/13 |
| D761,999 S ‡ | 7/2016 | Liu | D27/10 |
| D762,000 S ‡ | 7/2016 | Liu | D27/10 |
| D762,001 S ‡ | 7/2016 | Liu | D27/10 |
| D762,003 S ‡ | 7/2016 | Lomeli | D27/16 |
| D762,326 S ‡ | 7/2016 | Liu | D27/10 |
| 9,380,810 B2 ‡ | 7/2016 | Rose | A24F 47/008 |
| 9,380,812 B2 ‡ | 7/2016 | Chung | A24F 47/008 |
| 9,383,053 B2 ‡ | 7/2016 | Liu | A24F 47/008 |
| 9,385,554 B2 ‡ | 7/2016 | Xiang | H02J 7/0052 |
| 9,386,803 B2 ‡ | 7/2016 | Burke | A24D 3/062 |
| 9,386,805 B2 | 7/2016 | Liu | |
| D763,203 S ‡ | 8/2016 | Ikegaya | D13/16 |
| D763,204 S ‡ | 8/2016 | Ikegaya | D13/16 |
| D763,502 S ‡ | 8/2016 | Verleur | D27/16 |
| D764,098 S ‡ | 8/2016 | Liu | D27/10 |
| D764,703 S ‡ | 8/2016 | Liu | D27/10 |
| D765,307 S ‡ | 8/2016 | Liu | D27/10 |
| D765,308 S ‡ | 8/2016 | Liu | D27/10 |
| D765,309 S ‡ | 8/2016 | Liu | D27/10 |
| 9,408,416 B2 ‡ | 8/2016 | Monsees | A61M 15/06 |
| 9,413,180 B2 ‡ | 8/2016 | Liu | H02J 7/0045 |
| 9,414,627 B2 ‡ | 8/2016 | Liu | A24F 7/00 |
| 9,414,628 B2 ‡ | 8/2016 | Liu | A24F 47/008 |
| 9,414,629 B2 | 8/2016 | Egoyants et al. | |
| 9,415,929 B2 ‡ | 8/2016 | Liu | A24F 15/12 |
| 9,417,107 B2 ‡ | 8/2016 | Xiang | G01F 25/0007 |
| 9,420,829 B2 | 8/2016 | Thorens et al. | |
| 9,420,831 B2 ‡ | 8/2016 | Liu | A61M 15/06 |
| 9,423,152 B2 | 8/2016 | Ampolini et al. | |
| 9,427,022 B2 ‡ | 8/2016 | Levin | A24F 47/008 |
| 9,427,023 B2 ‡ | 8/2016 | Liu | A24F 47/008 |
| 9,427,024 B2 ‡ | 8/2016 | Liu | H02J 7/0044 |
| 9,427,025 B2 ‡ | 8/2016 | Liu | A24F 47/008 |
| 9,427,026 B2 ‡ | 8/2016 | Wu | A61M 15/06 |
| D765,907 S ‡ | 9/2016 | Liu | D27/10 |
| D766,503 S ‡ | 9/2016 | Liu | D27/16 |
| D766,873 S ‡ | 9/2016 | Washio | D14/21 |
| D767,200 S ‡ | 9/2016 | Liu | D27/10 |
| D767,201 S ‡ | 9/2016 | Starr | D27/16 |
| D767,820 S ‡ | 9/2016 | Jordan | D27/17 |
| D767,822 S ‡ | 9/2016 | Jordan | D27/19 |
| 9,433,242 B1 ‡ | 9/2016 | Buffone | A24F 47/002 |
| 9,438,049 B2 ‡ | 9/2016 | Xiang | H02J 7/007 |
| 9,438,051 B2 ‡ | 9/2016 | Firman, II | H01R 13/6675 |
| 9,439,455 B2 ‡ | 9/2016 | Alarcon | A24F 47/00 |
| 9,439,456 B2 ‡ | 9/2016 | Liu | A24F 47/008 |
| 9,440,035 B2 ‡ | 9/2016 | Chung | A61M 15/002 |
| 9,451,790 B2 ‡ | 9/2016 | Liu | A24F 47/008 |
| 9,451,793 B2 ‡ | 9/2016 | Zhou | A24F 47/008 |
| 9,455,579 B2 ‡ | 9/2016 | Xiang | H02J 7/0013 |
| D768,331 S ‡ | 10/2016 | Chen | D27/10 |
| D768,920 S ‡ | 10/2016 | Jones | D27/18 |
| D768,980 S ‡ | 10/2016 | Alexander | D3/210 |
| D769,518 S ‡ | 10/2016 | Liu | D27/10 |
| D769,519 S ‡ | 10/2016 | Chen | D27/10 |
| D769,520 S ‡ | 10/2016 | Hua | D27/16 |
| D769,830 S ‡ | 10/2016 | Clymer | D13/16 |
| D770,088 S ‡ | 10/2016 | Abadi | D27/16 |
| 9,456,632 B2 ‡ | 10/2016 | Hon | A24F 47/008 |
| 9,456,633 B2 ‡ | 10/2016 | Liu | A24F 47/008 |
| 9,456,634 B2 ‡ | 10/2016 | Wang | B01F 3/04085 |
| 9,459,021 B2 ‡ | 10/2016 | Greim | A24F 47/008 |
| 9,462,832 B2 ‡ | 10/2016 | Lord | A24F 47/008 |
| 9,465,081 B2 ‡ | 10/2016 | Xiang | G01R 31/3842 |
| 9,474,305 B2 ‡ | 10/2016 | Liu | A24F 47/008 |
| D770,395 S ‡ | 11/2016 | Clymer | D13/16 |
| D770,676 S ‡ | 11/2016 | Bennett | D27/16 |
| D770,678 S ‡ | 11/2016 | Shin | D27/16 |
| D770,679 S ‡ | 11/2016 | Weigensberg | D27/18 |
| D771,219 S ‡ | 11/2016 | Gilbarte | D22/11 |
| D771,307 S ‡ | 11/2016 | Wu | D27/10 |
| D771,308 S ‡ | 11/2016 | Saydar | A61M 15/00 D27/16 |
| D772,477 S ‡ | 11/2016 | Shin | D27/16 |
| D772,478 S ‡ | 11/2016 | Liu | D27/16 |
| D772,479 S ‡ | 11/2016 | Stowers | D27/16 |
| D772,480 S ‡ | 11/2016 | Hua | D27/18 |
| D772,879 S ‡ | 11/2016 | Eliyahu | D14/43 |
| D773,115 S ‡ | 11/2016 | Liu | D27/16 |
| D773,116 S ‡ | 11/2016 | Liu | D27/16 |
| 9,480,285 B2 ‡ | 11/2016 | Liu | A24F 47/008 |
| 9,480,286 B2 ‡ | 11/2016 | Liu | A24F 47/008 |
| 9,497,993 B2 ‡ | 11/2016 | Vallar | A24B 15/00 |
| 9,497,994 B2 ‡ | 11/2016 | Liu | A61M 15/06 |

(56) References Cited

U.S. PATENT DOCUMENTS

| | | | |
|---|---|---|---|
| 9,497,995 B2 ‡ | 11/2016 | Liu | A24F 47/008 |
| 9,497,997 B2 ‡ | 11/2016 | Wu | A24F 47/008 |
| 9,497,998 B2 ‡ | 11/2016 | Chen | A24F 47/008 |
| 9,497,999 B2 ‡ | 11/2016 | Lord | A24F 47/008 |
| 9,498,001 B2 ‡ | 11/2016 | Wu | A24F 47/008 |
| 9,498,002 B1 ‡ | 11/2016 | Soreide | A61M 15/06 |
| 9,498,588 B2 ‡ | 11/2016 | Benassayag | A61M 15/06 |
| 9,502,917 B2 ‡ | 11/2016 | Xiang | H02J 7/0077 |
| 9,504,278 B2 ‡ | 11/2016 | Liu | A24F 15/18 |
| 9,504,279 B2 ‡ | 11/2016 | Chen | A24F 47/008 |
| D773,391 S ‡ | 12/2016 | Haarburger | D13/10 |
| D773,729 S ‡ | 12/2016 | Jordan | D27/19 |
| D774,247 S ‡ | 12/2016 | Chen | D27/10 |
| D774,248 S ‡ | 12/2016 | Jordan | D27/19 |
| D774,514 S ‡ | 12/2016 | Turksu | D14/48 |
| D774,693 S ‡ | 12/2016 | Liu | D27/16 |
| D774,892 S ‡ | 12/2016 | Liu | D9/418 |
| D775,412 S ‡ | 12/2016 | Di Bari | D27/19 |
| D775,413 S ‡ | 12/2016 | Liu | D27/10 |
| 9,510,623 B2 | 12/2016 | Tucker et al. | |
| 9,510,624 B2 ‡ | 12/2016 | Li | A61M 11/041 |
| 9,516,898 B2 ‡ | 12/2016 | Liu | A24F 47/008 |
| 9,516,899 B2 | 12/2016 | Plojoux et al. | |
| 9,521,867 B2 ‡ | 12/2016 | Xiang | A24F 47/008 |
| 9,526,272 B2 ‡ | 12/2016 | Liu | A24F 47/008 |
| 9,526,273 B2 ‡ | 12/2016 | Liu | A24F 47/008 |
| 9,531,183 B2 ‡ | 12/2016 | Xiang | H02H 3/202 |
| D776,051 S ‡ | 1/2017 | Wang | D13/10 |
| D776,162 S ‡ | 1/2017 | Beck | D14/20 |
| D776,270 S ‡ | 1/2017 | Wilcox | D24/12 |
| D776,338 S ‡ | 1/2017 | Lomeli | D27/16 |
| D776,340 S ‡ | 1/2017 | Seibel | D27/18 |
| D776,659 S ‡ | 1/2017 | Hou | D14/43 |
| D777,372 S ‡ | 1/2017 | Liu | D27/16 |
| D777,976 S ‡ | 1/2017 | Mahlmeister | D27/16 |
| 9,532,598 B2 ‡ | 1/2017 | Liu | A24F 47/008 |
| 9,532,599 B2 ‡ | 1/2017 | Liu | A24F 47/008 |
| 9,532,601 B2 ‡ | 1/2017 | Liu | A24F 47/008 |
| 9,532,602 B2 ‡ | 1/2017 | Liu | A24F 47/008 |
| 9,532,604 B2 ‡ | 1/2017 | Conley | A24F 47/008 |
| 9,532,605 B2 ‡ | 1/2017 | Yamada | A24F 47/008 |
| 9,538,781 B2 ‡ | 1/2017 | Zheng | A61K 9/007 |
| 9,538,783 B2 ‡ | 1/2017 | Xiang | A24F 15/18 |
| 9,538,787 B2 ‡ | 1/2017 | Liu | A24F 47/008 |
| 9,538,789 B2 ‡ | 1/2017 | Liu | A24F 47/008 |
| 9,545,489 B2 ‡ | 1/2017 | Turner | A61M 15/009 |
| 9,549,572 B2 ‡ | 1/2017 | Dincer | A24F 47/002 |
| 9,549,573 B2 ‡ | 1/2017 | Monsees | H05B 3/04 |
| 9,554,596 B2 ‡ | 1/2017 | Liu | A24F 47/008 |
| 9,554,597 B2 ‡ | 1/2017 | Liu | A24F 47/008 |
| 9,555,203 B2 ‡ | 1/2017 | Terry | A24F 47/008 |
| D778,493 S ‡ | 2/2017 | Scott | D27/10 |
| D778,831 S ‡ | 2/2017 | Chen | D13/10 |
| D779,677 S ‡ | 2/2017 | Chen | D24/21 |
| D779,719 S ‡ | 2/2017 | Qiu | D27/10 |
| D780,179 S ‡ | 2/2017 | Bae | D14/13 |
| D780,372 S ‡ | 2/2017 | Liu | D27/10 |
| 9,560,882 B2 ‡ | 2/2017 | Xiang | A24F 47/008 |
| 9,565,873 B2 ‡ | 2/2017 | Zheng | A24B 15/16 |
| 9,565,876 B2 ‡ | 2/2017 | Tsai | A24F 47/008 |
| 9,572,372 B2 ‡ | 2/2017 | Liu | A24F 47/008 |
| 9,572,373 B2 ‡ | 2/2017 | Chen | A24F 47/008 |
| 9,572,374 B2 ‡ | 2/2017 | Gabbay | A24F 47/008 |
| 9,573,751 B2 ‡ | 2/2017 | Liu | A24F 15/18 |
| 9,578,002 B2 ‡ | 2/2017 | Wu | G06F 21/35 |
| 9,578,898 B2 ‡ | 2/2017 | Liu | A24F 47/008 |
| D780,990 S ‡ | 3/2017 | Liu | D27/10 |
| D780,991 S ‡ | 3/2017 | Liu | D27/10 |
| D782,108 S ‡ | 3/2017 | Jordan | D27/16 |
| D782,728 S ‡ | 3/2017 | Pinder | D27/10 |
| D782,729 S ‡ | 3/2017 | Wright | D27/10 |
| 9,591,876 B2 ‡ | 3/2017 | Alima | A24F 47/008 |
| 9,596,881 B2 ‡ | 3/2017 | Chiolini | A61K 47/10 |
| 9,596,884 B2 ‡ | 3/2017 | Liu | A24F 47/008 |
| 9,596,885 B2 ‡ | 3/2017 | Liu | A24F 47/008 |
| 9,596,886 B2 ‡ | 3/2017 | Liu | A24F 47/008 |
| 9,596,887 B2 ‡ | 3/2017 | Newton | A24F 47/008 |
| 9,602,646 B2 ‡ | 3/2017 | Stanimirovic | H04M 1/185 |
| 9,603,198 B2 ‡ | 3/2017 | Liu | A24F 47/008 |
| 9,603,386 B2 ‡ | 3/2017 | Xiang | A24F 47/008 |
| 9,603,387 B2 ‡ | 3/2017 | Liu | A24F 47/008 |
| 9,603,389 B2 ‡ | 3/2017 | Chen | A61M 15/06 |
| 9,603,390 B2 ‡ | 3/2017 | Li | A24F 47/008 |
| D784,609 S ‡ | 4/2017 | Liu | D27/10 |
| D785,234 S ‡ | 4/2017 | Liu | D27/16 |
| D785,237 S ‡ | 4/2017 | Wu | D27/16 |
| 9,609,893 B2 ‡ | 4/2017 | Novak, III | A24F 47/008 |
| 9,615,605 B2 ‡ | 4/2017 | Liu | A24F 47/008 |
| 9,615,606 B2 ‡ | 4/2017 | Liu | A24F 47/008 |
| 9,615,607 B2 ‡ | 4/2017 | Liu | A24F 47/008 |
| 9,620,958 B2 ‡ | 4/2017 | Liu | H02H 11/003 |
| 9,622,511 B2 ‡ | 4/2017 | Zhu | A24F 47/008 |
| 9,623,592 B2 ‡ | 4/2017 | Liu | C08K 3/22 |
| 9,627,611 B2 ‡ | 4/2017 | Liu | H01M 2/0404 |
| 9,629,391 B2 ‡ | 4/2017 | Dube | A24B 15/302 |
| 9,629,394 B2 ‡ | 4/2017 | Aronie | A24F 47/008 |
| D785,859 S ‡ | 5/2017 | Pang | D27/10 |
| D785,862 S ‡ | 5/2017 | Wu | D27/16 |
| D786,789 S ‡ | 5/2017 | Jordan | D13/10 |
| D787,114 S ‡ | 5/2017 | Scott | D27/19 |
| D788,362 S ‡ | 5/2017 | Qiu | D27/10 |
| 9,635,886 B2 ‡ | 5/2017 | Tu | A24F 47/008 |
| 9,641,208 B2 ‡ | 5/2017 | Sela | H04B 1/3888 |
| 9,642,396 B2 ‡ | 5/2017 | Liu | A24F 47/008 |
| 9,642,397 B2 ‡ | 5/2017 | Dai | A61M 15/06 |
| 9,645,134 B1 ‡ | 5/2017 | Farmen | G01N 33/49 |
| 9,648,905 B2 ‡ | 5/2017 | Levitz | A24F 13/22 |
| 9,648,908 B1 ‡ | 5/2017 | Rinehart | A24F 47/00 |
| 9,648,909 B2 ‡ | 5/2017 | Zhou | B05B 17/00 |
| 9,655,383 B2 ‡ | 5/2017 | Holzherr | A24F 47/008 |
| 9,655,890 B2 ‡ | 5/2017 | Hearn | A24B 15/16 |
| 9,661,878 B2 ‡ | 5/2017 | Liu | A61M 15/06 |
| 9,663,266 B2 ‡ | 5/2017 | Schwester | B65D 5/38 |
| D788,697 S ‡ | 6/2017 | Verleur | D13/10 |
| D790,122 S ‡ | 6/2017 | Hawes | D27/10 |
| D790,126 S ‡ | 6/2017 | Bennett | D27/10 |
| D790,129 S ‡ | 6/2017 | Bennett | D27/18 |
| D790,766 S ‡ | 6/2017 | Li | D27/16 |
| 9,668,517 B2 ‡ | 6/2017 | Liu | A24F 47/008 |
| 9,668,518 B2 ‡ | 6/2017 | Esses | A24F 47/008 |
| 9,668,519 B2 ‡ | 6/2017 | Mishra | A24B 15/283 |
| 9,668,520 B2 ‡ | 6/2017 | Boldrini | A24B 15/16 |
| 9,668,521 B2 ‡ | 6/2017 | Kuczaj | A24F 47/008 |
| 9,668,522 B2 ‡ | 6/2017 | Memari | A24F 15/12 |
| 9,668,523 B2 ‡ | 6/2017 | Tucker | H01C 17/00 |
| 9,675,108 B2 ‡ | 6/2017 | Liu | A24F 47/002 |
| 9,675,109 B2 | 6/2017 | Monsees et al. | |
| 9,675,113 B2 ‡ | 6/2017 | Liu | A24F 47/008 |
| 9,675,114 B2 ‡ | 6/2017 | Timmermans | A24F 47/008 |
| 9,675,115 B2 ‡ | 6/2017 | Liu | A24F 47/008 |
| 9,675,116 B2 ‡ | 6/2017 | Liu | A24F 47/008 |
| 9,675,117 B2 ‡ | 6/2017 | Li | A61M 15/06 |
| 9,675,118 B2 ‡ | 6/2017 | Chen | A24F 47/008 |
| 9,681,687 B2 ‡ | 6/2017 | Liu | A24F 47/008 |
| 9,681,688 B1 ‡ | 6/2017 | Rinehart | A61M 15/06 |
| 9,682,203 B2 ‡ | 6/2017 | Dahne | A61M 15/06 |
| 9,682,204 B2 ‡ | 6/2017 | Matsumoto | A61M 15/06 |
| 9,682,800 B2 ‡ | 6/2017 | Xiang | B65D 25/00 |
| 9,687,025 B2 ‡ | 6/2017 | Cyphert | A24F 1/00 |
| 9,687,027 B2 ‡ | 6/2017 | Poston | A24F 47/008 |
| 9,687,028 B2 ‡ | 6/2017 | Park | A24F 47/008 |
| 9,687,029 B2 ‡ | 6/2017 | Liu | H05B 3/16 |
| D792,021 S ‡ | 7/2017 | Beer | D27/10 |
| D792,022 S ‡ | 7/2017 | Li | D27/16 |
| D792,644 S ‡ | 7/2017 | Jordan | D27/10 |
| D793,004 S ‡ | 7/2017 | Liu | D27/18 |
| 9,693,584 B2 ‡ | 7/2017 | Hearn | A24F 47/002 |
| 9,693,586 B2 ‡ | 7/2017 | Liu | A24F 47/008 |
| 9,693,587 B2 ‡ | 7/2017 | Plojoux | A61M 15/06 |
| 9,693,588 B2 ‡ | 7/2017 | Zhu | A24F 47/008 |
| 9,695,033 B1 ‡ | 7/2017 | Alshouse | B67D 7/302 |
| 9,700,074 B2 ‡ | 7/2017 | Liu | A24F 47/008 |
| 9,700,075 B2 ‡ | 7/2017 | Liu | A24F 47/008 |
| 9,700,076 B2 ‡ | 7/2017 | Xiang | A24F 47/008 |

(56) References Cited

U.S. PATENT DOCUMENTS

| | | | |
|---|---|---|---|
| 9,713,345 B2 ‡ | 7/2017 | Farine | A24F 47/008 |
| 9,713,346 B2 ‡ | 7/2017 | Hon | A24F 47/002 |
| 9,714,878 B2 ‡ | 7/2017 | Powers | G01L 7/08 |
| D793,620 S ‡ | 8/2017 | Bennett | D27/19 |
| 9,717,274 B2 ‡ | 8/2017 | Daehne | A24F 47/002 |
| 9,717,275 B2 ‡ | 8/2017 | Liu | A24F 47/008 |
| 9,717,276 B2 ‡ | 8/2017 | Brammer | H05B 3/02 |
| 9,717,277 B2 ‡ | 8/2017 | Mironov | A24F 47/008 |
| 9,717,278 B2 ‡ | 8/2017 | Hon | A24F 47/008 |
| 9,717,279 B2 ‡ | 8/2017 | Hon | A24F 47/002 |
| 9,723,872 B2 ‡ | 8/2017 | Liu | A24F 47/008 |
| 9,723,873 B2 ‡ | 8/2017 | Liu | A24F 47/008 |
| 9,723,874 B2 ‡ | 8/2017 | Liu | A24F 47/008 |
| 9,723,875 B2 ‡ | 8/2017 | Liu | A24F 47/008 |
| 9,723,876 B2 ‡ | 8/2017 | Cadieux | A24F 47/008 |
| 9,723,877 B2 ‡ | 8/2017 | Wong | A24F 47/008 |
| 9,730,471 B2 ‡ | 8/2017 | Li | A24F 47/008 |
| 9,763,478 B2 ‡ | 9/2017 | Cameron | F01K 5/00 |
| 9,770,055 B2 ‡ | 9/2017 | Cameron | H04M 1/7253 |
| 9,772,216 B2 ‡ | 9/2017 | Poole | B65B 1/12 |
| 9,772,245 B2 | 9/2017 | Besling et al. | |
| 9,775,380 B2 ‡ | 10/2017 | Fernando | A24F 47/008 |
| 9,781,953 B2 | 10/2017 | Verleur et al. | |
| 9,795,168 B2 | 10/2017 | Zhu | |
| 9,801,413 B2 | 10/2017 | Zhu | |
| 9,802,011 B2 ‡ | 10/2017 | Davidson | A61K 9/007 |
| 9,806,549 B2 ‡ | 10/2017 | Liberti | A24F 47/00 |
| 9,814,263 B2 ‡ | 11/2017 | Cochand | A61M 11/041 |
| 9,814,265 B2 ‡ | 11/2017 | Rinker | A24F 47/008 |
| 9,814,272 B2 ‡ | 11/2017 | Li | B67D 99/00 |
| 9,820,508 B2 ‡ | 11/2017 | Arnel | A24F 47/002 |
| 9,844,234 B2 | 12/2017 | Thorens et al. | |
| 9,861,135 B2 | 1/2018 | Chen | |
| 9,974,743 B2 | 5/2018 | Rose et al. | |
| 10,039,321 B2 | 8/2018 | Verleur et al. | |
| 10,045,568 B2 | 8/2018 | Monsees et al. | |
| 10,058,122 B2 | 8/2018 | Steingraber et al. | |
| 10,058,124 B2 | 8/2018 | Monsees et al. | |
| 10,058,129 B2 | 8/2018 | Monsees et al. | |
| 10,085,481 B2 | 10/2018 | Verleur et al. | |
| 10,092,713 B2 | 10/2018 | Terry et al. | |
| 10,104,915 B2 | 10/2018 | Bowen et al. | |
| 10,111,470 B2 | 10/2018 | Monsees et al. | |
| 10,117,465 B2 | 11/2018 | Monsees et al. | |
| 10,117,466 B2 | 11/2018 | Monsees et al. | |
| 10,143,233 B2 | 12/2018 | Dubief et al. | |
| 10,195,345 B2 | 2/2019 | Senior et al. | |
| 10,195,370 B2 | 2/2019 | Chen | |
| 10,264,823 B2 | 4/2019 | Monsees et al. | |
| 2001/0015209 A1 ‡ | 8/2001 | Zielke | A24C 5/18 131/28 |
| 2001/0032643 A1 ‡ | 10/2001 | Hochrainer | A61K 9/0078 128/20 |
| 2001/0032795 A1 ‡ | 10/2001 | Weinstein | B65D 11/02 206/32 |
| 2001/0052480 A1 ‡ | 12/2001 | Kawaguchi | B65D 5/0227 206/73 |
| 2002/0029779 A1 ‡ | 3/2002 | Schmidt | A61M 15/0086 128/20 |
| 2002/0043262 A1 | 4/2002 | Langford et al. | |
| 2002/0043554 A1 ‡ | 4/2002 | White | A47F 5/112 229/23 |
| 2002/0078951 A1 ‡ | 6/2002 | Nichols | A61M 11/041 128/20 |
| 2002/0088469 A1 ‡ | 7/2002 | Rennecamp | A24F 1/00 131/33 |
| 2002/0142291 A1 ‡ | 10/2002 | Bauer | G01N 33/64386 435/5 |
| 2002/0175164 A1 ‡ | 11/2002 | Dees | B65D 11/188 220/4 |
| 2003/0004426 A1 ‡ | 1/2003 | Melker | G01N 29/022 600/53 |
| 2003/0005926 A1 ‡ | 1/2003 | Jones | A61M 15/0028 128/20 |
| 2003/0033055 A1 | 2/2003 | McRae et al. | |
| 2003/0089377 A1 ‡ | 5/2003 | Hajaligol | A24D 1/02 131/36 |
| 2003/0096542 A1 | 5/2003 | Kojima | |
| 2003/0149372 A1 ‡ | 8/2003 | Smith | A61B 5/083 600/53 |
| 2003/0150451 A1 ‡ | 8/2003 | Shayan | A61M 11/041 128/20 |
| 2003/0154991 A1 ‡ | 8/2003 | Fournier | A24D 1/02 131/19 |
| 2003/0226837 A1 | 12/2003 | Blake et al. | |
| 2004/0031495 A1 ‡ | 2/2004 | Steinberg | A61M 15/06 131/19 |
| 2004/0050382 A1 ‡ | 3/2004 | Goodchild | A61M 15/0065 128/20 |
| 2004/0099266 A1 ‡ | 5/2004 | Cross | A61M 11/041 128/20 |
| 2004/0129280 A1 ‡ | 7/2004 | Woodson | A24B 15/284 131/19 |
| 2004/0149296 A1 ‡ | 8/2004 | Rostami | A24F 47/008 131/19 |
| 2004/0149624 A1 ‡ | 8/2004 | Wischusen | B65D 5/54 206/73 |
| 2004/0173224 A1 ‡ | 9/2004 | Burgard | C07D 291/06 131/27 |
| 2004/0173229 A1 ‡ | 9/2004 | Crooks | A24B 15/165 131/35 |
| 2004/0182403 A1 ‡ | 9/2004 | Andersson | A24F 47/002 131/27 |
| 2004/0191322 A1 ‡ | 9/2004 | Hansson | A61K 9/0058 424/48 |
| 2004/0221857 A1 ‡ | 11/2004 | Dominguez | A24F 13/04 131/27 |
| 2004/0226569 A1 ‡ | 11/2004 | Yang | A24D 3/0225 131/20 |
| 2004/0237974 A1 ‡ | 12/2004 | Min | A24D 3/045 131/18 |
| 2005/0016549 A1 ‡ | 1/2005 | Banerjee | A24B 15/16 131/19 |
| 2005/0016550 A1 ‡ | 1/2005 | Katase | A24F 47/002 131/19 |
| 2005/0029137 A1 ‡ | 2/2005 | Wang | H05K 5/0278 206/32 |
| 2005/0034723 A1 ‡ | 2/2005 | Bennett | A61K 9/007 128/20 |
| 2005/0061759 A1 ‡ | 3/2005 | Doucette | B65D 75/367 211/85 |
| 2005/0069831 A1 ‡ | 3/2005 | St. Charles | F23D 14/105 431/35 |
| 2005/0081601 A1 ‡ | 4/2005 | Lawson | G01N 33/497 73/23 |
| 2005/0090798 A1 ‡ | 4/2005 | Clark | A61K 9/0073 604/50 |
| 2005/0118545 A1 ‡ | 6/2005 | Wong | F23Q 2/40 431/14 |
| 2005/0145533 A1 ‡ | 7/2005 | Seligson | B65D 77/0446 206/57 |
| 2005/0172976 A1 ‡ | 8/2005 | Newman | A24F 47/008 131/19 |
| 2005/0229918 A1 ‡ | 10/2005 | Shim | F23D 14/72 126/39 |
| 2005/0236006 A1 ‡ | 10/2005 | Cowan | A24F 47/004 131/27 |
| 2005/0244521 A1 ‡ | 11/2005 | Strickland | A24B 13/00 424/75 |
| 2005/0252511 A1 | 11/2005 | Pentafragas | |
| 2005/0266365 A1 ‡ | 12/2005 | Xie | F23Q 2/16 431/13 |
| 2005/0268911 A1 ‡ | 12/2005 | Cross | A61M 15/0045 128/20 |
| 2006/0016453 A1 ‡ | 1/2006 | Kim | A24F 47/008 131/19 |
| 2006/0018840 A1 ‡ | 1/2006 | Lechuga-Ballesteros | A01N 43/40 424/45 |

(56) References Cited

U.S. PATENT DOCUMENTS

| | | | |
|---|---|---|---|
| 2006/0054676 A1‡ | 3/2006 | Wischusen, III | B65D 5/4266 229/23 |
| 2006/0102175 A1‡ | 5/2006 | Nelson | A61M 15/0045 128/20 |
| 2006/0141344 A1 | 6/2006 | Chen et al. | |
| 2006/0150991 A1‡ | 7/2006 | Lee | A24D 1/02 131/33 |
| 2006/0185687 A1‡ | 8/2006 | Hearn | A24B 15/282 131/36 |
| 2006/0191546 A1‡ | 8/2006 | Takano | A24F 47/002 131/27 |
| 2006/0191548 A1‡ | 8/2006 | Strickland | A24B 3/14 131/34 |
| 2006/0191594 A1‡ | 8/2006 | Py | A61J 1/18 141/32 |
| 2006/0196518 A1‡ | 9/2006 | Hon | A24F 47/002 131/36 |
| 2006/0207466 A1 | 9/2006 | McNulty et al. | |
| 2006/0254948 A1‡ | 11/2006 | Herbert | A47J 47/02 206/51 |
| 2006/0255105 A1‡ | 11/2006 | Sweet | B65D 5/0005 229/10 |
| 2007/0006889 A1‡ | 1/2007 | Kobal | A24F 47/002 131/32 |
| 2007/0045288 A1‡ | 3/2007 | Nelson | A61M 11/041 219/53 |
| 2007/0062548 A1‡ | 3/2007 | Horstmann | A24F 47/002 131/27 |
| 2007/0074734 A1‡ | 4/2007 | Braunshteyn | A24F 47/008 131/32 |
| 2007/0089757 A1‡ | 4/2007 | Bryman | A24F 3/00 131/33 |
| 2007/0098148 A1‡ | 5/2007 | Sherman | H04M 1/21 379/45 |
| 2007/0102013 A1‡ | 5/2007 | Adams | A24F 47/008 131/27 |
| 2007/0119450 A1 | 5/2007 | Wharton et al. | |
| 2007/0125765 A1‡ | 6/2007 | Nelson | A61M 11/041 219/53 |
| 2007/0144514 A1‡ | 6/2007 | Yeates | A61M 15/0086 128/20 |
| 2007/0163610 A1‡ | 7/2007 | Lindell | A61K 9/0002 131/27 |
| 2007/0191756 A1‡ | 8/2007 | Tapper | A61N 1/0436 604/20 |
| 2007/0215164 A1‡ | 9/2007 | Mehio | A24F 1/30 131/17 |
| 2007/0215168 A1‡ | 9/2007 | Banerjee | A24B 15/165 131/33 |
| 2007/0235046 A1‡ | 10/2007 | Gedevanishvili | A24D 3/046 131/20 |
| 2007/0267033 A1‡ | 11/2007 | Mishra | A24B 15/283 131/27 |
| 2007/0277816 A1‡ | 12/2007 | Morrison | A61M 11/005 128/20 |
| 2007/0280652 A1‡ | 12/2007 | Williams | A24F 1/30 392/38 |
| 2007/0283972 A1‡ | 12/2007 | Monsees | A24F 47/006 131/27 |
| 2007/0295347 A1‡ | 12/2007 | Paine, III | A24D 3/163 131/34 |
| 2008/0000763 A1‡ | 1/2008 | Cove | H01H 13/023 200/31 |
| 2008/0023003 A1‡ | 1/2008 | Rosenthal | A61M 11/041 128/20 |
| 2008/0029095 A1‡ | 2/2008 | Esser | A61M 15/06 128/20 |
| 2008/0068602 A1 | 3/2008 | Delaage et al. | |
| 2008/0092912 A1‡ | 4/2008 | Robinson | A24F 47/008 131/20 |
| 2008/0138423 A1‡ | 6/2008 | Gonda | A24F 47/002 424/48 |
| 2008/0149118 A1‡ | 6/2008 | Oglesby | A61M 11/047 131/19 |
| 2008/0207276 A1‡ | 8/2008 | Burrell | B60R 11/0241 455/57 |
| 2008/0216828 A1‡ | 9/2008 | Wensley | A61K 9/0009 128/20 |
| 2008/0241255 A1‡ | 10/2008 | Rose | A61K 31/4439 424/48 |
| 2008/0257367 A1‡ | 10/2008 | Paterno | A24F 47/008 131/32 |
| 2008/0276947 A1‡ | 11/2008 | Martzel | A24F 47/008 131/27 |
| 2008/0286340 A1‡ | 11/2008 | Andersson | A23G 3/44 424/44 |
| 2008/0302374 A1 | 12/2008 | Wengert et al. | |
| 2008/0302375 A1‡ | 12/2008 | Andersson | A24F 47/002 131/27 |
| 2009/0004249 A1‡ | 1/2009 | Gonda | A24F 47/002 424/44 |
| 2009/0095287 A1‡ | 4/2009 | Emarlou | A61M 11/041 128/20 |
| 2009/0095311 A1‡ | 4/2009 | Han | A24F 47/008 131/19 |
| 2009/0111287 A1‡ | 4/2009 | Lindberg | H01R 13/6205 439/39 |
| 2009/0126745 A1‡ | 5/2009 | Hon | A24F 47/008 131/27 |
| 2009/0133691 A1‡ | 5/2009 | Yamada | A61M 11/041 128/20 |
| 2009/0133703 A1‡ | 5/2009 | Strickland | A24B 13/00 131/11 |
| 2009/0133704 A1‡ | 5/2009 | Strickland | A24B 13/00 131/11 |
| 2009/0151717 A1‡ | 6/2009 | Bowen | A61M 11/041 128/20 |
| 2009/0188490 A1‡ | 7/2009 | Han | A61M 11/041 128/20 |
| 2009/0230117 A1‡ | 9/2009 | Fernando | A24F 47/008 219/49 |
| 2009/0255534 A1‡ | 10/2009 | Paterno | A61M 15/0028 128/20 |
| 2009/0260641 A1‡ | 10/2009 | Monsees | A24F 47/006 131/19 |
| 2009/0260642 A1‡ | 10/2009 | Monsees | A24F 47/006 131/19 |
| 2009/0267252 A1‡ | 10/2009 | Ikeyama | B29C 45/14336 264/40 |
| 2009/0272379 A1‡ | 11/2009 | Thorens | A24F 47/008 128/20 |
| 2009/0283103 A1‡ | 11/2009 | Nielsen | A24F 1/30 131/27 |
| 2009/0288668 A1‡ | 11/2009 | Inagaki | A24F 47/008 131/17 |
| 2009/0288669 A1‡ | 11/2009 | Hutchens | A24D 3/0212 131/27 |
| 2009/0293892 A1‡ | 12/2009 | Williams | A24F 47/008 131/32 |
| 2009/0293895 A1‡ | 12/2009 | Axelsson | A24B 15/14 131/35 |
| 2010/0000672 A1‡ | 1/2010 | Fogle | B65D 5/5445 156/25 |
| 2010/0006092 A1‡ | 1/2010 | Hale | A61M 11/041 128/20 |
| 2010/0024834 A1‡ | 2/2010 | Oglesby | A24F 47/006 131/19 |
| 2010/0031968 A1‡ | 2/2010 | Sheikh | A24F 47/008 131/34 |
| 2010/0059073 A1‡ | 3/2010 | Hoffmann | A24F 47/002 131/27 |
| 2010/0156193 A1‡ | 6/2010 | Rhodes | G06F 1/1632 307/10 |
| 2010/0163063 A1‡ | 7/2010 | Fernando | A24F 47/008 131/18 |
| 2010/0163065 A1 | 7/2010 | Chang | |
| 2010/0186757 A1‡ | 7/2010 | Crooks | A24F 47/006 131/58 |

(56) References Cited

U.S. PATENT DOCUMENTS

| | | | |
|---|---|---|---|
| 2010/0192949 A1 | 8/2010 | Wright et al. | |
| 2010/0200006 A1‡ | 8/2010 | Robinson | A24F 47/008 131/19 |
| 2010/0200008 A1‡ | 8/2010 | Taieb | A24F 47/008 131/36 |
| 2010/0236562 A1‡ | 9/2010 | Hearn | A61K 9/0043 131/33 |
| 2010/0242974 A1‡ | 9/2010 | Pan | A24F 47/008 131/27 |
| 2010/0242976 A1‡ | 9/2010 | Katayama | A24B 15/16 131/27 |
| 2010/0275938 A1‡ | 11/2010 | Roth | A24F 47/002 131/27 |
| 2010/0276333 A1‡ | 11/2010 | Couture | B65D 5/5445 206/77 |
| 2010/0307116 A1‡ | 12/2010 | Fisher | B65D 51/28 53/492 |
| 2010/0307518 A1‡ | 12/2010 | Wang | A24F 47/008 131/32 |
| 2010/0313901 A1‡ | 12/2010 | Fernando | A24F 47/008 131/33 |
| 2011/0005535 A1‡ | 1/2011 | Xiu | A24F 47/008 131/27 |
| 2011/0011396 A1‡ | 1/2011 | Fang | A24F 47/008 128/20 |
| 2011/0030706 A1‡ | 2/2011 | Gibson | A61M 11/041 131/32 |
| 2011/0036346 A1‡ | 2/2011 | Cohen | A61M 11/042 128/20 |
| 2011/0036363 A1‡ | 2/2011 | Urtsev | A24F 47/002 131/27 |
| 2011/0041861 A1‡ | 2/2011 | Sebastian | A24F 47/004 131/36 |
| 2011/0049226 A1‡ | 3/2011 | Moreau | B65D 5/5445 229/11 |
| 2011/0083684 A1‡ | 4/2011 | Luan | A24B 15/24 131/29 |
| 2011/0094523 A1‡ | 4/2011 | Thorens | A24F 47/008 131/19 |
| 2011/0097060 A1‡ | 4/2011 | Michael Buzzetti | A61M 11/042 392/39 |
| 2011/0108023 A1‡ | 5/2011 | McKinney | A61M 11/005 128/20 |
| 2011/0120482 A1‡ | 5/2011 | Brenneise | A24F 47/008 131/32 |
| 2011/0125146 A1 | 5/2011 | Greeley et al. | |
| 2011/0126831 A1‡ | 6/2011 | Fernandez Pernia | A61M 11/041 128/20 |
| 2011/0155151 A1‡ | 6/2011 | Newman | A24F 47/008 131/27 |
| 2011/0155153 A1‡ | 6/2011 | Thorens | H05B 3/58 131/32 |
| 2011/0162667 A1‡ | 7/2011 | Burke | A24D 3/062 131/33 |
| 2011/0168194 A1‡ | 7/2011 | Hon | A24F 47/008 131/27 |
| 2011/0180433 A1‡ | 7/2011 | Rennecamp | A24F 9/16 206/26 |
| 2011/0192397 A1‡ | 8/2011 | Saskar | A61M 15/0045 128/20 |
| 2011/0226236 A1‡ | 9/2011 | Buchberger | A61M 11/041 128/20 |
| 2011/0226266 A1‡ | 9/2011 | Tao | A24F 3/00 131/18 |
| 2011/0232654 A1‡ | 9/2011 | Mass | A61M 15/06 131/27 |
| 2011/0232655 A1‡ | 9/2011 | Chan | A24C 5/00 131/27 |
| 2011/0236002 A1‡ | 9/2011 | Oglesby | A61M 15/06 392/38 |
| 2011/0240047 A1‡ | 10/2011 | Adamic | A24F 1/00 131/32 |
| 2011/0263947 A1‡ | 10/2011 | Utley | A61B 5/4845 600/30 |
| 2011/0265806 A1‡ | 11/2011 | Alarcon | A24F 47/00 131/27 |
| 2011/0268809 A1‡ | 11/2011 | Brinkley | A61K 9/0056 424/49 |
| 2011/0277780 A1‡ | 11/2011 | Terry | A24F 47/008 131/27 |
| 2011/0278189 A1‡ | 11/2011 | Terry | A24F 47/008 206/45 |
| 2011/0290248 A1‡ | 12/2011 | Schennum | A24F 47/002 128/20 |
| 2011/0290269 A1‡ | 12/2011 | Shimizu | A24F 47/004 131/33 |
| 2011/0308521 A1‡ | 12/2011 | Kofford | A61M 11/041 128/20 |
| 2011/0315152 A1‡ | 12/2011 | Hearn | A24F 47/002 131/27 |
| 2011/0315701 A1‡ | 12/2011 | Everson | B65D 43/162 220/78 |
| 2012/0006342 A1‡ | 1/2012 | Rose | A24F 47/008 131/27 |
| 2012/0018529 A1 | 1/2012 | Gammon et al. | |
| 2012/0060853 A1‡ | 3/2012 | Robinson | A24F 47/008 131/19 |
| 2012/0077849 A1‡ | 3/2012 | Howson | A61M 11/00 514/34 |
| 2012/0086391 A1‡ | 4/2012 | Smith | H02J 7/0044 320/10 |
| 2012/0111346 A1‡ | 5/2012 | Powell | A41D 13/082 2/20 |
| 2012/0111347 A1‡ | 5/2012 | Hon | A24F 47/008 131/32 |
| 2012/0118301 A1‡ | 5/2012 | Montaser | A61M 15/0085 131/27 |
| 2012/0118307 A1‡ | 5/2012 | Tu | A24F 47/008 131/33 |
| 2012/0125353 A1‡ | 5/2012 | Wollin | A24F 47/00 131/27 |
| 2012/0138052 A1‡ | 6/2012 | Hearn | A24F 47/002 128/20 |
| 2012/0174914 A1‡ | 7/2012 | Pirshafiey | A61M 11/041 128/20 |
| 2012/0186594 A1 | 7/2012 | Liu | |
| 2012/0188687 A1 | 7/2012 | Yamamoto | |
| 2012/0199146 A1‡ | 8/2012 | Marangos | A24F 47/008 131/32 |
| 2012/0199663 A1‡ | 8/2012 | Qiu | A61M 11/041 239/8 |
| 2012/0204889 A1‡ | 8/2012 | Xiu | A24F 47/008 131/27 |
| 2012/0211015 A1‡ | 8/2012 | Li | A24B 15/32 131/27 |
| 2012/0227753 A1‡ | 9/2012 | Newton | A24F 47/008 131/34 |
| 2012/0234315 A1‡ | 9/2012 | Li | A24F 47/008 128/20 |
| 2012/0234821 A1‡ | 9/2012 | Shimizu | A24F 13/00 219/22 |
| 2012/0247494 A1‡ | 10/2012 | Oglesby | A24F 47/006 131/32 |
| 2012/0255567 A1‡ | 10/2012 | Rose | A61K 9/12 131/27 |
| 2012/0260926 A1‡ | 10/2012 | Tu | A24F 47/008 131/32 |
| 2012/0260927 A1‡ | 10/2012 | Liu | A24F 47/008 131/32 |
| 2012/0261286 A1‡ | 10/2012 | Holloway | B65D 85/1054 206/26 |
| 2012/0267383 A1‡ | 10/2012 | Van Rooyen | A45C 13/08 220/69 |
| 2012/0279512 A1‡ | 11/2012 | Hon | A24F 47/008 131/32 |

(56) References Cited

U.S. PATENT DOCUMENTS

| | | | |
|---|---|---|---|
| 2012/0285475 A1‡ | 11/2012 | Liu | A24F 47/008 131/32 |
| 2012/0291791 A1‡ | 11/2012 | Pradeep | A24F 47/008 131/27 |
| 2012/0312313 A1‡ | 12/2012 | Frija | A24F 47/002 131/32 |
| 2012/0318882 A1‡ | 12/2012 | Abehasera | A61M 11/041 239/1 |
| 2012/0325227 A1‡ | 12/2012 | Robinson | A61M 15/06 131/32 |
| 2012/0325228 A1‡ | 12/2012 | Williams | A24B 15/16 131/32 |
| 2013/0008457 A1‡ | 1/2013 | Zheng | A24B 15/24 131/29 |
| 2013/0014755 A1‡ | 1/2013 | Kumar | A24F 47/006 128/20 |
| 2013/0014772 A1‡ | 1/2013 | Liu | A24F 47/008 131/32 |
| 2013/0019887 A1‡ | 1/2013 | Liu | A24F 47/008 131/32 |
| 2013/0025609 A1‡ | 1/2013 | Liu | A24F 47/008 131/32 |
| 2013/0037041 A1‡ | 2/2013 | Worm | A24F 47/008 131/32 |
| 2013/0042865 A1‡ | 2/2013 | Monsees | A61M 5/06 128/20 |
| 2013/0047984 A1‡ | 2/2013 | Dahne | A24F 47/002 128/20 |
| 2013/0056012 A1‡ | 3/2013 | Hearn | A24F 47/002 131/27 |
| 2013/0056013 A1‡ | 3/2013 | Terry | A24F 47/008 131/32 |
| 2013/0068239 A1‡ | 3/2013 | Youn | A24F 47/008 131/27 |
| 2013/0074857 A1‡ | 3/2013 | Buchberger | A61M 5/06 131/32 |
| 2013/0081642 A1‡ | 4/2013 | Safari | A24F 47/008 131/32 |
| 2013/0087160 A1‡ | 4/2013 | Gherghe | A24F 1/00 131/32 |
| 2013/0099725 A1 | 4/2013 | Burrell et al. | |
| 2013/0115821 A1 | 5/2013 | Golko et al. | |
| 2013/0140200 A1‡ | 6/2013 | Scatterday | A24F 15/00 206/26 |
| 2013/0146489 A1‡ | 6/2013 | Scatterday | A24F 15/20 206/24 |
| 2013/0152922 A1‡ | 6/2013 | Benassayag | A61M 15/06 128/20 |
| 2013/0152954 A1‡ | 6/2013 | Youn | A61M 15/06 131/27 |
| 2013/0167854 A1‡ | 7/2013 | Shin | A24F 47/008 131/32 |
| 2013/0168880 A1‡ | 7/2013 | Duke | A24F 47/008 261/78 |
| 2013/0182421 A1 | 7/2013 | Popper et al. | |
| 2013/0186416 A1‡ | 7/2013 | Gao | A24F 47/002 131/27 |
| 2013/0192615 A1 | 8/2013 | Tucker et al. | |
| 2013/0192618 A1‡ | 8/2013 | Li | A24F 47/008 131/32 |
| 2013/0192619 A1 | 8/2013 | Tucker et al. | |
| 2013/0192623 A1 | 8/2013 | Tucker et al. | |
| 2013/0199528 A1‡ | 8/2013 | Goodman | F22B 1/282 128/20 |
| 2013/0213417 A1‡ | 8/2013 | Chong | A24B 15/30 131/31 |
| 2013/0213418 A1‡ | 8/2013 | Tucker | A24F 47/008 131/32 |
| 2013/0213419 A1‡ | 8/2013 | Tucker | A24F 47/008 131/32 |
| 2013/0220314 A1 | 8/2013 | Bottom | |
| 2013/0220315 A1‡ | 8/2013 | Conley | A24F 47/008 128/20 |
| 2013/0220316 A1 | 8/2013 | Oglesby et al. | |
| 2013/0228190 A1‡ | 9/2013 | Weiss | A24F 47/002 131/32 |
| 2013/0228191 A1‡ | 9/2013 | Newton | A24F 47/008 131/32 |
| 2013/0233086 A1‡ | 9/2013 | Besling | G01L 9/0073 73/724 |
| 2013/0247924 A1‡ | 9/2013 | Scatterday | A61M 15/06 131/32 |
| 2013/0248385 A1‡ | 9/2013 | Scatterday | A24F 15/12 206/86 |
| 2013/0253433 A1 | 9/2013 | Senior et al. | |
| 2013/0255675 A1 | 10/2013 | Liu | |
| 2013/0255702 A1‡ | 10/2013 | Griffith, Jr. | A24F 47/008 131/32 |
| 2013/0263869 A1‡ | 10/2013 | Zhu | A24F 47/002 131/32 |
| 2013/0276802 A1‡ | 10/2013 | Scatterday | A61M 15/06 131/32 |
| 2013/0284190 A1‡ | 10/2013 | Scatterday | A61M 15/06 131/32 |
| 2013/0284191 A1‡ | 10/2013 | Scatterday | A61M 15/06 131/32 |
| 2013/0298905 A1‡ | 11/2013 | Levin | A24F 47/008 128/20 |
| 2013/0306065 A1‡ | 11/2013 | Thorens | A24F 47/008 128/20 |
| 2013/0306084 A1 | 11/2013 | Flick | |
| 2013/0312742 A1‡ | 11/2013 | Monsees | A61M 15/06 128/20 |
| 2013/0319431 A1‡ | 12/2013 | Cyphert | A24F 47/008 131/27 |
| 2013/0319435 A1‡ | 12/2013 | Flick | A24F 47/008 131/32 |
| 2013/0319436 A1‡ | 12/2013 | Liu | A24F 47/008 131/32 |
| 2013/0319437 A1‡ | 12/2013 | Liu | A24F 1/30 131/32 |
| 2013/0319438 A1 | 12/2013 | Liu | |
| 2013/0319440 A1‡ | 12/2013 | Capuano | A61M 15/06 131/32 |
| 2013/0323941 A1 | 12/2013 | Zeliff et al. | |
| 2013/0333700 A1‡ | 12/2013 | Buchberger | A24F 47/008 128/20 |
| 2013/0333711 A1‡ | 12/2013 | Liu | A24F 47/002 131/32 |
| 2013/0336358 A1‡ | 12/2013 | Liu | G01K 13/002 374/15 |
| 2013/0340775 A1‡ | 12/2013 | Juster | H01L 67/42 131/27 |
| 2013/0342157 A1‡ | 12/2013 | Liu | A24F 15/18 320/10 |
| 2014/0000638 A1‡ | 1/2014 | Sebastian | A24F 47/008 131/32 |
| 2014/0007891 A1‡ | 1/2014 | Liu | A24F 47/002 131/32 |
| 2014/0007892 A1‡ | 1/2014 | Liu | G08C 23/02 131/32 |
| 2014/0014124 A1‡ | 1/2014 | Glasberg | A24F 47/008 131/32 |
| 2014/0014126 A1‡ | 1/2014 | Peleg | A24F 47/008 131/32 |
| 2014/0020697 A1‡ | 1/2014 | Liu | A24F 15/00 131/32 |
| 2014/0034071 A1‡ | 2/2014 | Levitz | A24F 47/008 131/32 |
| 2014/0035391 A1‡ | 2/2014 | Kitani | H02J 15/005 307/10 |
| 2014/0041655 A1‡ | 2/2014 | Barron | A61M 11/042 128/20 |
| 2014/0041658 A1‡ | 2/2014 | Goodman | F22B 1/282 128/20 |
| 2014/0048086 A1‡ | 2/2014 | Zhanghua | A24F 47/008 131/32 |

(56) References Cited

U.S. PATENT DOCUMENTS

| | | | |
|---|---|---|---|
| 2014/0053856 A1‡ | 2/2014 | Liu | A24F 47/008 131/32 |
| 2014/0053858 A1‡ | 2/2014 | Liu | A24F 15/18 131/32 |
| 2014/0060528 A1‡ | 3/2014 | Liu | A24F 47/002 128/20 |
| 2014/0060529 A1‡ | 3/2014 | Zhang | A24F 47/008 128/20 |
| 2014/0060552 A1‡ | 3/2014 | Cohen | A24F 47/008 131/27 |
| 2014/0060556 A1‡ | 3/2014 | Liu | A24F 47/008 131/32 |
| 2014/0062417 A1‡ | 3/2014 | Li | H02J 7/007 320/13 |
| 2014/0069424 A1‡ | 3/2014 | Poston | A24F 47/008 128/20 |
| 2014/0069425 A1‡ | 3/2014 | Zhang | A24F 47/008 128/20 |
| 2014/0083442 A1‡ | 3/2014 | Scatterday | A24F 47/008 131/32 |
| 2014/0096782 A1‡ | 4/2014 | Ampolini | A24F 47/008 131/32 |
| 2014/0107815 A1‡ | 4/2014 | LaMothe | A24F 15/18 700/90 |
| 2014/0109898 A1‡ | 4/2014 | Li | A24F 47/008 128/20 |
| 2014/0109921 A1‡ | 4/2014 | Chen | A24F 47/008 131/27 |
| 2014/0116455 A1‡ | 5/2014 | Youn | A24F 47/008 131/32 |
| 2014/0123989 A1‡ | 5/2014 | LaMothe | A24F 47/008 131/32 |
| 2014/0123990 A1‡ | 5/2014 | Timmermans | A24F 47/008 131/32 |
| 2014/0130796 A1‡ | 5/2014 | Liu | A24F 47/008 128/20 |
| 2014/0130797 A1‡ | 5/2014 | Liu | A24F 47/008 128/20 |
| 2014/0130816 A1‡ | 5/2014 | Liu | A24F 47/008 131/32 |
| 2014/0130817 A1‡ | 5/2014 | Li | A24F 47/008 131/32 |
| 2014/0144429 A1‡ | 5/2014 | Wensley | A61M 15/06 128/20 |
| 2014/0144453 A1‡ | 5/2014 | Capuano | A24F 47/008 131/32 |
| 2014/0150784 A1‡ | 6/2014 | Liu | A24F 47/008 128/20 |
| 2014/0150785 A1‡ | 6/2014 | Malik | A61M 15/06 128/20 |
| 2014/0150810 A1‡ | 6/2014 | Hon | A24F 47/008 131/32 |
| 2014/0161301 A1‡ | 6/2014 | Merenda | B65H 75/48 381/38 |
| 2014/0166028 A1‡ | 6/2014 | Fuisz | A24D 1/002 131/32 |
| 2014/0166029 A1‡ | 6/2014 | Weigensberg | A24F 47/008 131/32 |
| 2014/0166030 A1‡ | 6/2014 | Li | A24F 47/008 131/32 |
| 2014/0166032 A1‡ | 6/2014 | Gindrat | A24B 3/14 131/35 |
| 2014/0174458 A1‡ | 6/2014 | Katz | A24F 47/008 131/20 |
| 2014/0174459 A1‡ | 6/2014 | Burstyn | A24F 47/008 131/27 |
| 2014/0175081 A1‡ | 6/2014 | Hwa | F23Q 7/16 219/26 |
| 2014/0178461 A1‡ | 6/2014 | Rigas | A61K 31/661 424/45 |
| 2014/0182609 A1‡ | 7/2014 | Liu | A24F 47/008 131/32 |
| 2014/0182610 A1‡ | 7/2014 | Liu | A24F 47/008 131/32 |
| 2014/0182611 A1‡ | 7/2014 | Liu | A24F 47/008 131/32 |
| 2014/0182612 A1‡ | 7/2014 | Chen | A24F 47/008 131/32 |
| 2014/0190477 A1‡ | 7/2014 | Qiu | A61M 11/042 128/20 |
| 2014/0190478 A1‡ | 7/2014 | Liu | A24F 47/008 128/20 |
| 2014/0190496 A1‡ | 7/2014 | Wensley | A24F 47/008 131/27 |
| 2014/0190501 A1‡ | 7/2014 | Liu | A24F 47/008 131/32 |
| 2014/0190502 A1‡ | 7/2014 | Liu | A24F 47/008 131/32 |
| 2014/0190503 A1‡ | 7/2014 | Li | A61M 15/06 131/32 |
| 2014/0196716 A1‡ | 7/2014 | Liu | A24F 47/008 128/20 |
| 2014/0196718 A1‡ | 7/2014 | Li | A61M 11/041 128/20 |
| 2014/0196731 A1‡ | 7/2014 | Scatterday | A45C 13/005 131/32 |
| 2014/0196733 A1‡ | 7/2014 | Liu | A24F 47/008 131/32 |
| 2014/0196734 A1‡ | 7/2014 | Liu | A24F 47/008 131/32 |
| 2014/0196735 A1‡ | 7/2014 | Liu | A24F 47/008 131/32 |
| 2014/0202454 A1‡ | 7/2014 | Buchberger | A24F 47/008 128/20 |
| 2014/0202474 A1‡ | 7/2014 | Peleg | G01N 25/72 131/32 |
| 2014/0202475 A1‡ | 7/2014 | Liu | A24F 47/008 131/32 |
| 2014/0202477 A1‡ | 7/2014 | Qi | A24F 47/008 131/32 |
| 2014/0209096 A1‡ | 7/2014 | Cheyene | A61M 15/08 128/20 |
| 2014/0209106 A1‡ | 7/2014 | Liu | A24F 47/008 131/32 |
| 2014/0209107 A1‡ | 7/2014 | Liu | A24F 47/008 131/32 |
| 2014/0209108 A1‡ | 7/2014 | Li | A24F 47/008 131/32 |
| 2014/0209109 A1‡ | 7/2014 | Larson | A61K 9/007 131/32 |
| 2014/0216450 A1‡ | 8/2014 | Liu | A24F 47/008 128/20 |
| 2014/0216483 A1‡ | 8/2014 | Alima | A24F 47/008 131/32 |
| 2014/0216484 A1‡ | 8/2014 | Liu | A24F 47/008 131/32 |
| 2014/0224244 A1‡ | 8/2014 | Liu | H03B 3/14 128/20 |
| 2014/0224267 A1‡ | 8/2014 | Levitz | A24F 47/008 131/32 |
| 2014/0230835 A1‡ | 8/2014 | Saliman | A24F 47/008 131/32 |
| 2014/0238421 A1‡ | 8/2014 | Shapiro | A24F 47/008 131/32 |
| 2014/0238422 A1‡ | 8/2014 | Plunkett | A24F 47/008 131/32 |
| 2014/0238423 A1‡ | 8/2014 | Tucker | A24F 47/008 131/32 |
| 2014/0238424 A1‡ | 8/2014 | Macko | A24F 47/008 131/32 |
| 2014/0246031 A1‡ | 9/2014 | Liu | A24F 47/008 131/26 |
| 2014/0246033 A1‡ | 9/2014 | Daehne | A24F 47/002 131/32 |
| 2014/0251324 A1‡ | 9/2014 | Xiang | A24F 47/008 128/20 |
| 2014/0251325 A1‡ | 9/2014 | Liu | A24F 47/008 128/20 |

(56) References Cited

U.S. PATENT DOCUMENTS

| | | | |
|---|---|---|---|
| 2014/0251356 A1‡ | 9/2014 | Xiang | A24F 47/008 131/32 |
| 2014/0253144 A1‡ | 9/2014 | Novak, III | A24F 47/008 324/55 |
| 2014/0254055 A1‡ | 9/2014 | Xiang | H05H 7/20 361/86 |
| 2014/0259026 A1‡ | 9/2014 | Xiang | G06F 9/4887 718/10 |
| 2014/0261408 A1‡ | 9/2014 | DePiano | A24F 47/008 128/20 |
| 2014/0261474 A1‡ | 9/2014 | Gonda | A61M 15/06 131/27 |
| 2014/0261479 A1‡ | 9/2014 | Xu | A24B 15/38 131/29 |
| 2014/0261483 A1‡ | 9/2014 | Hopps | A24B 15/24 131/29 |
| 2014/0261486 A1‡ | 9/2014 | Potter | A24F 47/008 131/32 |
| 2014/0261487 A1‡ | 9/2014 | Chapman | D04C 1/06 131/32 |
| 2014/0261488 A1‡ | 9/2014 | Tucker | A24F 47/008 131/32 |
| 2014/0261489 A1‡ | 9/2014 | Cadieux | A24F 47/008 131/32 |
| 2014/0261490 A1‡ | 9/2014 | Kane | A24F 47/008 131/32 |
| 2014/0261491 A1‡ | 9/2014 | Hawes | A24F 47/008 131/32 |
| 2014/0261492 A1‡ | 9/2014 | Kane | A24F 47/008 131/32 |
| 2014/0261493 A1‡ | 9/2014 | Smith | A24F 47/008 131/32 |
| 2014/0261494 A1‡ | 9/2014 | Scatterday | A24F 47/008 131/32 |
| 2014/0261495 A1 | 9/2014 | Novak, III et al. | |
| 2014/0261497 A1‡ | 9/2014 | Liu | A24F 47/008 131/32 |
| 2014/0261498 A1‡ | 9/2014 | Liu | A24F 47/008 131/32 |
| 2014/0261500 A1‡ | 9/2014 | Park | A24F 47/008 131/32 |
| 2014/0270727 A1‡ | 9/2014 | Ampolini | A24F 47/008 392/38 |
| 2014/0270729 A1‡ | 9/2014 | DePiano | A24F 47/008 392/39 |
| 2014/0270730 A1‡ | 9/2014 | DePiano | A24F 47/008 392/40 |
| 2014/0274940 A1‡ | 9/2014 | Mishra | A24B 15/30 514/54 |
| 2014/0276536 A1‡ | 9/2014 | Estes | A61M 5/14244 604/50 |
| 2014/0278250 A1‡ | 9/2014 | Smith | A24F 47/002 702/18 |
| 2014/0278258 A1‡ | 9/2014 | Shafer | G01N 21/17 702/18 |
| 2014/0283823 A1‡ | 9/2014 | Liu | A24F 47/008 128/20 |
| 2014/0283855 A1‡ | 9/2014 | Hawes | A24F 47/008 131/32 |
| 2014/0283856 A1‡ | 9/2014 | Xiang | A24F 47/008 131/32 |
| 2014/0283857 A1‡ | 9/2014 | Liu | A24F 47/008 131/32 |
| 2014/0283858 A1‡ | 9/2014 | Liu | A24F 47/008 131/32 |
| 2014/0290673 A1‡ | 10/2014 | Liu | A24F 47/002 131/32 |
| 2014/0290676 A1‡ | 10/2014 | Liu | A24F 47/008 131/32 |
| 2014/0290677 A1‡ | 10/2014 | Liu | A24F 47/008 131/32 |
| 2014/0299125 A1 | 10/2014 | Buchberger | |
| 2014/0299137 A1‡ | 10/2014 | Kieckbusch | A24F 47/008 131/32 |
| 2014/0299138 A1‡ | 10/2014 | Xiang | G06Q 10/00 131/32 |
| 2014/0299139 A1‡ | 10/2014 | Liu | A24F 47/008 131/32 |
| 2014/0299140 A1‡ | 10/2014 | Liu | A24F 47/008 131/32 |
| 2014/0299141 A1 | 10/2014 | Flick | |
| 2014/0301721 A1‡ | 10/2014 | Ruscio | A24F 47/008 392/38 |
| 2014/0305450 A1‡ | 10/2014 | Xiang | A24F 47/008 131/32 |
| 2014/0305451 A1‡ | 10/2014 | Liu | A24F 47/008 131/32 |
| 2014/0305452 A1‡ | 10/2014 | Liu | A24F 47/008 131/32 |
| 2014/0305454 A1‡ | 10/2014 | Rinker | A24F 47/008 131/32 |
| 2014/0311503 A1‡ | 10/2014 | Liu | A24F 47/008 131/32 |
| 2014/0311504 A1‡ | 10/2014 | Liu | A24F 47/008 131/32 |
| 2014/0311505 A1‡ | 10/2014 | Liu | A24F 47/008 131/32 |
| 2014/0332016 A1‡ | 11/2014 | Bellinger | A61M 11/041 131/32 |
| 2014/0332017 A1‡ | 11/2014 | Liu | A24F 47/008 131/32 |
| 2014/0332018 A1‡ | 11/2014 | Liu | A24F 47/008 131/32 |
| 2014/0332019 A1‡ | 11/2014 | Liu | A61M 15/06 131/32 |
| 2014/0332020 A1‡ | 11/2014 | Li | A24F 47/008 131/32 |
| 2014/0332022 A1‡ | 11/2014 | Li | A24F 47/008 131/32 |
| 2014/0334803 A1‡ | 11/2014 | Li | H05B 3/03 392/39 |
| 2014/0334804 A1 | 11/2014 | Choi | |
| 2014/0338680 A1‡ | 11/2014 | Abramov | A24F 47/008 131/32 |
| 2014/0338681 A1‡ | 11/2014 | Liu | A24F 47/008 131/32 |
| 2014/0338682 A1‡ | 11/2014 | Liu | A24F 47/008 131/32 |
| 2014/0338683 A1‡ | 11/2014 | Liu | A24F 47/008 131/32 |
| 2014/0338684 A1‡ | 11/2014 | Liu | A24F 48/008 131/32 |
| 2014/0338685 A1‡ | 11/2014 | Amir | A24F 47/008 131/32 |
| 2014/0345631 A1‡ | 11/2014 | Bowen | A24B 15/16 131/32 |
| 2014/0345632 A1‡ | 11/2014 | Scatterday | A24F 47/008 131/32 |
| 2014/0345633 A1‡ | 11/2014 | Talon | A24F 47/008 131/32 |
| 2014/0345635 A1‡ | 11/2014 | Rabinowitz | A24B 15/16 131/35 |
| 2014/0352177 A1‡ | 12/2014 | Rehkemper | A43B 23/24 36/114 |
| 2014/0352705 A1‡ | 12/2014 | Liu | H02H 11/003 131/27 |
| 2014/0352707 A1‡ | 12/2014 | Liu | A24F 47/008 131/32 |
| 2014/0353856 A1‡ | 12/2014 | Dubief | A24D 3/041 261/12 |
| 2014/0353867 A1‡ | 12/2014 | Liu | C08K 3/22 264/51 |
| 2014/0354215 A1‡ | 12/2014 | Xiang | H02J 7/0052 320/10 |
| 2014/0355969 A1‡ | 12/2014 | Stern | A24F 47/008 392/39 |
| 2014/0356607 A1‡ | 12/2014 | Woodcock | A24F 47/006 428/22 |

(56) References Cited

U.S. PATENT DOCUMENTS

| | | | |
|---|---|---|---|
| 2014/0360512 A1‡ | 12/2014 | Xiang | H02J 7/0077 131/32 |
| 2014/0360516 A1‡ | 12/2014 | Liu | A61M 15/06 131/32 |
| 2014/0363145 A1 | 12/2014 | Plojoux et al. | |
| 2014/0366894 A1‡ | 12/2014 | Liu | A24F 47/008 131/32 |
| 2014/0366895 A1‡ | 12/2014 | Li | H01M 2/1055 131/32 |
| 2014/0366896 A1‡ | 12/2014 | Li | A24F 47/008 131/32 |
| 2014/0366897 A1‡ | 12/2014 | Liu | A24F 47/008 131/32 |
| 2014/0366898 A1‡ | 12/2014 | Monsees | A24F 47/008 131/32 |
| 2014/0366902 A1‡ | 12/2014 | Chiolini | A61K 47/10 131/35 |
| 2014/0373833 A1‡ | 12/2014 | Liu | A61M 15/06 128/20 |
| 2014/0373855 A1‡ | 12/2014 | Zheng | A61K 9/007 131/27 |
| 2014/0373857 A1 | 12/2014 | Steinberg | |
| 2014/0373858 A1‡ | 12/2014 | Liu | A24F 47/008 131/32 |
| 2014/0376895 A1‡ | 12/2014 | Han | A24F 47/008 392/39 |
| 2014/0378790 A1‡ | 12/2014 | Cohen | A61B 5/486 600/30 |
| 2015/0000682 A1‡ | 1/2015 | Liu | A24F 47/008 131/32 |
| 2015/0000683 A1‡ | 1/2015 | Liu | A24F 47/008 131/32 |
| 2015/0007834 A1‡ | 1/2015 | Liu | A24F 47/008 131/32 |
| 2015/0007835 A1‡ | 1/2015 | Liu | A24F 47/008 131/32 |
| 2015/0007836 A1‡ | 1/2015 | Li | A24F 47/008 131/32 |
| 2015/0013692 A1‡ | 1/2015 | Liu | A24F 47/008 131/27 |
| 2015/0013693 A1‡ | 1/2015 | Fuisz | A24B 15/28 131/27 |
| 2015/0013696 A1‡ | 1/2015 | Plojoux | A61M 15/06 131/32 |
| 2015/0013700 A1‡ | 1/2015 | Liu | A24F 47/008 131/32 |
| 2015/0013701 A1‡ | 1/2015 | Liu | A24F 47/008 131/32 |
| 2015/0013702 A1‡ | 1/2015 | Liu | A24F 47/008 131/32 |
| 2015/0015187 A1‡ | 1/2015 | Xiang | H02J 7/007 320/10 |
| 2015/0020822 A1‡ | 1/2015 | Janardhan | A24F 47/008 131/32 |
| 2015/0020823 A1‡ | 1/2015 | Lipowicz | A24B 15/167 131/32 |
| 2015/0020824 A1‡ | 1/2015 | Bowen | A24B 15/16 131/32 |
| 2015/0020825 A1‡ | 1/2015 | Galloway | A24F 47/008 131/32 |
| 2015/0020826 A1‡ | 1/2015 | Liu | A24F 47/008 131/32 |
| 2015/0020827 A1‡ | 1/2015 | Liu | A24F 47/008 131/32 |
| 2015/0020828 A1‡ | 1/2015 | Liu | A24F 47/008 131/32 |
| 2015/0020829 A1‡ | 1/2015 | Li | A24F 47/008 131/32 |
| 2015/0020830 A1‡ | 1/2015 | Koller | A24F 47/008 131/32 |
| 2015/0020831 A1‡ | 1/2015 | Weigensberg | A24F 47/008 131/32 |
| 2015/0020833 A1‡ | 1/2015 | Conley | A24F 47/008 131/32 |
| 2015/0027454 A1‡ | 1/2015 | Li | A24F 47/008 131/32 |
| 2015/0027455 A1‡ | 1/2015 | Peleg | A24F 47/008 131/32 |
| 2015/0027456 A1‡ | 1/2015 | Janardhan | A24F 47/008 131/32 |
| 2015/0027457 A1‡ | 1/2015 | Janardhan | A24F 47/008 131/32 |
| 2015/0027460 A1‡ | 1/2015 | Liu | A24F 47/008 131/32 |
| 2015/0027461 A1‡ | 1/2015 | Liu | A24F 47/008 131/32 |
| 2015/0027462 A1‡ | 1/2015 | Liu | A24F 47/008 131/32 |
| 2015/0027463 A1‡ | 1/2015 | Liu | A24F 47/008 131/32 |
| 2015/0027464 A1‡ | 1/2015 | Liu | A24F 47/008 131/32 |
| 2015/0027465 A1‡ | 1/2015 | Liu | A24F 47/008 131/32 |
| 2015/0027466 A1‡ | 1/2015 | Xiang | H02J 7/0013 131/32 |
| 2015/0027467 A1‡ | 1/2015 | Liu | A24F 47/008 131/32 |
| 2015/0027468 A1‡ | 1/2015 | Li | A24F 47/008 131/32 |
| 2015/0027469 A1‡ | 1/2015 | Tucker | A24F 47/008 131/32 |
| 2015/0027470 A1‡ | 1/2015 | Kane | A24F 47/008 131/32 |
| 2015/0027471 A1‡ | 1/2015 | Feldman | H03B 3/16 131/32 |
| 2015/0027472 A1‡ | 1/2015 | Amir | A24F 47/008 131/32 |
| 2015/0027473 A1‡ | 1/2015 | Graf | F22B 1/288 131/32 |
| 2015/0034102 A1‡ | 2/2015 | Faramarzian | A24F 47/008 131/32 |
| 2015/0034103 A1‡ | 2/2015 | Hon | H05B 3/22 131/32 |
| 2015/0034104 A1‡ | 2/2015 | Zhou | A24F 47/008 131/32 |
| 2015/0034105 A1‡ | 2/2015 | Liu | A24F 47/008 131/32 |
| 2015/0034106 A1‡ | 2/2015 | Liu | H01M 2/20 131/32 |
| 2015/0034107 A1‡ | 2/2015 | Liu | A24F 47/008 131/32 |
| 2015/0034507 A1‡ | 2/2015 | Liu | A24F 15/12 206/25 |
| 2015/0035540 A1‡ | 2/2015 | Xiang | G01R 31/3842 324/42 |
| 2015/0038567 A1‡ | 2/2015 | Herkenroth | C07D 311/80 514/45 |
| 2015/0040927 A1‡ | 2/2015 | Li | A24F 47/008 131/32 |
| 2015/0040928 A1‡ | 2/2015 | Saydar | A61M 15/00 131/32 |
| 2015/0040929 A1‡ | 2/2015 | Hon | A24F 47/008 131/32 |
| 2015/0041482 A1‡ | 2/2015 | Liu | B65D 43/163 220/84 |
| 2015/0047658 A1‡ | 2/2015 | Cyphert | A24F 47/008 131/32 |
| 2015/0047659 A1‡ | 2/2015 | Liu | A24F 47/008 131/32 |
| 2015/0047660 A1‡ | 2/2015 | Liu | A24F 47/008 131/32 |
| 2015/0047661 A1‡ | 2/2015 | Blackley | H05B 3/12 131/32 |
| 2015/0047663 A1‡ | 2/2015 | Liu | H01M 2/1055 131/32 |
| 2015/0053214 A1 | 2/2015 | Alarcon et al. | |

(56) References Cited

U.S. PATENT DOCUMENTS

| | | | |
|---|---|---|---|
| 2015/0053215 A1‡ | 2/2015 | Liu | A24F 47/008 131/32 |
| 2015/0053216 A1‡ | 2/2015 | Liu | A24F 47/008 131/32 |
| 2015/0053217 A1‡ | 2/2015 | Steingraber | A24F 47/008 131/32 |
| 2015/0053220 A1‡ | 2/2015 | Levy | A24F 47/008 131/32 |
| 2015/0057341 A1‡ | 2/2015 | Perry | A61K 31/352 514/45 |
| 2015/0059779 A1‡ | 3/2015 | Alarcon | A24F 47/00 131/27 |
| 2015/0059780 A1‡ | 3/2015 | Davis | A24F 47/008 131/32 |
| 2015/0059782 A1‡ | 3/2015 | Liu | A24F 47/008 131/32 |
| 2015/0059783 A1‡ | 3/2015 | Liu | A24F 47/008 131/32 |
| 2015/0059784 A1‡ | 3/2015 | Liu | A24F 47/008 131/32 |
| 2015/0059785 A1‡ | 3/2015 | Liu | A24F 47/008 131/32 |
| 2015/0059787 A1 | 3/2015 | Qiu | |
| 2015/0068523 A1‡ | 3/2015 | Powers | G01L 7/08 128/20 |
| 2015/0068543 A1‡ | 3/2015 | Liu | A24F 47/002 131/32 |
| 2015/0068545 A1‡ | 3/2015 | Moldoveanu | A24B 13/00 131/35 |
| 2015/0070832 A1 | 3/2015 | Schneider et al. | |
| 2015/0075545 A1‡ | 3/2015 | Xiang | A24F 47/008 131/32 |
| 2015/0075546 A1‡ | 3/2015 | Kueny, Sr. | A24F 47/008 131/32 |
| 2015/0078735 A1‡ | 3/2015 | Cormack | A61M 15/06 392/39 |
| 2015/0080265 A1‡ | 3/2015 | Elzinga | C11B 9/0038 506/15 |
| 2015/0082859 A1‡ | 3/2015 | Xiang | G01F 25/0007 73/1.3 |
| 2015/0083144 A1‡ | 3/2015 | Xiang | A24F 47/008 131/32 |
| 2015/0083145 A1‡ | 3/2015 | Li | H01M 2/1055 131/32 |
| 2015/0083146 A1‡ | 3/2015 | Goldman | A24F 47/008 131/32 |
| 2015/0083147 A1‡ | 3/2015 | Schiff | A24F 47/008 131/32 |
| 2015/0090253 A1‡ | 4/2015 | Farrow | A24F 47/008 128/20 |
| 2015/0090256 A1‡ | 4/2015 | Chung | A61M 15/002 128/20 |
| 2015/0090277 A1‡ | 4/2015 | Xiang | A24F 47/008 131/32 |
| 2015/0090278 A1‡ | 4/2015 | Schiff | A24F 47/008 131/32 |
| 2015/0090279 A1‡ | 4/2015 | Chen | A61M 15/06 131/32 |
| 2015/0090280 A1‡ | 4/2015 | Chen | A24F 47/008 131/32 |
| 2015/0090281 A1‡ | 4/2015 | Chen | A24F 47/008 131/32 |
| 2015/0100441 A1‡ | 4/2015 | Alarcon | G06Q 20/18 705/16 |
| 2015/0101606 A1 | 4/2015 | White | |
| 2015/0101622 A1‡ | 4/2015 | Liu | A24F 47/008 131/32 |
| 2015/0101623 A1‡ | 4/2015 | Liu | A24F 47/008 131/32 |
| 2015/0101625 A1‡ | 4/2015 | Newton | H05B 1/0244 131/32 |
| 2015/0101626 A1‡ | 4/2015 | Li | A24F 47/008 131/32 |
| 2015/0101945 A1‡ | 4/2015 | Scatterday | A24F 13/14 206/26 |
| 2015/0102777 A1‡ | 4/2015 | Cooper | H02J 7/0042 320/11 |
| 2015/0105455 A1‡ | 4/2015 | Bjorncrantz | A61K 9/007 514/45 |
| 2015/0107609 A1‡ | 4/2015 | Liu | A24F 47/008 131/32 |
| 2015/0107610 A1‡ | 4/2015 | Metrangolo | A24B 3/14 131/32 |
| 2015/0107611 A1‡ | 4/2015 | Metrangolo | A24B 13/00 131/32 |
| 2015/0107612 A1‡ | 4/2015 | Liu | A24F 15/12 131/32 |
| 2015/0108019 A1‡ | 4/2015 | Liu | A24F 15/12 206/26 |
| 2015/0114407 A1‡ | 4/2015 | Duncan | A24F 47/004 131/32 |
| 2015/0117842 A1‡ | 4/2015 | Brammer | H05B 3/02 392/38 |
| 2015/0122252 A1‡ | 5/2015 | Frija | A24F 47/008 128/20 |
| 2015/0122274 A1‡ | 5/2015 | Cohen | G01K 13/00 131/32 |
| 2015/0122278 A1‡ | 5/2015 | Hardgrove | A24F 47/008 131/32 |
| 2015/0128965 A1‡ | 5/2015 | Lord | A24F 47/008 131/32 |
| 2015/0128966 A1‡ | 5/2015 | Lord | A24F 47/002 131/32 |
| 2015/0128967 A1‡ | 5/2015 | Robinson | A24F 47/008 131/32 |
| 2015/0128969 A1‡ | 5/2015 | Chapman | A24F 47/008 131/32 |
| 2015/0128970 A1‡ | 5/2015 | Liu | A24F 47/008 131/32 |
| 2015/0128971 A1‡ | 5/2015 | Verleur | A24F 47/008 131/32 |
| 2015/0128972 A1‡ | 5/2015 | Verleur | A24F 47/008 131/32 |
| 2015/0128973 A1‡ | 5/2015 | Li | A24F 47/008 131/32 |
| 2015/0128976 A1‡ | 5/2015 | Verleur | A24F 47/008 131/32 |
| 2015/0128977 A1‡ | 5/2015 | Li | H05B 3/06 131/32 |
| 2015/0136153 A1‡ | 5/2015 | Lord | A24F 47/008 131/32 |
| 2015/0136155 A1‡ | 5/2015 | Verleur | A24F 47/008 131/32 |
| 2015/0136156 A1‡ | 5/2015 | Liu | A24F 47/008 131/32 |
| 2015/0136157 A1‡ | 5/2015 | Liu | A24F 47/008 131/32 |
| 2015/0136158 A1‡ | 5/2015 | Stevens | A24F 47/008 131/32 |
| 2015/0142387 A1‡ | 5/2015 | Alarcon | A61M 11/042 702/18 |
| 2015/0144145 A1‡ | 5/2015 | Chang | A24F 47/008 131/32 |
| 2015/0144147 A1‡ | 5/2015 | Li | A24F 47/008 131/32 |
| 2015/0144148 A1‡ | 5/2015 | Chen | A24F 47/008 131/32 |
| 2015/0150302 A1‡ | 6/2015 | Metrangolo | A24B 13/00 131/77 |
| 2015/0150303 A1‡ | 6/2015 | Jensen | A24B 15/16 131/27 |
| 2015/0150305 A1‡ | 6/2015 | Shenkal | A24F 47/008 131/32 |
| 2015/0150306 A1‡ | 6/2015 | Chen | A24F 47/008 131/32 |
| 2015/0150307 A1‡ | 6/2015 | Liu | H05B 1/0244 131/32 |

(56) References Cited

U.S. PATENT DOCUMENTS

| | | | |
|---|---|---|---|
| 2015/0150308 A1‡ | 6/2015 | Monsees | A24F 47/006 131/32 |
| 2015/0157053 A1‡ | 6/2015 | Mayor | A24F 47/008 131/32 |
| 2015/0157054 A1‡ | 6/2015 | Liu | A24F 47/008 131/32 |
| 2015/0157055 A1‡ | 6/2015 | Lord | A24F 47/008 131/32 |
| 2015/0157056 A1‡ | 6/2015 | Bowen | A61M 11/041 131/32 |
| 2015/0163859 A1‡ | 6/2015 | Schneider | A24F 47/008 131/32 |
| 2015/0164138 A1‡ | 6/2015 | Liu | H01M 2/1044 206/26 |
| 2015/0164141 A1‡ | 6/2015 | Newton | A24F 47/008 131/32 |
| 2015/0164142 A1‡ | 6/2015 | Li | F22B 1/288 131/32 |
| 2015/0164143 A1‡ | 6/2015 | Maas | A24F 47/008 131/32 |
| 2015/0164144 A1‡ | 6/2015 | Liu | A24F 47/008 131/32 |
| 2015/0164145 A1‡ | 6/2015 | Zhou | A24F 47/008 131/32 |
| 2015/0164146 A1‡ | 6/2015 | Li | A24F 47/008 131/32 |
| 2015/0164147 A1‡ | 6/2015 | Verleur | A24F 47/008 131/32 |
| 2015/0167976 A1‡ | 6/2015 | Recio | F23Q 7/16 219/20 |
| 2015/0173124 A1‡ | 6/2015 | Qiu | A24F 47/008 131/32 |
| 2015/0173417 A1‡ | 6/2015 | Gennrich | A24D 1/042 131/32 |
| 2015/0173419 A1‡ | 6/2015 | Tu | A24F 47/008 131/32 |
| 2015/0173421 A1‡ | 6/2015 | Hsieh | A24F 47/008 131/32 |
| 2015/0173422 A1‡ | 6/2015 | Liu | A24F 47/008 131/32 |
| 2015/0181928 A1‡ | 7/2015 | Liu | A24F 47/008 131/32 |
| 2015/0181937 A1‡ | 7/2015 | Dubief | A24F 47/008 131/32 |
| 2015/0181939 A1‡ | 7/2015 | Liu | A24F 47/008 131/32 |
| 2015/0181940 A1 | 7/2015 | Liu | |
| 2015/0181941 A1‡ | 7/2015 | Liu | A24F 47/008 131/32 |
| 2015/0181943 A1‡ | 7/2015 | Li | H05B 3/48 131/32 |
| 2015/0181944 A1‡ | 7/2015 | Li | A24F 47/008 131/32 |
| 2015/0184846 A1‡ | 7/2015 | Liu | F22B 1/284 131/32 |
| 2015/0186837 A1‡ | 7/2015 | Bianco | G06Q 10/087 235/38 |
| 2015/0189695 A1‡ | 7/2015 | Xiang | G06K 7/10861 219/20 |
| 2015/0189915 A1‡ | 7/2015 | Liu | A24F 47/008 131/32 |
| 2015/0189918 A1‡ | 7/2015 | Liu | H05B 3/03 131/32 |
| 2015/0189919 A1‡ | 7/2015 | Liu | A24F 47/008 131/32 |
| 2015/0189920 A1‡ | 7/2015 | Liu | A24D 3/043 131/32 |
| 2015/0196055 A1‡ | 7/2015 | Liu | A24F 47/008 131/32 |
| 2015/0196056 A1‡ | 7/2015 | Liu | H05B 1/0244 131/32 |
| 2015/0196057 A1‡ | 7/2015 | Wu | A24F 47/008 131/32 |
| 2015/0196058 A1‡ | 7/2015 | Lord | A24F 47/008 131/32 |
| 2015/0196059 A1‡ | 7/2015 | Liu | H05B 3/06 131/32 |
| 2015/0196060 A1‡ | 7/2015 | Wensley | F22B 1/288 392/39 |
| 2015/0196062 A1‡ | 7/2015 | Li | A24F 47/008 131/32 |
| 2015/0200385 A1‡ | 7/2015 | Liu | H01M 2/0404 131/32 |
| 2015/0201674 A1‡ | 7/2015 | Dooly | B65B 5/06 53/432 |
| 2015/0201675 A1‡ | 7/2015 | Lord | A24F 47/008 131/32 |
| 2015/0201676 A1‡ | 7/2015 | Shin | A24F 47/008 131/32 |
| 2015/0208724 A1‡ | 7/2015 | Wu | A24F 47/008 131/32 |
| 2015/0208725 A1‡ | 7/2015 | Tsai | A24F 47/008 392/29 |
| 2015/0208726 A1‡ | 7/2015 | Liu | A24F 47/008 131/32 |
| 2015/0208728 A1‡ | 7/2015 | Lord | A24F 7/00 131/32 |
| 2015/0208729 A1‡ | 7/2015 | Monsees | A24F 47/008 131/32 |
| 2015/0208730 A1‡ | 7/2015 | Li | A61M 15/06 131/32 |
| 2015/0208731 A1‡ | 7/2015 | Malamud | H05B 1/0244 131/32 |
| 2015/0216232 A1‡ | 8/2015 | Bless | A24F 47/008 131/32 |
| 2015/0216233 A1‡ | 8/2015 | Sears | A23F 47/008 362/23 |
| 2015/0216234 A1‡ | 8/2015 | Chung | A24F 47/008 131/32 |
| 2015/0216235 A1‡ | 8/2015 | Liu | A24F 47/008 131/32 |
| 2015/0216237 A1‡ | 8/2015 | Wensley | A24F 47/008 131/27 |
| 2015/0217067 A1‡ | 8/2015 | Hearn | A24F 47/002 128/20 |
| 2015/0217068 A1‡ | 8/2015 | Wakalopulos | A61M 15/06 128/20 |
| 2015/0223520 A1‡ | 8/2015 | Phillips | A61M 15/06 131/32 |
| 2015/0223521 A1‡ | 8/2015 | Menting | A24F 47/008 131/27 |
| 2015/0223522 A1‡ | 8/2015 | Ampolini | A24F 47/008 131/32 |
| 2015/0223523 A1‡ | 8/2015 | McCullough | A61M 15/06 131/32 |
| 2015/0224268 A1‡ | 8/2015 | Henry | A24F 47/008 128/20 |
| 2015/0227471 A1‡ | 8/2015 | Stafford | G06F 12/1441 711/16 |
| 2015/0237914 A1‡ | 8/2015 | Han | A24F 47/008 131/32 |
| 2015/0237916 A1 | 8/2015 | Farine et al. | |
| 2015/0237917 A1‡ | 8/2015 | Lord | A24F 47/008 131/32 |
| 2015/0237918 A1‡ | 8/2015 | Liu | A24F 47/002 131/32 |
| 2015/0238723 A1‡ | 8/2015 | Knudsen | A24F 47/002 128/20 |
| 2015/0245654 A1‡ | 9/2015 | Memari | A24F 15/12 141/2 |
| 2015/0245655 A1‡ | 9/2015 | Memari | A24F 15/12 206/24 |
| 2015/0245657 A1‡ | 9/2015 | Memari | A24F 15/12 141/18 |
| 2015/0245658 A1‡ | 9/2015 | Worm | A24F 47/008 131/32 |

(56) References Cited

U.S. PATENT DOCUMENTS

| | | | | |
|---|---|---|---|---|
| 2015/0245659 A1‡ | 9/2015 | Depiano | A24F 47/008 | 392/39 |
| 2015/0245660 A1‡ | 9/2015 | Lord | H04W 8/24 | 131/32 |
| 2015/0245661 A1‡ | 9/2015 | Milin | A24F 47/008 | 131/32 |
| 2015/0245665 A1‡ | 9/2015 | Memari | A24F 15/12 | 131/32 |
| 2015/0245666 A1‡ | 9/2015 | Memari | A24F 15/12 | 131/32 |
| 2015/0245667 A1‡ | 9/2015 | Memari | A24F 15/12 | 131/32 |
| 2015/0245668 A1‡ | 9/2015 | Memari | A24F 15/12 | 206/25 |
| 2015/0245669 A1‡ | 9/2015 | Cadieux | A61M 15/06 | 131/32 |
| 2015/0257441 A1‡ | 9/2015 | Gerkin | A24F 15/08 | 206/22 |
| 2015/0257444 A1‡ | 9/2015 | Chung | A24F 47/008 | 131/32 |
| 2015/0257445 A1‡ | 9/2015 | Henry, Jr. | A24F 47/008 | 131/32 |
| 2015/0257446 A1‡ | 9/2015 | Chung | A24F 47/008 | 131/32 |
| 2015/0257447 A1‡ | 9/2015 | Sullivan | A24F 47/008 | 131/32 |
| 2015/0257449 A1‡ | 9/2015 | Gabbay | A24F 47/008 | 392/38 |
| 2015/0257451 A1‡ | 9/2015 | Brannon | A24F 47/008 | 131/32 |
| 2015/0258289 A1‡ | 9/2015 | Henry, Jr. | A61M 15/06 | 128/20 |
| 2015/0272211 A1‡ | 10/2015 | Chung | A24F 15/00 | 206/24 |
| 2015/0272215 A1‡ | 10/2015 | Esses | A24F 47/008 | 320/10 |
| 2015/0272217 A1‡ | 10/2015 | Chen | A24F 47/008 | 131/32 |
| 2015/0272218 A1‡ | 10/2015 | Chen | H05B 3/44 | 131/32 |
| 2015/0272220 A1‡ | 10/2015 | Spinka | A24F 47/008 | 131/32 |
| 2015/0272221 A1‡ | 10/2015 | Liu | A24F 47/008 | 131/27 |
| 2015/0272222 A1‡ | 10/2015 | Spinka | A24F 47/008 | 131/27 |
| 2015/0272223 A1‡ | 10/2015 | Weigensberg | A24F 47/008 | 131/32 |
| 2015/0276262 A1‡ | 10/2015 | Dai | A24F 47/008 | 392/38 |
| 2015/0280273 A1‡ | 10/2015 | Liu | H01M 10/0422 | 429/16 |
| 2015/0282524 A1‡ | 10/2015 | Elhalwani | A24F 1/30 | 131/32 |
| 2015/0282525 A1‡ | 10/2015 | Plojoux | A24F 47/008 | 131/18 |
| 2015/0282526 A1‡ | 10/2015 | Wu | A61M 15/06 | 131/32 |
| 2015/0282527 A1‡ | 10/2015 | Henry, Jr. | A24F 47/008 | 131/32 |
| 2015/0282529 A1‡ | 10/2015 | Li | A24F 47/008 | 131/27 |
| 2015/0282530 A1‡ | 10/2015 | Johnson | A61M 15/06 | 392/38 |
| 2015/0288468 A1‡ | 10/2015 | Xiang | H04W 84/18 | 455/50 |
| 2015/0289565 A1‡ | 10/2015 | Cadieux | A24F 47/002 | 131/32 |
| 2015/0289567 A1‡ | 10/2015 | Liu | A24F 47/008 | 131/32 |
| 2015/0295921 A1‡ | 10/2015 | Cao | H04L 63/0853 | 726/7 |
| 2015/0296883 A1‡ | 10/2015 | Wu | A24F 47/008 | 131/32 |
| 2015/0296885 A1‡ | 10/2015 | Liu | A24F 47/008 | 131/32 |
| 2015/0296886 A1‡ | 10/2015 | Li | A24F 47/008 | 131/32 |
| 2015/0296887 A1‡ | 10/2015 | Zhu | A24F 47/008 | 131/32 |
| 2015/0296888 A1‡ | 10/2015 | Liu | A24F 47/008 | 131/32 |
| 2015/0296889 A1‡ | 10/2015 | Liu | A24F 47/008 | 131/32 |
| 2015/0304401 A1‡ | 10/2015 | Liu | A24F 47/008 | 709/21 |
| 2015/0304402 A1‡ | 10/2015 | Liu | A24F 47/008 | 709/20 |
| 2015/0305403 A1‡ | 10/2015 | Coelho Belo Fernandes De Carvalho | F22B 1/284 | 131/32 |
| 2015/0305404 A1‡ | 10/2015 | Rosales | A24F 47/008 | 131/24 |
| 2015/0305406 A1‡ | 10/2015 | Li | A24F 47/008 | 131/32 |
| 2015/0305407 A1‡ | 10/2015 | Li | A61M 11/08 | 131/27 |
| 2015/0305408 A1‡ | 10/2015 | Liu | H05B 3/44 | 131/32 |
| 2015/0305409 A1‡ | 10/2015 | Verleur | H02J 7/0022 | 131/32 |
| 2015/0305464 A1‡ | 10/2015 | Nelson, Jr. | A24F 47/008 | 206/23 |
| 2015/0313275 A1‡ | 11/2015 | Anderson | A24B 15/10 | 131/35 |
| 2015/0313282 A1‡ | 11/2015 | Ademe | A24F 47/008 | 131/32 |
| 2015/0313283 A1‡ | 11/2015 | Collett | A24F 47/008 | 131/32 |
| 2015/0313284 A1‡ | 11/2015 | Liu | H05B 1/0244 | 131/32 |
| 2015/0313285 A1‡ | 11/2015 | Waller | A24B 15/165 | 131/32 |
| 2015/0313287 A1‡ | 11/2015 | Verleur | A24F 47/008 | 131/32 |
| 2015/0313288 A1‡ | 11/2015 | Liu | A24F 47/008 | 131/32 |
| 2015/0313868 A1‡ | 11/2015 | Morgan | A61K 31/352 | 514/22 |
| 2015/0320114 A1‡ | 11/2015 | Wu | A24F 47/002 | 131/32 |
| 2015/0320116 A1‡ | 11/2015 | Bleloch et al. | A61M 15/06 | 219/62 |
| 2015/0322451 A1‡ | 11/2015 | Kudithipudi | C12N 15/8261 | 131/32 |
| 2015/0327595 A1‡ | 11/2015 | Scatterday | A24F 47/008 | 128/20 |
| 2015/0327596 A1‡ | 11/2015 | Alarcon | A24F 47/008 | 131/32 |
| 2015/0327597 A1‡ | 11/2015 | Li | A24F 47/008 | 131/32 |
| 2015/0327598 A1‡ | 11/2015 | Xiang | A24F 47/004 | 131/32 |
| 2015/0328415 A1‡ | 11/2015 | Minskoff | A61M 15/06 | 128/20 |
| 2015/0332379 A1‡ | 11/2015 | Alarcon | A24F 15/19 | 705/26 |
| 2015/0333542 A1‡ | 11/2015 | Alarcon | H02J 7/007 | 131/32 |
| 2015/0333552 A1‡ | 11/2015 | Alarcon | H02J 7/0052 | 131/32 |
| 2015/0333561 A1‡ | 11/2015 | Alarcon | H02J 7/0042 | 131/32 |
| 2015/0335071 A1‡ | 11/2015 | Brinkley | F22B 1/284 | 131/32 |
| 2015/0335072 A1‡ | 11/2015 | Giller | F21V 33/0004 | 131/32 |

(56) References Cited

U.S. PATENT DOCUMENTS

| | | | |
|---|---|---|---|
| 2015/0335074 A1‡ | 11/2015 | Leung | A61M 15/06 131/32 |
| 2015/0335075 A1‡ | 11/2015 | Minskoff | A24F 47/008 131/32 |
| 2015/0336689 A1‡ | 11/2015 | Brown | B65B 3/12 141/98 |
| 2015/0342254 A1‡ | 12/2015 | Mironov | A24F 47/006 131/33 |
| 2015/0342255 A1‡ | 12/2015 | Wu | A61M 15/06 131/32 |
| 2015/0342256 A1‡ | 12/2015 | Chen | H05B 3/06 392/40 |
| 2015/0342257 A1‡ | 12/2015 | Chen | H05B 3/06 392/39 |
| 2015/0342258 A1‡ | 12/2015 | Chen | H05B 3/06 131/32 |
| 2015/0342259 A1‡ | 12/2015 | Baker | A24F 47/008 131/32 |
| 2015/0351449 A1‡ | 12/2015 | Righetti | A24B 15/167 131/32 |
| 2015/0351454 A1‡ | 12/2015 | Huang | F22B 1/284 392/39 |
| 2015/0351455 A1‡ | 12/2015 | Liu | H05B 1/0244 131/32 |
| 2015/0351456 A1‡ | 12/2015 | Johnson | A24F 47/008 131/32 |
| 2015/0351457 A1‡ | 12/2015 | Liu | A24F 47/008 131/32 |
| 2015/0357608 A1‡ | 12/2015 | Huang | A24F 47/008 131/32 |
| 2015/0357839 A1‡ | 12/2015 | Cai | A24F 47/008 131/32 |
| 2015/0359258 A1‡ | 12/2015 | Mishra | A24B 15/282 131/32 |
| 2015/0359261 A1‡ | 12/2015 | Li | A24F 47/008 392/39 |
| 2015/0359262 A1‡ | 12/2015 | Liu | A24F 47/008 131/32 |
| 2015/0359263 A1‡ | 12/2015 | Bellinger | H05B 1/0244 392/39 |
| 2015/0359264 A1‡ | 12/2015 | Fernando | A24F 47/008 131/32 |
| 2015/0359265 A1‡ | 12/2015 | Liu | A24F 47/008 131/32 |
| 2015/0366250 A1‡ | 12/2015 | Landau | A24F 47/002 426/2 |
| 2015/0366265 A1‡ | 12/2015 | Lansing | A24F 47/004 131/32 |
| 2015/0366266 A1‡ | 12/2015 | Chen | H05B 1/0244 131/32 |
| 2015/0366267 A1‡ | 12/2015 | Liu | H01M 2/1055 131/32 |
| 2015/0366268 A1‡ | 12/2015 | Shabat | H04M 1/21 131/32 |
| 2015/0374035 A1‡ | 12/2015 | Sanchez | A24F 47/008 131/32 |
| 2015/0374039 A1‡ | 12/2015 | Zhu | A24F 47/008 131/32 |
| 2015/0374040 A1‡ | 12/2015 | Chen | A24F 47/008 131/32 |
| 2016/0000147 A1‡ | 1/2016 | Li | A24F 47/008 131/32 |
| 2016/0000148 A1‡ | 1/2016 | Liu | A24F 47/008 131/32 |
| 2016/0000149 A1‡ | 1/2016 | Scatterday | A24F 47/008 392/39 |
| 2016/0002649 A1‡ | 1/2016 | Kudithipudi | A24B 13/00 131/32 |
| 2016/0007650 A1‡ | 1/2016 | Duncan | A24F 47/004 131/32 |
| 2016/0007651 A1‡ | 1/2016 | Ampolini | A24F 47/008 131/32 |
| 2016/0007653 A1‡ | 1/2016 | Tu | A24F 47/008 392/40 |
| 2016/0007654 A1‡ | 1/2016 | Zhu | A24F 47/008 131/32 |
| 2016/0007655 A1‡ | 1/2016 | Li | A61M 15/06 392/39 |
| 2016/0010103 A1‡ | 1/2016 | Kudithipudi | A01H 1/04 800/26 |
| 2016/0013143 A1‡ | 1/2016 | Fujii | B65D 85/70 206/22 |
| 2016/0015082 A1‡ | 1/2016 | Liu | A24F 47/008 131/32 |
| 2016/0020048 A1‡ | 1/2016 | Ware | H01H 36/004 131/32 |
| 2016/0021771 A1‡ | 1/2016 | Zhang | G06F 1/163 361/75 |
| 2016/0021931 A1‡ | 1/2016 | Hawes | A24F 47/008 131/32 |
| 2016/0021932 A1‡ | 1/2016 | Silvestrini | A24F 47/004 131/32 |
| 2016/0021933 A1‡ | 1/2016 | Thorens | A24F 47/008 131/32 |
| 2016/0021934 A1‡ | 1/2016 | Cadieux | A24F 47/008 131/32 |
| 2016/0029225 A1‡ | 1/2016 | Hu | H04W 16/28 455/56 |
| 2016/0029694 A1‡ | 2/2016 | Clements | A24F 47/004 131/32 |
| 2016/0029697 A1‡ | 2/2016 | Shafer | A24F 47/008 131/32 |
| 2016/0029698 A1‡ | 2/2016 | Xiang | A24F 47/008 131/32 |
| 2016/0029699 A1‡ | 2/2016 | Li | A24F 47/008 131/32 |
| 2016/0029700 A1‡ | 2/2016 | Li | A24F 47/008 131/32 |
| 2016/0037826 A1‡ | 2/2016 | Hearn | A24F 47/002 141/3 |
| 2016/0044961 A1‡ | 2/2016 | Liu | A24F 47/008 131/32 |
| 2016/0044962 A1 | 2/2016 | Thorens et al. | |
| 2016/0044964 A1‡ | 2/2016 | Liu | A24F 47/008 392/39 |
| 2016/0044965 A1‡ | 2/2016 | Liu | A24F 47/008 131/32 |
| 2016/0044966 A1‡ | 2/2016 | Li | A24F 47/008 131/32 |
| 2016/0044967 A1‡ | 2/2016 | Bowen | A24B 15/16 131/32 |
| 2016/0044968 A1‡ | 2/2016 | Bowen | A24B 15/16 131/32 |
| 2016/0049682 A1‡ | 2/2016 | Won | H01M 2/021 429/18 |
| 2016/0051716 A1‡ | 2/2016 | Wheelock | F22B 1/28 392/38 |
| 2016/0053988 A1‡ | 2/2016 | Quintana | A24F 47/008 392/39 |
| 2016/0057811 A1‡ | 2/2016 | Alarcon | A24F 47/008 219/49 |
| 2016/0058066 A1‡ | 3/2016 | Banks | A24B 15/10 131/32 |
| 2016/0058071 A1‡ | 3/2016 | Hearn | A24F 47/002 131/32 |
| 2016/0058072 A1‡ | 3/2016 | Liu | A24F 47/008 131/32 |
| 2016/0058073 A1‡ | 3/2016 | Chen | A24F 47/008 131/32 |
| 2016/0058074 A1‡ | 3/2016 | Liu | A24F 47/008 131/32 |
| 2016/0073677 A1‡ | 3/2016 | Kappel | A24B 15/16 206/24 |
| 2016/0073678 A1‡ | 3/2016 | Fujisawa | A24B 15/24 131/29 |
| 2016/0073690 A1‡ | 3/2016 | Liu | A24F 47/008 131/32 |

(56) References Cited

U.S. PATENT DOCUMENTS

| | | | |
|---|---|---|---|
| 2016/0073691 A1‡ | 3/2016 | Liu | A24F 47/008 131/32 |
| 2016/0073692 A1‡ | 3/2016 | Alarcon | A24F 47/008 131/32 |
| 2016/0073693 A1‡ | 3/2016 | Reevell | H05B 1/0244 131/32 |
| 2016/0073694 A1‡ | 3/2016 | Liu | H05B 3/40 131/32 |
| 2016/0080469 A1‡ | 3/2016 | Liu | H04W 12/08 709/21 |
| 2016/0081393 A1‡ | 3/2016 | Black | A24F 47/008 392/38 |
| 2016/0081394 A1‡ | 3/2016 | Alarcon | A24D 3/04 131/32 |
| 2016/0081395 A1‡ | 3/2016 | Thorens | A24F 47/008 128/20 |
| 2016/0088874 A1‡ | 3/2016 | Lipowicz | A24F 47/008 131/32 |
| 2016/0089508 A1‡ | 3/2016 | Smith | A61M 15/06 128/20 |
| 2016/0091194 A1‡ | 3/2016 | Liu | A24F 15/18 206/23 |
| 2016/0095352 A1‡ | 4/2016 | Liu | H01M 2/34 131/32 |
| 2016/0095353 A1‡ | 4/2016 | Liu | A24F 15/10 206/86 |
| 2016/0095354 A1‡ | 4/2016 | Wu | A24F 47/008 131/32 |
| 2016/0095355 A1‡ | 4/2016 | Hearn | A24F 47/008 131/27 |
| 2016/0095356 A1‡ | 4/2016 | Chan | A24F 47/008 131/32 |
| 2016/0095357 A1‡ | 4/2016 | Burton | A24F 47/008 131/32 |
| 2016/0099592 A1‡ | 4/2016 | Gatta | H02J 7/0042 320/10 |
| 2016/0100456 A1‡ | 4/2016 | Tsai | H05B 3/06 219/53 |
| 2016/0100632 A1‡ | 4/2016 | Debono | A24F 47/008 219/49 |
| 2016/0101909 A1‡ | 4/2016 | Schennum | A45C 13/007 206/26 |
| 2016/0106144 A1‡ | 4/2016 | Muehlbauer | A24F 47/008 131/29 |
| 2016/0106151 A1‡ | 4/2016 | Swepston | A24F 47/002 |
| 2016/0106152 A1‡ | 4/2016 | Liu | G01F 1/661 392/40 |
| 2016/0106153 A1 | 4/2016 | Zhu | |
| 2016/0106154 A1‡ | 4/2016 | Lord | A24F 47/008 131/32 |
| 2016/0106155 A1‡ | 4/2016 | Reevell | A24F 47/008 131/32 |
| 2016/0106156 A1‡ | 4/2016 | Qiu | A24F 47/008 392/40 |
| 2016/0106936 A1‡ | 4/2016 | Kimmel | A24F 47/008 128/20 |
| 2016/0109115 A1‡ | 4/2016 | Lipowicz | F22B 1/282 392/39 |
| 2016/0113323 A1‡ | 4/2016 | Liu | A24F 15/12 206/26 |
| 2016/0113325 A1‡ | 4/2016 | Liu | A24F 47/008 131/32 |
| 2016/0113326 A1‡ | 4/2016 | Li | A24F 47/008 131/32 |
| 2016/0113327 A1‡ | 4/2016 | Wu | H05B 3/06 131/32 |
| 2016/0120218 A1‡ | 5/2016 | Schennum | A24F 15/12 206/26 |
| 2016/0120220 A1‡ | 5/2016 | Malgat | A24F 47/004 128/20 |
| 2016/0120222 A1‡ | 5/2016 | Bagai | H05B 3/00 131/32 |
| 2016/0120223 A1‡ | 5/2016 | Keen | A24F 47/00 |
| 2016/0120224 A1‡ | 5/2016 | Mishra | A24F 47/008 392/39 |
| 2016/0120225 A1‡ | 5/2016 | Mishra | A24F 47/008 392/38 |
| 2016/0120226 A1‡ | 5/2016 | Rado | A24F 47/008 131/32 |
| 2016/0120227 A1‡ | 5/2016 | Levitz | A24F 47/008 219/38 |
| 2016/0120228 A1‡ | 5/2016 | Rostami | A24F 47/008 131/32 |
| 2016/0121058 A1‡ | 5/2016 | Chen | A61M 11/04 |
| 2016/0128384 A1‡ | 5/2016 | Luciani | A24F 47/008 131/32 |
| 2016/0128385 A1‡ | 5/2016 | Lin | A24F 47/008 131/32 |
| 2016/0128387 A1‡ | 5/2016 | Chen | A24F 47/008 392/39 |
| 2016/0128388 A1‡ | 5/2016 | Liu | H05B 3/00 392/40 |
| 2016/0128389 A1‡ | 5/2016 | Lamb | G01L 9/0072 131/32 |
| 2016/0128390 A1‡ | 5/2016 | Liu | A24F 47/008 392/38 |
| 2016/0129205 A1‡ | 5/2016 | Shahaf | A61M 11/02 128/20 |
| 2016/0131629 A1‡ | 5/2016 | Cadieux, Jr. | G01N 21/94 436/60 |
| 2016/0132898 A1‡ | 5/2016 | Cadieux | G06Q 30/0185 705/31 |
| 2016/0135494 A1‡ | 5/2016 | Liu | A24B 15/284 131/32 |
| 2016/0135500 A1‡ | 5/2016 | Hearn | A24F 47/002 131/32 |
| 2016/0135501 A1‡ | 5/2016 | Liu | A24F 47/002 131/32 |
| 2016/0135503 A1‡ | 5/2016 | Liu | A24F 47/002 392/40 |
| 2016/0135504 A1‡ | 5/2016 | Li | A24F 47/008 392/39 |
| 2016/0135505 A1‡ | 5/2016 | Li | H05B 3/44 131/32 |
| 2016/0135506 A1‡ | 5/2016 | Sanchez | A24F 47/008 131/32 |
| 2016/0135507 A1‡ | 5/2016 | Thorens | A24F 47/008 131/32 |
| 2016/0136153 A1‡ | 5/2016 | Jenkins | A61K 31/485 |
| 2016/0136213 A1‡ | 5/2016 | Paul | A61K 36/185 131/35 |
| 2016/0138795 A1‡ | 5/2016 | Meinhart | A61L 9/037 392/39 |
| 2016/0143354 A1‡ | 5/2016 | Liu | A24F 47/008 131/32 |
| 2016/0143357 A1‡ | 5/2016 | Liu | H02J 7/0045 206/22 |
| 2016/0143358 A1‡ | 5/2016 | Zhu | A24F 47/008 131/32 |
| 2016/0143359 A1‡ | 5/2016 | Xiang | H05B 1/0227 392/38 |
| 2016/0143360 A1‡ | 5/2016 | Sanchez | A24F 47/008 239/30 |
| 2016/0143361 A1‡ | 5/2016 | Juster | A24F 47/008 392/40 |
| 2016/0143362 A1‡ | 5/2016 | Boldrini | A24F 47/008 29/611 |
| 2016/0143363 A1‡ | 5/2016 | Boldrini | A24F 47/008 29/874 |
| 2016/0143365 A1‡ | 5/2016 | Liu | A24F 47/008 131/32 |
| 2016/0144458 A1‡ | 5/2016 | Boldrini | B23K 31/02 228/17 |
| 2016/0150820 A1‡ | 6/2016 | Liu | A24F 47/002 137/23 |
| 2016/0150821 A1‡ | 6/2016 | Liu | A24F 47/002 131/32 |

(56) References Cited

U.S. PATENT DOCUMENTS

| | | | |
|---|---|---|---|
| 2016/0150823 A1‡ | 6/2016 | Liu | H05B 3/46 131/32 |
| 2016/0150824 A1‡ | 6/2016 | Memari | A24F 15/12 131/32 |
| 2016/0150826 A1‡ | 6/2016 | Liu | A24F 47/008 392/40 |
| 2016/0150827 A1‡ | 6/2016 | Liu | A24F 47/008 131/32 |
| 2016/0150828 A1‡ | 6/2016 | Goldstein | A24F 47/008 392/38 |
| 2016/0150872 A1‡ | 6/2016 | Zayat | A45F 5/02 248/69 |
| 2016/0157523 A1‡ | 6/2016 | Liu | A24F 47/008 392/39 |
| 2016/0157524 A1‡ | 6/2016 | Bowen | A24F 47/008 128/20 |
| 2016/0157525 A1‡ | 6/2016 | Tucker | A24F 47/008 392/39 |
| 2016/0158782 A1‡ | 6/2016 | Henry, Jr. | B05B 12/08 700/27 |
| 2016/0165952 A1‡ | 6/2016 | Liu | A24F 15/12 206/25 |
| 2016/0165955 A1‡ | 6/2016 | Horne | A45F 5/02 131/32 |
| 2016/0166564 A1‡ | 6/2016 | Myers | A61K 9/004 514/34 |
| 2016/0167846 A1‡ | 6/2016 | Zahr | B65D 50/046 222/15 |
| 2016/0174076 A1‡ | 6/2016 | Wu | H04W 12/12 455/41 |
| 2016/0174609 A1‡ | 6/2016 | Mironov | A24F 47/006 131/32 |
| 2016/0174611 A1‡ | 6/2016 | Monsees | H05B 3/04 392/38 |
| 2016/0174613 A1‡ | 6/2016 | Zuber | A24F 47/008 392/39 |
| 2016/0176564 A1‡ | 6/2016 | Garthaffner | A24F 47/002 156/21 |
| 2016/0177285 A1‡ | 6/2016 | Voerman | A61K 38/1767 131/32 |
| 2016/0183592 A1‡ | 6/2016 | Liu | H05B 1/0244 131/32 |
| 2016/0183593 A1‡ | 6/2016 | Liu | A24F 47/008 392/38 |
| 2016/0183594 A1‡ | 6/2016 | Liu | A24F 47/008 392/38 |
| 2016/0183595 A1‡ | 6/2016 | Grimandi | A24F 47/008 29/428 |
| 2016/0183597 A1‡ | 6/2016 | Li | H05B 1/0244 392/40 |
| 2016/0189216 A1‡ | 6/2016 | Liu | A24F 47/008 705/14 |
| 2016/0192705 A1‡ | 7/2016 | Borkovec | A24F 47/008 131/32 |
| 2016/0192706 A1‡ | 7/2016 | Kananen | H05B 1/0244 128/20 |
| 2016/0192707 A1‡ | 7/2016 | Li | H05B 3/00 131/32 |
| 2016/0192708 A1‡ | 7/2016 | DeMeritt | H05B 3/40 131/32 |
| 2016/0192709 A1‡ | 7/2016 | Liu | H05B 3/40 131/32 |
| 2016/0192710 A1‡ | 7/2016 | Liu | H05B 3/40 131/32 |
| 2016/0198759 A1‡ | 7/2016 | Kuntawala | A24B 15/284 131/35 |
| 2016/0198763 A1‡ | 7/2016 | Adkins | A24F 15/12 224/18 |
| 2016/0198765 A1‡ | 7/2016 | Liu | H05B 1/0244 392/38 |
| 2016/0198766 A1‡ | 7/2016 | Liu | H02J 7/0042 392/38 |
| 2016/0198767 A1‡ | 7/2016 | Verleur | H05B 1/0202 392/38 |
| 2016/0198768 A1‡ | 7/2016 | Liu | H05B 1/0244 392/40 |
| 2016/0198769 A1‡ | 7/2016 | Liu | F22B 1/284 131/32 |
| 2016/0198770 A1‡ | 7/2016 | Alarcon | A24F 47/008 392/4 |
| 2016/0200463 A1‡ | 7/2016 | Hodges | G07F 13/02 53/415 |
| 2016/0201224 A1‡ | 7/2016 | Xiang | D01D 5/08 425/7 |
| 2016/0204637 A1‡ | 7/2016 | Alarcon | A24F 47/008 320/11 |
| 2016/0205998 A1‡ | 7/2016 | Matsumoto | A61M 15/06 |
| 2016/0205999 A1‡ | 7/2016 | Liu | A24F 47/008 |
| 2016/0206000 A1‡ | 7/2016 | Lord | A24F 47/008 |
| 2016/0206002 A1‡ | 7/2016 | Borkovec | A24F 47/008 |
| 2016/0206005 A1‡ | 7/2016 | Yamada | A24F 47/008 |
| 2016/0206006 A1‡ | 7/2016 | Li | H05B 1/0202 |
| 2016/0211693 A1‡ | 7/2016 | Stevens | A24F 47/008 |
| 2016/0212520 A1‡ | 7/2016 | Merenda | B65H 75/48 |
| 2016/0213060 A1‡ | 7/2016 | Thaler | A24F 47/00 |
| 2016/0213061 A1‡ | 7/2016 | Liu | A24F 47/008 |
| 2016/0213062 A1‡ | 7/2016 | Doyle | A24F 47/002 |
| 2016/0213065 A1‡ | 7/2016 | Wensley | A24F 47/008 |
| 2016/0213066 A1‡ | 7/2016 | Zitzke | A24F 47/008 |
| 2016/0213067 A1‡ | 7/2016 | Hon | A24F 47/008 |
| 2016/0213866 A1‡ | 7/2016 | Tan | A61M 11/005 |
| 2016/0219932 A1‡ | 8/2016 | Glaser | A24F 47/008 |
| 2016/0219933 A1‡ | 8/2016 | Henry, Jr. | A24F 47/008 |
| 2016/0219934 A1‡ | 8/2016 | Li | A24F 47/008 |
| 2016/0219936 A1‡ | 8/2016 | Alarcon | A24F 47/008 |
| 2016/0219937 A1‡ | 8/2016 | Rado | A24F 47/008 |
| 2016/0219938 A1‡ | 8/2016 | Mamoun | G05B 15/02 |
| 2016/0221707 A1‡ | 8/2016 | Xu | B65D 1/09 |
| 2016/0226286 A1‡ | 8/2016 | Xiang | A24F 47/002 |
| 2016/0227837 A1‡ | 8/2016 | Hammel | A24F 47/008 |
| 2016/0227838 A1‡ | 8/2016 | Johnson | H04R 1/028 |
| 2016/0227839 A1‡ | 8/2016 | Zuber | A24F 47/004 |
| 2016/0227840 A1‡ | 8/2016 | Xiang | A24F 47/008 |
| 2016/0227841 A1‡ | 8/2016 | Li | A61M 15/06 |
| 2016/0227842 A1‡ | 8/2016 | Xiang | A24F 47/008 |
| 2016/0233705 A1‡ | 8/2016 | Liu | H02J 7/0044 |
| 2016/0233708 A1‡ | 8/2016 | Liu | H02J 17/0042 |
| 2016/0235119 A1‡ | 8/2016 | Liu | H02J 7/0042 |
| 2016/0235120 A1‡ | 8/2016 | Liu | A24F 47/008 |
| 2016/0235121 A1‡ | 8/2016 | Rogan | A24D 3/041 |
| 2016/0235124 A1‡ | 8/2016 | Krietzman | A24F 47/008 |
| 2016/0235125 A1‡ | 8/2016 | Safari | A24F 47/008 |
| 2016/0242463 A1‡ | 8/2016 | Liu | A24F 47/008 |
| 2016/0242464 A1‡ | 8/2016 | Liu | A24F 47/008 |
| 2016/0242465 A1‡ | 8/2016 | Zheng | A24F 47/008 |
| 2016/0242466 A1‡ | 8/2016 | Lord | G06F 1/3296 |
| 2016/0242467 A1‡ | 8/2016 | Vaughn | A24F 47/008 |
| 2016/0242468 A1‡ | 8/2016 | Liu | H01M 2/20 |
| 2016/0249680 A1‡ | 9/2016 | Liu | A24F 47/008 131/32 |
| 2016/0249682 A1‡ | 9/2016 | Leadley | A24F 47/008 131/32 |
| 2016/0249683 A1‡ | 9/2016 | Li | A24F 47/008 131/32 |
| 2016/0249684 A1‡ | 9/2016 | Liu | A24F 47/008 131/32 |
| 2016/0255876 A1‡ | 9/2016 | Rostami | A24F 47/008 |
| 2016/0255878 A1‡ | 9/2016 | Huang | A24F 47/008 |
| 2016/0260156 A1‡ | 9/2016 | Liu | G07F 17/3239 |
| 2016/0261021 A1‡ | 9/2016 | Marion | A24F 47/008 |
| 2016/0262443 A1‡ | 9/2016 | Piccirilli | A24B 15/16 |
| 2016/0262445 A1‡ | 9/2016 | Benjak | A24B 3/04 |
| 2016/0262449 A1‡ | 9/2016 | Liu | A24D 1/02 |
| 2016/0262450 A1‡ | 9/2016 | Liu | H01M 2/1055 |
| 2016/0262451 A1‡ | 9/2016 | Liu | A24F 47/008 |
| 2016/0262452 A1‡ | 9/2016 | Zhu | A24F 47/008 |
| 2016/0262453 A1‡ | 9/2016 | Ampolini | A24F 47/008 |
| 2016/0262454 A1‡ | 9/2016 | Sears | A24F 47/008 |
| 2016/0262455 A1‡ | 9/2016 | Chen | A24F 47/008 |
| 2016/0262456 A1‡ | 9/2016 | Borkovec | A24F 47/008 |

(56) References Cited

U.S. PATENT DOCUMENTS

| | | | |
|---|---|---|---|
| 2016/0262457 A1‡ | 9/2016 | Borkovec | A24F 47/008 |
| 2016/0262459 A1‡ | 9/2016 | Monsees | A61M 11/042 |
| 2016/0262526 A1‡ | 9/2016 | Gonzalez | A45F 5/00 |
| 2016/0268824 A1‡ | 9/2016 | Liu | H02J 7/0045 |
| 2016/0270441 A1‡ | 9/2016 | Lewis | A24F 47/002 |
| 2016/0270442 A1‡ | 9/2016 | Liu | A24F 47/008 |
| 2016/0270443 A1‡ | 9/2016 | Liu | G05B 15/02 |
| 2016/0270444 A1‡ | 9/2016 | Lin | A24F 47/008 |
| 2016/0270445 A1‡ | 9/2016 | Liu | H01M 2/105 |
| 2016/0270446 A1‡ | 9/2016 | Shenkal | A24F 47/008 |
| 2016/0270447 A1‡ | 9/2016 | Borkovec | A24F 47/008 |
| 2016/0271347 A1‡ | 9/2016 | Raichman | A61M 15/06 |
| 2016/0278163 A1‡ | 9/2016 | Chen | A61M 11/042 |
| 2016/0278431 A1‡ | 9/2016 | Liu | G06K 9/325 |
| 2016/0278432 A1‡ | 9/2016 | Liu | H02J 7/0042 |
| 2016/0278433 A1‡ | 9/2016 | Xiang | H02J 7/0042 |
| 2016/0278434 A1‡ | 9/2016 | Liu | A24F 47/008 |
| 2016/0278435 A1‡ | 9/2016 | Choukroun | A24F 47/008 |
| 2016/0278436 A1‡ | 9/2016 | Verleur | A24F 47/008 |
| 2016/0280450 A1‡ | 9/2016 | Hearn | A61M 15/0091 |
| 2016/0284197 A1‡ | 9/2016 | Liu | G08B 21/182 |
| 2016/0285983 A1‡ | 9/2016 | Liu | A24F 47/002 |
| 2016/0286856 A1‡ | 10/2016 | Liu | A24F 47/008 |
| 2016/0286858 A1‡ | 10/2016 | Liu | A24F 47/008 |
| 2016/0286859 A1‡ | 10/2016 | Liu | A24F 47/008 |
| 2016/0286860 A1‡ | 10/2016 | Flayler | A24F 47/008 |
| 2016/0286862 A1‡ | 10/2016 | Silvetrini | A24B 15/16 |
| 2016/0286863 A1‡ | 10/2016 | Lin | A24F 47/008 |
| 2016/0286864 A1‡ | 10/2016 | Lin | A24F 47/008 |
| 2016/0286865 A1‡ | 10/2016 | King | A24F 47/008 |
| 2016/0295913 A1‡ | 10/2016 | Guo | B05B 17/0615 |
| 2016/0295915 A1‡ | 10/2016 | Jochnowitz | A24F 47/004 |
| 2016/0295916 A1‡ | 10/2016 | Malgat | A24B 3/14 |
| 2016/0295917 A1‡ | 10/2016 | Malgat | A24F 47/004 |
| 2016/0295918 A1‡ | 10/2016 | Liu | A24F 47/008 |
| 2016/0295920 A1‡ | 10/2016 | Liu | H05B 3/0014 |
| 2016/0295922 A1‡ | 10/2016 | John | A24F 47/008 |
| 2016/0295923 A1‡ | 10/2016 | Lin | A24F 47/008 |
| 2016/0295924 A1‡ | 10/2016 | Liu | A24F 47/008 |
| 2016/0295925 A1‡ | 10/2016 | Chen | A24F 47/008 |
| 2016/0295926 A1‡ | 10/2016 | Zuber | A24B 15/165 |
| 2016/0297341 A1‡ | 10/2016 | Wallace | B60N 3/12 |
| 2016/0302471 A1‡ | 10/2016 | Bowen | A24B 15/16 |
| 2016/0302483 A1‡ | 10/2016 | Liu | A24F 47/008 |
| 2016/0302484 A1‡ | 10/2016 | Gupta | A24F 47/002 |
| 2016/0302485 A1‡ | 10/2016 | Alima | A24F 47/008 |
| 2016/0302486 A1‡ | 10/2016 | Eroch | A24F 47/008 |
| 2016/0302487 A1‡ | 10/2016 | Chen | A24F 47/00 |
| 2016/0302488 A1‡ | 10/2016 | Fernando | A24F 47/008 |
| 2016/0309775 A1‡ | 10/2016 | Parker | A24B 15/26 |
| 2016/0309779 A1‡ | 10/2016 | Liu | A24F 47/008 |
| 2016/0309780 A1‡ | 10/2016 | Chen | H02J 7/025 |
| 2016/0309781 A1‡ | 10/2016 | Malgat | A24F 47/008 |
| 2016/0309783 A1‡ | 10/2016 | Hopps | A24F 47/008 |
| 2016/0309784 A1‡ | 10/2016 | Silvestrini | A61M 15/0066 |
| 2016/0309785 A1‡ | 10/2016 | Holtz | A24F 47/008 |
| 2016/0309786 A1‡ | 10/2016 | Holtz | F22B 1/284 |
| 2016/0309789 A1‡ | 10/2016 | Thomas, Jr. | A24F 47/008 |
| 2016/0315488 A1‡ | 10/2016 | Moon | H02J 7/0042 |
| 2016/0316818 A1‡ | 11/2016 | Liu | A24F 47/008 |
| 2016/0316820 A1‡ | 11/2016 | Liu | A24F 47/008 |
| 2016/0316821 A1‡ | 11/2016 | Liu | A24F 47/008 |
| 2016/0316822 A1‡ | 11/2016 | Liu | A24F 47/008 |
| 2016/0321879 A1‡ | 11/2016 | Oh | A24F 47/008 |
| 2016/0323404 A1‡ | 11/2016 | Liu | A24F 47/008 |
| 2016/0324211 A1‡ | 11/2016 | Yankelevich | A24F 1/00 |
| 2016/0324213 A1‡ | 11/2016 | Liu | A24F 47/008 |
| 2016/0324215 A1‡ | 11/2016 | Mironov | H05B 3/06 |
| 2016/0324217 A1‡ | 11/2016 | Cameron | A24F 47/008 |
| 2016/0324218 A1‡ | 11/2016 | Wang | A24F 47/00 |
| 2016/0324219 A1‡ | 11/2016 | Li | F16J 15/021 |
| 2016/0325055 A1‡ | 11/2016 | Cameron | A61M 11/005 |
| 2016/0325858 A1‡ | 11/2016 | Ampolini | A24F 47/008 |
| 2016/0331022 A1‡ | 11/2016 | Cameron | A24F 47/002 |
| 2016/0331023 A1‡ | 11/2016 | Cameron | A24F 47/002 |
| 2016/0331024 A1‡ | 11/2016 | Cameron | A24F 47/002 |
| 2016/0331025 A1‡ | 11/2016 | Cameron | A24F 47/002 |
| 2016/0331026 A1‡ | 11/2016 | Cameron | A24F 47/002 |
| 2016/0331027 A1‡ | 11/2016 | Cameron | A24F 47/002 |
| 2016/0331028 A1‡ | 11/2016 | Xu | A24F 47/006 |
| 2016/0331029 A1‡ | 11/2016 | Contreras | A24F 47/008 |
| 2016/0331030 A1‡ | 11/2016 | Ampolini | A24F 47/008 |
| 2016/0331032 A1‡ | 11/2016 | Malgat | A24F 47/004 |
| 2016/0331033 A1‡ | 11/2016 | Hopps | A24F 47/008 |
| 2016/0331034 A1‡ | 11/2016 | Cameron | A24F 47/008 |
| 2016/0331035 A1‡ | 11/2016 | Cameron | F01K 5/00 |
| 2016/0331037 A1‡ | 11/2016 | Cameron | H04L 67/12 |
| 2016/0331038 A1‡ | 11/2016 | Farine | A24F 47/008 |
| 2016/0331039 A1‡ | 11/2016 | Thorens | A24F 47/008 |
| 2016/0331040 A1‡ | 11/2016 | Nakano | A61M 15/06 |
| 2016/0332754 A1‡ | 11/2016 | Brown | B65B 3/10 |
| 2016/0334847 A1‡ | 11/2016 | Cameron | G06F 1/266 |
| 2016/0337141 A1‡ | 11/2016 | Cameron | H01L 12/185 |
| 2016/0337362 A1‡ | 11/2016 | Cameron | H04L 63/10 |
| 2016/0337444 A1‡ | 11/2016 | Cameron | H04L 67/10 |
| 2016/0338402 A1‡ | 11/2016 | Buehler | A24F 47/004 |
| 2016/0338405 A1‡ | 11/2016 | Liu | A24F 47/008 |
| 2016/0338406 A1‡ | 11/2016 | Liu | A24F 47/008 |
| 2016/0338407 A1‡ | 11/2016 | Kerdemelidis | A24F 47/008 |
| 2016/0338408 A1‡ | 11/2016 | Guenther, Jr. | B23P 19/002 |
| 2016/0338409 A1‡ | 11/2016 | Varone | A24F 47/008 |
| 2016/0338410 A1‡ | 11/2016 | Batista | A24F 47/008 |
| 2016/0338411 A1‡ | 11/2016 | Liu | A24F 47/008 |
| 2016/0338412 A1‡ | 11/2016 | Monsees | A24F 47/008 |
| 2016/0338413 A1‡ | 11/2016 | Li | A24F 47/008 |
| 2016/0338945 A1‡ | 11/2016 | Knight | A61K 9/007 |
| 2016/0345621 A1‡ | 12/2016 | Li | H05B 3/141 |
| 2016/0345625 A1‡ | 12/2016 | Liu | A24F 47/008 |
| 2016/0345626 A1‡ | 12/2016 | Wong | A24F 47/008 |
| 2016/0345627 A1‡ | 12/2016 | Liu | A24F 47/008 |
| 2016/0345628 A1‡ | 12/2016 | Sabet | A24B 15/18 |
| 2016/0345630 A1‡ | 12/2016 | Mironov | A24F 47/008 |
| 2016/0345631 A1‡ | 12/2016 | Monsees | A24F 47/008 |
| 2016/0345632 A1‡ | 12/2016 | Lipowicz | A24F 47/008 |
| 2016/0345633 A1‡ | 12/2016 | DePiano | A24F 47/008 |
| 2016/0345634 A1‡ | 12/2016 | Fernando | A24F 47/008 |
| 2016/0345636 A1‡ | 12/2016 | Liu | A24F 47/008 |
| 2016/0351044 A1‡ | 12/2016 | Liu | G08B 21/24 |
| 2016/0353798 A1‡ | 12/2016 | Liu | A24F 47/008 |
| 2016/0353800 A1‡ | 12/2016 | Di Carlo | A24F 47/008 |
| 2016/0353805 A1‡ | 12/2016 | Hawes | A24F 47/008 |
| 2016/0356751 A1‡ | 12/2016 | Blackley | G01N 33/0036 |
| 2016/0360784 A1‡ | 12/2016 | Liu | A24F 47/008 |
| 2016/0360785 A1‡ | 12/2016 | Bless | H05B 1/0244 |
| 2016/0360786 A1‡ | 12/2016 | Bellinger | A24F 47/008 |
| 2016/0360787 A1‡ | 12/2016 | Bailey | A24F 47/008 |
| 2016/0360788 A1‡ | 12/2016 | Wang | A24F 47/008 |
| 2016/0360789 A1‡ | 12/2016 | Hawes | H05B 3/12 |
| 2016/0360792 A1‡ | 12/2016 | Liu | A24F 47/008 |
| 2016/0360793 A1‡ | 12/2016 | Liu | H01M 2/1055 |
| 2016/0363570 A1‡ | 12/2016 | Blackley | G01N 33/0006 |
| 2016/0363917 A1‡ | 12/2016 | Blackley | G05B 19/042 |
| 2016/0366725 A1‡ | 12/2016 | Tucker | H05B 3/06 |
| 2016/0366927 A1‡ | 12/2016 | Liu | A24B 15/16 |
| 2016/0366928 A1‡ | 12/2016 | Liu | A24B 15/16 |
| 2016/0366933 A1‡ | 12/2016 | Liu | A24F 15/18 |
| 2016/0366935 A1‡ | 12/2016 | Liu | A24F 47/008 |
| 2016/0366936 A1‡ | 12/2016 | Liu | A24F 47/008 |
| 2016/0366937 A1‡ | 12/2016 | Liu | A24F 47/008 |
| 2016/0366938 A1‡ | 12/2016 | Wu | A24F 47/008 |
| 2016/0366939 A1‡ | 12/2016 | Alarcon | G01F 1/6888 |
| 2016/0366940 A1‡ | 12/2016 | Liu | A24F 47/008 |
| 2016/0366941 A1‡ | 12/2016 | Lin | A24F 47/008 |
| 2016/0366942 A1‡ | 12/2016 | Liu | H01M 2/1055 |
| 2016/0366943 A1‡ | 12/2016 | Li | A24F 47/008 |
| 2016/0366945 A1‡ | 12/2016 | Rado | A24F 47/008 |
| 2016/0366947 A1‡ | 12/2016 | Monsees | H05B 3/04 |
| 2016/0367925 A1‡ | 12/2016 | Blackley | A24F 47/008 |
| 2016/0368670 A1‡ | 12/2016 | Beardsall | B65D 43/0212 |
| 2016/0368677 A1‡ | 12/2016 | Parsons | A24F 23/02 |
| 2016/0370335 A1‡ | 12/2016 | Blackley | G01N 33/0013 |
| 2016/0371437 A1‡ | 12/2016 | Alarcon | G06Q 50/24 |
| 2016/0371464 A1‡ | 12/2016 | Bricker | A24F 47/00 |

(56) References Cited

U.S. PATENT DOCUMENTS

| | | | |
|---|---|---|---|
| 2016/0374390 A1‡ | 12/2016 | Liu | A24F 15/18 340/87 |
| 2016/0374391 A1‡ | 12/2016 | Liu | A24F 47/008 392/38 |
| 2016/0374392 A1‡ | 12/2016 | Liu | A61M 15/06 392/40 |
| 2016/0374393 A1‡ | 12/2016 | Chen | A24F 47/008 131/32 |
| 2016/0374394 A1‡ | 12/2016 | Hawes | A24F 47/008 131/32 |
| 2016/0374395 A1‡ | 12/2016 | Jordan | A24F 47/008 131/32 |
| 2016/0374396 A1‡ | 12/2016 | Jordan | A24F 47/008 392/38 |
| 2016/0374397 A1‡ | 12/2016 | Jordan | A24F 47/008 131/32 |
| 2016/0374398 A1‡ | 12/2016 | Amir | A24F 47/008 392/38 |
| 2016/0374399 A1‡ | 12/2016 | Monsees | A24F 47/008 131/32 |
| 2016/0374400 A1‡ | 12/2016 | Monsees | A61M 15/06 131/32 |
| 2016/0374401 A1‡ | 12/2016 | Liu | A24F 47/008 131/32 |
| 2017/0000190 A1‡ | 1/2017 | Wu | H05B 3/44 |
| 2017/0000192 A1‡ | 1/2017 | Li | A24F 47/008 |
| 2017/0006915 A1‡ | 1/2017 | Li | B67D 3/0025 |
| 2017/0006916 A1‡ | 1/2017 | Liu | A24F 47/008 |
| 2017/0006917 A1‡ | 1/2017 | Alvarez | A24F 47/008 |
| 2017/0006918 A1‡ | 1/2017 | Chen | A24F 47/008 |
| 2017/0006919 A1‡ | 1/2017 | Liu | A24F 47/008 |
| 2017/0006920 A1‡ | 1/2017 | Liu | A24F 47/008 |
| 2017/0006921 A1‡ | 1/2017 | Lemay | A24F 47/008 |
| 2017/0006922 A1‡ | 1/2017 | Wang | H05B 3/04 |
| 2017/0013875 A1‡ | 1/2017 | Schennum | A24F 15/18 |
| 2017/0013876 A1‡ | 1/2017 | Schennum | H02J 7/0044 |
| 2017/0013878 A1‡ | 1/2017 | Schuler | H05B 1/0244 |
| 2017/0013880 A1‡ | 1/2017 | O'Brien | A24F 47/008 |
| 2017/0013881 A1‡ | 1/2017 | Liu | A24F 47/008 |
| 2017/0013882 A1‡ | 1/2017 | Liu | A24F 47/008 |
| 2017/0013883 A1‡ | 1/2017 | Han | A24F 47/008 |
| 2017/0013885 A1‡ | 1/2017 | Qiu | A24F 47/008 |
| 2017/0014582 A1‡ | 1/2017 | Skoda | A61M 11/042 |
| 2017/0018000 A1‡ | 1/2017 | Cameron | G06Q 30/0255 |
| 2017/0019951 A1‡ | 1/2017 | Louveau | A24F 47/008 |
| 2017/0020188 A1‡ | 1/2017 | Cameron | H04L 67/025 |
| 2017/0020191 A1‡ | 1/2017 | Lamb | A24F 47/008 |
| 2017/0020193 A1‡ | 1/2017 | Davis | A24F 47/008 |
| 2017/0020194 A1‡ | 1/2017 | Rehders | A24F 47/008 |
| 2017/0020195 A1‡ | 1/2017 | Cameron | A24F 47/008 |
| 2017/0020196 A1‡ | 1/2017 | Cameron | A24F 47/008 |
| 2017/0020197 A1‡ | 1/2017 | Cameron | A24F 47/008 |
| 2017/0020198 A1‡ | 1/2017 | Naqwi | G01M 99/008 |
| 2017/0020201 A1‡ | 1/2017 | Xiang | A24F 47/008 |
| 2017/0020791 A1‡ | 1/2017 | Moszner | A61K 6/0017 |
| 2017/0021969 A1‡ | 1/2017 | Smith | B65D 25/108 |
| 2017/0023952 A1‡ | 1/2017 | Henry, Jr. | G05D 7/0676 |
| 2017/0027221 A1‡ | 2/2017 | Liu | H02J 7/0044 |
| 2017/0027223 A1‡ | 2/2017 | Eksouzian | A24F 47/008 |
| 2017/0027224 A1‡ | 2/2017 | Volodarsky | H05B 1/0227 |
| 2017/0027227 A1‡ | 2/2017 | Lipowicz | A24F 47/008 |
| 2017/0027228 A1‡ | 2/2017 | Rastogi | A24F 47/008 |
| 2017/0027229 A1‡ | 2/2017 | Cameron | H04L 67/04 |
| 2017/0027230 A1‡ | 2/2017 | Fornarelli | A24F 47/008 |
| 2017/0027231 A1‡ | 2/2017 | Xiang | A24F 47/008 |
| 2017/0027232 A1‡ | 2/2017 | Scheck | A24F 47/008 |
| 2017/0027233 A1‡ | 2/2017 | Mironov | A24F 47/008 |
| 2017/0027234 A1‡ | 2/2017 | Farine | A24F 47/008 |
| 2017/0033568 A1‡ | 2/2017 | Holzherr | H02J 7/0088 |
| 2017/0033836 A1‡ | 2/2017 | Bernauer | A24F 47/008 |
| 2017/0035101 A1‡ | 2/2017 | Balder | A24F 47/008 |
| 2017/0035109 A1‡ | 2/2017 | Liu | H05B 3/24 |
| 2017/0035110 A1‡ | 2/2017 | Keen | F22B 1/28 |
| 2017/0035111 A1‡ | 2/2017 | Slurink | A24F 47/008 |
| 2017/0035112 A1‡ | 2/2017 | Thorens | A24F 47/008 |
| 2017/0035113 A1‡ | 2/2017 | Thorens | A24F 47/008 |
| 2017/0035114 A1‡ | 2/2017 | Lord | A24F 47/008 |
| 2017/0035115 A1‡ | 2/2017 | Monsees | H05B 1/0244 |
| 2017/0035117 A1‡ | 2/2017 | Lin | A24F 47/00 |
| 2017/0035118 A1‡ | 2/2017 | Liu | A24F 47/008 |
| 2017/0035119 A1‡ | 2/2017 | Otto | A24F 47/008 |
| 2017/0041646 A1‡ | 2/2017 | Pizzurro | H04N 21/64322 |
| 2017/0042225 A1‡ | 2/2017 | Liu | A24F 47/008 |
| 2017/0042227 A1‡ | 2/2017 | Gavrielov | A24F 47/008 |
| 2017/0042228 A1‡ | 2/2017 | Liu | A24F 47/008 |
| 2017/0042229 A1‡ | 2/2017 | Liu | B65D 25/26 |
| 2017/0042230 A1‡ | 2/2017 | Cameron | A24F 47/008 |
| 2017/0042231 A1‡ | 2/2017 | Cameron | A24F 47/008 |
| 2017/0042242 A1‡ | 2/2017 | Hon | A24F 47/008 |
| 2017/0042243 A1‡ | 2/2017 | Plojoux | H05B 3/42 |
| 2017/0042245 A1‡ | 2/2017 | Buchberger | A61M 15/0021 |
| 2017/0042246 A1‡ | 2/2017 | Lau | B65D 25/04 |
| 2017/0042247 A1‡ | 2/2017 | Xiang | A24F 47/00 |
| 2017/0042248 A1‡ | 2/2017 | Xiang | A24F 47/00 |
| 2017/0042250 A1‡ | 2/2017 | Takeuchi | A24F 47/00 |
| 2017/0046357 A1‡ | 2/2017 | Cameron | A24F 47/008 |
| 2017/0046722 A1‡ | 2/2017 | Ertugrul | H04B 5/0056 |
| 2017/0046738 A1‡ | 2/2017 | Cameron | G06Q 30/0255 |
| 2017/0047756 A1‡ | 2/2017 | Xiang | A24F 47/008 |
| 2017/0048691 A1‡ | 2/2017 | Liu | A24F 47/00 |
| 2017/0049149 A1‡ | 2/2017 | Carty | A24F 47/008 |
| 2017/0049150 A1‡ | 2/2017 | Xue | A24F 47/008 |
| 2017/0049151 A1‡ | 2/2017 | Xue | H05B 1/0244 |
| 2017/0049152 A1‡ | 2/2017 | Liu | A24F 47/008 |
| 2017/0049153 A1‡ | 2/2017 | Guo | A24F 47/008 |
| 2017/0049154 A1‡ | 2/2017 | Batista | A24F 47/008 |
| 2017/0049155 A1‡ | 2/2017 | Liu | A24F 47/008 |
| 2017/0049156 A1‡ | 2/2017 | Wang | A24F 47/008 |
| 2017/0050798 A1‡ | 2/2017 | Ludewig | B65D 85/54 |
| 2017/0055577 A1‡ | 3/2017 | Batista | A24B 15/165 |
| 2017/0055579 A1‡ | 3/2017 | Kuna | A24F 47/008 |
| 2017/0055586 A1‡ | 3/2017 | Liu | A24F 47/008 |
| 2017/0055588 A1‡ | 3/2017 | Cameron | H05B 3/44 |
| 2017/0055589 A1‡ | 3/2017 | Fernando | A24F 47/008 |
| 2017/0064994 A1‡ | 3/2017 | Xu | A24F 47/002 |
| 2017/0064999 A1‡ | 3/2017 | Perez | A24F 47/008 |
| 2017/0065000 A1‡ | 3/2017 | Sears | H05B 1/0288 |
| 2017/0065001 A1‡ | 3/2017 | Li | F16K 15/14 |
| 2017/0066556 A1‡ | 3/2017 | Liu | A24F 15/12 |
| 2017/0071249 A1‡ | 3/2017 | Ampolini | A24F 47/008 |
| 2017/0071251 A1‡ | 3/2017 | Goch | A24F 47/008 |
| 2017/0071252 A1‡ | 3/2017 | Liu | A24F 47/008 |
| 2017/0071256 A1‡ | 3/2017 | Verleur | A24F 47/008 |
| 2017/0071257 A1‡ | 3/2017 | Lin | A24F 47/00 |
| 2017/0071258 A1‡ | 3/2017 | Li | A24F 47/008 |
| 2017/0071260 A1‡ | 3/2017 | Li | A24F 47/008 |
| 2017/0071262 A1‡ | 3/2017 | Liu | A24F 47/00 |
| 2017/0079110 A1‡ | 3/2017 | Plattner | A61M 15/06 |
| 2017/0079319 A1‡ | 3/2017 | Muhammed | A24B 15/16 |
| 2017/0079321 A1‡ | 3/2017 | Golz | A24F 47/008 |
| 2017/0079322 A1‡ | 3/2017 | Li | A24B 15/16 |
| 2017/0079323 A1‡ | 3/2017 | Wang | A24F 47/008 |
| 2017/0079324 A1‡ | 3/2017 | Eksouzian | A24F 47/008 |
| 2017/0079327 A1‡ | 3/2017 | Wu | A24F 47/008 |
| 2017/0079328 A1‡ | 3/2017 | Wu | A24F 47/008 |
| 2017/0079329 A1‡ | 3/2017 | Zitzke | A24F 47/008 |
| 2017/0079330 A1‡ | 3/2017 | Mironov | A24F 47/008 |
| 2017/0079331 A1‡ | 3/2017 | Monsees | A61M 15/06 |
| 2017/0079332 A1‡ | 3/2017 | Li | A24F 47/008 |
| 2017/0086496 A1‡ | 3/2017 | Cameron | B25F 1/04 |
| 2017/0086497 A1‡ | 3/2017 | Cameron | A24F 3/00 |
| 2017/0086498 A1‡ | 3/2017 | Daryani | A24F 7/02 |
| 2017/0086499 A1‡ | 3/2017 | Mize | A24F 47/002 |
| 2017/0086500 A1‡ | 3/2017 | Li | A24B 15/16 |
| 2017/0086501 A1‡ | 3/2017 | Buehler | A24F 47/008 |
| 2017/0086502 A1‡ | 3/2017 | Hearn | A61M 15/0065 |
| 2017/0086503 A1‡ | 3/2017 | Cameron | A24F 47/008 |
| 2017/0086504 A1‡ | 3/2017 | Cameron | A24F 47/008 |
| 2017/0086505 A1‡ | 3/2017 | Cameron | A24F 47/008 |
| 2017/0086506 A1‡ | 3/2017 | Rado | A24F 47/008 |
| 2017/0086507 A1‡ | 3/2017 | Rado | A24F 47/008 |
| 2017/0086508 A1‡ | 3/2017 | Mironov | H05B 6/108 |
| 2017/0091490 A1‡ | 3/2017 | Cameron | G06F 21/84 |

(56) References Cited

U.S. PATENT DOCUMENTS

| | | | |
|---|---|---|---|
| 2017/0091853 A1‡ | 3/2017 | Cameron | G06Q 30/0631 |
| 2017/0092106 A1‡ | 3/2017 | Cameron | G08B 21/24 |
| 2017/0092900 A1‡ | 3/2017 | Yang | H01M 2/022 |
| 2017/0093960 A1‡ | 3/2017 | Cameron | H04L 67/10 |
| 2017/0093981 A1‡ | 3/2017 | Cameron | H04L 67/12 |
| 2017/0094998 A1‡ | 4/2017 | Bernauer | B23P 19/00 |
| 2017/0094999 A1‡ | 4/2017 | Hearn | A24F 47/008 |
| 2017/0095000 A1‡ | 4/2017 | Spirito | A24F 47/008 |
| 2017/0095001 A1‡ | 4/2017 | Liu | A24F 47/00 |
| 2017/0095002 A1‡ | 4/2017 | Silvestrini | A24F 47/008 |
| 2017/0095003 A1‡ | 4/2017 | Mironov | A24F 47/008 |
| 2017/0095004 A1‡ | 4/2017 | Liu | A24F 47/008 |
| 2017/0095005 A1‡ | 4/2017 | Monsees | A24F 47/008 |
| 2017/0095518 A1‡ | 4/2017 | Bjorncrantz | A61K 9/007 |
| 2017/0095623 A1‡ | 4/2017 | Trzecieski | A61M 11/042 |
| 2017/0099877 A1‡ | 4/2017 | Worm | A61M 11/042 |
| 2017/0099879 A1‡ | 4/2017 | Heidl | F16L 15/00 |
| 2017/0099880 A1‡ | 4/2017 | Hawes | A24F 47/008 |
| 2017/0101256 A1‡ | 4/2017 | Zeitlin | A24F 15/20 |
| 2017/0102013 A1‡ | 4/2017 | Wallman | F15B 15/1447 |
| 2017/0105448 A1‡ | 4/2017 | Scarpulla | A24F 47/002 |
| 2017/0105449 A1‡ | 4/2017 | Hearn | A24F 15/18 |
| 2017/0105450 A1‡ | 4/2017 | Reed | A24F 47/008 |
| 2017/0105451 A1‡ | 4/2017 | Fornarelli | A24F 47/008 |
| 2017/0105452 A1‡ | 4/2017 | Mironov | A24F 47/008 |
| 2017/0105453 A1‡ | 4/2017 | Li | A24F 47/008 |
| 2017/0105454 A1‡ | 4/2017 | Li | H05B 1/0244 |
| 2017/0105455 A1‡ | 4/2017 | Qiu | C04B 35/64 |
| 2017/0108210 A1‡ | 4/2017 | Meinhart | F22B 1/30 |
| 2017/0108840 A1‡ | 4/2017 | Hawes | G05B 15/02 |
| 2017/0109877 A1‡ | 4/2017 | Peleg | G01N 25/72 |
| 2017/0112182 A1‡ | 4/2017 | Arnold | A24B 15/167 |
| 2017/0112190 A1‡ | 4/2017 | Buchberger | A61M 15/06 |
| 2017/0112192 A1‡ | 4/2017 | Shan | A24F 47/008 |
| 2017/0112193 A1‡ | 4/2017 | Chen | A24F 47/008 |
| 2017/0112196 A1‡ | 4/2017 | Sur | A24F 47/008 |
| 2017/0112197 A1‡ | 4/2017 | Li | A24F 47/008 |
| 2017/0113819 A1‡ | 4/2017 | Marz | B65B 3/12 |
| 2017/0117654 A1‡ | 4/2017 | Cruz | H01R 13/2421 |
| 2017/0118292 A1‡ | 4/2017 | Xiang | A24F 47/008 |
| 2017/0118584 A1‡ | 4/2017 | Xiang | H04W 4/80 |
| 2017/0119040 A1‡ | 5/2017 | Cameron | A24B 15/167 |
| 2017/0119044 A1‡ | 5/2017 | Oligschlaeger | A24F 15/00 |
| 2017/0119050 A1‡ | 5/2017 | Blandino | A24B 15/165 |
| 2017/0119052 A1‡ | 5/2017 | Williams | H05B 3/0014 |
| 2017/0119053 A1‡ | 5/2017 | Henry, Jr. | A61M 15/00 |
| 2017/0119054 A1‡ | 5/2017 | Zinovik | A24F 47/008 |
| 2017/0119055 A1‡ | 5/2017 | Liu | A24F 47/008 |
| 2017/0119057 A1‡ | 5/2017 | Liu | A24F 47/00 |
| 2017/0119058 A1‡ | 5/2017 | Cameron | A24F 47/008 |
| 2017/0119060 A1‡ | 5/2017 | Li | A24F 47/008 |
| 2017/0119061 A1‡ | 5/2017 | Li | A61M 11/042 |
| 2017/0127722 A1‡ | 5/2017 | Davis | A24F 47/008 |
| 2017/0127723 A1‡ | 5/2017 | Wu | B65D 85/70 |
| 2017/0127724 A1‡ | 5/2017 | Liu | A24F 47/008 |
| 2017/0127725 A1‡ | 5/2017 | Buchberger | A24F 47/008 |
| 2017/0127726 A1‡ | 5/2017 | Xiang | A24F 47/008 |
| 2017/0127728 A1‡ | 5/2017 | Li | B05B 7/1686 |
| 2017/0129661 A1‡ | 5/2017 | Van Tassell, III | B65D 47/18 |
| 2017/0135397 A1‡ | 5/2017 | Buehler | A24F 47/002 |
| 2017/0135398 A1‡ | 5/2017 | Scott | A24F 47/002 |
| 2017/0135399 A1‡ | 5/2017 | Gavrielov | A24F 47/008 |
| 2017/0135400 A1‡ | 5/2017 | Liu | A24F 47/008 |
| 2017/0135401 A1‡ | 5/2017 | Dickens | A24F 47/008 |
| 2017/0135402 A1‡ | 5/2017 | Zitzke | A24F 47/008 |
| 2017/0135403 A1‡ | 5/2017 | Liu | A24F 47/00 |
| 2017/0135407 A1‡ | 5/2017 | Cameron | A24F 47/008 |
| 2017/0135408 A1‡ | 5/2017 | Cameron | A24F 47/008 |
| 2017/0135409 A1‡ | 5/2017 | Cameron | A24F 47/008 |
| 2017/0135410 A1‡ | 5/2017 | Cameron | A24F 47/008 |
| 2017/0135411 A1‡ | 5/2017 | Cameron | A24F 47/008 |
| 2017/0135412 A1‡ | 5/2017 | Cameron | A24F 47/008 |
| 2017/0136193 A1‡ | 5/2017 | Cameron | A61M 11/042 |
| 2017/0136194 A1‡ | 5/2017 | Cameron | A61M 11/042 |
| 2017/0136301 A1‡ | 5/2017 | Cameron | G16H 40/67 |
| 2017/0143035 A1‡ | 5/2017 | Pucci | A24F 1/30 |
| 2017/0143037 A9‡ | 5/2017 | Larson | A24F 47/008 |
| 2017/0143038 A1‡ | 5/2017 | Dickens | A61M 15/06 |
| 2017/0143040 A1‡ | 5/2017 | Liu | A24F 47/008 |
| 2017/0143043 A1‡ | 5/2017 | Liu | A24F 47/008 |
| 2017/0143917 A1‡ | 5/2017 | Cohen | A61M 11/042 |
| 2017/0144827 A1‡ | 5/2017 | Batista | A24F 47/008 |
| 2017/0146005 A1‡ | 5/2017 | Edelen | B41J 2/175 |
| 2017/0150753 A1‡ | 6/2017 | Macko | A24F 47/008 |
| 2017/0150754 A1‡ | 6/2017 | Lin | A24F 47/00 |
| 2017/0150755 A1‡ | 6/2017 | Batista | A24F 47/008 |
| 2017/0150756 A1‡ | 6/2017 | Rexroad | A24F 47/008 |
| 2017/0150758 A1‡ | 6/2017 | Fernando | A24F 47/008 |
| 2017/0156397 A1‡ | 6/2017 | Sur | A24F 47/008 |
| 2017/0156398 A1‡ | 6/2017 | Sur | A24F 47/008 |
| 2017/0156400 A1‡ | 6/2017 | Liu | A24F 47/00 |
| 2017/0156401 A1‡ | 6/2017 | Liu | A24F 47/008 |
| 2017/0156402 A1‡ | 6/2017 | Liu | A24F 7/04 |
| 2017/0156403 A1‡ | 6/2017 | Gill | A24F 47/008 |
| 2017/0156404 A1‡ | 6/2017 | Novak, III | A24F 47/008 |
| 2017/0156408 A1‡ | 6/2017 | Li | A24F 47/008 |
| 2017/0157341 A1 | 6/2017 | Pandya et al. | |
| 2017/0158436 A1‡ | 6/2017 | Slurink | A24F 47/008 |
| 2017/0162523 A1‡ | 6/2017 | Hu | H01L 23/49833 |
| 2017/0162797 A1‡ | 6/2017 | Lee | A24F 2/12 |
| 2017/0164655 A1‡ | 6/2017 | Chen | A24F 47/008 |
| 2017/0164656 A1‡ | 6/2017 | Eusepi | A24F 47/008 |
| 2017/0164657 A1‡ | 6/2017 | Batista | H05B 3/34 |
| 2017/0164658 A1‡ | 6/2017 | Lin | A24F 47/00 |
| 2017/0170439 A1‡ | 6/2017 | Jarvis | H01M 2/12 |
| 2017/0172204 A1‡ | 6/2017 | Kane | A24B 15/16 |
| 2017/0172205 A1‡ | 6/2017 | Chang | A24F 47/008 |
| 2017/0172207 A1‡ | 6/2017 | Liu | A24F 47/008 |
| 2017/0172208 A1‡ | 6/2017 | Mironov | A24F 47/008 |
| 2017/0172209 A1‡ | 6/2017 | Saydar | A24F 47/008 |
| 2017/0172213 A1‡ | 6/2017 | Hon | A24F 47/008 |
| 2017/0172214 A1‡ | 6/2017 | Li | A24F 13/00 |
| 2017/0172215 A1‡ | 6/2017 | Li | H05B 3/42 |
| 2017/0181223 A1‡ | 6/2017 | Sur | H04B 5/0081 |
| 2017/0181467 A1‡ | 6/2017 | Cameron | A63F 13/90 |
| 2017/0181468 A1‡ | 6/2017 | Bowen | A24F 47/004 |
| 2017/0181470 A1‡ | 6/2017 | Li | A24F 47/008 |
| 2017/0181471 A1‡ | 6/2017 | Phillips | H02J 7/0029 |
| 2017/0181473 A1‡ | 6/2017 | Batista | H05B 1/0244 |
| 2017/0181474 A1‡ | 6/2017 | Cameron | A24F 47/008 |
| 2017/0181475 A1‡ | 6/2017 | Cameron | A24F 47/008 |
| 2017/0181476 A1‡ | 6/2017 | Li | A24F 47/008 |
| 2017/0181928 A1‡ | 6/2017 | Collins | A61J 1/035 |
| 2017/0185364 A1‡ | 6/2017 | Cameron | G06F 3/1446 |
| 2017/0186122 A1‡ | 6/2017 | Levings | G06Q 50/24 |
| 2017/0188626 A1‡ | 7/2017 | Davis | A24F 47/008 |
| 2017/0188627 A1‡ | 7/2017 | Sur | A24F 47/008 |
| 2017/0188628 A1‡ | 7/2017 | Montgomery | A24F 47/008 |
| 2017/0188629 A1‡ | 7/2017 | Dickens | A61M 11/042 |
| 2017/0188631 A1‡ | 7/2017 | Lin | A24F 47/00 |
| 2017/0188632 A1‡ | 7/2017 | Hon | A24F 47/008 |
| 2017/0188634 A1‡ | 7/2017 | Plojoux | A24F 47/008 |
| 2017/0188635 A1‡ | 7/2017 | Force | A24F 47/008 |
| 2017/0188636 A1‡ | 7/2017 | Li | A24F 47/008 |
| 2017/0196263 A1‡ | 7/2017 | Sur | A24F 47/008 |
| 2017/0196264 A1‡ | 7/2017 | Liu | A24F 47/008 |
| 2017/0196265 A1‡ | 7/2017 | Liu | A24F 47/008 |
| 2017/0196267 A1‡ | 7/2017 | Zou | B65B 3/04 |
| 2017/0196268 A1‡ | 7/2017 | Reevell | A24F 47/008 |
| 2017/0196269 A1‡ | 7/2017 | Bernauer | H05B 6/108 |
| 2017/0196270 A1‡ | 7/2017 | Vick | A24F 47/008 |
| 2017/0196271 A1‡ | 7/2017 | Levitz | A24F 13/22 |
| 2017/0196272 A1‡ | 7/2017 | Li | A24F 47/002 |
| 2017/0196273 A1‡ | 7/2017 | Qiu | A24F 47/008 |
| 2017/0202265 A1‡ | 7/2017 | Hawes | A24F 47/008 |
| 2017/0202266 A1‡ | 7/2017 | Sur | A24F 47/008 |
| 2017/0202267 A1‡ | 7/2017 | Liu | A24F 47/008 |
| 2017/0202268 A1‡ | 7/2017 | Li | A24F 7/02 |
| 2017/0207499 A1‡ | 7/2017 | Leadley | H01M 10/42 |
| 2017/0208857 A1‡ | 7/2017 | Branton | A24D 3/12 |
| 2017/0208858 A1‡ | 7/2017 | Li | A24F 1/24 |
| 2017/0208862 A1‡ | 7/2017 | Li | A24F 15/20 |
| 2017/0208863 A1‡ | 7/2017 | Davis | A24F 47/008 |
| 2017/0208864 A1‡ | 7/2017 | Anderson, Jr. | A61M 15/06 |

(56) References Cited

U.S. PATENT DOCUMENTS

| | | | |
|---|---|---|---|
| 2017/0208865 A1‡ | 7/2017 | Nettenstrom | H01M 2/30 |
| 2017/0208866 A1‡ | 7/2017 | Liu | A24F 47/00 |
| 2017/0208867 A1‡ | 7/2017 | Li | G08C 17/02 |
| 2017/0208868 A1‡ | 7/2017 | Li | A24F 47/008 |
| 2017/0208869 A1‡ | 7/2017 | Li | F16L 55/115 |
| 2017/0208870 A1‡ | 7/2017 | Liu | A24F 47/008 |
| 2017/0208882 A1‡ | 7/2017 | Lambertz | A41D 13/02 |
| 2017/0214261 A1‡ | 7/2017 | Gratton | H01M 10/446 |
| 2017/0215470 A1‡ | 8/2017 | Piccirilli | A24B 15/16 |
| 2017/0215473 A1‡ | 8/2017 | Nakano | A24B 13/00 |
| 2017/0215474 A1‡ | 8/2017 | Li | A24F 47/008 |
| 2017/0215476 A1‡ | 8/2017 | Dickens | |
| 2017/0215477 A1‡ | 8/2017 | Reevell | A24F 47/008 |
| 2017/0215478 A1‡ | 8/2017 | Harrison | A24F 7/02 |
| 2017/0215479 A1‡ | 8/2017 | Kies | A24F 3/00 |
| 2017/0215480 A1‡ | 8/2017 | Qiu | A24F 47/008 |
| 2017/0215481 A1‡ | 8/2017 | Li | H05B 3/42 |
| 2017/0215482 A1‡ | 8/2017 | Levitz | A24F 47/008 |
| 2017/0215483 A1‡ | 8/2017 | Li | A24F 47/008 |
| 2017/0215484 A1‡ | 8/2017 | Xiang | A24F 47/008 |
| 2017/0215485 A1‡ | 8/2017 | Zitzke | A24F 47/008 |
| 2017/0217607 A1‡ | 8/2017 | Slurink | B65B 39/12 |
| 2017/0219199 A1‡ | 8/2017 | Lou | F21V 29/70 |
| 2017/0219391 A1‡ | 8/2017 | Lin | G01D 5/42 |
| 2017/0222468 A1‡ | 8/2017 | Schennum | A24F 47/008 |
| 2017/0224013 A1‡ | 8/2017 | Huang | A24F 47/008 |
| 2017/0224014 A1‡ | 8/2017 | Fraser | H05B 1/0244 |
| 2017/0224016 A1‡ | 8/2017 | Reevell | H05B 1/0227 |
| 2017/0224017 A1‡ | 8/2017 | Li | A24F 47/008 |
| 2017/0224018 A1‡ | 8/2017 | Li | A24F 47/008 |
| 2017/0224022 A1‡ | 8/2017 | Liu | A24F 47/008 |
| 2017/0224023 A1‡ | 8/2017 | Lin | A24F 47/002 |
| 2017/0224024 A1‡ | 8/2017 | Jochnowitz | A24F 47/002 |
| 2017/0229885 A1‡ | 8/2017 | Bernauer | H01M 4/5825 |
| 2017/0229888 A1‡ | 8/2017 | Liu | H02J 7/0044 |
| 2017/0231266 A1‡ | 8/2017 | Mishra | A24B 15/283 131/27 |
| 2017/0231267 A1‡ | 8/2017 | Shi | A24B 15/26 131/29 |
| 2017/0231269 A1‡ | 8/2017 | Besso | A24D 1/02 131/33 |
| 2017/0231273 A1‡ | 8/2017 | Xiang | A24F 47/002 |
| 2017/0231275 A1‡ | 8/2017 | Guenther | A24F 9/00 362/25 |
| 2017/0231276 A1‡ | 8/2017 | Mironov | A24F 47/008 131/32 |
| 2017/0231277 A1‡ | 8/2017 | Mironov | A24F 47/008 392/40 |
| 2017/0231278 A1‡ | 8/2017 | Mironov | A24F 47/008 392/39 |
| 2017/0231279 A1‡ | 8/2017 | Watson | H01M 2/1055 131/32 |
| 2017/0231280 A1‡ | 8/2017 | Anton | A24F 47/008 392/40 |
| 2017/0231281 A1‡ | 8/2017 | Hatton | G01L 9/0072 131/32 |
| 2017/0231282 A1‡ | 8/2017 | Bowen | A61M 11/06 |
| 2017/0231283 A1‡ | 8/2017 | Gadas | A24F 7/02 131/32 |
| 2017/0231284 A1‡ | 8/2017 | Newns | A24F 47/008 |
| 2017/0231285 A1‡ | 8/2017 | Holzherr | A24F 47/008 |
| 2017/0231286 A1‡ | 8/2017 | Borkovec | A24F 47/008 131/32 |
| 2017/0233114 A1‡ | 8/2017 | Christensen | B65B 3/003 |
| 2017/0238596 A1‡ | 8/2017 | Matsumoto | A24B 15/167 |
| 2017/0238605 A1‡ | 8/2017 | Matsumoto | A24F 47/00 |
| 2017/0238606 A1‡ | 8/2017 | Matsumoto | A61M 11/003 |
| 2017/0238608 A1‡ | 8/2017 | Matsumoto | A24F 47/00 |
| 2017/0238609 A1‡ | 8/2017 | Schlipf | H05B 3/04 |
| 2017/0238611 A1‡ | 8/2017 | Buchberger | A61M 15/0091 |
| 2017/0238612 A1‡ | 8/2017 | Daryani | A24F 47/008 |
| 2017/0238613 A1‡ | 8/2017 | Suess | A24F 47/008 |
| 2017/0238614 A1‡ | 8/2017 | Li | A24F 47/008 |
| 2017/0238617 A1‡ | 8/2017 | Scatterday | A24F 47/008 |
| 2017/0241857 A1‡ | 8/2017 | Hearn | A24C 5/34 |
| 2017/0245543 A1‡ | 8/2017 | Karles | A24B 15/16 |
| 2017/0245546 A1‡ | 8/2017 | Huang | A24F 1/16 |
| 2017/0245547 A1‡ | 8/2017 | Lipowicz | A24F 47/008 |
| 2017/0245550 A1‡ | 8/2017 | Freelander | A61M 15/06 |
| 2017/0245551 A1‡ | 8/2017 | Reevell | G01F 23/22 |
| 2017/0245554 A1‡ | 8/2017 | Perez | A24F 47/008 |
| 2017/0246399 A1‡ | 8/2017 | Forlani | A61M 5/1684 |
| 2017/0246405 A1‡ | 8/2017 | Wensley | A24F 47/008 |
| 2017/0246407 A1‡ | 8/2017 | Matsumoto | A24F 47/002 |
| 2017/0250552 A1‡ | 8/2017 | Liu | H01M 10/48 |
| 2017/0251714 A1‡ | 9/2017 | Mishra | A24B 15/283 |
| 2017/0251718 A1‡ | 9/2017 | Armoush | A24F 1/30 |
| 2017/0251719 A1‡ | 9/2017 | Cyphert | A24F 1/00 |
| 2017/0251721 A1‡ | 9/2017 | Rostami | A24F 47/008 |
| 2017/0251722 A1‡ | 9/2017 | Kobal | A24F 47/008 |
| 2017/0251723 A1‡ | 9/2017 | Kobal | A24B 15/16 |
| 2017/0251724 A1‡ | 9/2017 | Lamb | A24F 47/008 |
| 2017/0251725 A1‡ | 9/2017 | Buchberger | A24F 47/008 |
| 2017/0251726 A1‡ | 9/2017 | Nielsen | A24F 47/008 |
| 2017/0251727 A1‡ | 9/2017 | Nielsen | A24F 47/008 |
| 2017/0251728 A1‡ | 9/2017 | Peleg | A24F 47/008 |
| 2017/0251729 A1‡ | 9/2017 | Li | A24F 47/008 |
| 2017/0258129 A1‡ | 9/2017 | Haun | A24F 9/16 |
| 2017/0258132 A1‡ | 9/2017 | Rostami | A24F 47/008 |
| 2017/0258134 A1‡ | 9/2017 | Kane | A24F 47/008 |
| 2017/0258137 A1‡ | 9/2017 | Smith | H05B 1/0244 |
| 2017/0258138 A1‡ | 9/2017 | Rostami | H04L 65/1069 |
| 2017/0258139 A1‡ | 9/2017 | Rostami | A24F 47/008 |
| 2017/0258140 A1‡ | 9/2017 | Rostami | A24F 47/008 |
| 2017/0258142 A1‡ | 9/2017 | Hatton | A24F 47/008 |
| 2017/0258143 A1‡ | 9/2017 | Lederer | A24F 47/008 |
| 2017/0259170 A1‡ | 9/2017 | Bowen | A24F 47/008 |
| 2017/0259954 A1‡ | 9/2017 | Schwester | B65D 5/503 |
| 2017/0261200 A1‡ | 9/2017 | Stultz | F22B 3/02 |
| 2017/0265517 A1‡ | 9/2017 | Swede | A24B 15/16 |
| 2017/0265522 A1‡ | 9/2017 | Li | A24F 7/00 |
| 2017/0265524 A1‡ | 9/2017 | Cadieux | A24F 47/008 |
| 2017/0265525 A1‡ | 9/2017 | Li | H05B 1/0244 |
| 2017/0266397 A1‡ | 9/2017 | Mayle | A61M 11/042 |
| 2017/0273353 A1‡ | 9/2017 | Gindrat | A24B 15/165 |
| 2017/0273354 A1‡ | 9/2017 | Tucker | A24F 47/008 |
| 2017/0273355 A1‡ | 9/2017 | Rogers | A24F 47/008 |
| 2017/0273357 A1‡ | 9/2017 | Barbuck | H05B 3/04 |
| 2017/0273358 A1‡ | 9/2017 | Batista | A24F 47/008 |
| 2017/0273359 A1‡ | 9/2017 | Liu | A61M 11/044 |
| 2017/0273360 A1‡ | 9/2017 | Brinkley | A24F 7/00 |
| 2017/0273361 A1‡ | 9/2017 | Li | A24F 47/008 |
| 2017/0273914 A1‡ | 9/2017 | Knudsen | A61K 36/81 |
| 2017/0280767 A1‡ | 10/2017 | Li | A24F 1/32 |
| 2017/0280768 A1‡ | 10/2017 | Lipowicz | A24F 1/32 |
| 2017/0280769 A1‡ | 10/2017 | Li | A24B 15/283 |
| 2017/0280770 A1‡ | 10/2017 | Wang | A24F 47/008 |
| 2017/0280771 A1‡ | 10/2017 | Courbat | A24F 47/008 |
| 2017/0280775 A1‡ | 10/2017 | Manca | A24F 47/008 |
| 2017/0280776 A1‡ | 10/2017 | Manca | A24F 47/008 |
| 2017/0280778 A1‡ | 10/2017 | Force | A24F 47/008 |
| 2017/0281883 A1‡ | 10/2017 | Li | A61M 15/001 |
| 2017/0283154 A1‡ | 10/2017 | Karles | B65D 81/32 |
| 2017/0285810 A1‡ | 10/2017 | Krah | G06F 3/0412 |
| 2017/0290368 A1‡ | 10/2017 | Hearn | A24F 47/002 |
| 2017/0290369 A1‡ | 10/2017 | Norasak | A24F 47/004 |
| 2017/0290370 A1‡ | 10/2017 | Garthaffner | A24F 47/008 |
| 2017/0290371 A1‡ | 10/2017 | Davis | A24F 47/008 |
| 2017/0290373 A1‡ | 10/2017 | Hon | A24F 47/008 |
| 2017/0290998 A1‡ | 10/2017 | Poston | A24F 47/008 |
| 2017/0295840 A1‡ | 10/2017 | Rath | A24D 1/18 |
| 2017/0295843 A1‡ | 10/2017 | Storch | A61M 11/041 |
| 2017/0295844 A1‡ | 10/2017 | Thevenaz | A24F 47/008 |
| 2017/0295845 A1‡ | 10/2017 | Bajpai | A24F 47/008 |
| 2017/0295846 A1‡ | 10/2017 | Liu | A24F 47/008 |
| 2017/0295847 A1‡ | 10/2017 | Liu | A24F 47/00 |
| 2017/0295848 A1‡ | 10/2017 | LaMothe | A24F 47/008 |
| 2017/0295849 A1‡ | 10/2017 | Cadieux | A24F 47/008 |
| 2017/0297892 A1‡ | 10/2017 | Li | B65D 47/265 |
| 2017/0301898 A1‡ | 10/2017 | Lin | A24F 47/00 |
| 2017/0302089 A1‡ | 10/2017 | Bernauer | H02J 7/0054 |
| 2017/0302324 A1‡ | 10/2017 | Stanimirovic | H01M 10/46 |
| 2017/0303597 A1‡ | 10/2017 | Tsui | H05B 1/0297 |

(56) References Cited

U.S. PATENT DOCUMENTS

| | | | |
|---|---|---|---|
| 2017/0311648 A1 ‡ | 11/2017 | Gill | A24F 47/008 |
| 2017/0318860 A1 ‡ | 11/2017 | Adair | A24F 47/008 |
| 2017/0318861 A1 ‡ | 11/2017 | Thorens | A24F 47/008 |
| 2017/0325503 A1 ‡ | 11/2017 | Liu | A61M 11/044 |
| 2017/0325504 A1 ‡ | 11/2017 | Liu | A24F 47/00 |
| 2017/0325506 A1 ‡ | 11/2017 | Batista | A24F 47/008 |
| 2017/0332695 A1 ‡ | 11/2017 | Zappoli | A24D 3/0229 |
| 2017/0333415 A1 ‡ | 11/2017 | Williams | A24B 15/167 |
| 2017/0333650 A1 ‡ | 11/2017 | Buchberger | A61M 15/06 |
| 2017/0333651 A1 ‡ | 11/2017 | Qiu | A24F 47/00 |
| 2017/0334605 A1 ‡ | 11/2017 | Murphy | A24F 15/18 |
| 2017/0367410 A1 | 12/2017 | Hon | |
| 2018/0070644 A1 | 3/2018 | Monsees et al. | |
| 2018/0117268 A1 ‡ | 5/2018 | Selby | A61M 15/06 |
| 2018/0160737 A1 ‡ | 6/2018 | Verleur | A24F 47/008 |
| 2019/0037926 A1 | 2/2019 | Qiu | |
| 2019/0046745 A1 * | 2/2019 | Nettenstrom | A61M 15/002 |

FOREIGN PATENT DOCUMENTS

| | | |
|---|---|---|
| AU | 2014208287 A1 ‡ | 8/2014 |
| AU | 2017202891 A1 ‡ | 5/2017 |
| CA | 2614869 A1 | 1/2006 |
| CA | 2641869 A1 ‡ | 5/2010 |
| CH | 105346 A | 6/1924 |
| CN | 1122213 A ‡ | 5/1996 |
| CN | 2643529 Y | 9/2004 |
| CN | 1906096 A | 1/2007 |
| CN | 201104488 Y | 8/2008 |
| CN | 101277622 A | 10/2008 |
| CN | 201430916 Y ‡ | 3/2010 |
| CN | 101869356 A ‡ | 10/2010 |
| CN | 101951796 A | 1/2011 |
| CN | 301485739 | 3/2011 |
| CN | 201781984 U | 4/2011 |
| CN | 301547686 S ‡ | 5/2011 |
| CN | 102160906 A | 8/2011 |
| CN | 102176941 A | 9/2011 |
| CN | 202004499 U | 10/2011 |
| CN | 202218034 U | 5/2012 |
| CN | 301970169 S ‡ | 6/2012 |
| CN | 202385728 U | 8/2012 |
| CN | 102655773 A | 9/2012 |
| CN | 102754924 A ‡ | 10/2012 |
| CN | 202603608 U | 12/2012 |
| CN | 202663148 U | 1/2013 |
| CN | 102920028 A | 2/2013 |
| CN | 102970885 A | 3/2013 |
| CN | 202890462 U | 4/2013 |
| CN | 302396126 | 4/2013 |
| CN | 302396126 S ‡ | 4/2013 |
| CN | 203040683 U | 7/2013 |
| CN | 203072896 U | 7/2013 |
| CN | 103237469 A | 8/2013 |
| CN | 103237470 A | 8/2013 |
| CN | 203327953 U | 12/2013 |
| CN | 203353689 U | 12/2013 |
| CN | 103750571 A ‡ | 4/2014 |
| CN | 302799554 S | 4/2014 |
| CN | 302810246 S | 4/2014 |
| CN | 302884434 S | 7/2014 |
| CN | 104010529 A | 8/2014 |
| CN | 302926289 S ‡ | 8/2014 |
| CN | 104055223 A | 9/2014 |
| CN | 302950830 S ‡ | 9/2014 |
| CN | 204120231 U | 1/2015 |
| CN | 303091331 S ‡ | 1/2015 |
| CN | 204132390 U | 2/2015 |
| CN | 303103390 S ‡ | 2/2015 |
| CN | 104382237 A | 3/2015 |
| CN | 204217907 U | 3/2015 |
| CN | 303210086 S ‡ | 5/2015 |
| CN | 104738816 A | 7/2015 |
| CN | 105011375 A | 11/2015 |
| CN | 204905326 U | 12/2015 |
| CN | 303568163 S ‡ | 1/2016 |
| DE | 1093936 B | 12/1960 |
| DE | 19619536 A1 | 10/1997 |
| DE | 19854005 A1 ‡ | 5/2000 |
| DE | 19854012 A1 ‡ | 5/2000 |
| DE | 102006004484 A1 | 8/2007 |
| DE | 102007011120 A1 | 9/2008 |
| DE | 102008046932 A1 | 5/2009 |
| EP | 0283672 A2 ‡ | 9/1988 |
| EP | 0503767 A1 ‡ | 9/1992 |
| EP | 0532194 A1 ‡ | 3/1993 |
| EP | 0535695 A2 ‡ | 4/1993 |
| EP | 0762258 A2 | 3/1997 |
| EP | 1093936 A1 | 4/2001 |
| EP | 1736177 A1 | 12/2006 |
| EP | 2113178 A1 | 11/2009 |
| EP | 2186507 A2 ‡ | 5/2010 |
| EP | 2399636 A1 ‡ | 12/2011 |
| EP | 2460424 A1 | 6/2012 |
| EP | 2489391 A1 | 8/2012 |
| EP | 2606756 A1 | 6/2013 |
| EP | 2609821 A1 | 7/2013 |
| EP | 2614731 A1 ‡ | 7/2013 |
| EP | 2711006 A1 ‡ | 3/2014 |
| EP | 2641669 B1 ‡ | 5/2014 |
| EP | 2789248 A1 ‡ | 10/2014 |
| EP | 2493342 B1 ‡ | 12/2014 |
| EP | 2856893 A1 ‡ | 4/2015 |
| EP | 2862454 A1 ‡ | 4/2015 |
| EP | 2862457 A1 ‡ | 4/2015 |
| EP | 2888964 A1 | 7/2015 |
| EP | 2895390 A1 | 7/2015 |
| EP | 2944206 A1 ‡ | 11/2015 |
| EP | 2944207 A1 | 11/2015 |
| EP | 2952110 A1 ‡ | 12/2015 |
| EP | 2989921 A1 ‡ | 3/2016 |
| EP | 3001918 A1 ‡ | 4/2016 |
| EP | 3007305 A1 ‡ | 4/2016 |
| EP | 3012213 A1 ‡ | 4/2016 |
| EP | 3016233 A1 ‡ | 5/2016 |
| EP | 3023016 A1 ‡ | 5/2016 |
| EP | 3023351 A1 ‡ | 5/2016 |
| EP | 3023947 A1 ‡ | 5/2016 |
| EP | 3024343 A2 | 6/2016 |
| EP | 3025598 A1 ‡ | 6/2016 |
| EP | 3026779 A1 | 6/2016 |
| EP | 3031338 A1 ‡ | 6/2016 |
| EP | 3031339 A1 ‡ | 6/2016 |
| EP | 3047742 A1 ‡ | 7/2016 |
| EP | 3056099 A1 | 8/2016 |
| EP | 3061358 A1 ‡ | 8/2016 |
| EP | 3075270 A1 ‡ | 10/2016 |
| EP | 3075271 A1 | 10/2016 |
| EP | 3081102 A1 ‡ | 10/2016 |
| EP | 3085638 A1 ‡ | 10/2016 |
| EP | 3087853 A1 ‡ | 11/2016 |
| EP | 3097803 A1 ‡ | 11/2016 |
| EP | 3103355 A1 ‡ | 12/2016 |
| EP | 3103356 A1 ‡ | 12/2016 |
| EP | 3111787 A1 ‡ | 1/2017 |
| EP | 3130238 A1 ‡ | 2/2017 |
| EP | 3132843 A1 ‡ | 2/2017 |
| EP | 3135139 A1 ‡ | 3/2017 |
| EP | 3135603 A1 ‡ | 3/2017 |
| EP | 3143882 A3 ‡ | 3/2017 |
| EP | 3143884 A3 ‡ | 4/2017 |
| EP | 3155908 A1 ‡ | 4/2017 |
| EP | 3158880 A1 ‡ | 4/2017 |
| EP | 3158881 A1 ‡ | 4/2017 |
| EP | 3195738 A2 ‡ | 7/2017 |
| EP | 3199043 A1 ‡ | 8/2017 |
| EP | 3205220 A1 ‡ | 8/2017 |
| EP | 3205597 A1 ‡ | 8/2017 |
| EP | 3213649 A1 ‡ | 9/2017 |
| EP | 3225118 A1 ‡ | 10/2017 |
| EP | 3228198 A1 ‡ | 10/2017 |
| EP | 3228345 A1 ‡ | 10/2017 |
| ES | 2118034 A1 ‡ | 9/1998 |
| GB | 1025630 A ‡ | 4/1966 |

(56) References Cited

FOREIGN PATENT DOCUMENTS

| | | | |
|---|---|---|---|
| GB | 1065678 A ‡ | 4/1967 |
| GB | 2264237 A | 8/1993 |
| GB | 2266466 A | 11/1993 |
| GB | 2504074 A | 1/2014 |
| GB | 2533174 A ‡ | 6/2016 |
| GB | 2560653 A | 9/2018 |
| IE | S20050615 ‡ | 9/2005 |
| JP | 62278975 ‡ | 12/1987 |
| JP | H06114105 A ‡ | 4/1994 |
| JP | 09-075058 ‡ | 3/1997 |
| JP | H09075058 A ‡ | 3/1997 |
| JP | 11178563 ‡ | 6/1999 |
| JP | 2000203639 A ‡ | 7/2000 |
| JP | 2000236865 A ‡ | 9/2000 |
| JP | 2009213428 A ‡ | 9/2000 |
| JP | 2001161819 A ‡ | 6/2001 |
| JP | 2001165437 A ‡ | 6/2001 |
| JP | 3325591 B2 | 9/2002 |
| JP | 2006320285 A ‡ | 11/2006 |
| JP | 2006320286 A ‡ | 11/2006 |
| JP | 2011024430 A ‡ | 2/2011 |
| JP | 2013507976 A | 3/2013 |
| JP | 2013516159 A | 5/2013 |
| KR | 100579783 B1 | 5/2006 |
| KR | 20120008751 A | 2/2012 |
| KR | 20120006582 U | 9/2012 |
| KR | 20120105655 A | 9/2012 |
| KR | 20120113519 A | 10/2012 |
| KR | 1020120132004 | 12/2012 |
| KR | 20130092252 A | 8/2013 |
| KR | 20130106741 A | 9/2013 |
| KR | 20130107658 A | 10/2013 |
| KR | 20130122713 A | 11/2013 |
| SG | 11201707778 | 10/2017 |
| TW | I320698 B | 2/2010 |
| TW | 201436722 A ‡ | 10/2014 |
| TW | 201438608 A ‡ | 10/2014 |
| TW | 201524383 A ‡ | 7/2015 |
| WO | WO-9712639 A1 ‡ | 4/1997 |
| WO | WO-2000005976 A1 ‡ | 2/2000 |
| WO | WO-0028842 A1 ‡ | 5/2000 |
| WO | WO-2007066374 A1 ‡ | 6/2000 |
| WO | WO-03055486 A1 ‡ | 7/2003 |
| WO | WO-03056948 A1 ‡ | 7/2003 |
| WO | WO-2003061716 A1 | 7/2003 |
| WO | WO-03082031 A1 ‡ | 10/2003 |
| WO | WO-03101454 A1 ‡ | 12/2003 |
| WO | WO-03103387 A2 | 12/2003 |
| WO | WO-2004064548 A1 ‡ | 8/2004 |
| WO | WO-2004080216 A1 ‡ | 9/2004 |
| WO | WO-2005020726 A1 ‡ | 3/2005 |
| WO | WO-2005060366 A2 ‡ | 7/2005 |
| WO | WO-2006021153 A1 ‡ | 3/2006 |
| WO | WO-2007078273 A1 ‡ | 7/2007 |
| WO | WO-2007095109 A2 ‡ | 8/2007 |
| WO | WO-2007117675 A2 ‡ | 10/2007 |
| WO | WO-2007/141520 A1 ‡ | 12/2007 |
| WO | WO-2008077271 A1 ‡ | 7/2008 |
| WO | WO-2008138650 A1 | 11/2008 |
| WO | WO-2008151777 A2 ‡ | 12/2008 |
| WO | WO-2009003204 A2 ‡ | 1/2009 |
| WO | WO-2009079641 A2 | 6/2009 |
| WO | WO-2009132793 A1 | 11/2009 |
| WO | 2010020929 A ‡ | 1/2010 |
| WO | WO-2010003480 A1 ‡ | 1/2010 |
| WO | WO-2010118122 A1 ‡ | 10/2010 |
| WO | WO-2010118644 A1 ‡ | 10/2010 |
| WO | WO-2010140841 A2 ‡ | 12/2010 |
| WO | WO-2010145805 A1 ‡ | 12/2010 |
| WO | WO-2011010334 A1 ‡ | 1/2011 |
| WO | WO-2011050964 A1 ‡ | 5/2011 |
| WO | WO-2011079932 A1 | 7/2011 |
| WO | WO-2011125058 A1 ‡ | 10/2011 |
| WO | WO-2011146174 A2 | 11/2011 |
| WO | WO-2011147691 A1 | 12/2011 |
| WO | 2012005412 A ‡ | 1/2012 |
| WO | WO-2012014490 A1 | 2/2012 |
| WO | WO-2012019533 A1 ‡ | 2/2012 |
| WO | WO-2012043941 A1 ‡ | 4/2012 |
| WO | WO-2012059726 A2 | 5/2012 |
| WO | WO-2012062600 A1 ‡ | 5/2012 |
| WO | WO-2012085203 A1 | 6/2012 |
| WO | WO-2012088675 A1 ‡ | 7/2012 |
| WO | WO-2012091249 A1 ‡ | 7/2012 |
| WO | WO-2010100523 A1 ‡ | 8/2012 |
| WO | WO-2012129812 A1 ‡ | 10/2012 |
| WO | WO-2012134117 A2 ‡ | 10/2012 |
| WO | WO-2012164033 A1 ‡ | 12/2012 |
| WO | WO-2012173322 A1 ‡ | 12/2012 |
| WO | WO-D079112-0010 ‡ | 12/2012 |
| WO | WO-2013012157 A1 ‡ | 1/2013 |
| WO | WO-2013020220 A1 ‡ | 2/2013 |
| WO | WO-2013030202 A1 ‡ | 3/2013 |
| WO | WO-2013034453 A1 ‡ | 3/2013 |
| WO | WO-2013034456 A1 | 3/2013 |
| WO | WO-2013040193 A2 ‡ | 3/2013 |
| WO | WO-2013044537 A1 ‡ | 4/2013 |
| WO | WO-2013045582 A2 | 4/2013 |
| WO | WO-2013060784 A2 | 5/2013 |
| WO | WO-2013068100 A1 | 5/2013 |
| WO | WO-2013075439 A1 | 5/2013 |
| WO | WO-2013076750 A1 ‡ | 5/2013 |
| WO | WO-2013083631 A1 | 6/2013 |
| WO | WO-2013083634 A1 | 6/2013 |
| WO | WO-2013083635 A1 ‡ | 6/2013 |
| WO | WO-2013089358 A1 | 6/2013 |
| WO | WO-2013089551 A1 ‡ | 6/2013 |
| WO | WO-2013093695 A1 | 6/2013 |
| WO | WO-2013098395 A1 | 7/2013 |
| WO | WO-2013110208 A1 ‡ | 8/2013 |
| WO | WO-2013110209 A1 ‡ | 8/2013 |
| WO | WO-2013110210 A1 ‡ | 8/2013 |
| WO | WO-2013113173 A1 ‡ | 8/2013 |
| WO | WO-2013113174 A1 ‡ | 8/2013 |
| WO | WO-2013113612 A1 ‡ | 8/2013 |
| WO | WO-2013116558 A1 | 8/2013 |
| WO | WO-2013116567 A1 | 8/2013 |
| WO | WO-2013116983 A1 ‡ | 8/2013 |
| WO | WO-2013131763 A1 ‡ | 9/2013 |
| WO | WO-2013142678 A1 ‡ | 9/2013 |
| WO | WO-2013147492 A1 | 10/2013 |
| WO | WO-2013150406 A2 ‡ | 10/2013 |
| WO | WO-2013155645 A1 | 10/2013 |
| WO | WO-2013155654 A1 | 10/2013 |
| WO | WO-2013156658 A1 ‡ | 10/2013 |
| WO | WO-2013159245 A1 | 10/2013 |
| WO | WO-2013171206 A1 ‡ | 11/2013 |
| WO | WO-2013174001 A1 ‡ | 11/2013 |
| WO | WO-2012174677 A1 ‡ | 12/2013 |
| WO | WO-2013190036 A1 | 12/2013 |
| WO | WO-2014012906 A1 | 1/2014 |
| WO | WO-2014020539 A1 ‡ | 2/2014 |
| WO | WO-2014020953 A1 ‡ | 2/2014 |
| WO | WO-2014023171 A1 ‡ | 2/2014 |
| WO | WO-2014032280 A1 ‡ | 3/2014 |
| WO | WO-2014039308 A1 | 3/2014 |
| WO | WO-2014040915 A1 ‡ | 3/2014 |
| WO | WO-2014047948 A1 ‡ | 4/2014 |
| WO | WO-2014047955 A1 ‡ | 4/2014 |
| WO | WO-2014067236 A1 ‡ | 5/2014 |
| WO | WO-2014071747 A1 ‡ | 5/2014 |
| WO | WO-2014101119 A1 ‡ | 7/2014 |
| WO | WO-2014101401 A1 ‡ | 7/2014 |
| WO | WO-2014101734 A1 ‡ | 7/2014 |
| WO | WO-2014106323 A1 ‡ | 7/2014 |
| WO | WO-2014113949 A1 ‡ | 7/2014 |
| WO | WO-2014114328 A1 ‡ | 7/2014 |
| WO | WO-2014440761 A1 ‡ | 7/2014 |
| WO | WO-2014117382 A1 ‡ | 8/2014 |
| WO | WO-2014121509 A1 ‡ | 8/2014 |
| WO | WO-2014125340 A1 ‡ | 8/2014 |
| WO | WO-2014127446 A1 ‡ | 8/2014 |
| WO | WO-2014134781 A1 ‡ | 9/2014 |
| WO | WO-2014138244 A1 ‡ | 9/2014 |

(56) References Cited

FOREIGN PATENT DOCUMENTS

| | | |
|---|---|---|
| WO | WO-2014139610 A1 | 9/2014 |
| WO | WO-2014144678 A2 ‡ | 9/2014 |
| WO | WO-2014146270 A1 ‡ | 9/2014 |
| WO | WO-2014147470 A2 ‡ | 9/2014 |
| WO | WO-2014150979 A2 | 9/2014 |
| WO | WO-2014151040 A2 | 9/2014 |
| WO | WO-2014153796 A1 | 10/2014 |
| WO | WO-2014159982 A1 | 10/2014 |
| WO | WO-2014161181 A1 ‡ | 10/2014 |
| WO | WO-2014166039 A1 ‡ | 10/2014 |
| WO | WO-2014167530 A1 ‡ | 10/2014 |
| WO | WO-2014169437 A1 ‡ | 10/2014 |
| WO | WO-2014169667 A1 ‡ | 10/2014 |
| WO | WO-2014185937 A1 ‡ | 11/2014 |
| WO | WO-2014186983 A1 ‡ | 11/2014 |
| WO | WO-2014194499 A1 ‡ | 12/2014 |
| WO | WO-2014195687 A1 ‡ | 12/2014 |
| WO | WO-2014198042 A1 ‡ | 12/2014 |
| WO | WO-2014201610 A1 ‡ | 12/2014 |
| WO | WO-2014201611 A1 ‡ | 12/2014 |
| WO | WO-2014201646 A1 ‡ | 12/2014 |
| WO | WO-2014201664 A1 ‡ | 12/2014 |
| WO | WO-2014201666 A1 ‡ | 12/2014 |
| WO | WO-2014201668 A1 ‡ | 12/2014 |
| WO | WO-2014205263 A1 | 12/2014 |
| WO | WO-2014205749 A1 ‡ | 12/2014 |
| WO | WO-2014205780 A1 ‡ | 12/2014 |
| WO | WO-2014205807 A1 ‡ | 12/2014 |
| WO | WO-2014205811 A1 ‡ | 12/2014 |
| WO | WO-2014206148 A1 ‡ | 12/2014 |
| WO | WO-2015000125 A1 ‡ | 1/2015 |
| WO | WO-2015000180 A1 ‡ | 1/2015 |
| WO | WO-2015003327 A1 ‡ | 1/2015 |
| WO | WO-2015003372 A1 ‡ | 1/2015 |
| WO | WO-2015003374 A1 ‡ | 1/2015 |
| WO | WO-2015006929 A1 ‡ | 1/2015 |
| WO | WO-2015010242 A1 ‡ | 1/2015 |
| WO | WO-2015010277 A1 ‡ | 1/2015 |
| WO | WO-2015010284 A1 ‡ | 1/2015 |
| WO | WO-2015010291 A1 ‡ | 1/2015 |
| WO | WO-2015010310 A1 ‡ | 1/2015 |
| WO | WO-2015010336 A1 ‡ | 1/2015 |
| WO | WO-2015010345 A1 ‡ | 1/2015 |
| WO | WO-2015010349 A1 ‡ | 1/2015 |
| WO | WO-2015013327 A2 | 1/2015 |
| WO | 2015504669 A ‡ | 2/2015 |
| WO | WO-2015013890 A1 ‡ | 2/2015 |
| WO | WO-2015013891 A1 ‡ | 2/2015 |
| WO | WO-2015013892 A1 ‡ | 2/2015 |
| WO | WO-2015013926 A1 ‡ | 2/2015 |
| WO | WO-2015013950 A1 ‡ | 2/2015 |
| WO | WO-2015013967 A1 ‡ | 2/2015 |
| WO | WO-2015015156 A1 ‡ | 2/2015 |
| WO | WO-2015017971 A1 ‡ | 2/2015 |
| WO | WO-2015018026 A1 ‡ | 2/2015 |
| WO | WO-2015018120 A1 ‡ | 2/2015 |
| WO | WO-2015021612 A1 ‡ | 2/2015 |
| WO | WO-2015021646 A1 ‡ | 2/2015 |
| WO | WO-2015021651 A1 ‡ | 2/2015 |
| WO | WO-2015021652 A1 ‡ | 2/2015 |
| WO | WO-2015021655 A1 ‡ | 2/2015 |
| WO | WO-2015021658 A1 ‡ | 2/2015 |
| WO | WO-2015024239 A1 ‡ | 2/2015 |
| WO | WO-2015024247 A1 ‡ | 2/2015 |
| WO | WO-2015026081 A1 ‡ | 2/2015 |
| WO | WO-2015027383 A1 ‡ | 3/2015 |
| WO | WO-2015027435 A1 ‡ | 3/2015 |
| WO | WO-2015027436 A1 ‡ | 3/2015 |
| WO | WO-2015027470 A1 ‡ | 3/2015 |
| WO | WO-2015028815 A1 ‡ | 3/2015 |
| WO | WO-2015032050 A1 ‡ | 3/2015 |
| WO | WO-2015032055 A1 ‡ | 3/2015 |
| WO | WO-2015032078 A1 ‡ | 3/2015 |
| WO | WO-2015032093 A1 ‡ | 3/2015 |
| WO | WO-2015035510 A1 ‡ | 3/2015 |
| WO | WO-2015035547 A1 ‡ | 3/2015 |
| WO | WO-2015035557 A1 ‡ | 3/2015 |
| WO | WO-2015035587 A1 ‡ | 3/2015 |
| WO | WO-2015035623 A1 ‡ | 3/2015 |
| WO | WO-2015035689 A1 ‡ | 3/2015 |
| WO | WO-2015037925 A1 ‡ | 3/2015 |
| WO | WO-2015039275 A1 ‡ | 3/2015 |
| WO | WO-2015039280 A1 ‡ | 3/2015 |
| WO | WO-2015039332 A1 ‡ | 3/2015 |
| WO | WO-2015042790 A1 ‡ | 4/2015 |
| WO | WO-2015042811 A1 ‡ | 4/2015 |
| WO | WO-2015042848 A1 ‡ | 4/2015 |
| WO | WO-2015042943 A1 ‡ | 4/2015 |
| WO | WO-2015051509 A1 ‡ | 4/2015 |
| WO | WO-2015051538 A1 ‡ | 4/2015 |
| WO | WO-2015052513 A2 | 4/2015 |
| WO | WO-2015054815 A1 ‡ | 4/2015 |
| WO | WO-2015054862 A1 | 4/2015 |
| WO | WO-2015054961 A1 ‡ | 4/2015 |
| WO | WO-2015055314 A1 ‡ | 4/2015 |
| WO | WO-2015058340 A1 ‡ | 4/2015 |
| WO | WO-2015058341 A1 ‡ | 4/2015 |
| WO | WO-2015058367 A1 ‡ | 4/2015 |
| WO | WO-2015058387 A1 ‡ | 4/2015 |
| WO | WO-2015062041 A1 ‡ | 5/2015 |
| WO | WO-2015066136 A1 ‡ | 5/2015 |
| WO | WO-2015066927 A1 ‡ | 5/2015 |
| WO | WO-2015070398 A1 ‡ | 5/2015 |
| WO | WO-2015070405 A1 ‡ | 5/2015 |
| WO | WO-2015071703 A1 ‡ | 5/2015 |
| WO | WO-2015073564 A1 | 5/2015 |
| WO | WO-2015073975 A1 ‡ | 5/2015 |
| WO | WO-2015074187 A1 ‡ | 5/2015 |
| WO | WO-2015074265 A1 ‡ | 5/2015 |
| WO | WO-2015074308 A1 ‡ | 5/2015 |
| WO | WO-2015077645 A1 | 5/2015 |
| WO | WO-2015077998 A1 ‡ | 6/2015 |
| WO | WO-2015077999 A1 ‡ | 6/2015 |
| WO | WO-2015078010 A1 ‡ | 6/2015 |
| WO | WO-2015078147 A1 | 6/2015 |
| WO | WO-2015079197 A1 ‡ | 6/2015 |
| WO | WO-2015089711 A1 ‡ | 6/2015 |
| WO | WO-2015091346 A2 ‡ | 6/2015 |
| WO | WO-2015013327 A3 ‡ | 7/2015 |
| WO | WO-2015106434 A1 ‡ | 7/2015 |
| WO | WO-2015106440 A1 ‡ | 7/2015 |
| WO | WO-2015107551 A2 ‡ | 7/2015 |
| WO | WO-2015107552 A1 ‡ | 7/2015 |
| WO | WO-2015109476 A1 ‡ | 7/2015 |
| WO | WO-2015109532 A1 ‡ | 7/2015 |
| WO | WO-2015109540 A1 ‡ | 7/2015 |
| WO | WO-2015109616 A1 ‡ | 7/2015 |
| WO | WO-2015109618 A1 ‡ | 7/2015 |
| WO | WO-2015114325 A1 | 8/2015 |
| WO | WO-2015117285 A1 ‡ | 8/2015 |
| WO | WO-2015120588 A1 ‡ | 8/2015 |
| WO | WO-2015120591 A1 ‡ | 8/2015 |
| WO | WO-2015120623 A1 ‡ | 8/2015 |
| WO | WO-2015123831 A1 ‡ | 8/2015 |
| WO | WO-2015127609 A1 ‡ | 9/2015 |
| WO | WO-2015128599 A1 ‡ | 9/2015 |
| WO | WO-2015137815 A1 ‡ | 9/2015 |
| WO | WO-2015140312 A1 ‡ | 9/2015 |
| WO | WO-2015140768 A2 | 9/2015 |
| WO | WO-2015143637 A1 ‡ | 10/2015 |
| WO | WO-2015143648 A1 ‡ | 10/2015 |
| WO | WO-2015143749 A1 ‡ | 10/2015 |
| WO | WO-2015143765 A1 ‡ | 10/2015 |
| WO | WO-2015144057 A1 ‡ | 10/2015 |
| WO | WO-2015144328 A1 | 10/2015 |
| WO | WO-2015149311 A1 ‡ | 10/2015 |
| WO | WO-2015149330 A1 ‡ | 10/2015 |
| WO | WO-2015149332 A1 ‡ | 10/2015 |
| WO | WO-2015149338 A1 ‡ | 10/2015 |
| WO | WO-2015149368 A1 ‡ | 10/2015 |
| WO | WO-2015149403 A1 ‡ | 10/2015 |
| WO | WO-2015149406 A1 ‡ | 10/2015 |
| WO | WO-2015150068 A1 ‡ | 10/2015 |
| WO | WO-2015154309 A1 ‡ | 10/2015 |

(56) References Cited

FOREIGN PATENT DOCUMENTS

| | | | |
|---|---|---|---|
| WO | WO-2015154619 A1 ‡ | 10/2015 |
| WO | WO-2015157891 A1 ‡ | 10/2015 |
| WO | WO-2015157893 A1 ‡ | 10/2015 |
| WO | WO-2015157900 A1 ‡ | 10/2015 |
| WO | WO-2015157901 A1 ‡ | 10/2015 |
| WO | WO-2015157928 A1 ‡ | 10/2015 |
| WO | WO-2015158522 A1 ‡ | 10/2015 |
| WO | WO-2015158548 A1 ‡ | 10/2015 |
| WO | WO-2015161406 A1 ‡ | 10/2015 |
| WO | WO-2015161407 A1 ‡ | 10/2015 |
| WO | WO-2015161485 A1 ‡ | 10/2015 |
| WO | WO-2015161486 A1 ‡ | 10/2015 |
| WO | WO-2015161491 A1 ‡ | 10/2015 |
| WO | WO-2015161514 A1 ‡ | 10/2015 |
| WO | WO-2015161553 A1 ‡ | 10/2015 |
| WO | WO-2015161555 A1 ‡ | 10/2015 |
| WO | WO-2015161557 A1 ‡ | 10/2015 |
| WO | WO-2015068044 A3 ‡ | 11/2015 |
| WO | WO-2015165067 A1 ‡ | 11/2015 |
| WO | WO-2015165081 A1 ‡ | 11/2015 |
| WO | WO-2015165083 A1 ‡ | 11/2015 |
| WO | WO-2015165086 A1 ‡ | 11/2015 |
| WO | WO-2015165105 A1 ‡ | 11/2015 |
| WO | WO-2015165146 A1 ‡ | 11/2015 |
| WO | WO-2015165747 A1 | 11/2015 |
| WO | WO-2015168827 A1 ‡ | 11/2015 |
| WO | WO-2015168828 A1 ‡ | 11/2015 |
| WO | WO-2015168853 A1 ‡ | 11/2015 |
| WO | WO-2015168904 A1 ‡ | 11/2015 |
| WO | WO-2015168912 A1 ‡ | 11/2015 |
| WO | WO-2015172224 A1 | 11/2015 |
| WO | WO-2015172331 A1 ‡ | 11/2015 |
| WO | WO-2015172361 A1 ‡ | 11/2015 |
| WO | WO-2015172368 A1 ‡ | 11/2015 |
| WO | WO-2015172382 A1 ‡ | 11/2015 |
| WO | WO-2015172383 A1 ‡ | 11/2015 |
| WO | WO-2015172384 A1 ‡ | 11/2015 |
| WO | WO-2015172387 A1 ‡ | 11/2015 |
| WO | WO-2015172388 A1 ‡ | 11/2015 |
| WO | WO-2015172389 A1 ‡ | 11/2015 |
| WO | WO-2015172390 A1 ‡ | 11/2015 |
| WO | WO-2015172606 A1 ‡ | 11/2015 |
| WO | WO-2015174657 A1 ‡ | 11/2015 |
| WO | WO-2015174708 A1 ‡ | 11/2015 |
| WO | WO-2015175979 A1 ‡ | 11/2015 |
| WO | WO-2015176210 A1 ‡ | 11/2015 |
| WO | WO-2015176230 A1 ‡ | 11/2015 |
| WO | WO-2015176300 A1 ‡ | 11/2015 |
| WO | WO-2015176580 A1 ‡ | 11/2015 |
| WO | WO-2015180027 A1 ‡ | 12/2015 |
| WO | WO-2015180061 A1 ‡ | 12/2015 |
| WO | WO-2015180062 A1 ‡ | 12/2015 |
| WO | WO-2015180071 A1 ‡ | 12/2015 |
| WO | WO-2015180088 A1 ‡ | 12/2015 |
| WO | WO-2015180089 A1 ‡ | 12/2015 |
| WO | WO-2015180145 A1 ‡ | 12/2015 |
| WO | WO-2015184580 A1 ‡ | 12/2015 |
| WO | WO-2015184590 A1 ‡ | 12/2015 |
| WO | WO-2015184620 A1 ‡ | 12/2015 |
| WO | WO-2015184747 A1 ‡ | 12/2015 |
| WO | WO-2015186000 A2 | 12/2015 |
| WO | WO-2015188295 A1 ‡ | 12/2015 |
| WO | WO-2015188296 A1 ‡ | 12/2015 |
| WO | WO-2015189613 A1 ‡ | 12/2015 |
| WO | WO-2015190810 A1 ‡ | 12/2015 |
| WO | WO-2015192301 A1 ‡ | 12/2015 |
| WO | WO-2015192326 A1 ‡ | 12/2015 |
| WO | WO-2015192336 A1 ‡ | 12/2015 |
| WO | WO-2015192337 A1 ‡ | 12/2015 |
| WO | WO-2015192377 A1 ‡ | 12/2015 |
| WO | WO-2015193456 A1 ‡ | 12/2015 |
| WO | WO-2015196331 A1 ‡ | 12/2015 |
| WO | WO-2015196332 A1 ‡ | 12/2015 |
| WO | WO-2015196357 A1 ‡ | 12/2015 |
| WO | WO-2015196367 A1 ‡ | 12/2015 |
| WO | WO-2015196395 A1 ‡ | 12/2015 |
| WO | WO-2015196463 A1 ‡ | 12/2015 |
| WO | WO-2015148649 A1 ‡ | 1/2016 |
| WO | WO-2016000113 A1 ‡ | 1/2016 |
| WO | WO-2016000130 A1 ‡ | 1/2016 |
| WO | WO-2016000135 A1 ‡ | 1/2016 |
| WO | WO-2016000136 A1 ‡ | 1/2016 |
| WO | WO-2016000139 A1 ‡ | 1/2016 |
| WO | WO-2016000206 A1 ‡ | 1/2016 |
| WO | WO-2016000207 A1 ‡ | 1/2016 |
| WO | WO-2016000214 A1 ‡ | 1/2016 |
| WO | WO-2016000232 A1 ‡ | 1/2016 |
| WO | WO-2016000233 A1 ‡ | 1/2016 |
| WO | WO-2016000305 A1 ‡ | 1/2016 |
| WO | WO-2016008067 A1 ‡ | 1/2016 |
| WO | WO-2016008096 A1 ‡ | 1/2016 |
| WO | WO-2016008217 A1 ‡ | 1/2016 |
| WO | WO-2016011573 A1 ‡ | 1/2016 |
| WO | WO-2016012769 A1 ‡ | 1/2016 |
| WO | WO-2016015196 A1 ‡ | 2/2016 |
| WO | WO-2016015245 A1 ‡ | 2/2016 |
| WO | WO-2016015246 A1 ‡ | 2/2016 |
| WO | WO-2016015247 A1 ‡ | 2/2016 |
| WO | WO-2016015264 A1 ‡ | 2/2016 |
| WO | WO-2016015712 A1 ‡ | 2/2016 |
| WO | WO-2016019508 A1 ‡ | 2/2016 |
| WO | WO-2016019550 A1 ‡ | 2/2016 |
| WO | WO-2016019573 A1 ‡ | 2/2016 |
| WO | WO-2016020675 A1 ‡ | 2/2016 |
| WO | WO-2016023173 A1 ‡ | 2/2016 |
| WO | WO-2016023176 A1 ‡ | 2/2016 |
| WO | WO-2016023177 A1 ‡ | 2/2016 |
| WO | WO-2016023181 A1 ‡ | 2/2016 |
| WO | WO-2016023182 A1 ‡ | 2/2016 |
| WO | WO-2016023183 A1 ‡ | 2/2016 |
| WO | WO-2016023212 A1 ‡ | 2/2016 |
| WO | WO-2016023651 A1 ‡ | 2/2016 |
| WO | WO-2016023824 A1 ‡ | 2/2016 |
| WO | WO-2016023965 A1 ‡ | 2/2016 |
| WO | WO-2016026104 A1 ‡ | 2/2016 |
| WO | WO-2016026105 A1 ‡ | 2/2016 |
| WO | WO-2016026156 A1 ‡ | 2/2016 |
| WO | WO-2016026811 A1 ‡ | 2/2016 |
| WO | WO-2016028544 A1 ‡ | 2/2016 |
| WO | WO-2016029344 A1 ‡ | 3/2016 |
| WO | WO-2016029382 A1 ‡ | 3/2016 |
| WO | WO-2016029386 A1 ‡ | 3/2016 |
| WO | WO-2016029389 A1 ‡ | 3/2016 |
| WO | WO-2016029429 A1 ‡ | 3/2016 |
| WO | WO-2016029464 A1 ‡ | 3/2016 |
| WO | WO-2016029468 A1 ‡ | 3/2016 |
| WO | WO-2016029470 A1 ‡ | 3/2016 |
| WO | WO-2016029473 A1 ‡ | 3/2016 |
| WO | WO-2016029567 A1 ‡ | 3/2016 |
| WO | WO-2016030661 A1 ‡ | 3/2016 |
| WO | WO-2016033721 A1 ‡ | 3/2016 |
| WO | WO-2016033734 A1 ‡ | 3/2016 |
| WO | WO-2016033783 A1 ‡ | 3/2016 |
| WO | WO-2016033817 A1 ‡ | 3/2016 |
| WO | WO-2016034100 A1 ‡ | 3/2016 |
| WO | WO-2016038029 A1 ‡ | 3/2016 |
| WO | WO-2016040575 A1 ‡ | 3/2016 |
| WO | WO-2016041114 A1 ‡ | 3/2016 |
| WO | WO-2016041140 A1 ‡ | 3/2016 |
| WO | WO-2016041141 A1 ‡ | 3/2016 |
| WO | WO-2016041207 A1 ‡ | 3/2016 |
| WO | WO-2016041209 A1 ‡ | 3/2016 |
| WO | WO-2016045058 A1 ‡ | 3/2016 |
| WO | WO-2016046116 A1 ‡ | 3/2016 |
| WO | WO-2015192834 A3 ‡ | 4/2016 |
| WO | WO-2016049822 A1 ‡ | 4/2016 |
| WO | WO-2016049823 A1 ‡ | 4/2016 |
| WO | WO-2016049855 A1 ‡ | 4/2016 |
| WO | WO-2016049863 A1 ‡ | 4/2016 |
| WO | WO-2016050246 A1 ‡ | 4/2016 |
| WO | WO-2016050247 A1 ‡ | 4/2016 |
| WO | WO-2016054793 A1 ‡ | 4/2016 |
| WO | WO-2016055653 A1 ‡ | 4/2016 |
| WO | WO-2016058139 A1 ‡ | 4/2016 |

(56) References Cited

FOREIGN PATENT DOCUMENTS

| | | |
|---|---|---|
| WO | WO-2016058187 A1 ‡ | 4/2016 |
| WO | WO-2016058189 A1 ‡ | 4/2016 |
| WO | WO-2016059000 A1 ‡ | 4/2016 |
| WO | WO-2016060576 A1 ‡ | 4/2016 |
| WO | WO-2016061729 A1 ‡ | 4/2016 |
| WO | WO-2016061730 A1 ‡ | 4/2016 |
| WO | WO-2016061822 A1 ‡ | 4/2016 |
| WO | WO-2016061859 A1 ‡ | 4/2016 |
| WO | WO-2016062168 A1 ‡ | 4/2016 |
| WO | WO-2016062777 A1 ‡ | 4/2016 |
| WO | WO-2016063775 A1 ‡ | 4/2016 |
| WO | WO-2016065520 A1 ‡ | 5/2016 |
| WO | WO-2016065521 A1 ‡ | 5/2016 |
| WO | WO-2016065532 A1 ‡ | 5/2016 |
| WO | WO-2016065533 A1 ‡ | 5/2016 |
| WO | WO-2016065596 A1 ‡ | 5/2016 |
| WO | WO-2016065598 A1 ‡ | 5/2016 |
| WO | WO-2016065599 A1 ‡ | 5/2016 |
| WO | WO-2016065605 A1 ‡ | 5/2016 |
| WO | WO-2016065606 A1 ‡ | 5/2016 |
| WO | WO-2016065607 A1 ‡ | 5/2016 |
| WO | WO-2016070553 A1 ‡ | 5/2016 |
| WO | WO-2016071027 A1 ‡ | 5/2016 |
| WO | WO-2016071705 A1 ‡ | 5/2016 |
| WO | WO-2016071706 A1 ‡ | 5/2016 |
| WO | WO-2016074228 A1 ‡ | 5/2016 |
| WO | WO-2016074229 A1 ‡ | 5/2016 |
| WO | WO-2016074230 A1 ‡ | 5/2016 |
| WO | WO-2016074234 A1 ‡ | 5/2016 |
| WO | WO-2016074237 A1 ‡ | 5/2016 |
| WO | WO-2016076178 A1 ‡ | 5/2016 |
| WO | WO-2016079001 A1 ‡ | 5/2016 |
| WO | WO-2016079151 A1 ‡ | 5/2016 |
| WO | WO-2016079152 A1 ‡ | 5/2016 |
| WO | WO-2016079155 A1 ‡ | 5/2016 |
| WO | WO-2016079468 A1 ‡ | 5/2016 |
| WO | WO-2016079533 A1 ‡ | 5/2016 |
| WO | WO-2016079729 A1 ‡ | 5/2016 |
| WO | WO-2016058992 A3 ‡ | 6/2016 |
| WO | WO-2016059003 A3 ‡ | 6/2016 |
| WO | WO-2016082074 A1 ‡ | 6/2016 |
| WO | WO-2016082103 A1 ‡ | 6/2016 |
| WO | WO-2016082116 A1 ‡ | 6/2016 |
| WO | WO-2016082136 A1 ‡ | 6/2016 |
| WO | WO-2016082158 A1 ‡ | 6/2016 |
| WO | WO-2016082179 A1 ‡ | 6/2016 |
| WO | WO-2016082180 A1 ‡ | 6/2016 |
| WO | WO-2016082183 A1 ‡ | 6/2016 |
| WO | WO-2016082217 A1 ‡ | 6/2016 |
| WO | WO-2016082232 A1 ‡ | 6/2016 |
| WO | WO-2016082479 A1 ‡ | 6/2016 |
| WO | WO-2016086382 A1 ‡ | 6/2016 |
| WO | WO-2016090426 A1 ‡ | 6/2016 |
| WO | WO-2016090531 A1 ‡ | 6/2016 |
| WO | WO-2016090533 A1 ‡ | 6/2016 |
| WO | WO-2016090593 A1 ‡ | 6/2016 |
| WO | WO-2016090601 A1 ‡ | 6/2016 |
| WO | WO-2016090602 A1 ‡ | 6/2016 |
| WO | WO-2016090962 A1 ‡ | 6/2016 |
| WO | WO-2016092259 A1 ‡ | 6/2016 |
| WO | WO-2016092261 A1 | 6/2016 |
| WO | WO-2016095101 A1 ‡ | 6/2016 |
| WO | WO-2016095206 A1 ‡ | 6/2016 |
| WO | WO-2016095220 A1 ‡ | 6/2016 |
| WO | WO-2016095234 A1 ‡ | 6/2016 |
| WO | WO-2016095297 A1 ‡ | 6/2016 |
| WO | WO-2016096337 A1 ‡ | 6/2016 |
| WO | WO-2016096482 A1 ‡ | 6/2016 |
| WO | WO-2016096497 A1 ‡ | 6/2016 |
| WO | WO-2016096733 A1 ‡ | 6/2016 |
| WO | WO-2016096762 A1 ‡ | 6/2016 |
| WO | WO-2016099045 A1 ‡ | 6/2016 |
| WO | WO-2016099276 A1 ‡ | 6/2016 |
| WO | WO-2016101141 A1 ‡ | 6/2016 |
| WO | WO-2016101142 A1 ‡ | 6/2016 |
| WO | WO-2016101143 A1 ‡ | 6/2016 |
| WO | WO-2016101144 A1 ‡ | 6/2016 |
| WO | WO-2016101150 A1 ‡ | 6/2016 |
| WO | WO-2016101183 A1 ‡ | 6/2016 |
| WO | WO-2016101200 A1 ‡ | 6/2016 |
| WO | WO-2016101202 A1 ‡ | 6/2016 |
| WO | WO-2016101203 A1 ‡ | 6/2016 |
| WO | WO-2016101248 A1 ‡ | 6/2016 |
| WO | WO-2016103202 A1 ‡ | 6/2016 |
| WO | WO-2016105191 A1 ‡ | 6/2016 |
| WO | WO-2016036236 A3 ‡ | 7/2016 |
| WO | WO-2016106476 A1 ‡ | 7/2016 |
| WO | WO-2016106483 A1 ‡ | 7/2016 |
| WO | WO-2016106493 A1 ‡ | 7/2016 |
| WO | WO-2016106495 A1 ‡ | 7/2016 |
| WO | WO-2016106499 A1 ‡ | 7/2016 |
| WO | WO-2016106500 A1 ‡ | 7/2016 |
| WO | WO-2016106512 A1 ‡ | 7/2016 |
| WO | WO-2016108693 A1 ‡ | 7/2016 |
| WO | WO-2016108694 A1 ‡ | 7/2016 |
| WO | WO-2016109929 A1 ‡ | 7/2016 |
| WO | WO-2016109930 A1 ‡ | 7/2016 |
| WO | WO-2016109931 A1 ‡ | 7/2016 |
| WO | WO-2016109932 A1 ‡ | 7/2016 |
| WO | WO-2016109933 A1 ‡ | 7/2016 |
| WO | WO-2016109942 A1 ‡ | 7/2016 |
| WO | WO-2016109964 A1 ‡ | 7/2016 |
| WO | WO-2016109965 A1 ‡ | 7/2016 |
| WO | WO-2016110522 A1 ‡ | 7/2016 |
| WO | WO-2016112491 A1 ‡ | 7/2016 |
| WO | WO-2016112493 A1 ‡ | 7/2016 |
| WO | WO-2016112533 A1 ‡ | 7/2016 |
| WO | WO-2016112534 A1 ‡ | 7/2016 |
| WO | WO-2016112541 A1 ‡ | 7/2016 |
| WO | WO-2016112542 A1 ‡ | 7/2016 |
| WO | WO-2016112561 A1 ‡ | 7/2016 |
| WO | WO-2016112579 A1 ‡ | 7/2016 |
| WO | WO-2016115689 A1 ‡ | 7/2016 |
| WO | WO-2016115691 A1 ‡ | 7/2016 |
| WO | WO-2016115701 A1 ‡ | 7/2016 |
| WO | WO-2016115715 A1 ‡ | 7/2016 |
| WO | WO-2016116754 A1 ‡ | 7/2016 |
| WO | WO-2016116755 A1 ‡ | 7/2016 |
| WO | WO-2016118005 A1 ‡ | 7/2016 |
| WO | WO-2016119098 A1 ‡ | 8/2016 |
| WO | WO-2016119099 A1 ‡ | 8/2016 |
| WO | WO-2016119101 A1 ‡ | 8/2016 |
| WO | WO-2016119119 A1 ‡ | 8/2016 |
| WO | WO-2016119121 A1 ‡ | 8/2016 |
| WO | WO-2016119144 A1 ‡ | 8/2016 |
| WO | WO-2016119145 A1 ‡ | 8/2016 |
| WO | WO-2016119163 A1 ‡ | 8/2016 |
| WO | WO-2016119167 A1 ‡ | 8/2016 |
| WO | WO-2016119170 A1 ‡ | 8/2016 |
| WO | WO-2016119225 A1 ‡ | 8/2016 |
| WO | WO-2016119248 A1 ‡ | 8/2016 |
| WO | WO-2016119273 A1 ‡ | 8/2016 |
| WO | WO-2016119496 A1 ‡ | 8/2016 |
| WO | WO-2016122417 A1 ‡ | 8/2016 |
| WO | WO-2016123763 A1 ‡ | 8/2016 |
| WO | WO-2016123764 A1 ‡ | 8/2016 |
| WO | WO-2016123770 A1 ‡ | 8/2016 |
| WO | WO-2016123779 A1 ‡ | 8/2016 |
| WO | WO-2016123780 A1 ‡ | 8/2016 |
| WO | WO-2016123781 A1 ‡ | 8/2016 |
| WO | WO-2016124017 A1 ‡ | 8/2016 |
| WO | WO-2016124019 A1 ‡ | 8/2016 |
| WO | WO-2016124695 A1 ‡ | 8/2016 |
| WO | WO-2016124740 A1 ‡ | 8/2016 |
| WO | WO-2016124741 A1 ‡ | 8/2016 |
| WO | WO-2016127287 A1 ‡ | 8/2016 |
| WO | WO-2016127293 A1 ‡ | 8/2016 |
| WO | WO-2016127327 A1 ‡ | 8/2016 |
| WO | WO-2016127360 A1 ‡ | 8/2016 |
| WO | WO-2016127361 A1 ‡ | 8/2016 |
| WO | WO-2016127389 A1 ‡ | 8/2016 |
| WO | WO-2016127390 A1 ‡ | 8/2016 |
| WO | WO-2016127396 A1 ‡ | 8/2016 |
| WO | WO-2016127397 A1 ‡ | 8/2016 |

(56) References Cited

FOREIGN PATENT DOCUMENTS

| | | |
|---|---|---|
| WO | WO-2016127401 A1 ‡ | 8/2016 |
| WO | WO-2016127406 A1 ‡ | 8/2016 |
| WO | WO-2016127468 A1 ‡ | 8/2016 |
| WO | WO-2016127839 A1 ‡ | 8/2016 |
| WO | WO-2016128562 A1 ‡ | 8/2016 |
| WO | WO-2016131755 A1 ‡ | 8/2016 |
| WO | WO-2016132026 A1 ‡ | 8/2016 |
| WO | WO-2016134544 A1 ‡ | 9/2016 |
| WO | WO-2016135503 A1 ‡ | 9/2016 |
| WO | WO-2016138608 A1 ‡ | 9/2016 |
| WO | WO-2016138665 A1 ‡ | 9/2016 |
| WO | WO-2016138689 A1 ‡ | 9/2016 |
| WO | WO-2016141508 A1 ‡ | 9/2016 |
| WO | WO-2016141555 A1 ‡ | 9/2016 |
| WO | WO-2016141556 A1 ‡ | 9/2016 |
| WO | WO-2016141581 A1 ‡ | 9/2016 |
| WO | WO-2016141592 A1 ‡ | 9/2016 |
| WO | WO-2016141593 A1 ‡ | 9/2016 |
| WO | WO-2016145611 A1 ‡ | 9/2016 |
| WO | WO-2016145612 A1 ‡ | 9/2016 |
| WO | WO-2016145613 A1 ‡ | 9/2016 |
| WO | WO-2016145634 A1 ‡ | 9/2016 |
| WO | WO-2016145656 A1 ‡ | 9/2016 |
| WO | WO-2016145663 A1 ‡ | 9/2016 |
| WO | WO-2016149896 A1 ‡ | 9/2016 |
| WO | WO-2016149932 A1 ‡ | 9/2016 |
| WO | WO-2016149942 A1 ‡ | 9/2016 |
| WO | WO-2016150019 A1 ‡ | 9/2016 |
| WO | WO-2016150979 A1 ‡ | 9/2016 |
| WO | WO-2016154792 A1 ‡ | 10/2016 |
| WO | WO-2016154797 A1 ‡ | 10/2016 |
| WO | WO-2016154798 A1 ‡ | 10/2016 |
| WO | WO-2016154815 A1 ‡ | 10/2016 |
| WO | WO-2016154895 A1 ‡ | 10/2016 |
| WO | WO-2016154896 A1 ‡ | 10/2016 |
| WO | WO-2016154897 A1 ‡ | 10/2016 |
| WO | WO-2016154900 A1 ‡ | 10/2016 |
| WO | WO-2016154994 A1 ‡ | 10/2016 |
| WO | WO-2016155003 A1 ‡ | 10/2016 |
| WO | WO-2016155103 A1 ‡ | 10/2016 |
| WO | WO-2016155104 A1 ‡ | 10/2016 |
| WO | WO-2016155105 A1 ‡ | 10/2016 |
| WO | WO-2016155316 A1 ‡ | 10/2016 |
| WO | WO-2016156103 A1 ‡ | 10/2016 |
| WO | WO-2016156217 A1 ‡ | 10/2016 |
| WO | WO-2016156413 A1 ‡ | 10/2016 |
| WO | WO-2016161554 A1 ‡ | 10/2016 |
| WO | WO-2016161673 A1 ‡ | 10/2016 |
| WO | WO-2016162446 A1 ‡ | 10/2016 |
| WO | WO-2016162492 A1 ‡ | 10/2016 |
| WO | WO-2016165055 A1 ‡ | 10/2016 |
| WO | WO-2016165057 A1 ‡ | 10/2016 |
| WO | WO-2016165063 A1 ‡ | 10/2016 |
| WO | WO-2016165125 A1 ‡ | 10/2016 |
| WO | WO-2016166049 A1 ‡ | 10/2016 |
| WO | WO-2016166456 A1 ‡ | 10/2016 |
| WO | WO-2016166661 A1 ‡ | 10/2016 |
| WO | WO-2016166670 A1 ‡ | 10/2016 |
| WO | WO-2016168986 A1 ‡ | 10/2016 |
| WO | WO-2016169019 A1 ‡ | 10/2016 |
| WO | WO-2016169052 A1 ‡ | 10/2016 |
| WO | WO-2016169063 A1 ‡ | 10/2016 |
| WO | WO-2016169669 A1 ‡ | 10/2016 |
| WO | WO-2016169796 A1 ‡ | 10/2016 |
| WO | WO-2016169797 A1 ‡ | 10/2016 |
| WO | WO-2016172802 A1 ‡ | 11/2016 |
| WO | WO-2016172821 A1 ‡ | 11/2016 |
| WO | WO-2016172843 A1 ‡ | 11/2016 |
| WO | WO-2016172847 A1 ‡ | 11/2016 |
| WO | WO-2016172867 A1 ‡ | 11/2016 |
| WO | WO-2016172898 A1 ‡ | 11/2016 |
| WO | WO-2016172907 A1 ‡ | 11/2016 |
| WO | WO-2016172908 A1 ‡ | 11/2016 |
| WO | WO-2016172909 A1 ‡ | 11/2016 |
| WO | WO-2016172954 A1 ‡ | 11/2016 |
| WO | WO-2016174179 A1 ‡ | 11/2016 |
| WO | WO-2016176800 A1 ‡ | 11/2016 |
| WO | WO-2016177604 A1 ‡ | 11/2016 |
| WO | WO-2016179356 A1 ‡ | 11/2016 |
| WO | WO-2016179664 A1 ‡ | 11/2016 |
| WO | WO-2016179776 A1 ‡ | 11/2016 |
| WO | WO-2016179828 A1 ‡ | 11/2016 |
| WO | WO-2016183724 A1 ‡ | 11/2016 |
| WO | WO-2016184247 A1 ‡ | 11/2016 |
| WO | WO-2016184824 A1 ‡ | 11/2016 |
| WO | WO-2016171997 A3 ‡ | 12/2016 |
| WO | WO-2016187803 A1 ‡ | 12/2016 |
| WO | WO-2016187943 A1 ‡ | 12/2016 |
| WO | WO-2016188140 A1 ‡ | 12/2016 |
| WO | WO-2016188141 A1 ‡ | 12/2016 |
| WO | WO-2016188142 A1 ‡ | 12/2016 |
| WO | WO-2016188967 A1 ‡ | 12/2016 |
| WO | WO-2016189086 A1 ‡ | 12/2016 |
| WO | WO-2016191946 A1 ‡ | 12/2016 |
| WO | WO-2016193336 A1 ‡ | 12/2016 |
| WO | WO-2016193365 A1 ‡ | 12/2016 |
| WO | WO-2016193743 A1 ‡ | 12/2016 |
| WO | WO-2016197485 A1 ‡ | 12/2016 |
| WO | WO-2016197658 A1 ‡ | 12/2016 |
| WO | WO-2016198417 A1 ‡ | 12/2016 |
| WO | WO-2016198459 A1 ‡ | 12/2016 |
| WO | WO-2016198879 A1 ‡ | 12/2016 |
| WO | WO-2016199062 A1 ‡ | 12/2016 |
| WO | WO-2016199065 A1 ‡ | 12/2016 |
| WO | WO-2016199066 A1 ‡ | 12/2016 |
| WO | WO-2016200252 A1 ‡ | 12/2016 |
| WO | WO-2016200253 A1 ‡ | 12/2016 |
| WO | WO-2016200255 A1 ‡ | 12/2016 |
| WO | WO-2016200382 A1 ‡ | 12/2016 |
| WO | WO-2016200529 A1 ‡ | 12/2016 |
| WO | WO-2016201602 A1 ‡ | 12/2016 |
| WO | WO-2016201606 A1 ‡ | 12/2016 |
| WO | WO-2016201911 A1 ‡ | 12/2016 |
| WO | WO-2016202028 A1 ‡ | 12/2016 |
| WO | WO-2016202033 A1 ‡ | 12/2016 |
| WO | WO-2016202301 A1 ‡ | 12/2016 |
| WO | WO-2016202302 A1 ‡ | 12/2016 |
| WO | WO-2016202303 A1 ‡ | 12/2016 |
| WO | WO-2016202304 A1 ‡ | 12/2016 |
| WO | WO-2016207357 A1 ‡ | 12/2016 |
| WO | WO-2016208757 A1 ‡ | 12/2016 |
| WO | WO-2016208760 A1 ‡ | 12/2016 |
| WO | WO-2016210242 A1 | 12/2016 |
| WO | 201712730 A ‡ | 1/2017 |
| WO | WO-2016193705 A1 ‡ | 1/2017 |
| WO | WO-2017000239 A1 ‡ | 1/2017 |
| WO | WO-2017001270 A1 ‡ | 1/2017 |
| WO | WO-2017001817 A1 ‡ | 1/2017 |
| WO | WO-2017001818 A1 ‡ | 1/2017 |
| WO | WO-2017001819 A1 ‡ | 1/2017 |
| WO | WO-2017001820 A1 ‡ | 1/2017 |
| WO | WO-2017005835 A1 ‡ | 1/2017 |
| WO | WO-2017007252 A1 ‡ | 1/2017 |
| WO | WO-2017008616 A1 ‡ | 1/2017 |
| WO | WO-2017009002 A1 ‡ | 1/2017 |
| WO | WO-2017011419 A1 ‡ | 1/2017 |
| WO | WO-2017012099 A1 ‡ | 1/2017 |
| WO | WO-2017012105 A1 ‡ | 1/2017 |
| WO | WO-2017012257 A1 ‡ | 1/2017 |
| WO | WO-2017012335 A1 ‡ | 1/2017 |
| WO | WO-2016172921 A8 ‡ | 2/2017 |
| WO | WO-2016178098 A3 ‡ | 2/2017 |
| WO | WO-2017015791 A1 ‡ | 2/2017 |
| WO | WO-2017015794 A1 ‡ | 2/2017 |
| WO | WO-2017015832 A1 ‡ | 2/2017 |
| WO | WO-2017015859 A1 ‡ | 2/2017 |
| WO | WO-2017016323 A1 ‡ | 2/2017 |
| WO | WO-2017017970 A1 ‡ | 2/2017 |
| WO | WO-2017020200 A1 ‡ | 2/2017 |
| WO | WO-2017020221 A1 ‡ | 2/2017 |
| WO | WO-2017020275 A1 ‡ | 2/2017 |
| WO | WO-2017020290 A1 ‡ | 2/2017 |
| WO | WO-2017023589 A1 ‡ | 2/2017 |
| WO | WO-2017024477 A1 ‡ | 2/2017 |

(56) References Cited

FOREIGN PATENT DOCUMENTS

| | | |
|---|---|---|
| WO | WO-2017024478 A1 ‡ | 2/2017 |
| WO | WO-2017024799 A1 ‡ | 2/2017 |
| WO | WO-2017024926 A1 ‡ | 2/2017 |
| WO | WO-2017025383 A1 ‡ | 2/2017 |
| WO | WO-2017028167 A1 ‡ | 2/2017 |
| WO | WO-2017028295 A1 ‡ | 2/2017 |
| WO | WO-2017029268 A1 ‡ | 2/2017 |
| WO | WO-2017029269 A1 ‡ | 2/2017 |
| WO | WO-2017029270 A1 ‡ | 2/2017 |
| WO | WO-2017021536 A3 ‡ | 3/2017 |
| WO | WO-2017031662 A1 ‡ | 3/2017 |
| WO | WO-2017031678 A1 ‡ | 3/2017 |
| WO | WO-2017031681 A1 ‡ | 3/2017 |
| WO | WO-2017033007 A1 ‡ | 3/2017 |
| WO | WO-2017033021 A1 ‡ | 3/2017 |
| WO | WO-2017033132 A1 ‡ | 3/2017 |
| WO | WO-2017035720 A1 ‡ | 3/2017 |
| WO | WO-2017036818 A1 ‡ | 3/2017 |
| WO | WO-2017036819 A1 ‡ | 3/2017 |
| WO | WO-2017036828 A1 ‡ | 3/2017 |
| WO | WO-2017036829 A1 ‡ | 3/2017 |
| WO | WO-2017036865 A1 ‡ | 3/2017 |
| WO | WO-2017036879 A1 ‡ | 3/2017 |
| WO | WO-2017041251 A1 ‡ | 3/2017 |
| WO | WO-2017042081 A1 ‡ | 3/2017 |
| WO | WO-2017045132 A1 ‡ | 3/2017 |
| WO | WO-2017045897 A1 ‡ | 3/2017 |
| WO | WO-2017045898 A1 ‡ | 3/2017 |
| WO | WO-2017045899 A1 ‡ | 3/2017 |
| WO | WO-2017046247 A1 ‡ | 3/2017 |
| WO | WO-2017046334 A1 ‡ | 3/2017 |
| WO | WO-2017046363 A1 ‡ | 3/2017 |
| WO | WO-2017046566 A1 ‡ | 3/2017 |
| WO | WO-2017049653 A1 ‡ | 3/2017 |
| WO | WO-2017049654 A1 ‡ | 3/2017 |
| WO | WO-2017051150 A1 ‡ | 3/2017 |
| WO | WO-2017051174 A1 ‡ | 3/2017 |
| WO | WO-2017051348 A1 ‡ | 3/2017 |
| WO | WO-2017051349 A1 ‡ | 3/2017 |
| WO | WO-2017046593 A3 ‡ | 4/2017 |
| WO | WO-2017054424 A1 ‡ | 4/2017 |
| WO | WO-2017054627 A1 ‡ | 4/2017 |
| WO | WO-2017054634 A1 ‡ | 4/2017 |
| WO | WO-2017055564 A1 ‡ | 4/2017 |
| WO | WO-2017055584 A1 ‡ | 4/2017 |
| WO | WO-2017055793 A1 ‡ | 4/2017 |
| WO | WO-2017055795 A1 ‡ | 4/2017 |
| WO | WO-2017055799 A1 ‡ | 4/2017 |
| WO | WO-2017055801 A1 ‡ | 4/2017 |
| WO | WO-2017055802 A1 ‡ | 4/2017 |
| WO | WO-2017055803 A1 ‡ | 4/2017 |
| WO | WO-2017055866 A1 ‡ | 4/2017 |
| WO | WO-2017056103 A1 ‡ | 4/2017 |
| WO | WO-2017057286 A1 ‡ | 4/2017 |
| WO | WO-2017059571 A1 ‡ | 4/2017 |
| WO | WO-2017060279 A1 ‡ | 4/2017 |
| WO | WO-2017063256 A1 ‡ | 4/2017 |
| WO | WO-2017063535 A1 ‡ | 4/2017 |
| WO | WO-2017064051 A1 ‡ | 4/2017 |
| WO | WO-2017064322 A1 ‡ | 4/2017 |
| WO | WO-2017064323 A1 ‡ | 4/2017 |
| WO | WO-2017064324 A1 ‡ | 4/2017 |
| WO | WO-2017064487 A1 ‡ | 4/2017 |
| WO | WO-2017066938 A1 ‡ | 4/2017 |
| WO | WO-2017066955 A1 ‡ | 4/2017 |
| WO | WO-2017067066 A1 ‡ | 4/2017 |
| WO | WO-2017067326 A1 ‡ | 4/2017 |
| WO | WO-2017068098 A1 ‡ | 4/2017 |
| WO | WO-2017068099 A1 ‡ | 4/2017 |
| WO | WO-2017068100 A1 ‡ | 4/2017 |
| WO | WO-2016096745 A9 ‡ | 5/2017 |
| WO | WO-2016173568 A3 ‡ | 5/2017 |
| WO | WO-2016198026 A3 ‡ | 5/2017 |
| WO | WO-2017051350 A3 ‡ | 5/2017 |
| WO | WO-2017070871 A1 ‡ | 5/2017 |
| WO | WO-2017071297 A1 ‡ | 5/2017 |
| WO | WO-2017071298 A1 ‡ | 5/2017 |
| WO | WO-2017072239 A1 ‡ | 5/2017 |
| WO | WO-2017072277 A1 ‡ | 5/2017 |
| WO | WO-2017072284 A1 ‡ | 5/2017 |
| WO | WO-2017075753 A1 ‡ | 5/2017 |
| WO | WO-2017075759 A1 ‡ | 5/2017 |
| WO | WO-2017075827 A1 ‡ | 5/2017 |
| WO | WO-2017075883 A1 ‡ | 5/2017 |
| WO | WO-2017075975 A1 ‡ | 5/2017 |
| WO | WO-2017076247 A1 ‡ | 5/2017 |
| WO | WO-2017076590 A1 ‡ | 5/2017 |
| WO | WO-2017081480 A1 ‡ | 5/2017 |
| WO | WO-2017082728 A1 ‡ | 5/2017 |
| WO | WO-2017084107 A1 ‡ | 5/2017 |
| WO | WO-2017084488 A1 ‡ | 5/2017 |
| WO | WO-2017084489 A1 ‡ | 5/2017 |
| WO | WO-2017084818 A1 ‡ | 5/2017 |
| WO | WO-2017084848 A1 ‡ | 5/2017 |
| WO | WO-2017084849 A1 ‡ | 5/2017 |
| WO | WO-2017084920 A2 ‡ | 5/2017 |
| WO | WO-2017085240 A1 ‡ | 5/2017 |
| WO | WO-2017085242 A1 ‡ | 5/2017 |
| WO | WO-2017081176 A3 ‡ | 6/2017 |
| WO | WO-2017088660 A1 ‡ | 6/2017 |
| WO | WO-2017089931 A1 ‡ | 6/2017 |
| WO | WO-2017091926 A1 ‡ | 6/2017 |
| WO | WO-2017092144 A1 ‡ | 6/2017 |
| WO | WO-2017093452 A1 ‡ | 6/2017 |
| WO | WO-2017093535 A1 ‡ | 6/2017 |
| WO | WO-2017096512 A1 ‡ | 6/2017 |
| WO | WO-2017096971 A1 ‡ | 6/2017 |
| WO | WO-2017096988 A1 ‡ | 6/2017 |
| WO | WO-2017097172 A1 ‡ | 6/2017 |
| WO | WO-2017097173 A1 ‡ | 6/2017 |
| WO | WO-2017097821 A1 ‡ | 6/2017 |
| WO | WO-2017101030 A1 ‡ | 6/2017 |
| WO | WO-2017101058 A1 ‡ | 6/2017 |
| WO | WO-2017101705 A1 ‡ | 6/2017 |
| WO | WO-2017102633 A1 ‡ | 6/2017 |
| WO | WO-2017102686 A1 ‡ | 6/2017 |
| WO | WO-2017102969 A1 ‡ | 6/2017 |
| WO | WO-2017107546 A1 ‡ | 6/2017 |
| WO | WO-2017108268 A1 ‡ | 6/2017 |
| WO | WO-2017108392 A1 ‡ | 6/2017 |
| WO | WO-2017108394 A1 ‡ | 6/2017 |
| WO | WO-2017108429 A1 ‡ | 6/2017 |
| WO | WO-2017109448 A2 ‡ | 6/2017 |
| WO | WO-2017109868 A1 ‡ | 6/2017 |
| WO | WO-2017110713 A1 ‡ | 6/2017 |
| WO | WO-2017036426 A3 ‡ | 7/2017 |
| WO | WO-2017113106 A1 ‡ | 7/2017 |
| WO | WO-2017113513 A1 ‡ | 7/2017 |
| WO | WO-2017113845 A1 ‡ | 7/2017 |
| WO | WO-2017114389 A1 ‡ | 7/2017 |
| WO | WO-2017117725 A1 ‡ | 7/2017 |
| WO | WO-2017117742 A1 ‡ | 7/2017 |
| WO | WO-2017118135 A1 ‡ | 7/2017 |
| WO | WO-2017118138 A1 ‡ | 7/2017 |
| WO | WO-2017118347 A1 ‡ | 7/2017 |
| WO | WO-2017121156 A1 ‡ | 7/2017 |
| WO | WO-2017121253 A1 ‡ | 7/2017 |
| WO | WO-2017121296 A1 ‡ | 7/2017 |
| WO | WO-2017121546 A1 ‡ | 7/2017 |
| WO | WO-2017121979 A1 ‡ | 7/2017 |
| WO | WO-2017122196 A1 ‡ | 7/2017 |
| WO | WO-2017124419 A1 ‡ | 7/2017 |
| WO | WO-2017124662 A1 ‡ | 7/2017 |
| WO | WO-2017124957 A1 ‡ | 7/2017 |
| WO | 3165102 A3 ‡ | 8/2017 |
| WO | WO-2017128038 A1 ‡ | 8/2017 |
| WO | WO-2017130138 A1 | 8/2017 |
| WO | WO-2017133056 A1 ‡ | 8/2017 |
| WO | WO-2017137138 A1 ‡ | 8/2017 |
| WO | WO-2017137554 A1 ‡ | 8/2017 |
| WO | WO-2017139595 A1 | 8/2017 |
| WO | WO-2017139662 A1 | 8/2017 |
| WO | WO-2017139963 A1 ‡ | 8/2017 |
| WO | WO-2017141017 A1 ‡ | 8/2017 |

(56) References Cited

FOREIGN PATENT DOCUMENTS

| WO | WO-2017141018 A1 ‡ | 8/2017 |
|---|---|---|
| WO | WO-2017141358 A1 ‡ | 8/2017 |
| WO | WO-2017143494 A1 ‡ | 8/2017 |
| WO | WO-2017143495 A1 ‡ | 8/2017 |
| WO | WO-2017143515 A1 ‡ | 8/2017 |
| WO | WO-2017143865 A1 ‡ | 8/2017 |
| WO | WO-2017143953 A1 ‡ | 8/2017 |
| WO | WO-2017144400 A1 ‡ | 8/2017 |
| WO | WO-2017144861 A1 ‡ | 8/2017 |
| WO | WO-2017149288 A1 ‡ | 9/2017 |
| WO | WO-2017152481 A1 ‡ | 9/2017 |
| WO | WO-2017153051 A1 ‡ | 9/2017 |
| WO | WO-2017153270 A1 ‡ | 9/2017 |
| WO | WO-2017156694 A1 ‡ | 9/2017 |
| WO | WO-2017156695 A1 ‡ | 9/2017 |
| WO | WO-2017156696 A1 ‡ | 9/2017 |
| WO | WO-2017156733 A1 ‡ | 9/2017 |
| WO | WO-2017156743 A1 ‡ | 9/2017 |
| WO | WO-2017161715 A1 ‡ | 9/2017 |
| WO | WO-2017161725 A1 ‡ | 9/2017 |
| WO | WO-2017163044 A1 ‡ | 9/2017 |
| WO | WO-2017163045 A1 ‡ | 9/2017 |
| WO | WO-2017163046 A1 ‡ | 9/2017 |
| WO | WO-2017163047 A1 ‡ | 9/2017 |
| WO | WO-2017163050 A1 ‡ | 9/2017 |
| WO | WO-2017163051 A1 ‡ | 9/2017 |
| WO | WO-2017163052 A1 ‡ | 9/2017 |
| WO | WO-2017164474 A1 ‡ | 9/2017 |
| WO | WO-2017166263 A1 ‡ | 10/2017 |
| WO | WO-2017166334 A1 ‡ | 10/2017 |
| WO | WO-2017167169 A1 ‡ | 10/2017 |
| WO | WO-2017167513 A1 ‡ | 10/2017 |
| WO | WO-2017173669 A1 ‡ | 10/2017 |
| WO | WO-2017173947 A1 ‡ | 10/2017 |
| WO | WO-2017173951 A1 ‡ | 10/2017 |
| WO | WO-2017174754 A1 ‡ | 10/2017 |
| WO | WO-2017175166 A1 ‡ | 10/2017 |
| WO | WO-2017176111 A1 ‡ | 10/2017 |
| WO | WO-2017176113 A1 ‡ | 10/2017 |
| WO | WO-2017177897 A1 ‡ | 10/2017 |

OTHER PUBLICATIONS

"Guideline Accompanying Commission Regulation (EC) No. 1275/2008," Official Journal of the European Union, Oct. 2009.‡

"Lighter." Merriam-Webster Online Dictionary. 2009. Merriam-Webster Online. Jun. 8, 2009 [http://www.merriam-webster.com/dictionary/lighter.‡

AMB. Manual:TranX160/Rev.10-06. published 2004-2006.‡

Baker et al., "The pyrolysis of tobacco ingredients," J. Anal. Appl. Pyrolysis, vol. 71, pp. 223-311 (2004).‡

Bombick, et al. Chemical and biological studies of a new cigarette that primarily heats tobacco. Part 2. In vitro toxicology of mainstream smoke condensate. Food and Chemical Toxicology. 1997; 36:183-190.‡

Bombick, et al. Chemical and biological studies of a new cigarette that primarily heats tobacco. Part 3. In vitro toxicity of whole smoke. Food and Chemical Toxicology. 1998; 36:191-197.‡

Borgerding, et al. Chemical and biological studies of a new cigarette that primarily heats tobacco. Part 1. Chemical composition of mainstream smoke. Food and Chemical Toxicology; 1997; 36:169-182.‡

Breland, Alison, et al. "Electronic cigarettes: what are they and what do they do?." Annals of the New York Academy of Sciences 1394.1 (2017): 5-30.‡

Brown, Christopher J., and James M. Cheng. "Electronic cigarettes: product characterisation and design considerations." Tobacco control 23.suppl 2 (2014): ii4-ii10.‡

Bullen, et al., "Effect of an electronic nicotine delivery device (e cigarette) on desire to smoke and withdrawal, user preferences and nicotine delivery: randomized cross-over trial," Tobacco Control, 19(2), pp. 98-103. Apr. 2010.‡

Burch, et al., "Effect of pH on nicotine absorption and side effects produced by areosolized nicotine," Journal of Aerosol Medicine: Deposition, Clearance, and Effects in the Lung, 6(1), pp. 45-52. 1993.‡

Capponnetto, et al., "Successful smoking cessation with cigarettes in smokers with a documented history of recurring relapses: a case series," Journal of Medical Case Reports; 5(1), 6 pages. 2011.‡

Davis & Nielsen, "Marketing, Processing and Storage: Green Leaf Threshing and Redrying Tobacco," Tobacco Production, Chemistry and Technology, (1999) Section 10B, pp. 330-333, Bill Ward, Expert Leaf Tobacco Company, Wilson, North Carolina, USA.‡

E-Cigarette Forum; pg-gv-peg (discussion/posting); retrieved from the Internet: https://e-cigarette-forum.com/forum/threads/pg-vg-peg.177551; 7 pgs.; Apr. 8, 2011.‡

ECF; Any interest in determining nicotine—by DVAP; (https://www.e-cigarette-forum.com/forum/threads/any-interest-in-determining-nicotine-by-dvap.35922/); blog posts dated: 2009; 8 pgs.; print/retrieval date: Jul. 31, 2014.‡

Electronic Vaporization Device with Cartridge | JUUL Pod | JUUL Vapor, Posted Jun. 3, 2015, © 2015, Juulvapor.com, retrieved Nov. 24, 2015, https://www.'uulvapor.com/shopjuul/.‡

Electronic Vaporization Device/ Gizmodo Pax 2 Vaporizer/ Gizmodo; retrieved from http://gizmodo.com/pax-2-vaporizer-reviews-its-like-smoking-in-the-future-1718310779; posted Jul. 23, 2015, retrieved Oct. 17, 2016.‡

Farsalinos, et al., "Electronic cigarettes do not damage the heart," European Society of Cardiology, 4 pages, (http://www.escardio.org/The-ESC/Press-Office/Press-releases/Electronic-cigarettes-do-not-damage-the-heart). Aug. 25, 2012.‡

Farsalinos, Konstantinos E., et al. "Protocol proposal for, and evaluation of, consistency in nicotine delivery from the liquid to the aerosol of electronic cigarettes atomizers: regulatory implications." Addiction 111.6 (2016): 1069-1076.‡

FC Vaporizer Review Forum; Pax Vaporizer by Ploom; retrieved from: http://fuckcombustion.com/threads/pax-vaporizer-by-ploom.6223/; pp. 2 & 11 (2 pgs.); retrieval date: Nov. 16, 2015.‡

Flouris, et al., "Acute impact of active and passive electronic cigarette smoking on serum cotinine and lung function," Inhal. Toxicol., 25(2), pp. 91-101. Feb. 2013.‡

Food & Drug Administration; Warning letter to the Compounding Pharmacy, retrieved Oct. 10, 2014 from http://www.fda.gov/ICECI/EnforcementActions/WarningLetters/2002/ucm144843.htm, 3 pages. Apr. 9, 2002.‡

Goniewicz, et al., "Nicotine levels in electronic cigarettes," Nicotine Tobacco Research, 15(1), pp. 158-166, Jan. 2013.‡

Gregory, Andrew, "E-cigarettes to go on prescription under move to class them as medicines," Mirror, Jun. 12, 2013. http://www.mirror.co.uk/news/uk-news/e-cigarettes-go-prescription-under-move-1949018.‡

Grotenhermen, et al., Developing science-based per se limits for driving under the influence of cannabis (DUIC): findings and recommendations by an expert panel; retreived Feb. 9, 2017 from (http://www.canorml.org/healthfacts/DUICreport.2005.pdf); Sep. 2005.‡

Harvest Vapor, American Blend Tobacco (product info), retrieved from the internet (http://harvestvapor.com/), 2 pages. Oct. 10, 2014.‡

Hurt, et al., "Treating tobacco dependence in a medical setting," CA: A Cancer Journal for Clinicians, 59(5), pp. 314-326. Sep. 2009.‡

INCHEM; Benzoic Acid; JECFA Evaluation Summary; retrieved Oct. 10, 2014 from http://www.inchem.org/documents/'ecfa/feceval/'ec 184.htm, 2 pages. May 28, 2005.‡

INCHEM; Levulinic Acid; JECFA Evaluation Summary; retrieved Oct. 10, 2014 from http://www.inchem.org/documentslecfa/feceval/lec 1266.htm, 2 pages. Mar. 10, 2003.‡

INCHEM; Pyruvic Acid; JECFA Evaluation Summary; retrieved Oct. 10, 2014 from http://www.inchem.org/documents/ecfa/feceval/ec 2072.htm, 2 pages. Jan. 29, 2003.‡

INCHEM; Sorbic Acid; JECFA Evaluation Summary; retrieved Oct. 10, 2014 from http://www.inchem.org/documents/'ecfa/'eceval/'ec 2181.htm, 2 pages. May 29, 2005.‡

(56) References Cited

OTHER PUBLICATIONS

Ingebrethsen et al., "Electronic Cigarette aerosol particle size distribution measurements", Inhalation Toxicology, 2012; 24 (14): 976-984.‡
Kuo et al. Applications of Turbulent and Multiphase Combustion, Appendix D: Particle Size—U.S. Sieve Size and Tyler Screen Mesh Equivalents, 2012, p. 541-543.‡
McCann et al., "Detection of carcinogens as mutagens in the Salmonella/microsome test: Assay of 300 chemicals: discussion." Proct. Nat. Acad. Sci, USA, Mar. 1976, vol. 73 (3), 950-954.‡
MYLAPS, "Rechargeable Transponder Battery Status and Charging Instructions," Sep. 9, 2010.‡
Nicoli et al., Mammalian tumor xenografts induce neovascularization in Zebrafish embryos. Cancer Research, 67:2927-2931 (2007).‡
PAX Labs, Inc.; Juul product information © 2016; retrieved from https://www.juulvapor.com/shop-'uul; 6pgs.; retrieved Mar. 9, 2016.‡
Perfetti, "Structural study of nicotine salts," Beitrage Zur Tabakforschung International, Contributions to Tobacco Research, 12(2), pp. 43-54. Jun. 1983.‡
Poynton, Simon, et al. "A novel hybrid tobacco product that delivers a tobacco flavour note with vapour aerosol (part 1): Product operation and preliminary aerosol chemistry assessment." Food and Chemical Toxicology (2017).‡
Seeman, et al., "The form of nicotine in tobacco. Thermal transfer of nicotine and nicotine acid salts to nicotine in the gas phase," J Aric Food Chem, 47(12), pp. 5133-5145. Dec. 1999.‡
SRNT Subcommittee on Biochemical Verification, "Biochemical verification of tobacco use and cessation," Nicotine & Tobacco Research 4, pp. 149-159, 2002.‡
Torikai et al., "Effects of temperature, atmosphere and pH on the generation of smoke compounds during tobacco pyrolysis," Food and Chemical Toxicology 42 (2004) 1409-1417.‡
Vansickel, et al. "A clinical laboratory model for evaluating the acute effects of electronic cigarettes: Nicotine delivery profile and cardiovascular and subjective effects," Cancer Epidemiology Biomarkers Prevention, 19(9), pp. 1945-1953. Jul. 20, 2010.‡
Vansickel, et al., "Electronic cigarettes: effective nicotine delivery after acute administration," Nicotine & Tobacco Research, 15(1), pp. 267-270. Jan. 2013.‡
VapeWorld; Original PAX Vaporizers for Portable and Home Use; retrieved from: https://www.vapeworld.com/pax-vaporizer-by-ploom?gclid=CPCi1PKojskC- FU06gQodPr; 9 pgs.; retrieved Nov. 13, 2015.‡
Wells. "Glycerin as a Constituent of Cosmetics and Toilet Preparations." Journal of Society of Cosmetic Chemists, 1958; 9(1): 19-25.‡
Williams, Monique, and Prue Talbot. "Variability among electronic cigarettes in the pressure drop, airflow rate, and aerosol production." Nicotine & Tobacco Research 13.12 (2011).‡
YouTube; Firefly Vaporizor Review w/ Usage Tips by the Vape Critic; retrieved from the internet (http://www.youtube.com/watch?v=1J38N0AV7w1); published Dec. 10, 2013; download/ print date: Feb. 18, 2015.‡
Youtube; Pax by Ploom Vaporizer Review; posted Aug. 14, 2013, retrieved Sep. 8, 2016, https://www.youtube.com/watch?v=Jm06zW3-cxQ.‡
Zhang, et al., "In vitro partical size distributions in electronic and conventional cigarette aerosols suggest comparable deposition patterns," Nicotine Tobacci Research, 15(2), pp. 501508. Feb. 2013.‡
"2011 New E-Cigarette GS-360With 1.2ml Clearomizer(Id:5861467) Product Details—View 2011 New E-Cigarette GS-360With 1.2m1Clearomizer from Green Sound High-Tech Co.Ltd-EC21." EC21 Global B2B Marketplace—Connecting Global Buyers with Manufacturers Suppliers Exporters Worldwide (2011) wo1138.en.ec21.com/2011_New_E-Cigarette_GS-360_With--5366965_5861467.html.
"Electronic Cigarette Refillable Cartridge GS-PUSHHold 1.5ml(Id:5722612) Product Details—View Electronic Cigarette Refillable Cartridge GS-PUSHHold 1.5ml from Green Sound High-Tech Co.Ltd-EC21." EC21 Global B2B Marketplace—Connecting Global Buyers with Manufacturers Suppliers Exporters Worldwide (2011) wo1138.en.ec21.com/Electronic_Cigarette_Refillable_Cartridge_GS--5366965_5722612.html.
"Esteam and J-Series Owner's Manual." Allbrands.com, 2002, www.allbrands.com/misc_files/pdfs/JiffySteamerOwnersManual.pdf.
"Hacking the Vuse E-Cig to Fully Use Cartridges and Allow Refills," Hacking the Vuse E-Cig to Fully Use Cartridges and Allow Refills, Oct. 16, 2015, se.azinstall.net/2015/10/hacking-vuse-e-cig-puff-counter.html?m=1.
"Lenmar CB0104 Battery for Panasonic Cordless Phones." Amazon, Amazon, first reviewed Jan. 5, 2011, www.amazon.com/Lenmar-CB0104-Battery-Panasonic-Cordless/dp/B000BS6078/.
"New Tank E-Cigarette:innokin 510T." From China Manufacturer, Manufactory, Factory and Supplier on ECVV.com, Nov. 15, 2011, www.ecvv.com.product/3118191.html.
"Terminal and Splices Selection Guide." TE.com, TE, 2013, www.te.com/commerce/DocumentDelivery/DDEController?Action=srchrtv& DocNm=2-1773700-5TerminalAndSplicesSelection &DocType=DS?DocLang=English&s_cid=1046.
"Uniden BT-990 Cordless Phone Battery Ni-CD, 3.6 Volt, 800 MAh—Ultra Hi-Capacity—Replacement for Uniden BP-990, Toshiba, GE TL96550, TL96556, Panasonic HHR-P505 Rechargeable Batteries," Amazon, Amazon, first reviewed on Feb. 8, 2017, www.amazon.com/Uniden-BT-990-Cordless-Phone-Battery/dp/B01HDV75YW.
513official4. "Glade Plug-Ins Scented Oils 2011." YouTube, YouTube, Jun. 29, 2011, www.youtube.com/watch?v=zW9acp4NOK8.
CannabisReviewTV™. "Official: Cloud Vape Pen Review #CRTV420." YouTube, YouTube, Apr. 17, 2013, www.youtube.com/watch?v=oujMMZ6I_tA&has_verified=1.
Chinabuye. "Innokin ITaste VV Tank Starter Kit Electronic Cigarette with Clearomizer." YouTube, YouTube, Jul. 23, 2013, www.youtube.com/watch?v=mz414d8MU20.
Cloud pen vaporizer unboxing review by vaporizer blog // VaporizeBlog.com, https://www.youtube.com/watch?v=ixHMkXoWKNg.
cutlerylover. "Electronic Cigarette (Vaping) Review: HALO G6 Basic Starter Kit." YouTube, YouTube, Oct. 10, 2012, www.youtube.com.watch?v=kUprxsQUPCU.
Darth Vapor Reviews, "Halo Cigs: Triton Starter Kit Review." YouTube, YouTube, Aug. 11, 2013, www.youtube.com/watch?v=KkVzsGsDDMY.
El Mono Vapeador. "EVic Joyetech—Revision." YouTube YouTube Dec. 12, 2012 www.youtube.com/watch?v=WNLVfgwb4Gs.
Following the Vapor Trail, https://www.nytimes.com/2013/12/19/fashion/for-vaporizers-new-technology-and-product-design.html.
Frakes, Dan. "Lightning: the IPhone's New Connector." Macworld, Macworld, Sep. 13, 2012, www.macworld.com/article/1168555/what-apples-new-lightning-connector-means-for-you.html.
Glory Vapes. "Glory Vapes TV: Kanger S1 Cubica Series Starter Kit Unboxing." YouTube, YouTube, Aug. 8, 2013, www.youtube.com/watch?v=NQjvJ6YhdbA.
infocentre101. "Jiffy Steamer . . . No1 Seller." YouTube, YouTube, Dec. 31, 2011, www.youtube.com/watch?v=9ge8phdU6WY.
iWand Rectangular Pen Shape Design Flat Short Mouth Holder 1.0ML Tank Atomizer LED Display 800mAh Rechargeable E-Cigarette Set—Colorful, https://www.gearbest.com/electronic-cigarettes/pp_15466.html.
Joye eGo-Tank System XXL 1000mAh Starter Kit, https://www.myvaporstore.com/eGo-Tank-System-XXL-1000mAh-Starter-Kit-p/ego-t-xxlkit.htm.
Marino, Michelle. "Review—Glade PlugIns Scented Oil Fragrancers." YouTube, YouTube, Feb. 18, 2013, www.youtube.com/watch?v=lzEpGdwKSA4.
Prater, Bill. "Crown Seven Hydro Imperial Menthol Review." YouTube, YouTube, Jan. 12, 2013, www.youtube.com/watch?v=YT-ycf6mEa0.
Purity Home Fragrance—How to refill your plug in air freshener.wmv, https://www.youtube.com/watch?v=OreNgPBUwaY&t=66s.
Rose Plastic. Rose Plastic: Innovations in Plastic Packaging, www.rose-plastic./2030.0.html?&L=4p?id=2337id=2345iel25% worldwide unique plastic packaging with remarkable diversity, retrieved Mar. 17, 2019.

(56) References Cited

OTHER PUBLICATIONS ruyanchina. "RUYAN—The New Way to Smoke(English) E-Cigarette-Blog.com." YouTube, YouTube, Jun. 9, 2007, www.youtube.com/watch?v=ia2997x_kog.
Smith, Chris. "Next USB Connector Will Finally Be Reversible, like Apple's Lightning Plug." BGR, Dec. 5, 2013, bgr.com/2013/12/05/reversible-usb-connector-apple-lightning/.
SourDieselManCO. "O.pen Vape Pen Vaporizer Hybrid and Indica 250mg Cartridges." YouTube, YouTube, Apr. 8, 2013, www.youtube.com/watch?v=5_jWTQVQbEw.
TechVitaminsTV. "E-Cigarettes: How It Works (Blu Premium E-Cig Social Kit Review) Must See!!" YouTube, YouTube, Mar. 14, 2012, www.youtube.com/watch?v=mFAYxw6csjg.
VapeandBake. "NJOY Electronic Cigarette Review." YouTube, YouTube, Apr. 9, 2013, www.youtube.com/watch?v=qUynQFK_Xpo.
Vaporizers Reviewed. "AtmosRX Optimus 510 Vaporizer Review." YouTube, YouTube, Oct. 10, 2013, www.youtube.com/watch?v=wsyQncG8FB8.
VapXtream. "The Elips by LSK." YouTube, YouTube, Jan. 13, 2013, www.youtube.com/watch?v=PTfJlsrfqWI.
Engadget. *Juul is the e-cig that will finally stop me from smoking (I hope)*. [online], published on Jun. 3, 2015. Available at: https://www.engadget.com/2015/06/03/pax-labs-juul-ecigarette/#/.
Pierce, D. *This Might Just Be the First Great E-Cig*. {online} Wired, Published on Apr. 21, 2015. Available at: https://www.wired.com/2015/04/pax-juul-ecig/?mbid=social_twitter.
The Verge. *Startup behind the Lambo of vaporizers just launched an intelligent e-cigarette*. [online], published on Apr. 21, 2015. Available at: https://www.theverge.com/2015/4/21/8458629/pax-labs-e-cigarette-juul.
EnsembleIQ "Vuse Product Reel" Youtube Jun. 6 2013 https://www.youtube.com/watch?v=lgo_bBY8tNM.
Maiocco Roberto. "Modello IWand." YouTube YouTube Dec. 28, 2012 www.youtube.com/watch?v=_brQOLDqHX0.
Press Release by R.J. Reynolds https://www.reynoldsamerican.com/about-us/press-releases/Press-Release-Details-/2013/RJ-Reynolds-Vapor-Company-bringing-VUSE-Digital-Vapor-Cigarette-to-Colorado-/default.aspx Jun. 6 2013.
Uptoyou Fromeme. "Elips Ego Sole Electronic Cigarette Kit Patent Elipse Flat Upgrade F6 Section with Atomizer CE4." YouTube YouTube Sep. 12, 2013 www.youtube.com/watch?v=cnPcqDzFm0Q.
Uptoyou Fromeme. "F8 iWand Penstyle Adjustable Voltage Itaste VV Power Display Electronic Cigarette." YouTube Sep. 25, 2013. www.youtube.com/watch?v=5nqtHWJvWWo.
Vaporizers Reviewed. "MicroG Pen Vaporizer Review." YouTube YouTube Nov. 6, 2013 www.youtube.com/watch?v=pLhtL8vosrs.
Wholesale Consumer electronics. "Elips Ego Sole Electronic Cigarette Kit Patent E-Cigarette E-Cig Elipse Flat Upgrade F6 Section." YouTube YouTube Sep. 13, 2013 www.youtube.com/watch?v=iCeE-O1scDg.

\* cited by examiner
‡ imported from a related application

FIG. 5A
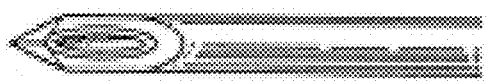
Quincke
FIG. 5B
FIG. 6A
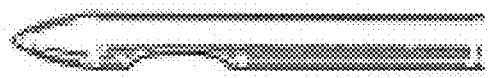
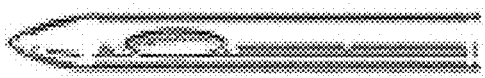
Sprotte
FIG. 6B
FIG. 7A
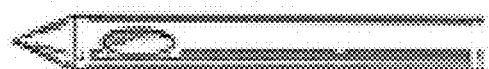
Whitacre
FIG. 7B

FILLABLE VAPORIZER CARTRIDGE AND METHOD OF FILLING

CROSS REFERENCE TO RELATED APPLICATIONS

This application is a continuation of U.S. patent application Ser. No. 15/430,284, filed on Feb. 10, 2017 and titled "FILLABLE VAPORIZER CARTRIDGE AND METHOD OF FILLING," which claims priority to U.S. provisional application No. 62/294,285, filed on Feb. 11, 2016 and titled "FILLABLE ELECTRONIC CIGARETTE CARTRIDGE AND METHOD OF FILLING," each of which are incorporated herein by reference in their entirety.

This application may be related to or may be used with the inventions in one or more of the following patent applications: U.S. patent application Ser. No. 14/578,193, filed on Dec. 19, 2014 and titled "METHOD AND SYSTEM FOR VAPORIZATION OF A SUBSTANCE"; U.S. patent application Ser. No. 14/625,042, filed on Feb. 18, 2015, and titled "AEROSOL DEVICES AND METHODS FOR INHALING A SUBSTANCE AND USES THEREOF"; U.S. patent application Ser. No. 13/837,438, filed on Mar. 15, 2013, and titled "LOW TEMPERATURE ELECTRONIC VAPORIZATION DEVICE AND METHODS"; U.S. patent application Ser. No. 14/271,071, filed on May 6, 2014, and titled "NICOTINE SALT FORMULATIONS FOR AEROSOL DEVICES AND METHODS THEREOF"; U.S. patent application Ser. No. 14/304,847, filed on Jun. 13, 2014, and titled "MULTIPLE HEATING ELEMENTS WITH SEPARATE VAPORIZABLE MATERIALS IN AN ELECTRIC VAPORIZATION DEVICE"; U.S. patent application Ser. No. 14/461,284, filed on Aug. 15, 2014 and titled "METHODS AND DEVICES FOR DELIVERING AND MONITORING OF TOBACCO, NICOTINE, OR OTHER SUBSTANCES"; U.S. patent application Ser. No. 14/581,666, filed on Dec. 23, 2014, and titled "VAPORIZATION DEVICE SYSTEMS AND METHODS"; PCT Patent Application No. PCT/US2015/031152, filed on May 15, 2015, and titled "SYSTEMS AND METHODS FOR AEROSOLIZING A SMOKEABLE MATERIAL"; PCT Patent Application No. PCT/US2014/064690, filed on Nov. 7, 2014, and titled "NICOTINE LIQUID FORMULATIONS FOR AEROSOL DEVICES AND METHODS THEREOF"; U.S. patent application Ser. No. 14/960,259, filed on Dec. 4, 2015, and titled "CALIBRATED DOSE CONTROL". Each of these applications is herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This invention relates to electronic cigarette cartridges, and in particular to cartridges and methods of filling of electronic cartridges.

BACKGROUND

Electronic cigarettes and cartridges that contain their vaporizable liquid in a "tank" structure or reservoir have performance and usability advantages over those which hold the liquid inside of a sponge or other medium. Unfortunately, tank-type cigarettes and cartridges have some unique difficulties associated with filling them. These problems are particularly acute because of the need for a porous wick that is in contact with the tank in the cartridge and/or electronic cigarette.

For example, tank-type cartridges may leak when subjected to a change in atmospheric pressure (such as may occur during air shipment), which can cause liquid to leak through the necessary porous wick, due to expansion of any captive air. If the cartridge could be filled completely with no captive air, this issue can be eliminated, at least at the time of initial shipment. As a result there is significant incentive to attempt to fill the cartridge as completely as possible.

There are currently two main approaches to filling a tank-type cartridge. The first approach is to make use of one or more elastomeric "plug" components that are removed and leave sufficient clearance at the time of filling that any air that is captured in the cartridge is able to freely vent through the same hole or holes that liquid is being added to. A secondary operation is required to install the plug, along with in many cases an additional cosmetic part that conceals the plug.

Unfortunately, the approach of filling with a plug part removed has a few problems. First, it requires that the cartridge be partially disassembled at the time of filling. This can result in supply chain complexity of shipping components separately as well as additional costs associated with the additional capping operation, especially if the cartridges are assembled in different locations as is often the case where it may be cheaper to manufacture in a first location and assemble in a second location. Second, a plug may potentially take up volume in the cartridge, and finally, inserting the cap my itself displace fluid and introduce air; inserting the plug may force the displaced volume of liquid through the porous wick to the outside of the tank area. The non-zero time between the filling operation and the capping operation can create a potential failure mode where liquid is allowed to slowly leak out through the wick without the negative backpressure provided by the sealed reservoir. The amount of liquid that can leak through during even a controlled time frame is a function of the viscosity of the liquid (which can be variable based on the liquid used) and therefore can be difficult to control.

The second approach, discussed in patent application no. WO2015028815 A1, is to use a sufficiently large elastomeric component of sufficiently low durometer that it can be pierced simultaneously by two hypodermic style needles whose pierce sites will reseal sufficiently after the needles are removed. This approach assumes an effective seal between the elastomeric component and the filling needle but requires a second, venting needle. One needle is described as being the inlet for liquid into the interior of the cartridge, while the other for the evacuation of the air that is inside the cartridge before filling. This approach allows the cartridges to be fully assembled at the time of fill.

Although this two needle approach may alleviate the need to perform a separate capping operation, it also has issues in terms of its ability to fill the cartridge completely and with a precise volume of liquid. Each pierce location is a potential failure site in the final product, and thus using a secondary vent pierce site doubles the chance of a problem with the final product and during the piercing process. In addition, if passive venting is chosen through the second needle, the level of fill must be sufficiently low to prevent liquid ever reaching the second needle, because although air can easily vent through the small diameter needle; liquid in the needle constitutes a significant blockage. Once liquid enters the second needle, air may no longer flow, even if still trapped within the electronic cigarette or cartridge reservoir. If active venting is chosen, there is a similar risk that the vacuum will pull liquid out of the cartridge, causing waste and introducing additional randomness to the final fill volume.

Finally, in all cases the secondary vent pierce limits how full the container can be filled since the needle has to pierce sufficiently deeply to ensure that it's opening is fully below the surface of the elastomeric component, which inherently means that there is some cavity of air left above it that can never be displaced. This issue persists even if a production method is created that can tolerate the liquid front reaching all the way to the vent location. Once the liquid front reaches the vent location any incremental liquid added to the system either gets forced through the vents or through the porous wick to the outside of the tank.

For example, FIGS. 1A-1G illustrate the use of the current two-needle approach and its shortcomings. In this example, the cartridge includes an elastomeric cap, and is preassembled with the wick, polymeric reservoir (rigid tank), and elastomeric (piercible) resealable cap. In FIG. 1A the assembled cartridge is ready to be filled by receiving the needles. In FIG. 1B the needle pierces the elastomeric cap to a distance that is large enough to ensure that the needle opening is exposed and open within the cartridge, then begins to fill. In FIG. 1C, the front of liquid being filled reaches one end of the cartridge and one side of the wick. In FIG. 1D the liquid front has occluded both sides of the porous wick. In FIG. 1E the liquid front has risen until it is nearly at the vent needle. This may be an ideal time to stop if (e.g., passive filling) the needle will clog and stop passing air once fluid contacts it (e.g., cannot tolerate liquid in the vent line). In FIG. 1F the liquid front has occluded all of the vent locations, and any incremental liquid pumped into the cartridge past this point (even with active venting through the vent needle) will either pass through the vent needle or leak out of the porous wick. No additional air can be displaced. Finally in FIG. 1G, once no more liquid can be added to the system, the needles are retracted and the filling is complete, leaving a substantial amount of captive air.

Thus, there is a need for methods and apparatuses (e.g., cartridges, filling devices and the like) for filling electronic cigarette and/or cartridge reservoirs so that they do not trap any air within the otherwise sealed reservoir, and particularly in reservoirs including a porous wick. Described herein are methods and apparatuses to address this need.

SUMMARY OF THE DISCLOSURE

Described herein are apparatuses including tanks to be filled with a vaporizable liquid and methods of filing them. Also described are systems for filling one or a plurality of cartridges having tanks without entrapping air within the tank volume. For example, described herein are methods of filling a tank volume of a cartridge for an electronic cigarette from a bottom or side surface opposite a wick so that the wick remains at least partially dry and can vent air during filling until the tank volume is full.

A method of filling a tank volume of an electronic cigarette cartridge with a liquid vaporizable material, wherein the cartridge includes a porous wick at a first end of the tank volume, may include: positioning the cartridge on a surface so that the porous wick is positioned on a top or side surface; inserting a needle into the tank volume from a bottom or side surface, opposite from the porous wick; injecting a vaporizable liquid into the tank volume; and venting air out of the tank through the porous wick until the tank volume is full of the vaporizable liquid and no air is entrapped within the tank volume.

A method of filling a tank volume of an electronic cigarette cartridge with a liquid vaporizable material, wherein the cartridge includes a porous wick at a first end of the tank volume, may include: positioning the cartridge on a surface so that the porous wick is oriented on a top opposite from the surface; inserting a needle into the tank volume from a bottom of the cartridge, opposite from the porous wick; injecting a vaporizable liquid into the tank volume through the needle; and venting air out of the tank through the porous wick as the tank volume fills, until the tank volume is full of the vaporizable liquid and no air is entrapped within the tank volume.

A method of filling a tank volume of an electronic cigarette cartridge with a liquid vaporizable material, wherein the cartridge includes a porous wick at a first end of the tank volume, may include: positioning the cartridge on a surface so that the porous wick is positioned on a side above the surface; inserting a needle into the tank volume from a side of the cartridge that is opposite from the porous wick; injecting a vaporizable liquid into the tank volume through the needle; and venting air out of the tank through the porous wick as the tank volume fills, until the tank volume is full of the vaporizable liquid and no air is entrapped within the tank volume.

In any of the methods described herein, the cartridge may be positioned flat against the surface, on a long side, on a short side, or on its top. In general the cartridges described herein may be rectangular in outer cross-section.

Any appropriate needle may be used. For example, the needle may have a beveled distal tip and a front-facing aperture. The needle may have a beveled distal tip and one or more side-facing aperture(s). The needle may be blunt.

Inserting the needle may include inserting through a septum, such as an elastomeric top or side. In some variations, inserting the needle may include inserting the needle through a pre-cut port or valve.

In any of the methods described herein, the temperature of the material being filled and/or the temperature of the filling device (including the needle(s), surface, stage or stand onto which the cartridges are held) or all or part of the cartridge itself (including just the tank and any internal components of the tank) may regulated by heating and/or warming. For example, when filling with a viscous material, the material may be warmed to lower the viscosity and/or cooled within the tank to increase the viscosity.

In general, the vaporizable liquid may comprise any appropriate material, including nicotine solutions (e.g., the vaporizable liquid may be a nicotine salt in an aqueous solution), a cannabis liquid (e.g., including a viscous cannabis-containing material), or any other pharmaceutical material. For example, the vaporizable material may contain a medicinal compound as an active ingredient. The medicinal compounds that are active ingredients for vaporization with the electronic vaporizer device utilizing the method herein, include drugs that can be heated without combustion to vaporization for inhalation delivery at a temperature range of, e.g., about 100° C. (e.g., for water-based carriers, e.g., about 100° C., 105° C., 110° C., 120° C., 130° C., 140° C., 150° C., 160° C., 170° C., etc.; for ethanol-based formulations, e.g., about 50° C., about 60° C., about 70° C., about 80° C., etc.) to about (e.g., below) the temperature at which the active ingredient thermally decomposes (e.g., less than about 150° C., 160° C., 170° C., 180° C., 190° C., 200° C., 210° C., 220° C., 230° C., 240° C., 250° C., 260° C., 270° C., 280° C., 290° C., 300° C., etc.). In certain embodiments, the drugs can be neat or are solubilized in a pharmaceutically acceptable solvent. In certain embodiments, the drugs can include over the counter (OTC) substances as aides for various ailments; wherein said drugs can include known respiratory aides for asthma or chronic obstructive pulmonary disease (COPD). The vaporizable materials that are active ingredients for vaporization with the device(s) herein described, can include drugs that can be heated to vaporization for inhalation delivery, without combustion; wherein said drugs can include over the counter (OTC) substances from the group comprising upper respiratory aides (like cetirizine), analgesics and internal medication aides (like ibuprofen, naproxen), heartburn aides (like omeprazole), sleeping aides (like doxylamine, diphenhydramine, melatonin), or motion sickness aides (like meclizine). In certain embodiments, the vaporizable material can contain respiratory aides for asthma or chronic obstructive pulmonary disease (COPD) such as short acting beta-agonist (like albuterol, levalbuterol, pirbuterol), long acting beta-agonist (like salmeterol, formoterol), anti-cholinergics (like atropine sulfate, ipratropium bromide), leukotriene modifiers (like montelukast, zafirlukast), cartico-steriods (like fluticasone, budesonide, mometasone), theophylline (like theophylline), or combination corticosteroid and beta agonist, long lasting (fluticasone and salmeterol, budesonide and formoterol, mometasone and formoterol). In certain embodiments, the vaporizable material can contain botanicals and/or nutraceuticals such as tea (polyphenols, flavonoids, green tea catechins +/- caffeine); horehound (phenol flavonoid glycosides, labdane diterpenoids, yohimbe, cranberry/grape (proanthocyanidins), black cohosh (terpene glycoside fraction (actine/cimifugoside), flax seed (omega fatty acids), echinacea (echinacoside), valerian (alkaloids, gabapentin, isovaleric acid, terpenes), senna (senna cglycosides), cinnamon (cinnamaldehyde, phenols, terpenes), vitamin D, saw palmetto (fatty acids), or caffeine. In certain embodiments, the vaporizable material is soluble to at least fifty percent by weight in any suitable carrier solvent such as glycols (such as propylene glycol and vegetable glycerin), ethylene glycol, dipropylene glycol, trimethylene glycol, ethanol, and combinations thereof. In certain embodiments, the medicinal compound is terpinolene. In certain embodiments, the medicinal compound is Linalool. In certain embodiments, the medicinal compound is phytol. In certain embodiments, the medicinal compound is beta myrcene. In certain embodiments, the medicinal compound is citronellol. In certain embodiments, the medicinal compound is caryophyllene oxide. In certain embodiments, the medicinal compound is alpha pinene. In certain embodiments, the medicinal compound is limonene. In certain embodiments, the medicinal compound is beta caryophyllene. In certain embodiments, the medicinal compound is humulene. In certain embodiments, the vaporizable material is an essential oil.

In any of these variations, the vaporizable liquid may be injected into the tank volume at any appropriate rate. For example, the vaporizable liquid may be injected into the tank volume at between about 0.1 ml/sec and 5 ml/sec, 0.5 ml/sec and 2 ml/sec, about 1 ml/sec, etc. (e.g., ata rate between a lower value in ml/sec of 0.05, 0.06, 0.07, 0.08, 0.09, 0.1, 0.2, 0.3, 0.4, 0.5, 0.6, 0.7, 0.8, 0.9 1.0, 1.1, 1.2, 1.3, 1.4, 1.5, 1.6, 1.7, 1.8, 1.9, 2, 3, 4, 5, 6, 7, 8, 9, 10, 12, 15, etc. and an upper value in ml/sec of 0.5, 0.6, 0.7, 0.8, 0.9 1.0, 1.1, 1.2, 1.3, 1.4, 1.5, 1.6, 1.7, 1.8, 1.9, 2, 3, 4, 5, 6, 7, 8, 9, 10, 12, 15, 20, etc. where the lower value is always less than the upper value).

In any of these variations, and particularly when the cartridge is oriented on its side and injected from the side, it may be beneficial for the tank volume to include one or more obstructions within the tank volume. The obstruction (e.g., central tube or cannula passing through the tank volume) may form sub-regions within the tank volume the preferentially fill first, without entrapping air, and allow the tank volume to be filled at high rates (e.g., between about 0.5 ml/sec and 2 ml/sec, greater than 0.5 ml/sec, etc.) without entrapping air within the tank volume.

In general, any of these methods may include keeping at least a portion of the wick that is within the tank dry until there is no air entrapped within the tank volume.

Once the filling is complete, the needle may be withdrawn. In any of these methods the needle may be reoriented, including rotating and/or moving laterally (further into or partially out of the tank volume) during filling to direct the filling and prevent entrapment of air.

In any of these variations, the method may be done in parallel to simultaneously fill a large number of cartridges. For example, the method may include positioning a plurality of cartridges in parallel and concurrently inserting a plurality of needles into each of the cartridges, and concurrently injecting the vaporizable liquid into each of the cartridges.

BRIEF DESCRIPTION OF THE DRAWINGS

FIGS. 5A and 5B illustrate side and top views, respectively, of one variation of a filling needle.

FIGS. 6A and 6B illustrate side and top views, respectively, of one variation of a filling.

FIGS. 7A and 7B illustrate side and top views, respectively, of one variation of a filling needle.

DETAILED DESCRIPTION

Described herein are methods of filling a reservoir of an electronic cigarette or cartridge for an electronic cigarette so that air is not trapped within the cartridge. In particular, described herein are methods of filing a reservoir for an electronic cigarette including a porous wick extending out of the reservoir at a first end, without leakage, or overflow, until there is no air within the reservoir.

Figures 1A, 1B, 1C, 1D, 1E, 1F, 1G:
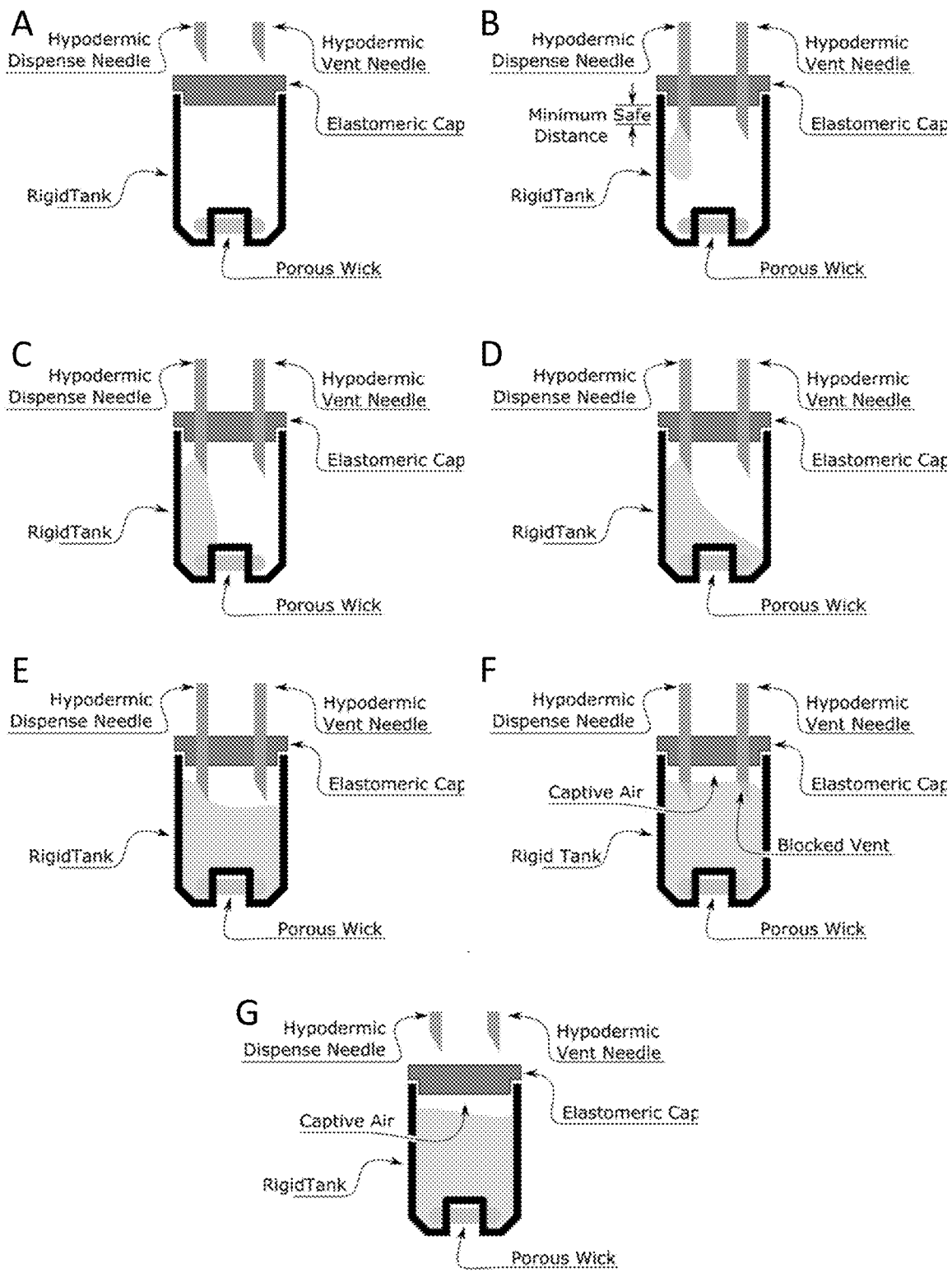
FIGS. 1A-1G illustrate a prior art method for filling a reservoir of an electronic cigarette cartridge which traps air within the cartridge.
Figure 2:
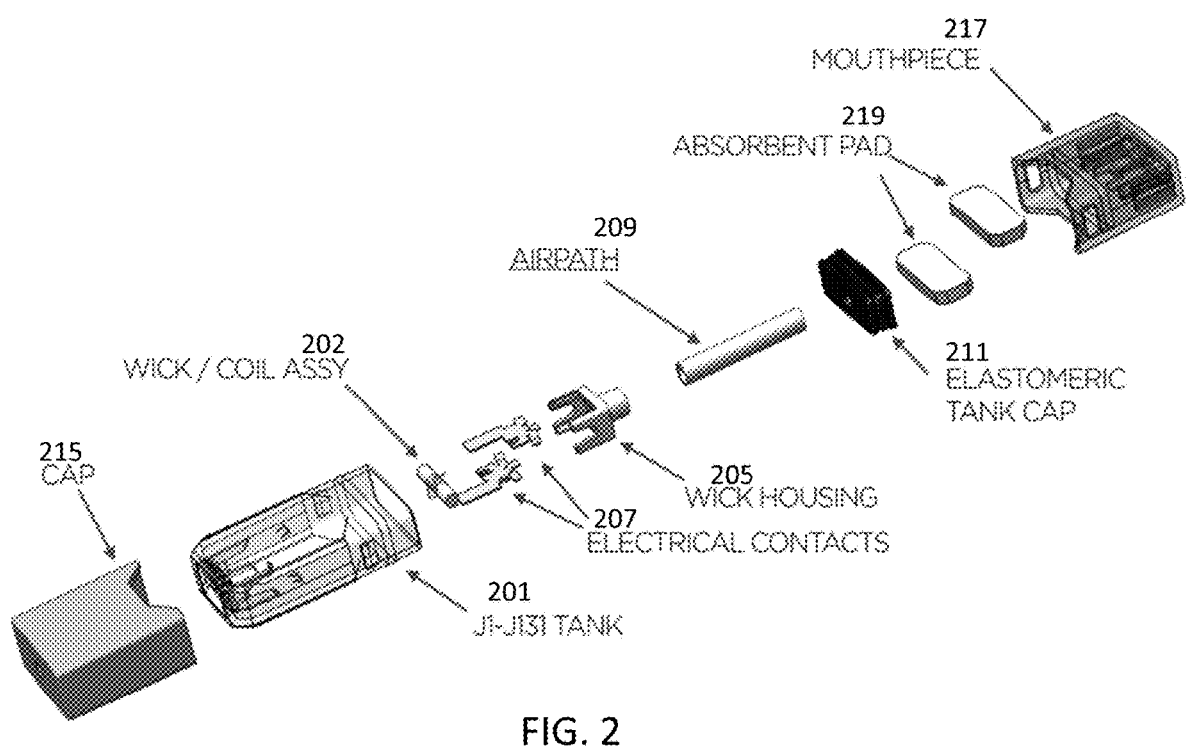
FIG. 2 is an exploded view of one example of a cartridge, including a reservoir, for an electronic cigarette.

In any of the variations described herein, the reservoir being filled may be a cartridge which may be filled vaporizable material (e.g., an aqueous solution of tobacco or any other liquid solution). For example, FIG. 2 shows one example of a cartridge including a reservoir that may be filled as described herein. FIGS. 1A-1G show a schematic illustration of another example of cartridge. In general a cartridge may include a reservoir into which fluid may be filled, a tank 201 (housing the reservoir), an elastomeric cap, and a porous wick at one end of the tank, which passes from within the tank to an external surface. The porous wick may be any appropriate material, including woven, braided, fibrous, and knitted materials. The wick may be coupled with or integral with a heating element. For example, a wire for resistive heating may be wrapped around an external portion of the wick, forming a wick/coil assembly 205 as shown in FIG. 2. The wick may be any appropriate material, including metals, polymers, natural fibers, synthetic fibers, or combinations of these. The wick is porous and provides a capillary pathway for fluid within the tank through and into the wick; the capillary pathway is generally large enough to permit wicking of sufficient material to replace vaporized liquid transferred from the tank by capillary action (wicking) during use of the electronic cigarette, but may be small enough to prevent leakage of the vaporizable fluid material out of the cartridge during normal operation, including when applying pressure (e.g., squeezing) the cartridge. The external portion of the wick may include a wick housing 205. The wick housing and/or wick may be treated to prevent leakage. For example, the wick and/or wick housing may be coated after filling to prevent leakage and/or evaporation through the wick until activated by connecting to an electronic cigarette and/or applying current through the electrical contacts 207 (e.g., operation in an electronic cigarette), or otherwise using the cartridge. Any appropriate coating may be used, including a heat-vaporizable coating (e.g., a wax or other material), a frangible material, or the like.

The cartridge may also include an air path through the tank (shown as a tube 209 in FIG. 2), which may at least partially partition the volume of the tank. The tank may include an elastomeric portion, such as all or a portion of the side, bottom, top, etc. In FIG. 2, the tank is covered by an elastomeric cap 211 (elastomeric tank cap). The elastomeric portion (e.g., cap) may, in some variations, be on an opposite side from the wick.

In the variation shown in FIG. 2, the cartridge including the tank also include a cover (cap 215) and is configured to be used as a mouthpiece, so includes a mouthpiece portion 217 that is separated from the tank 201 by one or more absorbent pads 219.

In general, the methods described herein may include filling the tank (e.g. of a cartridge) that includes a wick at one end. The method may generally include positioning the empty and fully assembled tank (e.g. cartridge) so that it may be filled by a single needle that is inserted from the bottom or side (but not the top) of the empty tank. For example, the tank may be held on its side or upside down.

Figure 3A:
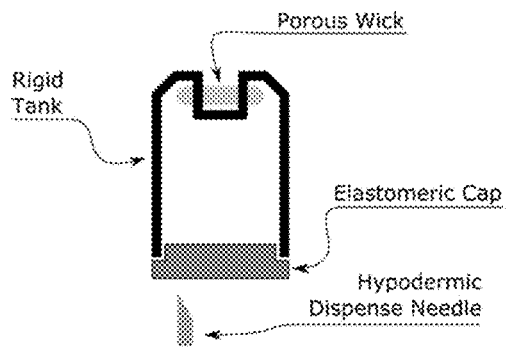
FIGS. 3A-3F illustrate a method filling a reservoir of a cartridge, similar to the cartridge shown in FIG. 2, of an electronic cigarette with a single needle.
Figure 3B:
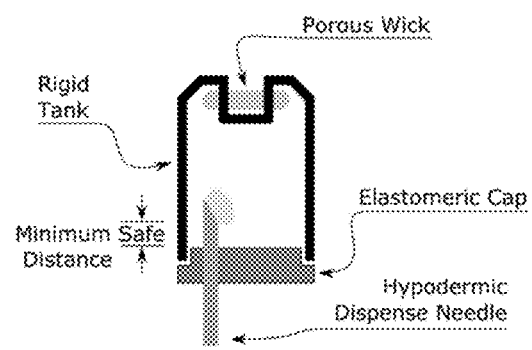
Figure 3C:
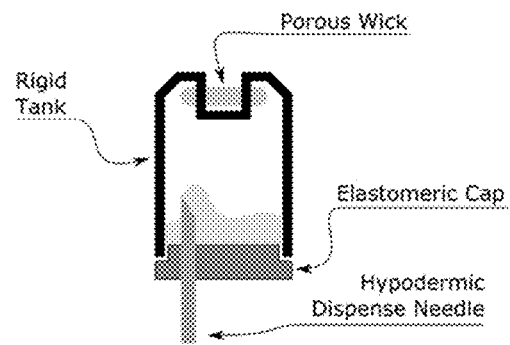
Figure 3D:
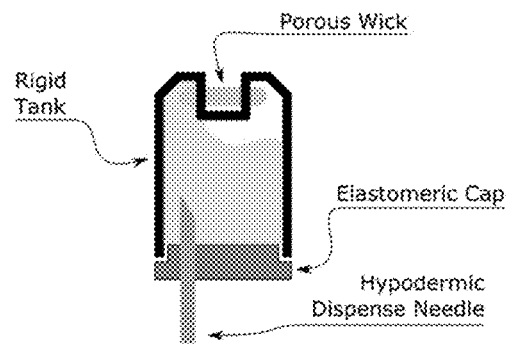
Figure 3E:
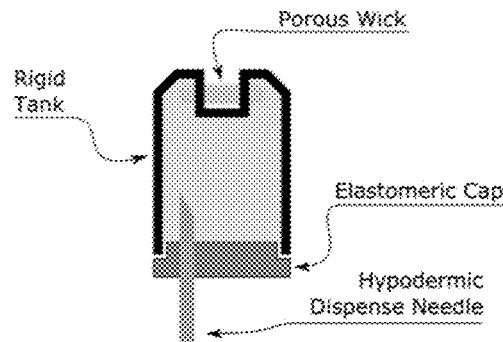
Figure 3F:
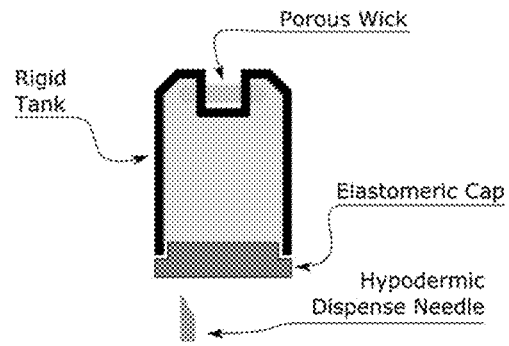

For example, FIGS. 3A-3F illustrate one example of filling as described herein, in which the tank is filled from a needle inserted into the bottom or lateral sides (where the lateral sides are not the top). In FIGS. 3A-3F, the filling system (e.g., needle, etc.) is inverted with respect to gravity so that the wick is not on the bottom. In FIG. 3A, the cartridge is ready to accept the dispensing needle through the elastomeric cap. During the first phase of fill liquid falls down around the needle that is injecting the liquid into the reservoir, immediately filling the reservoir in a way that the "additional vent" approach (shown in FIGS. 1A-1G) cannot. As filling progresses, air is displaced through the silica wick, at the top of the container in this example; the wick is dry, as shown in FIGS. 3B-3D. In FIG. 3B, the filling needle ("fill needle") pierces the elastomeric cap and begins dispensing. In this example a minimum safe distance for filling (e.g., the distance from the tip of the fill needle to the bottom of the opening of the needle opposite the tip) must be cleared by the needle before dispensing. In FIG. 3C the liquid fills the area between the needle opening and the elastomeric cap, and air is vented through the porous wick. By FIG. 3D, liquid being filled into the reservoir has reached one side of the wick, but venting may continue on the opposite side of the wick. In any of these examples the rate of filling may be controlled. For example, the rate of filling may be controlled to be relatively steady/constant and avoid splashing (e.g., by ramping up to the filling rate when initially filling). In FIG. 3E, the liquid front has finally reached the second side of the wick, and the cartridge is completely full, and (in FIG. 3F) the needle may be retraced, as shown.

In some variations, which may be used with tank-style electronic cigarettes, the wick may be as close to the bottom of the container as possible to ensure that as much liquid as possible can be drawn out of the container; when the cartridge is inverted this results in the wick being the highest point in the container and therefore an ideal location to vent from.

The area that surrounds the wick outside the tank may be configured to accommodate some amount of excess liquid during normal use (e.g., the wick housing), which means that it is often palatable to allow some small amount of liquid to be forced through the wick during filling, since any overflow ends up in a manageable location. This allows the possibility to fill a cartridge completely with no geometrically defined bubble zones.

Finally, it may be acceptable to allow some small amount of overfill in this configuration without having to deal with any messes or excess liquid, which allows for the addition of a subtle feature in the filling process. In some variations, the pumping system measures the pressure that it is applying during fill, and that pressure can be used to detect when the liquid front has reached the wick. The dramatic reduction in cross sectional area when passing through the wick typically results in a large change in fluid resistance, which in turn results in a relatively large spike in pressure in the tank and fill system when the flow front reaches the wick. This signal can be detected and used to switch off the pump, which allows the system to fill cartridges of variable sizes with no captive air.

As mentioned, in some variation the filling is performed when the tank is on its side, rather than upside down. This is shown in FIGS. 4A-4H. This variation may be employed to achieve the same effect as the inverted method discussed above, and may be particularly useful when machinery constraints provide a challenge to orienting the system so that the needles points upwards with respect to gravity. This variation may also be particularly useful if the cartridge is not a simple empty container and has additional features that can influence the liquid flow front as it is inserted. In general, it is desired to cause the wick to be the last point to become wetted when filling to completely fill the tank; this may be done when the cartridge (tank) is lying down or even vertical. When there are obstructions in the tank or connected sub-regions of the tank formed by projections into the tank, filing from different angles (e.g., side filling) may take advantage of different levels of fluid restriction in different areas of the cartridge. In any of these variations, the filling may also take advantage of the large difference in viscosity between air and the liquid being filled. Such differences can also be exaggerated by filling at very high speeds (around 1 ml/sec in the case of a cartridge that is between about 12 mm×about 4 mm×22 mm). See FIGS. 4A-4H for details of how the flow front advances in a cartridge during this horizontal fill process to avoid captured air.

Figure 4A:
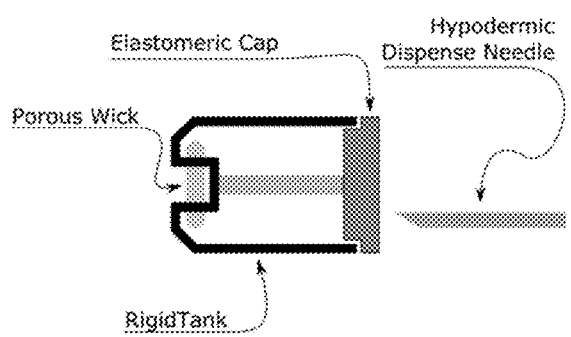
FIGS. 4A-4H illustrate a method of filling a reservoir of a cartridge, similar to the cartridge shown in FIG. 2, of an electronic cigarette with a single needle.
Figure 4B:
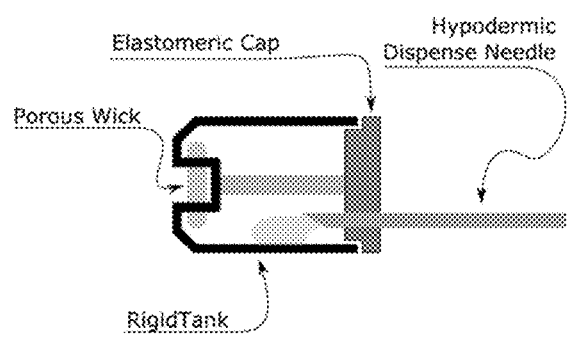
Figure 4C:
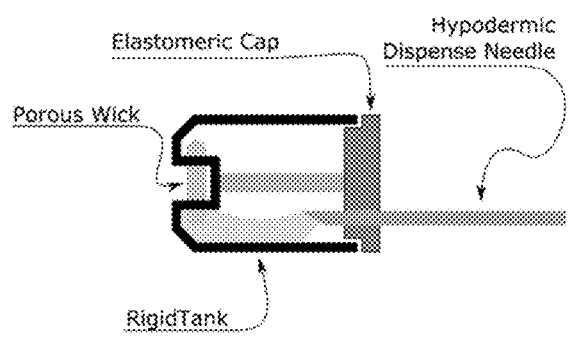
Figure 4D:
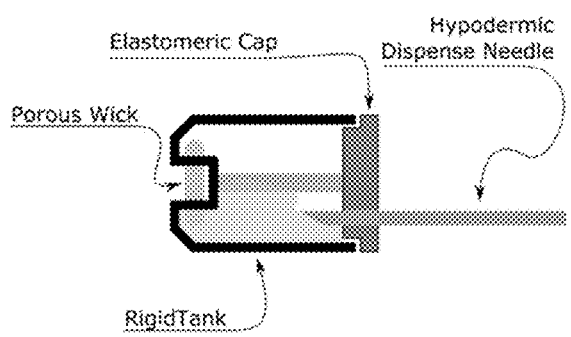
Figure 4E:
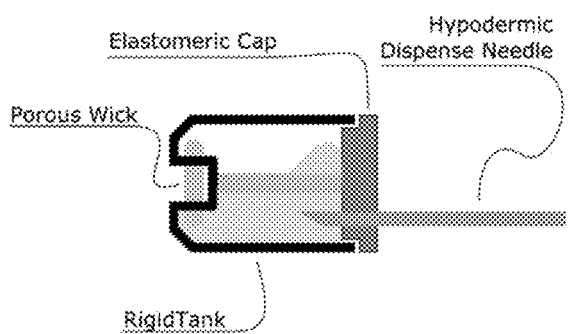
Figure 4F:
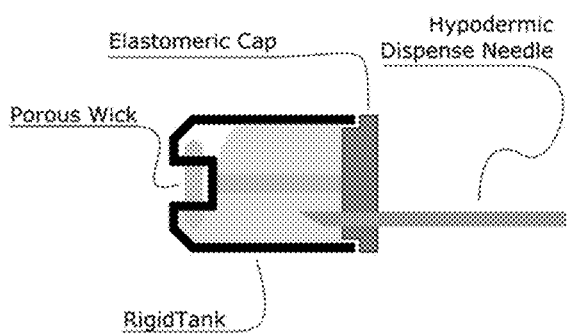
Figure 4G:
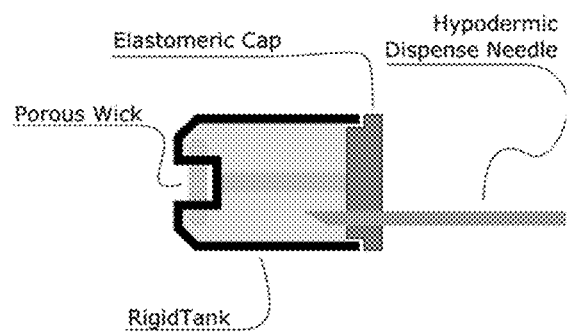
Figure 4H:
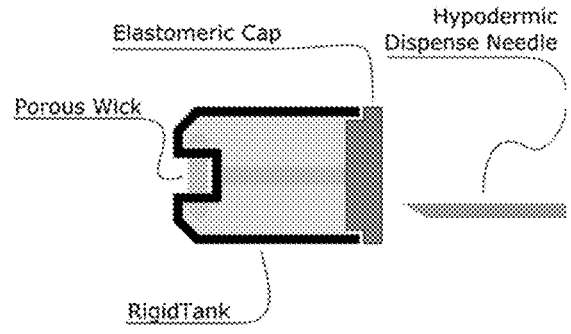

In FIG. 4A, the cartridge having an empty tank is fully assembled and positioned on its side, with the wick on a first side (perpendicular to the direction of gravity). In FIG. 4A, gravity is pointed in the direction of the page. Alternatively or additionally, the filling may be performed so quickly that viscous and inertial force dominate over the force of gravity. In FIG. 4B, the needle is inserted though the elastomeric cap opposite from the wick, and the filling may begin. The filling needle may be sharp and may include a beveled tip having the filling opening. The beveled opening may be oriented to direct the flow of filling liquid preferentially towards the bottom side of the cartridge (e.g., towards the page). In FIG. 4C, the flow front advances until it reaches the first wick end. The high rate of dispensing and fluid restricting of the wick may cause the flow front to advance within the cartridge instead of leaking out through the wick. In FIG. 4D, the internal tube restricts the flow of fluid from the side of the cartridge near the filling tube to the opposite side. In this example, fluid is restricted by the cannula (air path) to passing through the gap region between the walls of the tank and the cannula. This restriction may allow the filing to continue back towards the dispensing needle instead of starting to fill the opposite side from the needle (on the other side of the cannula). In FIG. 4E the proximity to the needle tip (dispensing head) may cause the flow front to finally cross the steel air path toward the end of the cartridge furthest from the wick (e.g., near the end from which the needle entered), eventually filling the furthest corner. In FIG. 4F, the flow front has advanced towards the wick as the top right (near the elastomeric cap) is filled, progressing towards the far side of the wick which is still venting. By FIG. 4G the flow front has reached the last free wick end at last, and after wetting it, no further air can escape (preventing it from venting captive air); by that point, filing is complete, as shown in FIG. 4H, and the hypodermic filling needle may be retracted, as shown.

This side-filling method may work well where there is some degree of fluid restriction (e.g., where, as here, a cannula or other obstruction is present in the tank). It also helps that fluid restriction through the wick is much higher when it is wetted than when it is dry, allowing it to behave effectively like a valve that creates a staged fill process. For example, filling the bottom, then the top. Similarly, the fluid restriction (governed in this case by the geometric arrangement or spacing) around the steel air path (cannula) is much higher than the fluid restriction back towards the needle, allowing the end far from the wick to fill in these examples, which, as shown in FIGS. 1A-1F is where air is trapped, forming a captive air zone in the 2 needle approach, even without gravity influencing that region to fill first as in the inverted filling technique show in FIGS. 3A-3H. Once the flow front reaches the far side of the air path it can simply fill towards the wick without risk of capturing any more air.

In cases in which the tank does not include an obstruction in the inner volume (e.g., where a feature similar to the steel air path in the cartridge shown in FIGS. 4A-4F is absent), a change to the needle geometry that causes the liquid to exit the needle in a direction normal to the axis of the needle (such as using a Witacre or Sprotte type needle, see FIGS. 6A-6B and 7A-B) may be used to influence the flow front to fill completely from the elastomer cap end to the wick end of the cartridge, as illustrated in FIGS. 8A-8F.

Figure 8A:
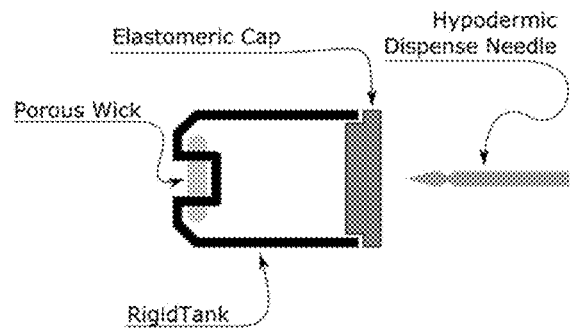
FIGS. 8A-8F illustrate a method of filling a reservoir of a cartridge, similar to the cartridge shown in FIG. 2, of an electronic cigarette with a single needle.
Figure 8B:
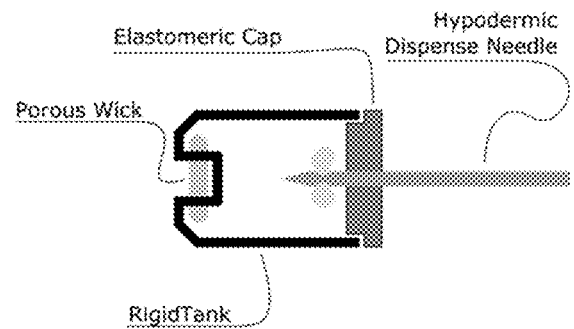
Figure 8C:
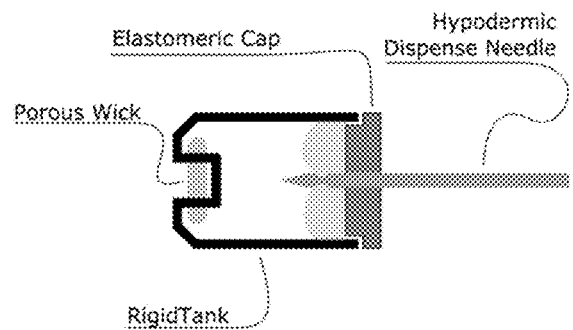
Figure 8D:
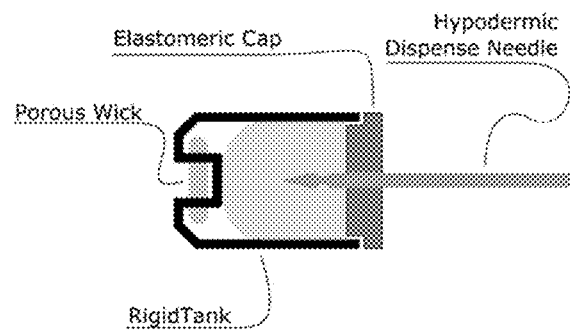

In this example, which is also a side-filling example, the cartridge including a tank is held sideways so that the wick is on one side and the needle is inserted from another side. The needle has a sharp distal tip and a more proximal side opening that directs the flow out of the needle perpendicular to the long axis of the needle. In FIG. 8A, a cartridge is viewed from above and ready for filling, otherwise fully assembled. In this example, gravity may be pointed down (towards the bottom of the page) or more preferable the cartridge is flat against a top surface and gravity is pointed into the page. Alternatively or additionally filling may be done rapidly so that viscous and inertial forces dominate over the gravitational forces. In FIG. 8B, the dispensing needle with side-exists (one or more preferably two side exits) is inserted into the tank reservoir and filing begins. The side exits (orifices) of the needle direct eh flow front to fill the area between the needle side exits and the elastomeric section. Filling then progresses from the right to left as shown in FIG. 8C. In FIG. 8D, the filling has further progressed and the dispensing needle may be adjusted to avoid air being captured between the wick housing and the needle (or between the needle and the wall of the tank. Preferably the needle is separated from the wall to entrap an air bubble.

Figure 8E:
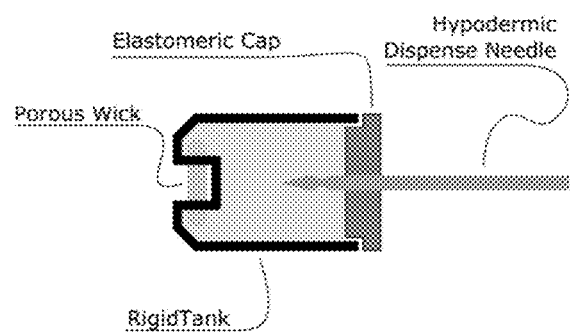
Figure 8F:
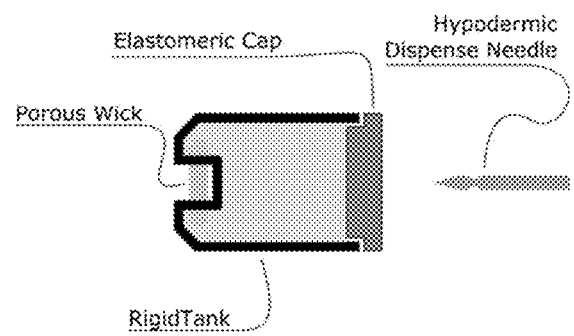

In FIG. 8E, the flow front has reached both wick ends at approximately the same time, and filling is complete in FIG. 8F and the needle may be retracted. Any of the filling methods described herein may be performed in parallel with multiple needles and multiple assembled cartridges/tanks.

Figure 9:
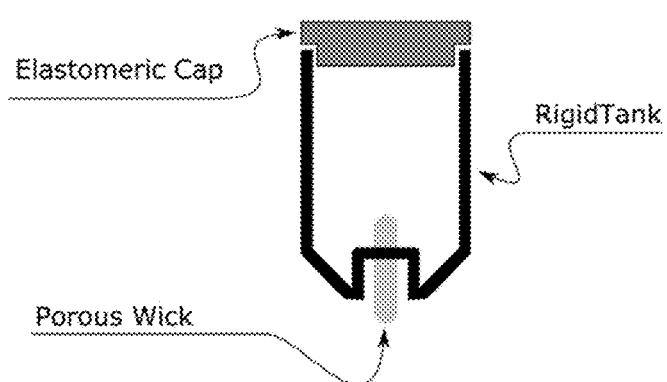
FIG. 9 is a front view of another variation of a cartridge, including a reservoir, for an electronic cigarette.

In all of these configurations we have depicted a style of tank with the wick reaching in to the tank in two locations. The risk of capturing air may be reduced if the wick reaches in to the tank in only one location, and the geometry of the tank may create a funnel towards that point, as would be the case with the variation shown in FIG. 9. All wick-venting filling methods and orientations described herein may work just as well or better with a cartridge of this format.

In general, the filling material (e.g., vaporizable material) that is injected into the tank may be any appropriate liquid. Examples of such liquid may include an aqueous solution of a nicotine salt (as incorporated by reference in its entirety above), or of a cannabis formulations. Any liquid solution may be used, including pharmaceutical solutions that may be vaporized for delivery (e.g., any liquid suitable for vaporization).

In some variations the cartridge may include a pre-pierced septum (e.g., elastomeric cap, etc.), and a blunt dispensing tip (filling needle) may be introduced through the existing septum flap to fill the tank reservoir. Alternatively or additionally any of these variations may include a resealable port of valve into which the needle is inserted for filling. This may reduce the required clearance of the needle (the minimum safe distance mentioned above). For example, a "star valve" may be formed (e.g., punched or laser cut, etc.) in a wall of the tank and/or the elastomeric top (septum), which may also allow liquid to be filled into the tank with a blunt dispensing tip. Alternatively or additionally, a mechanical fill port such as a poppet valve may be included in the cartridge and used for filling, rather than a penetrable septum like the elastomeric cap; this may also allow the use of a blunt dispensing tip, which may be designed to mate with the port.

As mentioned, any appropriate needle may be used, including those that direct the flow laterally (see e.g., FIGS. 6A-7B) or retrograde.

Figure 10C:
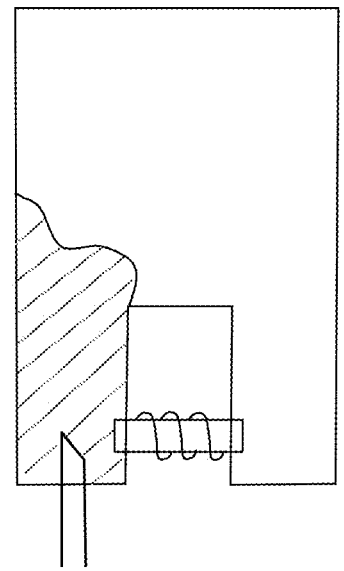
FIGS. 10A, 10B and 10C illustrate other variations of a method of filling a reservoir of a cartridge with a single needle. In these variations the liquid is filled from the same side as the wick, and the tank region (reservoir) is U-shaped. In general, one end of the wick may be confined to a smaller diameter region/smaller chamber so that it fills last, leaving the wick dry and able to vent air.
Figure 10A:
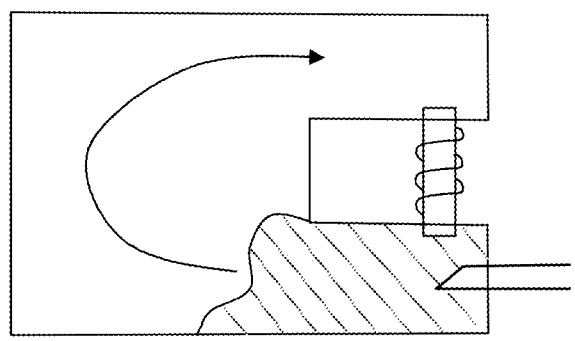
Figure 10B:
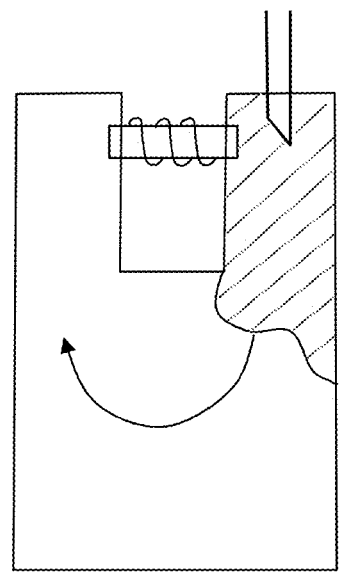

FIGS. 10A and 10B illustrate another variation of a filling method in which the needle is inserted from the same side as the wick. In this example, the filling may occur as described above, but may wrap around as shown in the arrow to fill the cartridge without leaving any air bubbles. In FIG. 10A, the cartridge is filled from the side (as described above) and may be lying flat (with a superior surface against a flat surface) so that gravity is into the page, or it may be inverted, as shown in FIG. 10B. Although it may be challenge. One or both of these filling arrangements. Note that a third variation is shown in FIG. 10C, where the liquid is filled from the bottom of the cartridge. In this case (as in FIGS. 10A-10B), liquid would preferentially flow into the tank vs. through the higher restriction of the wick, especially if filled slowly.

Alternative Cartridge Embodiments

Figure 11A:
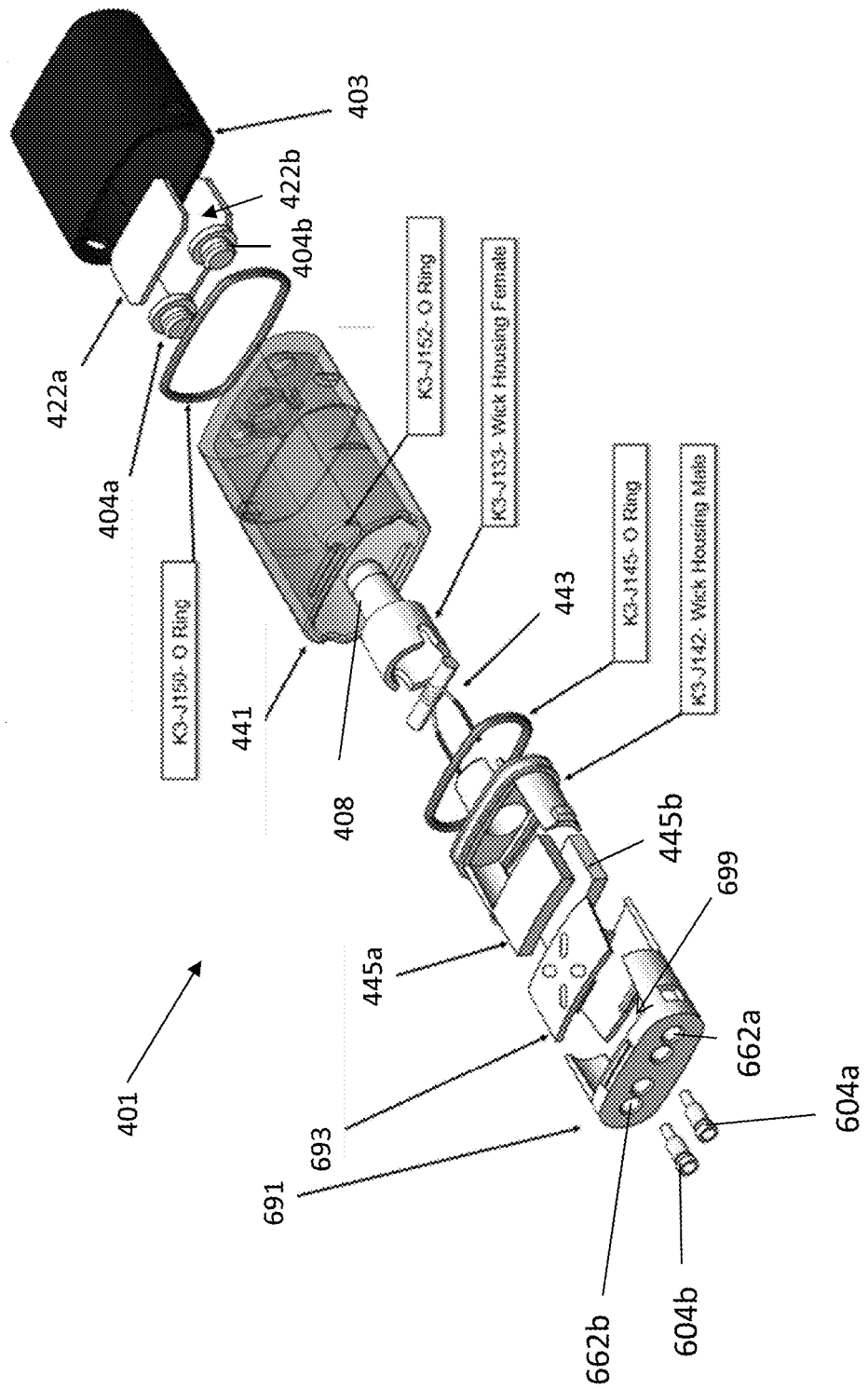
FIG. 11A illustrates an exploded view of a cartridge that may be filled as described herein.
Figure 11B:
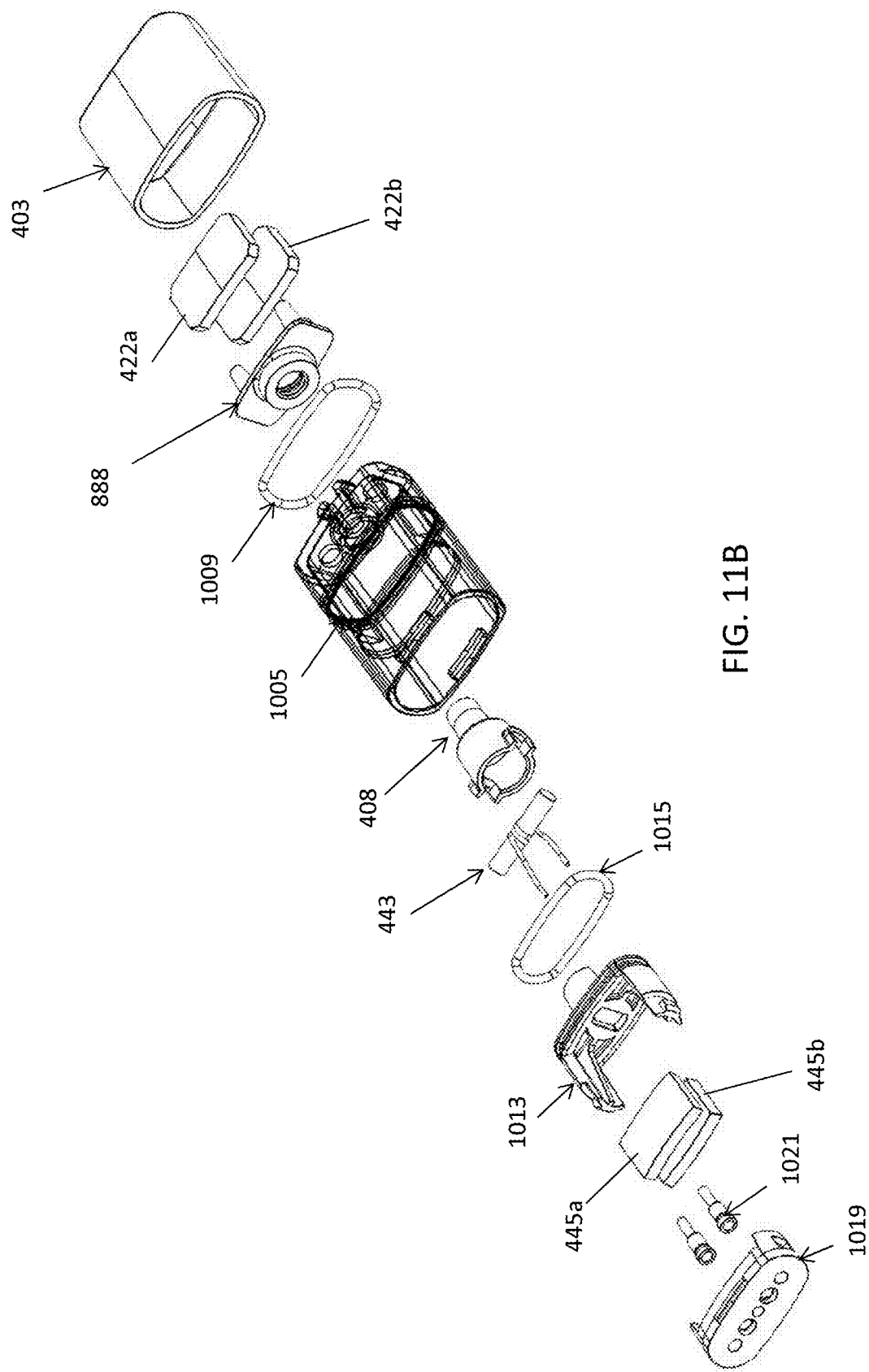
FIG. 11B is an alternative exploded view of a cartridge that may be filled as described herein.

The methods and apparatuses (including filling devices, systems, hardware and/or software for controlling filling) described herein may be used with any appropriate cartridge, including those shown in the exploded view of FIGS. 11A-11B.

For example, in FIG. 11A, the cartridge, whose components are described in greater detail below, may be filled by removing one or both plugs 404a, 404b, or by injection through these plugs, which may be formed of a self-healing material. In the exploded view of FIG. 11A the cartridge 401 includes a tank 441 configured to hold a liquid vaporizable material therein, a heater (e.g. a wick and coil assembly) 443 configured to heat the vaporizable material in the tank 441, and an air tube 408 extending from the tank to a mouthpiece 403. Contacts 535 are configured to connect with contacts 435 on the reusable component 411 to provide power to activate the wick and coil assembly 443. At the distal end of the cartridge the walls of the elongate and flattened tubular body 441 and a bottom cover piece 691 form an overflow leak chamber 699, which is shown with a pair of absorbent pads 495a,b are positioned along the long walls (along the diameter) of the overflow leak chamber. An option felt cover 693 may be included (also acting as an absorbent member). Parallel absorbent pads 422a,b can be positioned within the mouthpiece 403. The absorbent pads 422a,b are rectangular and parallel with one another. The absorbent pads 422a,b are positioned substantially parallel to the flat side of the device 400 (parallel with the plane of the length 1 and width w in FIG. 4A) and parallel with one another. In some embodiments, the pads 422a,b can be biased fully against the inside walls of the mouthpiece 403 so as to easily capture liquid that rolls along the walls (including during filling). A distance between the two pads 422a,b can be, for example, between 3 and 6 mm, such as between 4 and 5 mm, e.g., approximately 4.8 mm. The gap between the absorbent pads 422a,b advantageously prevents the pads from interfering with the air flow path when a user draws on the mouthpiece 403.

In general, over-flow pads, e.g., 445a,b may be positioned proximate to the tank 441, i.e., within an overflow leak chamber below the tank, to absorb liquid that may leak out of the tank 441 during filling and/or use. The over-flow pads 445a,b can be similarly placed parallel to one another and/or against the sides of the shell 431 as described above with respect to pads 422a,b.

Another example of a cartridge is shown in FIG. 11B. In this example, exemplary device 800 is similar to device 400 (similar reference numbers are therefore used) except that it includes a single plug 888 in the proximal section of the cartridge 801 (i.e., as opposed to the two tank seals 604a,b shown in FIG. 11A). The plug 888 is configured to simultaneously seal both outlets of the mouthpiece 403 while also sealing around the tube 408. As mentioned, filling may be performed as described herein, including injecting through the self-healing (e.g., a rubber or polymeric material).

In the exploded view of a cartridge shown in FIG. 11B, the apparatus includes a cartridge body 1005 that may be clear (transparent), opaque and/or translucent. The cartridge body may form a reservoir for the liquid vaporizable material, and particularly for a viscous liquid vaporizable material such as a cannabinoid oil, nicotine solution or other vaporizable material. The cartridge may include an outer seal (e.g., o-ring 1009) that seals the mouthpiece 403 over the body 1005. The reservoir (tank) may be sealed on the top (at the proximal end) under the mouthpiece by a single-piece plug 888 that covers multiple openings which may be used for filling the tank. The vaporization chamber may be formed at the bottom (distal end) of the cartridge; in exemplary cartridges described herein the vaporization chamber is formed from a cannula and housing piece 1011 that includes opening into which the wick (wick portion of wick and coil 443) passes into the chamber; the walls forming the vaporization chamber separate it from the tank and mate with a back piece 1013 that forms the bottom (distal end) of the tank within the cartridge body. This piece is also sealed (e.g., by an o-ring 1015) to the cartridge body from within the cartridge body, as shown. An air chamber is then formed between the bottom of the cartridge 1019 and the back piece 1013 of the tank. One or more (e.g., two) air openings 796, 796' through this bottom 1019 allow air to pass (after entering the cartridge receiver through one or more openings 894 in the side) into the distal end of the cartridge, into the air chamber region and then up through an opening into the vaporization chamber. The piece forming the bottom of the cartridge 1019 may also accommodate or include one or more (e.g., two) electrical connectors that are configured to mate with the connectors on the vaporizer base. As mentioned, these contacts may be wiper or scraping contacts. In FIG. 11B, they are shown as cans 1021, 1021' having openings into which the pins project to form an electrical contact.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A vaporizer device cartridge, comprising:
a storage compartment having a first end and a second end opposite the first end, the storage compartment configured to hold a liquid vaporizable material;
a sealing material sealing the second end, the sealing material configured for insertion of a needle through the sealing material for dispensing the liquid vaporizable material into the storage compartment; and
a wick positioned proximate to the first end, the wick comprising opposing ends in communication with the storage compartment, the wick configured to allow a volume of air to exit the storage compartment through the wick when the storage compartment is being filled with the liquid vaporizable material.

2. The vaporizer device cartridge of claim 1, wherein the wick is configured to allow the volume of air to exit the storage compartment through one or both of the opposing ends of the wick.

3. The vaporizer device cartridge of claim 2, wherein the opposing ends of the wick are disposed in the storage compartment.

4. The vaporizer device cartridge of claim 1, wherein the sealing material is further configured to seal after removal of the needle.

5. The vaporizer device cartridge of claim 1, wherein the sealing material comprises an elastomeric material.

6. The vaporizer device cartridge of claim 1, further comprising:
a heating element configured to heat the liquid vaporizable material to generate an aerosol, wherein the heating element is in thermal contact with the wick.

7. The vaporizer device cartridge of claim 6, further comprising:
electrical contacts electrically coupled to the heating element, the electrical contacts exposed proximate to the first end of the storage compartment.

8. The vaporizer device cartridge of claim 1, wherein the storage compartment comprises the liquid vaporizable material, and wherein the liquid vaporizable material comprises a nicotine formulation.

9. The vaporizer device cartridge of claim 8, wherein the nicotine formulation comprises nicotine and an organic acid.

10. The vaporizer device cartridge of claim 1, wherein the wick further comprises a central region between the opposing ends of the wick, and wherein the opposing ends of the wick are configured to draw the liquid vaporizable material towards the central region.

11. The vaporizer device cartridge of claim 10, further comprising:
a tank comprising the storage compartment and a chamber, wherein the chamber comprises the central region of the wick.

12. The vaporizer device cartridge of claim 1, wherein the wick comprises woven, braided, fibrous, or knitted material.

13. The vaporizer device cartridge of claim 1, wherein the storage compartment is translucent.

14. The vaporizer device cartridge of claim 1, further comprising:
a mouthpiece proximate to the second end of the storage compartment, the mouthpiece comprising at least one aerosol outlet.

15. The vaporizer cartridge of claim 14, further comprising:
a first absorbent pad; and
a second absorbent pad, the mouthpiece comprising a cavity, the first absorbent pad and the second absorbent pad held within the cavity, proximate to opposite sides of the mouthpiece.

16. The vaporizer device cartridge of claim 1, further comprising:
a tank comprising the storage compartment and a chamber, the chamber configured to receive and hold at least a portion of the wick.

17. The vaporizer device cartridge of claim 16, further comprising:
a heating element configured to heat the liquid vaporizable material within the chamber to generate an aerosol.

18. The vaporizer device cartridge of claim 17, further comprising:
a first electrical contact electrically coupled to the heating element, wherein part of the first electrical contact is disposed within the chamber; and
a second electrical contact electrically coupled to the heating element, wherein part of the second electrical contact is disposed within the chamber.

19. The vaporizer device cartridge of claim 16, further comprising:
a wick housing comprising a first pair of mating members, the tank further comprising a second pair of mating members, the first pair of mating members configured to mate with the second pair of mating members to define the chamber.

20. The vaporizer device cartridge of claim 19, wherein the first pair of mating members extends along part of at least one side wall of the tank.

21. The vaporizer device cartridge of claim 20, wherein the at least one side wall comprises a first side wall and a second side wall opposite the first side wall, and wherein the first pair of mating members extends along part of the first side wall and part of the second side wall.

22. The vaporizer device cartridge of claim 19, further comprising:
an airpath tube configured to provide fluid communication between the chamber and a mouthpiece.

23. The vaporizer device cartridge of claim 22, wherein the wick housing comprises a hole configured to receive the airpath tube.

24. The vaporizer device cartridge of claim 22, wherein the storage compartment comprises a first region and a second region, wherein the airpath tube is disposed to impede flow of the liquid vaporizable material from the first region of the storage compartment to the second region of the storage compartment.

25. The vaporizer device cartridge of claim 22, wherein the airpath tube comprises a cylindrical tube.

26. The vaporizer device cartridge of claim 25, wherein the storage compartment has a first dimension between the first end and the second end, wherein the storage compartment has a second dimension that is substantially perpendicular to the first dimension.

27. The vaporizer device cartridge of claim 26, wherein the storage compartment has a substantially rectangular cross-section along the second dimension.

28. The vaporizer device cartridge of claim 27, wherein the cylindrical tube extends along the first dimension, and wherein the wick extends along the second dimension.

* * * * *